(12) United States Patent
Hamblett et al.

(10) Patent No.: US 12,357,701 B2
(45) Date of Patent: Jul. 15, 2025

(54) ANTI-HER2 BIPARATOPIC ANTIBODY-DRUG CONJUGATES AND METHODS OF USE

(71) Applicant: Zymeworks BC Inc., Vancouver (CA)

(72) Inventors: Kevin Hamblett, Seattle, WA (US); Rupert H. Davies, Seattle, WA (US); James R. Rich, Vancouver (CA); Gerald J. Rowse, New Westminster (CA); Vincent K. C. Fung, Vancouver (CA); Stuart D. Barnscher, Vancouver (CA)

(73) Assignee: Zymeworks BC Inc., Vancouver (CA)

( * ) Notice: Subject to any disclaimer, the term of this patent is extended or adjusted under 35 U.S.C. 154(b) by 631 days.

(21) Appl. No.: 17/210,081

(22) Filed: Mar. 23, 2021

(65) Prior Publication Data
US 2021/0346508 A1     Nov. 11, 2021

Related U.S. Application Data

(60) Division of application No. 16/594,728, filed on Oct. 7, 2019, now Pat. No. 11,000,598, which is a
(Continued)

(51) Int. Cl.
*A61K 47/64* (2017.01)
*A61K 47/65* (2017.01)
(Continued)

(52) U.S. Cl.
CPC .......... *A61K 47/6425* (2017.08); *A61K 47/65* (2017.08); *A61K 47/6817* (2017.08);
(Continued)

(58) Field of Classification Search
None
See application file for complete search history.

(56) References Cited

U.S. PATENT DOCUMENTS

| 5,821,337 A | 10/1998 | Carter et al. |
| 6,884,869 B2 | 4/2005 | Senter et al. |

(Continued)

FOREIGN PATENT DOCUMENTS

| CN | 102884084 A | 1/2013 |
| CN | 106459214 A | 2/2017 |

(Continued)

OTHER PUBLICATIONS

Li et al., Cancer Cell (2016), 29(1), 117-129 (Year: 2016).*
(Continued)

*Primary Examiner* — Karl J Puttlitz
(74) *Attorney, Agent, or Firm* — Goodwin Procter LLP

(57) ABSTRACT

Anti-HER2 biparatopic antibody-drug conjugates (ADCs) in which the drug is an auristatin analogue and is conjugated to the antibody at a low average drug-to-antibody ratio (DAR), and methods of using the ADCs in the treatment of a HER2-expressing cancer. The low average DAR (<3.9) ADCs as described herein have improved tolerability and decreased toxicity as compared to a corresponding ADC having a DAR ≥3.9 when administered at the same toxin dose.

33 Claims, 25 Drawing Sheets

Specification includes a Sequence Listing.

Related U.S. Application Data continuation of application No. PCT/CA2019/050303, filed on Mar. 12, 2019.

(60) Provisional application No. 62/743,884, filed on Oct. 10, 2018, provisional application No. 62/658,477, filed on Apr. 16, 2018, provisional application No. 62/642,483, filed on Mar. 13, 2018.

(51) Int. Cl.

| | | |
|---|---|---|
| *A61K 47/68* | (2017.01) | |
| *A61P 35/00* | (2006.01) | |
| *C07K 16/30* | (2006.01) | |
| *C07K 16/32* | (2006.01) | |
| *A61K 38/00* | (2006.01) | |
| *A61K 39/00* | (2006.01) | |

(52) U.S. Cl.
CPC ...... *A61K 47/6855* (2017.08); *A61K 47/6857* (2017.08); *A61K 47/6863* (2017.08); *A61K 47/6869* (2017.08); *A61P 35/00* (2018.01); *C07K 16/3015* (2013.01); *C07K 16/3023* (2013.01); *C07K 16/3046* (2013.01); *C07K 16/3069* (2013.01); *C07K 16/32* (2013.01); *A61K 38/00* (2013.01); *A61K 2039/505* (2013.01); *C07K 2317/31* (2013.01); *C07K 2317/526* (2013.01); *C07K 2317/55* (2013.01); *C07K 2317/565* (2013.01); *C07K 2317/622* (2013.01); *C07K 2317/73* (2013.01)

(56) References Cited

U.S. PATENT DOCUMENTS

| | | |
|---|---|---|
| 7,098,308 B2 | 8/2006 | Senter et al. |
| 7,256,257 B2 | 8/2007 | Doronina et al. |
| 7,498,298 B2 | 3/2009 | Doronina et al. |
| 7,521,541 B2 | 4/2009 | Eigenbrot et al. |
| 7,659,241 B2 | 2/2010 | Senter et al. |
| 7,862,817 B2 | 1/2011 | Adams et al. |
| 8,455,622 B2 | 6/2013 | McDonagh et al. |
| 8,507,654 B2 | 8/2013 | Baker et al. |
| 9,000,130 B2 | 4/2015 | Bhakta et al. |
| 9,315,581 B2 | 4/2016 | Hudson et al. |
| 9,745,382 B1 | 8/2017 | Li et al. |
| 9,879,086 B2 | 1/2018 | Winters et al. |
| 10,000,576 B1 | 6/2018 | Weisser et al. |
| 10,092,559 B2 | 10/2018 | Rekhi et al. |
| 10,092,659 B2 | 10/2018 | Santin et al. |
| 10,383,948 B2 | 8/2019 | Allan et al. |
| 10,407,743 B2 | 9/2019 | Ariaans et al. |
| 10,414,822 B2 | 9/2019 | Winters et al. |
| 10,450,378 B2 | 10/2019 | Winters et al. |
| 10,457,739 B2 | 10/2019 | Berne et al. |
| 10,947,319 B2 | 3/2021 | Weisser et al. |
| 11,000,598 B2 | 5/2021 | Hamblett et al. |
| 2013/0195849 A1 | 8/2013 | Spreter Von Kreudenstein et al. |
| 2014/0170148 A1 | 6/2014 | De Goeij et al. |
| 2014/0286968 A1 | 9/2014 | Leanna et al. |
| 2015/0284463 A1 | 10/2015 | Tamaskovic et al. |
| 2016/0075735 A1 | 3/2016 | Winters et al. |
| 2016/0083480 A1 | 3/2016 | Ng et al. |
| 2016/0136298 A1 | 5/2016 | Grawunder et al. |
| 2016/0289335 A1 | 10/2016 | Weisser et al. |
| 2017/0029529 A1 | 2/2017 | Croasdale et al. |
| 2017/0291955 A1 | 10/2017 | Li et al. |
| 2017/0355779 A1 | 12/2017 | Wickman et al. |
| 2018/0022820 A1 | 1/2018 | Li et al. |
| 2018/0282429 A1 | 10/2018 | Weisser et al. |
| 2019/0345254 A1 | 11/2019 | Winters et al. |
| 2020/0297862 A1 | 9/2020 | Ng |
| 2021/0260210 A1 | 8/2021 | Hamblett et al. |

FOREIGN PATENT DOCUMENTS

| | | |
|---|---|---|
| CN | 107446045 A | 12/2017 |
| JP | 2015-521615 A | 7/2015 |
| JP | 2017-533886 A | 11/2017 |
| JP | 2018-501211 A | 1/2018 |
| RU | 2656161 | 12/2017 |
| WO | 2002/088172 A2 | 11/2002 |
| WO | 2012058768 A1 | 5/2012 |
| WO | 2013063702 A1 | 5/2013 |
| WO | 2013/190292 | 12/2013 |
| WO | 2015077891 * | 6/2015 |
| WO | 2015077891 A1 | 6/2015 |
| WO | 2015/095953 A1 | 7/2015 |
| WO | 2015095953 * | 7/2015 |
| WO | 2016/041082 A1 | 3/2016 |
| WO | 2016041082 * | 3/2016 |
| WO | 2016/082044 A1 | 6/2016 |
| WO | 2016/179707 A1 | 11/2016 |
| WO | 2017/095805 A1 | 6/2017 |
| WO | 2017/185177 A1 | 11/2017 |

OTHER PUBLICATIONS

Chen et al., Determination of Drug-to-Antibody Ratio for Antibody-Drug Conjugates Purified from Serum, Agilent Technologies, pp. 1-9, 2016 (Year: 2016).*
Jain et al., Pharm Res (2015) 32:3526-3540 (Year: 2015).*
Bange, J., et al., Molecular targets for breast cancer therapy and prevention. Nat Med. 2001;7(5):548-52.
Doi, T., et al., Safety, pharmacokinetics, and antitumour activity of trastuzumab deruxtecan (DS- 8201), a HER2-targeting antibody-drug conjugate, in patients with advanced breast and gastric or gastro-oesophageal tumours: a phase 1 dose-escalation study. Lancet Oncology. 2017; 18(11):1512-1522.
Donaghy, H., Effects of antibody, drug and linker on the preclinical and clinical toxicities of antibody-drug conjugates. MABS. 2016;8(4):659-671.
Hamblett, K. J., et al., Effects of Drug Loading on the Antitumor Activity of a Monoclonal Antibody Druo Coniuoate. Clin. Cancer Res. 2004; 10:7063-7070.
Hamblett, K., et al., "ZW49, a HER2-targeted biparatopic antibody-drug conjugate for the treatment of HER2-expressing cancers." Abstract 3914/14. AACR Annual Meeting, Apr. 17, 2018, Chicago, Illinois.
Kamath, A., et al., Preclinical Pharmacokinetic Considerations for the Development of Antibody Drug Conjugates. Pharm Res. Nov. 2015;32(11):3470-3479.
Li, J. Y., et al., A Biparatopic HER2-Targeting Antibody-Drug Conjugate Induces Tumor Regression in Primary Models Refractory to or Ineligible for HER2-Targeted Therapy. Cancer Cell. 2016;29(1):117-129.
Li. B., et al., Bispecific Antibody to ErbB2 Overcomes Trastuzumab Resistance through Comprehensive Blockade of ErbB2 Heterodimerization. Cancer Res. 2013;73(21):6471-6483.
Sun, X., et al., Effects of Drug-Antibody Ratio on Pharmacokinetics, Biodistribution, Efficacy, and Tolerability of Antibody-Maytansinoid Conjugates. Bioconj Chem. 2017;28(5): 1371-81.
Zymeworks Advances Clinical Candidate Incorporating Technology from Kairos Acquisition. Press release. Mar. 14, 2018. Retrieved from https://ir.zymeworks.com/file/Ind ex?KeyFile=39260084 7.
"ZW49, A HER2 Targeted Biparatopic Antibody Drug Conjugate for the Treatment of HER2 Expressing Cancers," Abstract, AACR Annual Meeting, Chicago, IL; Mar. 14, 2018, 1 page.
"ZW49, A HER2 Targeted Biparatopic Antibody Drug Conjugate for the Treatment of HER2 Expressing Cancers," Poster, AACR Annual Meeting, Chicago, IL; Apr. 17, 2018, 1 page.
"Redefining the Therapeutic Window for ADCs," Antibody Drug Conjugate Summit, Barcelona, Spain; May 18, 2018, 25 pages.
"ZymeLink: A Novel Drug Conjugate Platform—Redefining the Therapeutic Window for ADCs," Next Generation Protein Therapeutics & Bioconjugates Summit, San Francisco, CA; Jun. 13, 2018, 25 pages.

(56) References Cited

OTHER PUBLICATIONS

"ZW49: A Biparatopic HER2-Targeted ADC," Zymeworks' 2018 R&D Briefing, New York, NY; Oct. 11, 2018, 18 pages.
"ZW49, A HER2 Targeted Biparatopic Antibody Drug Conjugate for the Treatment of HER2 Expressing Cancers," Abstract, San Antonio Breast Cancer Conference, San Antonio, TX; Dec. 8, 2018, 1 page.
"ZW49, A HER2 Targeted Biparatopic Antibody Drug Conjugate for the Treatment of HER2 Expressing Cancers," Poster, San Antonio Breast Cancer Conference, San Antonio, TX; Dec. 8, 2018, 1 page.
International Preliminary Report of Patentability for Application PCT/CA2019/050303, received Sep. 24, 2020, 8 pages.
International Search Report and Written Opinion for PCT/CA2019/050303, 12 pages.
Trail, P.A., et al., "Antibody drug conjugates for treatment of breast cancer: novel targets and diverse approaches in ADS design", Pharmacology and Therapeutics 181 (2018) 126-142.
Jackson, D., et al., "In Vitro and In Vivo Evaluation of Cysteine and Site Specific Conjugated Herceptin Antibody-Drug Conjugates", Plos one, 2014, vol. 9, Issue 1, e83865.
Axup, J. Y., et al., Synthesis of site-specific antibody-drug conjugates using unnatural amino acids. PNAS USA. 2012; 109(40):16101-16106.
Alves, N.J., et al., Conjugation of a reactive thiol at the nucleotide binding site for site-specific antibody functionalization. Bioconjug Chem. 2014;25(7):1198-1202.
Badescu, G., et al., Bridging disulfides for stable and defined antibody drug conjugates. Bioconjug Chem. 2014;25 (6):1124-1136.
Behrens, C.R., et al., Antibody-Drug Conjugates (ADCs) Derived from Interchain Cysteine Cross-Linking Demonstrate Improved Homogeneity and Other Pharmacological Properties over Conventional Heterogeneous ADCs. Mol Pharm. 2015;12(11):3986-3998.
Bernardes, G. J., et al., Site-specific chemical modification of antibody fragments using traceless cleavable linkers. Nat Protoc. 2013;8(11):2079-2089.
Boutureira, O., et al., Advances in Chemical Protein Modification. Chem Rev. 2015;115(5):2174-2195.
Davies, R., et al., "Towards development of next-generation biparatopic ADCs using a novel linker-toxin with expanded therapeutic window." AACR Annual Meeting, Apr. 17, 2018, Chicago, Illinois. Poster Presentation.
Drake, P.M., et al. Aldehyde tag coupled with HIPS chemistry enables the production of ADCs conjugated site-specifically to different antibody regions with distinct in vivo efficacy and PK outcomes. Bioconjug Chem. 2014;25(7):1331-1341.
Hofer, T., et al., Molecularly defined antibody conjugation through a selenocysteine interface. Biochemistry. 2009;48 (50):12047-12057.
Jeger, S., et al., Site-specific and stoichiometric modification of antibodies by bacterial transglutaminase. Angew Chem Int Ed Engl. 2010;49(51):9995-9997.
Junutula, J. R., et al., Rapid identification of reactive cysteine residues for site-specific labeling of antibody—Fabs. J Immunol Methods. 2008;332(1-2):41-52.
Junutula, J. R., et al., Site-specific conjugation of a cytotoxic drug to an antibody improves the therapeutic index. Nat Biotechnol. 2008;26(8):925-932.
Kornberger, P., et al., Sortase-catalyzed in vitro functionalization of a HER2-specific recombinant Fab for tumor targeting of the plant cytotoxin gelonin. MAbs. 2014;6(2):354-366.
Lee, M.T.W., et al., Next-generation disulfide stapling: reduction and functional re-bridging all in one. Chem Sci. 2016;7(1):799-802.
Lyon, R.P., et al., Conjugation of anticancer drugs through endogenous monoclonal antibody cysteine residues. Methods Enzymol. 2012; 502:123-138.
McCombs, Osc., Antibody drug conjugates: design and selection of linker, payload and conjugation chemistry. AAPS J. 2015;17(2):339-351.
McDonagh, C.F., et al., Engineered antibody-drug conjugates with defined sites and stoichiometries of drug attachment. Protein Eng Des Sel. 2006; 19(7):299-307.
Maruani, A., et al., A plug-and-play approach to antibody-based therapeutics via a chemo selective dual click strategy. Nat Commun. 2015;6:6645.
Strop, P., et al., Location matters: site of conjugation modulates stability and pharmacokinetics of antibody drug conjugates. Chem Biol. 2013;20(2):161-167.
Thompson, P. et al., Hydrolytically Stable Site-Specific Conjugation at the N-Terminus of an Engineered Antibody. Bioconjug Chem. 2015;26(10):2085-2096.
Zhou, Q., et al. Site-specific antibody-drug conjugation through glycoengineering. Bioconjug Chem. 2014;25 (3):510-520.
Takegawa, N., et al., "DS-8201a, a new HER2-targeting antibody-drug conjugate incorportaing a novel DNA topoisomerase I inhibitor, overcomes HER2-positive gastric cancer T-DM1 resistance", International Journal of Cancer, vol. 141, No. 8, Jul. 12, 2017, 9 pages.
Yurkovetskiy, A, et al. "A Polymer-Based Antibody-Vinca Drug Conjugate Platform; Characterization and Preclinical Efficacy", Cancer Res; 75 (16); 3365-72, 2015.

\* cited by examiner

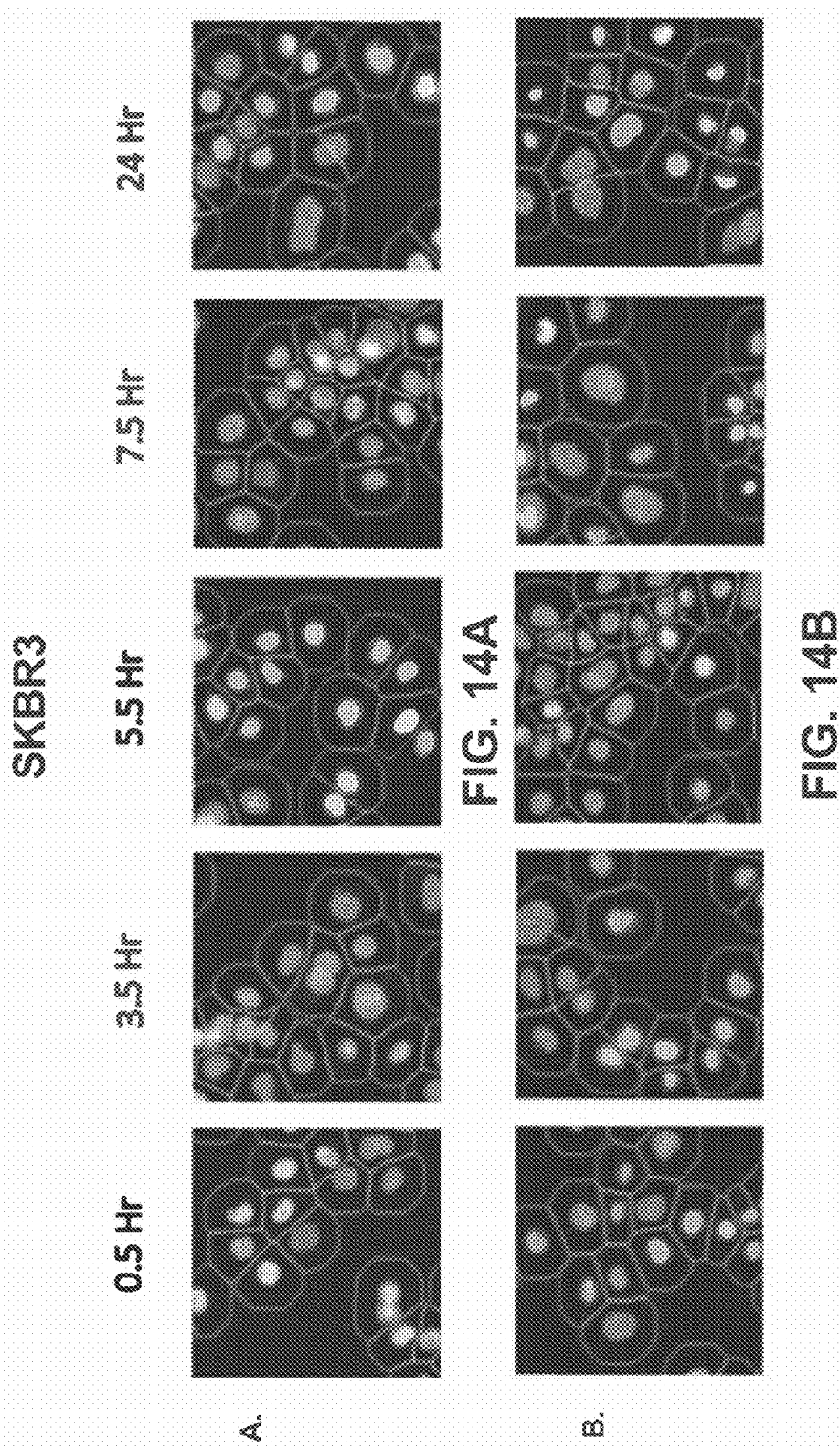

ANTI-HER2 BIPARATOPIC ANTIBODY-DRUG CONJUGATES AND METHODS OF USE

CROSS REFERENCE TO RELATED APPLICATIONS

This application is a divisional of U.S. application Ser. No. 16/594,728, filed Oct. 7, 2019, which is a continuation of International Application No. PCT/CA2019/050303, filed Mar. 12, 2019, which claims priority to U.S. Provisional Application No. 62/743,884, filed Oct. 10, 2018 and U.S. Provisional Application No. 62/658,477 filed Apr. 16, 2018 and U.S. Provisional Application No. 62/642,483, filed Mar. 13, 2018, each of which is herein incorporated in its entirety by reference.

SEQUENCE LISTING

The instant application contains a Sequence Listing with 89 sequences which has been submitted via EFS-Web and is hereby incorporated by reference in its entirety. Said ASCII copy, created on Mar. 23, 2021, is named ZWI047USD1_Sequencelisting.txt, and is 115,104 bytes in size

FIELD

The present disclosure relates to the field of cancer therapeutics and, in particular, to antibody-drug conjugates comprising a biparatopic anti-HER2 antibody and an auristatin analogue.

BACKGROUND

HER2 (ErbB2) is a transmembrane surface-bound receptor tyrosine kinase that is a member of the ErbB family of receptor tyrosine kinases and is normally involved in the signal transduction pathways leading to cell growth and differentiation. HER2 is a promising target for treatment of breast cancer as it was found to be overexpressed in about one-quarter of breast cancer patients (Bange et al, Nature Medicine 7:548 (2001)).

Herceptin® (trastuzumab, U.S. Pat. No. 5,821,337) was the first monoclonal antibody developed for the treatment of HER2-positive breast cancer and has increased survival times for patients so that they are now the same as for patients with HER2-negative breast cancer. Pertuzumab (Perjeta®, U.S. Pat. No. 7,862,817) is a humanized monoclonal antibody, which is designed specifically to prevent the HER2 receptor from pairing (dimerizing) with other HER receptors (EGFR/HER1, HER3 and HER4) on the surface of cells, a process that is believed to play a role in tumour growth and survival. The combination of Perjeta, Herceptin and chemotherapy is thought to provide a more comprehensive blockade of HER signaling pathways. Pertuzumab binds to domain II of HER2, essential for dimerization, while trastuzumab binds to extracellular domain IV of HER2.

Li et al (Cancer Res., 73:6471-6483 (2013)) describe bispecific, bivalent antibodies to HER2 that are based on the native trastuzumab and pertuzumab sequences and which overcome trastuzumab resistance. Other bispecific anti-HER2 antibodies have been described (International Patent Application Publication Nos. WO 2015/077891 and WO 2016/179707; U.S. Patent Application Publication Nos. 2014/0170148, 2015/0284463, 2017/0029529 and 2017/0291955; U.S. Pat. No. 9,745,382). An antibody-drug conjugate comprising a HER2-targeting biparatopic antibody site-specifically conjugated to a tubulysin derivative has also been described (Li et al., Cancer Cell, 29:117-129 (2016)).

Auristatins are synthetic analogues of dolastatin 10, which is a potent microtubule inhibitor with anti-cancer activity. Antibody-drug conjugates comprising auristatin payloads, such as monomethyl auristatin E (MMAE) or monomethyl auristatin F (MMAF), have been described (U.S. Pat. Nos. 7,498,298 and 7,659,241; International Patent Application Publication Nos. WO 2002/088172 and WO 2016/041082). International Patent Application Publication No. WO 2106/041082 describes N-acyl sulfonamide modified auristatins and their use as antibody-drug conjugate payloads.

This background information is provided for the purpose of making known information believed by the applicant to be of possible relevance to the present disclosure. No admission is necessarily intended, nor should be construed, that any of the preceding information constitutes prior art against the claimed invention.

SUMMARY

Described herein are anti-HER2 biparatopic antibody-drug conjugates and methods of use. In one aspect, the present disclosure relates to an antibody-drug conjugate comprising an anti-HER2 biparatopic antibody conjugated to an auristatin analogue via a linker (L) at a low average drug-to-antibody ratio (DAR), wherein the anti-HER2 biparatopic antibody comprises a first antigen-binding polypeptide construct which binds a first HER2 epitope and a second antigen-binding polypeptide construct which binds a second HER2 epitope, the first and second HER2 epitopes being different epitopes, and wherein the low average DAR is an average DAR of less than 3.9.

In certain embodiments of the antibody-drug conjugate the auristatin analogue-linker has general Formula (II):

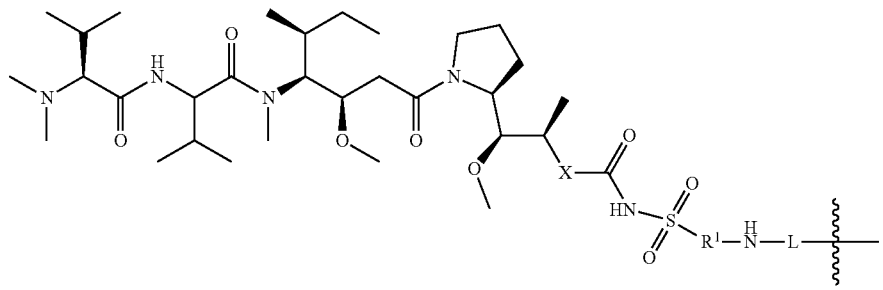

(II)

wherein:

X is —C(O)NHCH(CH$_2$R$^2$)—, or X is absent;

R$^1$ is selected from:

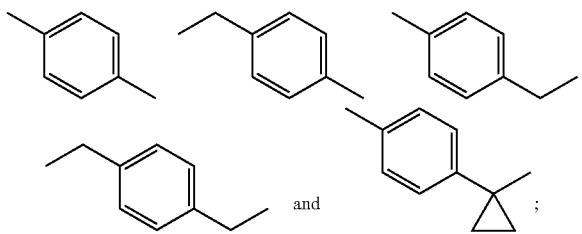

and

L is the linker, and

⸸ represents the point of attachment of the linker-toxin to the anti-HER2 biparatopic antibody;

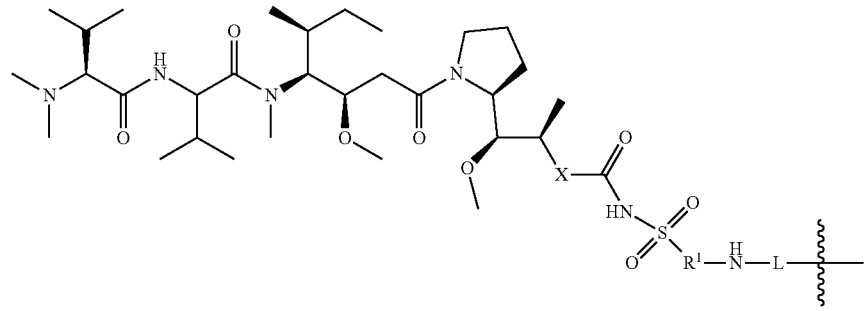

(II)

wherein the anti-HER2 biparatopic antibody comprises a first antigen-binding polypeptide construct which binds a first HER2 epitope and a second antigen-binding polypeptide construct which binds a second HER2 epitope, the first and second HER2 epitopes being different epitopes, and wherein the low average DAR is an average DAR of less than 3.9.

In certain embodiments, the low average DAR of the antibody-drug conjugate is between 0.5 and 3.5, or between 0.5 and 2.5.

In certain embodiments, the antibody-drug conjugate comprises 5% or more DAR0 species or 15% or more DAR0 species. In some embodiments, the antibody-drug conjugate comprises between about 5% and about 50% DAR0 species, or between about 10% and about 30% DAR0 species, or between about 10% and about 25% DAR0 species, or between about 15% and about 25% DAR0 species.

In certain embodiments, the antibody-drug conjugate comprises 25% or less DAR6 or greater species, or 15% or less DAR6 or greater species. In some embodiments, the antibody-drug conjugate comprises between 0% and about 15% DAR6 or greater species, or between about 0% and about 10% DAR6 or greater species.

Another aspect of the present disclosure relates to a pharmaceutical composition comprising an anti-HER2 biparatopic antibody-drug conjugate as described herein and a pharmaceutically acceptable carrier or diluent.

Another aspect relates to a method of inhibiting the growth of a HER2-expressing cancer cell, the method comprising contacting the cancer cell with an effective amount of an anti-HER2 biparatopic antibody-drug conjugate as described herein.

Another aspect relates to a method of treating a HER2-expressing cancer comprising administering to a subject having a HER2-expressing cancer an effective amount of an anti-HER2 biparatopic antibody-drug conjugate as described herein.

Another aspect relates to an antibody-drug conjugate as described herein for use in therapy.

Another aspect relates to an antibody-drug conjugate as described herein for use to treat a HER2-expressing cancer in a subject in need thereof.

Another aspect relates to a use of an antibody-drug conjugate as described herein in the manufacture of a medicament for the treatment of a HER2-expressing cancer.

Another aspect relates to an antibody-drug conjugate composition comprising an anti-HER2 biparatopic antibody conjugated to an auristatin analogue via a linker (L), the auristatin analogue-linker having general Formula (II):

wherein:

X is absent;

R$^1$ is selected from:

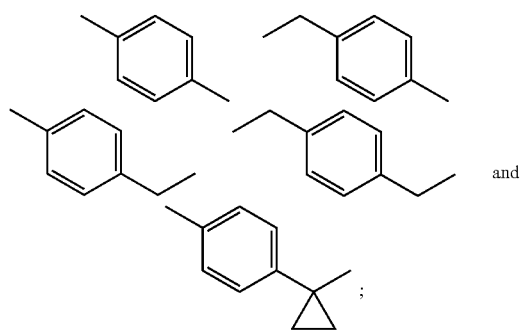

and

L is the linker, and

⸸ represents the point of attachment of the auristatin analogue-linker to the anti-HER2 biparatopic antibody;

wherein the anti-HER2 biparatopic antibody comprises a first antigen-binding polypeptide construct which binds a first HER2 epitope on ECD4 of HER2 and a second antigen-binding polypeptide construct which binds a second HER2 epitope on ECD2 of HER2, and wherein the antibody-drug conjugate composition has an average DAR of between 0.5 and 2.5 and comprises between about 10% and about 30% DAR0 species and between 0% and about 15% DAR6 or greater species.

BRIEF DESCRIPTION OF THE DRAWINGS

FIGS. 14A-14B show internalization of pHAb-conjugated v21252 (FIG. 14A) compared to pHAb-conjugated Trastuzumab-Linker-Toxin 001 (FIG. 14B) into SKBR3 cells at various time points as indicated. Nuclei are shown in grey, and pHAb is shown in white.

(FIG. 15A) exposure in cynomolgus monkeys and mice subcutaneously implanted with high HER2 patient derived tumour (HBCx-13b), (FIG. 15B) exposure in cynomolgus monkeys and mice subcutaneously implanted with low HER2 patient derived tumour (ST-910).

DETAILED DESCRIPTION

Figures 1A, 1B:
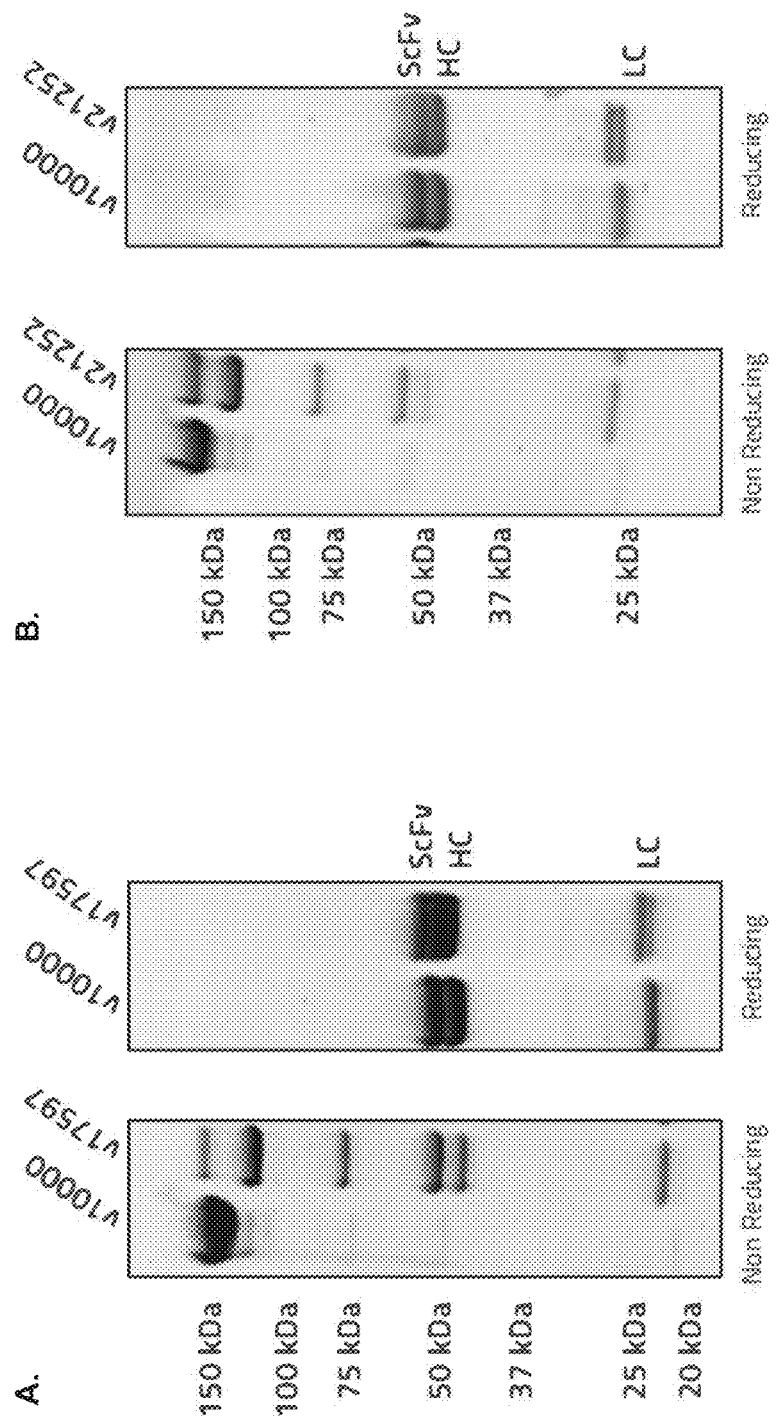
FIGS. 1A and 1B show non-reducing and reducing SDS-PAGE of (FIG. 1A) v17597 (anti-HER2 biparatopic antibody conjugated to Linker-Toxin 001 at DAR4), and (FIG. 1B) v21252 (anti-HER2 biparatopic antibody conjugated to Linker-Toxin 001 at DAR2), each compared to parent anti-HER2 biparatopic antibody (v10000).
Figure 2A:
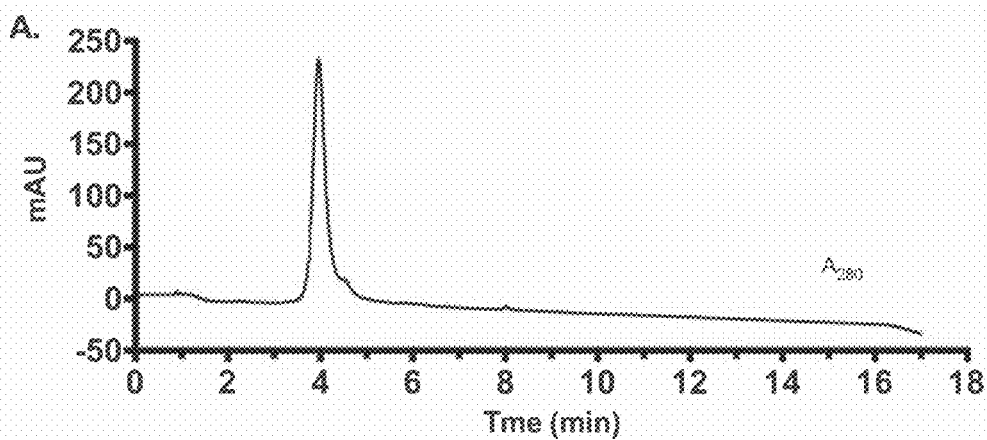
FIGS. 2A-2E show hydrophobic interaction chromatography (HIC) traces for (FIG. 2A) parent anti-HER2 biparatopic antibody v10000, (FIG. 2B) v17597 (anti-HER2 biparatopic antibody conjugated to Linker-Toxin 001 showing an average DAR of 3.92), and (FIG. 2C) v21252 (anti-HER2 biparatopic antibody conjugated to Linker-Toxin 001 showing an average DAR of 2.07). The individual contributions of the DAR0, DAR2, DAR4 and DAR6 species to the average DAR of the purified ADCs is shown in (FIG. 2D) and (FIG. 2E).
Figure 2B:
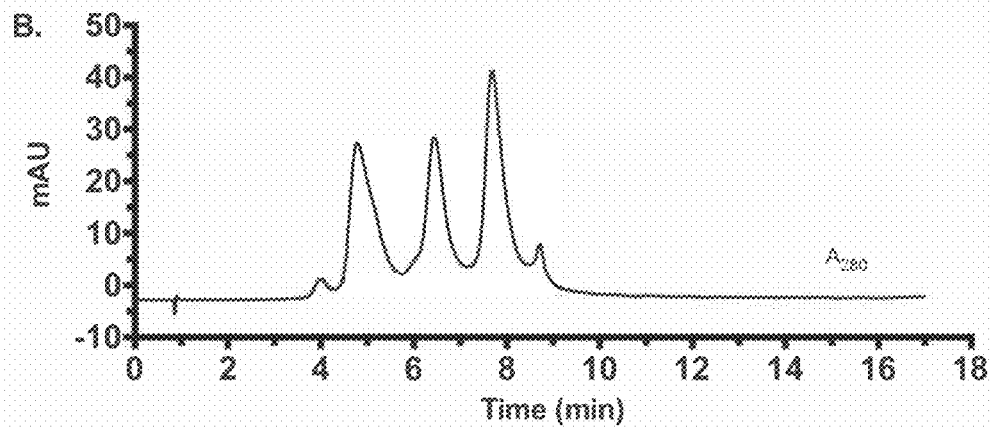
Figure 2C:
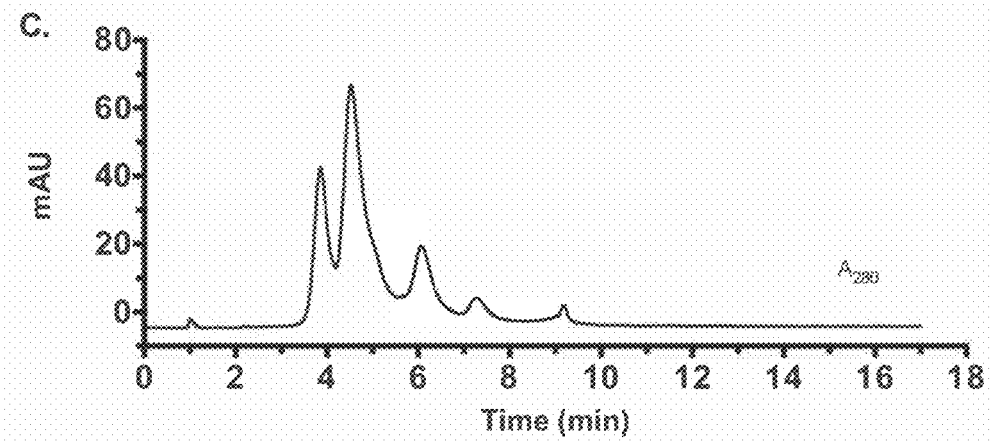
Figure 2D:
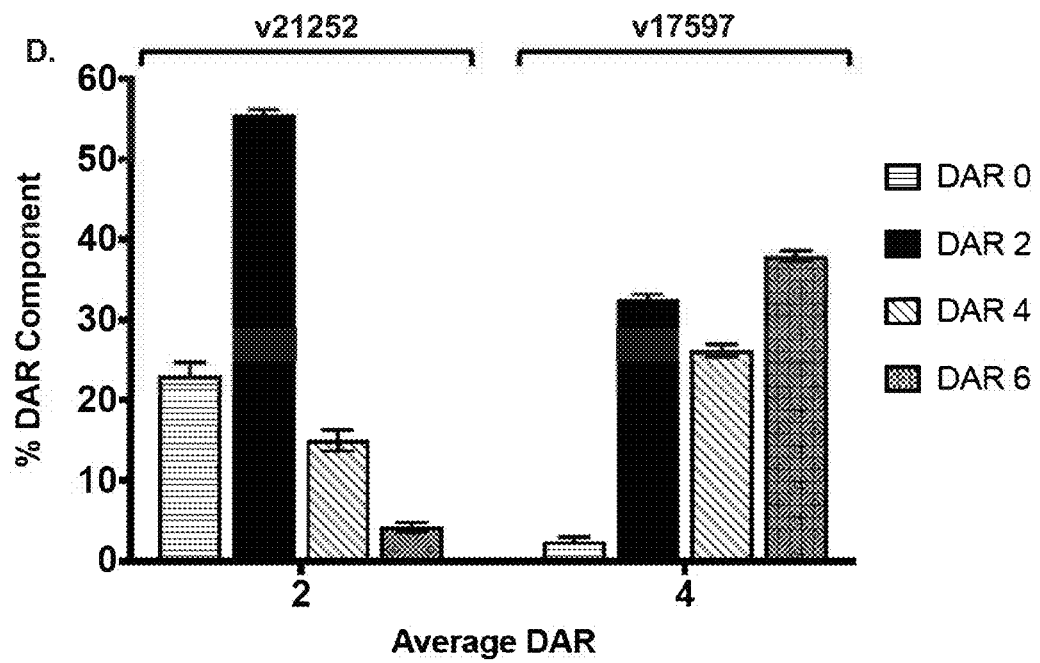
Figure 2E:
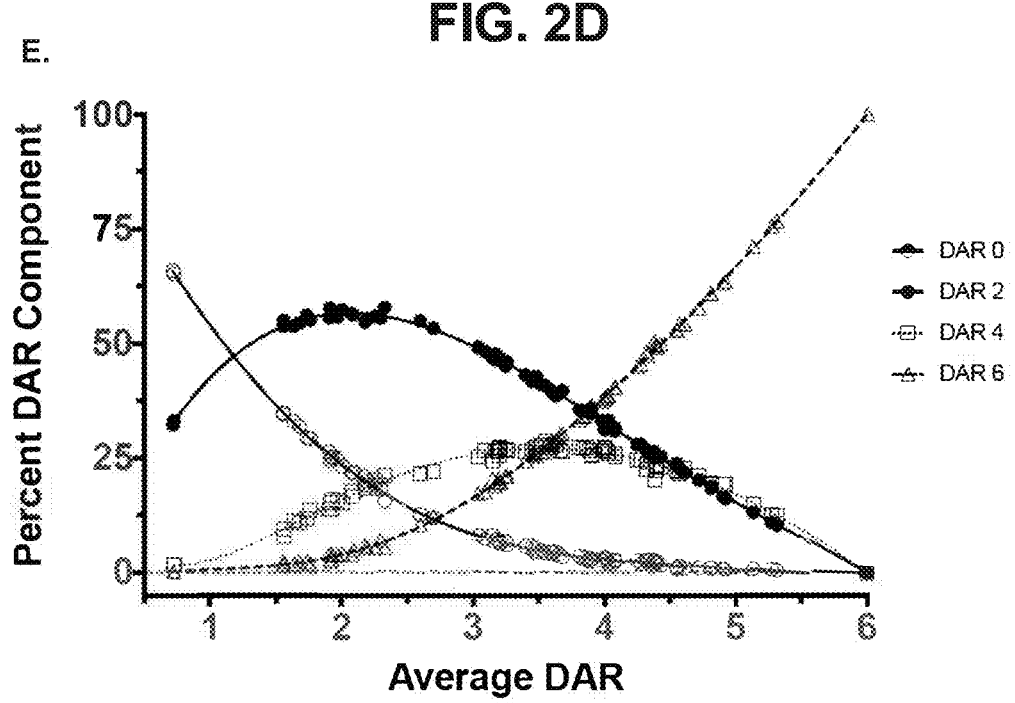

The present disclosure relates to anti-HER2 biparatopic antibody-drug conjugates (ADCs) in which the drug is an auristatin analogue and is conjugated to the antibody at a low average drug-to-antibody ratio (DAR). The low average DAR (<3.9) ADCs as described herein have improved tolerability and decreased toxicity as compared to a corresponding ADC having a DAR ≥3.9 when administered at the same toxin (auristatin analogue) dose. Of particular interest are ADCs having an average DAR of about 2.5 or less, such as between about 1.8 and 2.5.

The present disclosure also relates to methods of using the ADCs described herein in the treatment of a HER2-expressing cancer.

Definitions

Unless defined otherwise, all technical and scientific terms used herein have the same meaning as commonly understood by one of ordinary skill in the art.

The term "subject," as used herein, refers to an animal, in some embodiments a mammal, which is the object of treatment, observation or experiment. The animal may be a human, a non-human primate, a companion animal (for example, dog, cat, or the like), farm animal (for example, cow, sheep, pig, horse, or the like) or a laboratory animal (for example, rat, mouse, guinea pig, non-human primate, or the like). In certain embodiments, the subject is a human.

The term "mammal," as used herein, includes but is not limited to humans, non-human primates, canines, felines, murines, bovines, equines and porcines. In certain embodiments, the mammal is a human.

As used herein, the term "about" refers to an approximately +/−10% variation from a given value. It is to be understood that such a variation is always included in any given value provided herein, whether or not it is specifically referred to.

The use of the word "a" or "an" when used herein in conjunction with the term "comprising" may mean "one," but it is also consistent in certain embodiments with the meaning of "one or more," "at least one" or "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

It is contemplated that any embodiment discussed herein can be implemented with respect to any method, use or composition disclosed herein.

Particular features, structures and/or characteristics described in connection with an embodiment disclosed herein may be combined with features, structures and/or characteristics described in connection with another embodiment disclosed herein in any suitable manner to provide one or more further embodiments.

It is also to be understood that the positive recitation of a feature in one embodiment, serves as a basis for excluding the feature in an alternative embodiment. For example, where a list of options is presented for a given embodiment or claim, it is to be understood that one or more option may be deleted from the list and the shortened list may form an alternative embodiment, whether or not such an alternative embodiment is specifically referred to.

Anti-HER2 Biparatopic Antibody-Drug Conjugates

The antibody-drug conjugates (ADCs) of the present disclosure comprise an anti-HER2 biparatopic antibody conjugated to a toxin via a linker at a low average drug-to-antibody ratio (DAR), the toxin being an auristatin-based toxin (or "auristatin analogue"). Examples of auristatin-based toxins are known in the art.

In certain embodiments, the auristatin analogue is a compound of general Formula (I):

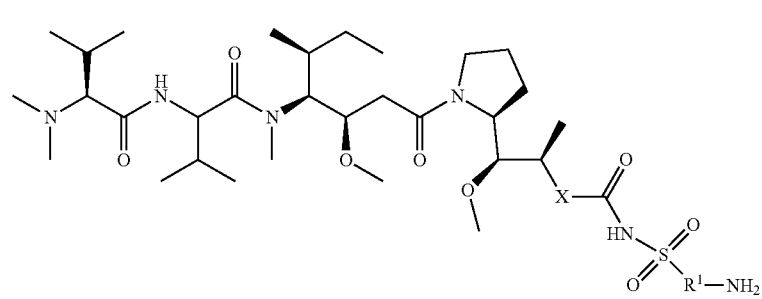

wherein:
X is —C(O)NHCH(CH$_2$R$^2$)—, or X is absent;
R$^1$ is selected from:

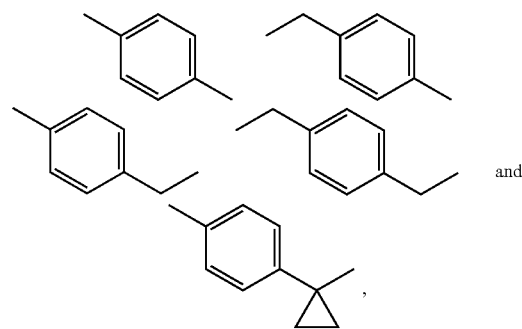

and
R$^2$ is phenyl.

"Low DAR" as used herein, is defined as an average DAR of less than 3.9, but more than 0.5. In some embodiments, the average DAR of the ADCs is less than 3.5. In some embodiments, the average DAR of the ADCs is less than 3.4, for example, less than 3.3, less than 3.2 or less than 3.1. In some embodiments, the average DAR of the ADCs is 3.0 or less. In some embodiments, the average DAR of the ADCs is 2.9 or less, for example, 2.8 or less, 2.7 or less, or 2.6 or less. In some embodiments, the average DAR of the ADCs is 2.5 or less, for example, 2.4 or less, 2.3 or less, or 2.2 or less. In some embodiments, the average DAR of the ADCs is about 2.0.

In some embodiments, the average DAR of the ADCs is between 0.5 and 3.8, for example, between 0.5 and 3.5, or between 0.5 and 2.5. In some embodiments, the average DAR of the ADCs is between 0.7 and 3.8, for example, between 0.7 and 3.5, between 0.7 and 3.0, or between 0.7 and 2.5. In some embodiments, the average DAR of the ADCs is between 1.0 and 3.8, for example, between 1.0 and 3.5, between 1.0 and 3.0, or between 1.0 and 2.5. In some embodiments, the average DAR of the ADCs is between 1.5 and 3.8, for example, between 1.5 and 3.5, between 1.5 and 3.0, or between 1.5 and 2.5. In some embodiments, the average DAR of the ADCs is between 1.6 and 3.8, for example, between 1.6 and 3.5, between 1.6 and 3.0, or between 1.6 and 2.5. In some embodiments, the average DAR of the ADCs is between 1.8 and 2.8, for example, between 1.8 and 2.5.

As noted above, the low average DAR (<3.9) ADCs as described herein have improved tolerability and decreased toxicity as compared to a corresponding ADC having a DAR ≥3.9 when administered at the same toxin dose. As is known in the art, the majority of conjugation methods yield an ADC composition that includes various DAR species, with the reported DAR being the average of the individual DAR species. Without being limited by any particular theory, the higher tolerability and decreased toxicity of the low DAR ADC may be due to one or both of a decrease in high DAR (6 or greater) species in the ADC composition and/or an increase in the DAR0 species in the ADC composition.

In certain embodiments, ADC compositions that include a proportion of DAR0 species above a certain threshold may be advantageous. Accordingly, in some embodiments, the low DAR ADC composition may include 5% or more DAR0 species. In some embodiments, the low DAR ADC composition may include 10% or more DAR0 species. In some embodiments, the low DAR ADC composition may include 15% or more DAR0 species, for example, 20% or more DAR0 species. In some embodiments, the low DAR ADC composition may include between about 5% and about 50% DAR0 species. In some embodiments, the low DAR ADC composition may include between about 10% and about 50% DAR0 species, for example, between about 10% and about 40%, between about 10% and about 30% DAR0 species, or between about 10% and about 25% DAR0 species. In some embodiments, the low DAR ADC composition may include between about 12% and about 28% DAR0 species, for example, between about 12% and about 28% DAR0 species, or between about 15% and about 25% DAR0 species.

In certain embodiments, ADC compositions that include a proportion of DAR6 or greater species below a certain threshold may be advantageous. Accordingly, in some embodiments, the low DAR ADC composition may include less than about 35% DAR6 or greater species. In some embodiments, the low DAR ADC composition may include 30% or less DAR6 or greater species. In some embodiments, the low DAR ADC composition may include 25% or less DAR6 or greater species, for example, 20% or less, 15% or less, or 10% or less DAR6 or greater species. In some embodiments, the low DAR ADC composition may include 9% or less DAR6 or greater species, for example, 8% or less, 7% or less, 6% or less, or 5% or less DAR6 or greater species. In some embodiments, the low DAR ADC composition may include between 0% and about 35% DAR6 or greater species. In some embodiments, the low DAR ADC composition may include between 0% and about 30% DAR6 or greater species, for example, between 0% and about 25%, or between 0% and about 20% DAR6 or greater species. In some embodiments, the low DAR ADC composition may include between 0% and about 15% DAR6 or greater species, for example, between about 0% and about 10%, between about 0% and about 8%, or between 0% and about 5% DAR6 or greater species.

Certain embodiments relate to ADCs that comprise an anti-HER2 biparatopic antibody conjugated to an auristatin analogue via a linker (L) at a low average drug-to-antibody ratio (DAR), the auristatin analogue-linker having general Formula (II):

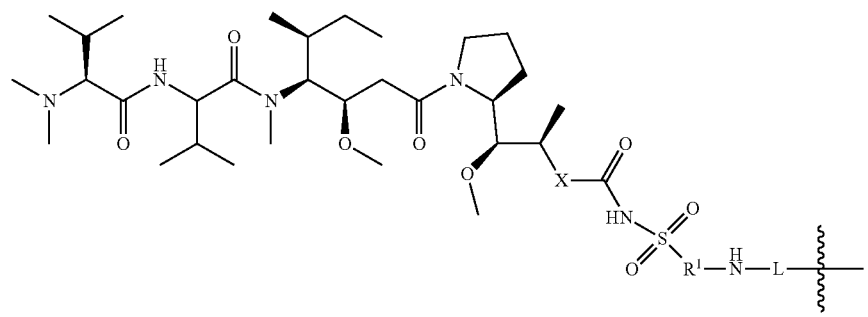

(II)

wherein X and R$^1$ are as defined for general Formula (I);

L is the linker, and

⸸ represents the point of attachment of the auristatin analogue-linker to the anti-HER2 biparatopic antibody.

Certain embodiments relate to an ADC having general Formula (III):

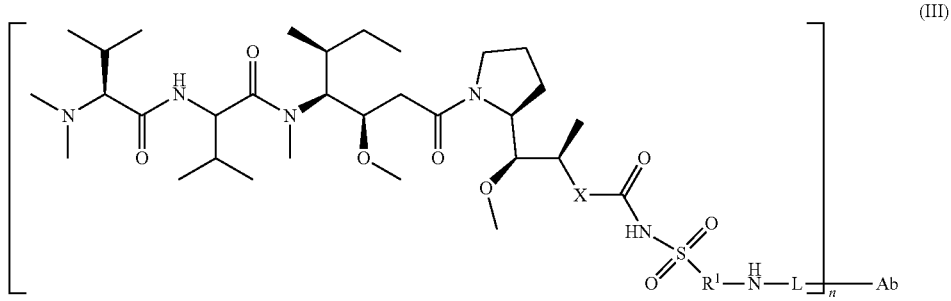

(III)

wherein X and $R^1$ are as defined for general Formula (I);
L is a linker;
n is the average drug-to-antibody ratio (DAR) and is less than 3.9, and
Ab is an anti-HER2 biparatopic antibody.

Anti-HER2 Biparatopic Antibodies

The ADCs described herein comprise an anti-HER2 biparatopic antibody that binds to two different epitopes of HER2.

The term "antibody," as used herein, generally refers to a proteinaceous binding molecule with immunoglobulin-like functions. Typical examples of an antibody are immunoglobulins, as well as derivatives or functional fragments thereof which still retain binding specificity. Techniques for the production of antibodies are well known in the art. The term "antibody" may also include immunoglobulins of different classes (i.e. IgA, IgG, IgM, IgD and IgE) and subclasses (such as $IgG_1$, $IgG_2$, $IgG_3$, $IgG_4$, $IgA_1$ and $IgA_2$). Illustrative examples of an antibody are whole antibodies and antigen-binding fragments thereof, such as Fab fragments, $F(ab')_2$, Fv fragments, single-chain Fv fragments (scFv), diabodies, domain antibodies, and combinations thereof. Domain antibodies may be single domain antibodies, single variable domain antibodies or immunoglobulin single variable domain having only one variable domain, which may be a heavy chain variable domain or a light chain variable domain, that specifically bind an antigen or epitope independently of other variable regions or domains. The term "antibody" also includes embodiments such as chimeric, single chain and humanized antibodies.

A typical whole antibody comprises at least two heavy (H) chains and two light (L) chains interconnected by disulfide bonds. Each heavy chain is comprised of a heavy chain variable region (VH) and a heavy chain constant region (CH). The heavy chain constant region comprises three domains: CH1, CH2 and CH3. The heavy chain constant domains that correspond to the different classes of immunoglobulins are known as α (IgA), δ (IgD), ε (IgE), γ (IgG) and μ (IgM). Each light chain is comprised of a light chain variable region (VL) and a light chain constant region. The light chain constant region comprises just one domain: CL. Light chains are classified as either kappa or lambda. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain (a paratope) that interacts with an antigen. The constant regions of the antibodies can mediate the binding of the immunoglobulin to host tissues or factors, including various cells of the immune system (such as effector cells) and C1q, which is a component of the complement system.

In certain embodiments, the anti-HER2 biparatopic antibodies for inclusion in the ADCs described herein comprise two antigen-binding polypeptide constructs, each of which binds to a different epitope of HER2. An "antigen-binding polypeptide construct," as used herein, may be an immunoglobulin-based construct, for example, an antibody fragment, or it may be a non-immunoglobulin-based antibody mimetic format, such as an anticalin, a fynomer, an affimer, an alphabody, a DARPin or an avimer. In some embodiments, the antigen-binding polypeptide constructs comprised by the anti-HER2 biparatopic antibody may be immunoglobulin-based constructs. In some embodiments, the antigen-binding polypeptide constructs comprised by the anti-HER2 biparatopic antibody may be antibody fragments.

In certain embodiments, the antigen-binding polypeptide constructs comprised by the anti-HER2 biparatopic antibody may each independently be a Fab fragment, a Fab' fragment, an scFv or an sdAb. In some embodiments, the antigen-binding polypeptide constructs comprised by the anti-HER2 biparatopic antibody may each independently be a Fab fragment or an scFv. In some embodiments, one antigen-binding polypeptide construct comprised by the anti-HER2 biparatopic antibody may be a Fab fragment and the other antigen-binding polypeptide construct may be an scFv.

In certain embodiments, at least one of the antigen-binding polypeptide constructs comprised by the anti-HER2 biparatopic antibody may be a Fab fragment or a Fab' fragment. A "Fab fragment" contains the constant domain of the light chain (CL) and the first constant domain of the heavy chain (CH1) along with the variable domains of the light and heavy chains (VL and VH, respectively). Fab' fragments differ from Fab fragments by the addition of a few amino acid residues at the C-terminus of the heavy chain CH1 domain, including one or more cysteines from the antibody hinge region. A Fab fragment may also be a single-chain Fab molecule, i.e. a Fab molecule in which the Fab light chain and the Fab heavy chain are connected by a peptide linker to form a single peptide chain. For example, the C-terminus of the Fab light chain may be connected to the N-terminus of the Fab heavy chain in the single-chain Fab molecule.

In certain embodiments, at least one of the antigen-binding polypeptide constructs comprised by the anti-HER2 biparatopic antibody may be a single-chain Fv (scFv). An "scFv" includes a heavy chain variable domain (VH) and a light chain variable domain (VL) of an antibody in a single polypeptide chain. The scFv may optionally further comprise a polypeptide linker between the VH and VL domains which enables the scFv to form a desired structure for antigen binding. For example, an scFv may include a VL connected from its C-terminus to the N-terminus of a VH by a polypeptide linker. Alternately, an scFv may comprise a VH connected through its C-terminus to the N-terminus of a VL by a polypeptide chain or linker (see review in Pluckthun in *The Pharmacology of Monoclonal Antibodies*, vol. 113, Rosenburg and Moore eds., Springer-Verlag, New York, pp. 269-315 (1994)).

In certain embodiments, at least one of the antigen-binding polypeptide constructs comprised by the anti-HER2 biparatopic antibody may be in a single domain antibody (sdAb) format. An sdAb format refers to a single immunoglobulin domain. The sdAb may be, for example, of camelid origin. Camelid antibodies lack light chains and their antigen-binding sites consist of a single domain, termed a "VHH." An sdAb comprises three CDR/hypervariable loops that form the antigen-binding site: CDR1, CDR2 and CDR3. sdAbs are fairly stable and easy to express, for example, as a fusion with the Fc chain of an antibody (see, for example, Harmsen & De Haard, Appl. Microbiol Biotechnol. 77(1): 13-22 (2007)).

Antibody Formats

The anti-HER2 biparatopic antibodies for inclusion in the ADCs described herein may have various formats. The minimal components of the anti-HER2 biparatopic antibody are a first antigen-binding polypeptide construct that binds to a first HER2 epitope and a second antigen-binding polypeptide construct that binds to a second HER2 epitope, with the first and second HER2 epitopes being different. An antibody that comprises two antigen-binding polypeptide constructs that bind to different HER2 epitopes may be considered to be a bivalent, biparatopic antibody. Certain embodiments relate to bivalent, anti-HER2 biparatopic antibodies. In some embodiments, the anti-HER2 biparatopic antibody may comprise one or more additional antigen-binding polypeptide constructs, each of which bind to either the first or second HER2 epitope. For example, in some embodiments, the anti-HER2 biparatopic antibody may be trivalent or tetravalent.

In some embodiments, the anti-HER2 biparatopic antibody further comprises a linker that links the first and second antigen-binding polypeptide constructs. In some embodiments, the anti-HER2 biparatopic antibody further comprises a scaffold and the first and second antigen-binding polypeptide constructs are operably linked to the scaffold. The term "operably linked," as used herein, means that the components described are in a relationship permitting them to function in their intended manner.

The anti-HER2 biparatopic antibodies may thus be considered to have a modular architecture that includes two antigen-binding polypeptide construct modules and optionally one or both of a linker module and a scaffold module. One skilled in the art will understand that these modules may be combined in various ways to provide anti-HER2 biparatopic antibodies having different formats. These formats are based generally on antibody formats known in the art (see, for example, review by Brinkmann & Kontermann, MABS, 9(2):182-212 (2017), and Müller & Kontermann, "Bispecific Antibodies" in *Handbook of Therapeutic Antibodies*, Wiley-VCH Verlag GmbH & Co. (2014)).

In certain embodiments, the anti-HER2 biparatopic antibody comprises two antigen-binding polypeptide constructs operably linked to a scaffold. Suitable scaffolds are described below. In some embodiments, the anti-HER2 biparatopic antibody comprises two antigen-binding polypeptide constructs operably linked to a scaffold, and at least one of the antigen-binding polypeptide constructs is an scFv. In some embodiments, the anti-HER2 biparatopic antibody comprises two antigen-binding polypeptide constructs operably linked to a scaffold, and at least one of the antigen-binding polypeptide constructs is a Fab.

In some embodiments, the anti-HER2 biparatopic antibody may comprise three or four antigen-binding polypeptide constructs and a scaffold. In this format, at least the first and second antigen-binding constructs are operably linked to the scaffold. The third and optional fourth antigen-binding polypeptide constructs may each independently be operably linked to the scaffold or to the first antigen-binding polypeptide construct or to the second antigen-binding polypeptide construct.

Anti-HER2 biparatopic antibodies that lack a scaffold typically comprise two antigen-binding polypeptide constructs operably linked by one or more linkers. The antigen-binding polypeptide constructs may be in the form of scFvs, Fabs, sdAbs, or a combination thereof. For example, using scFvs as the antigen-binding polypeptide constructs, formats such as a tandem scFv ((scFv)$_2$ or taFv) may be constructed, in which the scFvs are connected together by a flexible linker. scFvs may also be used to construct diabody formats, which comprise two scFvs connected by a short linker (usually about 5 amino acids in length). The restricted length of the linker results in dimerization of the scFvs in a head-to-tail manner. In any of the preceding formats, the scFvs may be further stabilized by inclusion of an interdomain disulfide bond. For example, a disulfide bond may be introduced between VL and VH through introduction of an additional cysteine residue in each chain (for example, at position 44 in VH and 100 in VL) (see, for example, Fitzgerald et al., Protein Engineering, 10:1221-1225 (1997)), or a disulfide bond may be introduced between two VHs to provide construct having a DART format (see, for example, Johnson et al., J Mol. Biol., 399:436-449 (2010)).

Similarly, formats comprising two sdAbs, such as VHs or VHHs, connected together through a suitable linker may be employed in some embodiments.

Other examples of anti-HER2 biparatopic antibody formats that lack a scaffold include those based on Fab fragments, for example, Fab$_2$ and F(ab')$_2$ formats, in which the Fab fragments are connected through a linker or an IgG hinge region.

Combinations of antigen-binding polypeptide constructs in different forms may also be employed to generate alternative scaffold-less formats. For example, an scFv or a sdAb may be fused to the C-terminus of either or both of the light and heavy chain of a Fab fragment resulting in a bivalent (Fab-scFv/sdAb) construct.

In certain embodiments, the anti-HER2 biparatopic antibody may comprise two antigen-binding polypeptide constructs and one or more linkers, and does not include a scaffold. In some embodiments, the anti-HER2 biparatopic antibody comprises two antigen-binding polypeptide constructs which are scFvs, Fabs, sdAbs, or a combination thereof, and one or more linkers, and does not include a scaffold.

Scaffolds

Anti-HER2 biparatopic antibodies comprising a scaffold may be constructed by linking the two antigen-binding polypeptide constructs to a suitable scaffold. The antigen-binding polypeptide constructs may be in one or a combination of the forms described above (for example, scFvs, Fabs and/or sdAbs). Examples of suitable scaffolds are described in more detail below and include, but are not limited to, immunoglobulin Fc regions, albumin, albumin analogs and derivatives, heterodimerizing peptides (such as leucine zippers, heterodimer-forming "zipper" peptides derived from Jun and Fos, IgG CH1 and CL domains or barnase-barstar toxins), cytokines, chemokines or growth factors. Other examples include antibodies based on the DOCK-AND-LOCK™ (DNL™) technology developed by IBC Pharmaceuticals, Inc. and Immunomedics, Inc. (see, for example, Chang, et al., Clin Cancer Res 13:5586s-5591s (2007)).

In some embodiments, the anti-HER2 biparatopic antibodies comprise two or more antigen-binding polypeptide constructs and a scaffold. In some embodiments, the anti-HER2 biparatopic antibodies comprise two antigen-binding polypeptide constructs operably linked to a scaffold.

A scaffold may be a peptide, polypeptide, polymer, nanoparticle or other chemical entity. Where the scaffold is a polypeptide, each antigen-binding polypeptide construct of the anti-HER2 biparatopic antibody may be linked to either the N- or C-terminus of the polypeptide scaffold. Anti-HER2 biparatopic antibodies comprising a polypeptide scaffold in which one or more of the antigen-binding polypeptide constructs are linked to a region other than the N- or C-terminus, for example, via the side chain of an amino acid with or without a linker, are also contemplated in certain embodiments.

In embodiments where the scaffold is a peptide or polypeptide, the antigen-binding polypeptide constructs may be linked to the scaffold by genetic fusion or chemical conjugation. Typically, when the scaffold is a peptide or polypeptide, the antigen-binding polypeptide constructs are linked to the scaffold by genetic fusion. In some embodiments, where the scaffold is a polymer or nanoparticle, the antigen-binding polypeptide constructs may be linked to the scaffold by chemical conjugation.

A number of protein domains are known in the art that comprise selective pairs of two different polypeptides and may be used to form a scaffold. An example is leucine zipper domains such as Fos and Jun that selectively pair together (Kostelny, et al., J Immunol, 148:1547-53 (1992); Wranik, et al., J. Biol. Chem., 287: 43331-43339 (2012)). Other selectively pairing molecular pairs include, for example, the barnase barstar pair (Deyev, et al., Nat Biotechnol, 21:1486-1492 (2003)), DNA strand pairs (Chaudri, et al., FEBS Letters, 450(1-2):23-26 (1999)) and split fluorescent protein pairs (International Patent Application Publication No. WO 2011/135040).

Other examples of protein scaffolds include immunoglobulin Fc regions, albumin, albumin analogues and derivatives, toxins, cytokines, chemokines and growth factors. The use of protein scaffolds in combination with antigen-binding moieties has been described (see, for example, Müller et al., J Biol Chem, 282:12650-12660 (2007); McDonaugh et al., Mol Cancer Ther, 11:582-593 (2012); Vallera et al., Clin Cancer Res, 11:3879-3888 (2005); Song et al., Biotech Appl Biochem, 45:147-154 (2006), and U.S. Patent Application Publication No. 2009/0285816).

For example, fusing antigen-binding moieties such as scFvs, diabodies or single chain diabodies to albumin has been shown to improve the serum half-life of the antigen-binding moieties (Müller et al., ibid.). Antigen-binding moieties may be fused at the N- and/or C-termini of albumin, optionally via a linker.

Derivatives of albumin in the form of heteromultimers that comprise two transporter polypeptides obtained by segmentation of an albumin protein such that the transporter polypeptides self-assemble to form quasi-native albumin have been described (see International Patent Application Publication Nos. WO 2012/116453 and WO 2014/012082). As a result of the segmentation of albumin, the heteromultimer includes four termini and thus can be fused to up to four different antigen-binding moieties, optionally via linkers.

In certain embodiments, the anti-HER2 biparatopic antibody may comprise a protein scaffold. In some embodiments, the anti-HER2 biparatopic antibody may comprise a protein scaffold that is based on an immunoglobulin Fc region, an albumin or an albumin analogue or derivative. In some embodiments, the anti-HER2 biparatopic antibody may comprise a protein scaffold that is based on an immunoglobulin Fc region, for example, an IgG Fc region.

In some embodiments, the anti-HER2 biparatopic antibody may comprise a protein scaffold that is based on an albumin, for example human serum albumin (HSA), or an albumin analogue or derivative. In some embodiments, the anti-HER2 biparatopic antibody may comprise a protein scaffold that is based on an albumin derivative as described in International Patent Application Publication No. WO 2012/116453 or WO 2014/012082.

Fc Regions

The terms "Fc region," "Fc" or "Fc domain" as used herein refer to a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD (1991).

In certain embodiments, the anti-HER2 biparatopic antibodies may comprise a scaffold that is based on an immunoglobulin Fc region. In some embodiments, the Fc region may be dimeric and composed of two Fc polypeptides. In some embodiments, the Fc region may be composed of a single polypeptide.

An "Fc polypeptide" of a dimeric Fc refers to one of the two polypeptides forming the dimeric Fc domain, i.e. a polypeptide comprising one or more C-terminal constant regions of an immunoglobulin heavy chain that is capable of stable self-association. The terms "first Fc polypeptide" and "second Fc polypeptide" may be used interchangeably provided that the Fc region comprises one first Fc polypeptide and one second Fc polypeptide.

An Fc region comprises a CH3 domain or both a CH3 and a $CH_2$ domain. For example, an Fc polypeptide of a dimeric IgG Fc region comprises an IgG CH2 and an IgG CH3 constant domain sequence. The CH3 domain comprises two CH3 sequences, one from each of the two Fc polypeptides of the dimeric Fc region. The CH2 domain comprises two CH2 sequences, one from each of the two Fc polypeptides of the dimeric Fc region.

In some embodiments, the anti-HER2 biparatopic antibody may comprise a scaffold that is based on an IgG Fc region. In some embodiments, the anti-HER2 biparatopic antibody may comprise a scaffold that is based on a human Fc region. In some embodiments, the anti-HER2 biparatopic antibody may comprise a scaffold based on a human IgG Fc region, for example a human IgG1 Fc region.

In certain embodiments, the anti-HER2 biparatopic antibody may comprise a scaffold based on an IgG Fc region, which is a heterodimeric Fc region, comprising a first Fc polypeptide and a second Fc polypeptide, each comprising a CH3 sequence, and optionally a CH2 sequence.

In some embodiments, the anti-HER2 biparatopic antibody may comprise a scaffold based on an Fc region which comprises first and second Fc polypeptides, and the first antigen-binding polypeptide construct is operably linked to the first Fc polypeptide and the second antigen-binding polypeptide construct is operably linked to the second Fc polypeptide.

In some embodiments, the anti-HER2 biparatopic antibody may comprise a scaffold based on an Fc region which comprises first and second Fc polypeptides, in which the first antigen-binding polypeptide construct is operably linked to the first Fc polypeptide and the second antigen-binding polypeptide construct is operably linked to the second Fc polypeptide, and in which the first and second antigen-binding polypeptide constructs are independently a Fab fragment or an scFv.

In some embodiments, the anti-HER2 biparatopic antibody may comprise a scaffold based on an Fc region which comprises two CH3 sequences, at least one of which comprises one or more amino acid modifications. In some embodiments, the anti-HER2 biparatopic antibody may comprise a scaffold based on an Fc region which comprises two CH3 sequences and two CH2 sequences, at least one of the CH2 sequences comprising one or more amino acid modifications.

In some embodiments, the anti-HER2 biparatopic antibody comprises a heterodimeric Fc region comprising a modified CH3 domain, wherein the modified CH3 domain is an asymmetrically modified CH3 domain. Generally, the first Fc polypeptide of the heterodimeric Fc comprises a first CH3 sequence and the second Fc polypeptide comprises a second CH3 sequence.

As used herein, "asymmetric amino acid modification" refers to a modification where an amino acid at a specific position on a first CH3 sequence is different to the amino acid on a second CH3 sequence at the same position. For CH3 sequences comprising asymmetric amino acid modifications, the first and second CH3 sequence will typically preferentially pair to form a heterodimer, rather than a homodimer. These asymmetric amino acid modifications can be a result of modification of only one of the two amino acids at the same respective amino acid position on each sequence, or different modifications of both amino acids on each sequence at the same respective position on each of the first and second CH3 sequences. Each of the first and second CH3 sequence of a heterodimeric Fc may comprise one or more than one asymmetric amino acid modification.

In some embodiments, the anti-HER2 biparatopic antibody may comprise a scaffold based on a modified Fc region as described in International Patent Application Publication No. WO 2012/058768 or WO 2013/063702.

Table 1 provides the amino acid sequence of the human IgG1 Fc sequence (SEQ ID NO:1), corresponding to amino acids 231 to 447 of the full-length human IgG1 heavy chain. The CH3 sequence comprises amino acids 341-447 of the full-length human IgG1 heavy chain.

In certain embodiments, the anti-HER2 biparatopic antibody may comprise a heterodimeric Fc scaffold comprising a modified CH3 domain that comprises asymmetric amino acid modifications that promote formation of a heterodimeric Fc rather than a homodimeric Fc. In some embodiments, the anti-HER2 biparatopic antibody may comprise a heterodimeric Fc scaffold which includes modifications at one or more of the following positions: L351, F405, Y407, T366, K392, T394, T350, S400 and/or N390, using EU numbering.

In certain embodiments, the anti-HER2 biparatopic antibody may comprise a heterodimeric Fc comprising a modified CH3 domain having a first polypeptide sequence that comprises amino acid modifications at positions F405 and Y407, and optionally further comprises an amino acid modification at position L351, and a second polypeptide sequence that comprises amino acid modifications at positions T366 and T394, and optionally further comprises an amino acid modification at position K392. In some embodiments, a first polypeptide sequence of the modified CH3 domain may comprise amino acid modifications at positions F405 and Y407, and optionally further comprises an amino acid modification at position L351, and a second polypeptide sequence of the modified CH3 domain comprises amino acid modifications at positions T366 and T394, and optionally further comprises an amino acid modification at position K392, and the amino acid modification at position F405 is F405A, F405I, F405M, F405S, F405T or F405V; the amino acid modification at position Y407 is Y407I or Y407V; the amino acid modification at position T366 is T366I, T366L or T366M; the amino acid modification at position T394 is T394W; the amino acid modification at position L351 is L351Y, and the amino acid modification at position K392 is K392F, K392L or K392M. In some embodiments, the amino acid modification at position F405 is F405A, F405S, F405T or F405V.

In some embodiments, the anti-HER2 biparatopic antibody may comprise a heterodimeric Fc comprising a modified CH3 domain having a first Fc polypeptide sequence comprising amino acid modifications at positions F405 and Y407, and optionally further comprises an amino acid modification at position L351, and a second Fc polypeptide sequence comprising amino acid modifications at positions T366 and T394, and optionally further comprises an amino acid modification at position K392, and the amino acid modification at position F405 is F405A, F405I, F405M, F405S, F405T or F405V; the amino acid modification at position Y407 is Y407I or Y407V; the amino acid modification at position T366 is T366I, T366L or T366M; the amino acid modification at position T394 is T394W; the amino acid modification at position L351 is L351Y, and the amino acid modification at position K392 is K392F, K392L or K392M, and one or both of the first and second Fc polypeptide sequences further comprises the amino acid modification T350V. In some embodiments, the amino acid modification at position F405 is F405A, F405S, F405T or F405V.

In certain embodiments, the anti-HER2 biparatopic antibody may comprise a heterodimeric Fc comprising a modified CH3 domain as described above, in which the first Fc polypeptide sequence comprises amino acid modifications at positions F405 and Y407, and optionally further comprises an amino acid modification at position L351, and the second Fc polypeptide sequence comprises amino acid modifications at positions T366 and T394, and optionally further comprises an amino acid modification at position K392, and in which the first Fc polypeptide sequence further comprises an amino acid modification at one or both of positions S400 or Q347 and/or the second Fc polypeptide sequence further comprises an amino acid modification at one or both of positions K360 or N390, where the amino acid modification at position S400 is S400E, S400D, S400R or S400K; the amino acid modification at position Q347 is Q347R, Q347E or Q347K; the amino acid modification at position K360 is K360D or K360E, and the amino acid modification at position N390 is N390R, N390K or N390D. In some embodiments, the amino acid modification at position F405 is F405A, F405S, F405T or F405V.

In some embodiments, the anti-HER2 biparatopic antibody may comprise a heterodimeric Fc scaffold having a modified CH3 domain comprising the modifications of any one of Variant 1, Variant 2, Variant 3, Variant 4 or Variant 5, as shown in Table 1.

TABLE 1

| IgG1 Fc sequences | | |
|---|---|---|
| Human IgG1 Fc sequence 231-447 (EU-numbering) | APELLGGPSVFLFPPKPKDTLMISRTPEVTCVVVDVSH EDPEVKFNWYVDGVEVHNAKTKPREEQYNSTYRVVS VLTVLHQDWLNGKEYKCKVSNKALPAPIEKTISKAKG QPREPQVYTLPPSRDELTKNQVSLTCLVKGFYPSDIAV EWESNGQPENNYKTTPPVLDSDGSFFLYSKLTVDKSR WQQGNVFSCSVMHEALHNHYTQKSLSLSPGK (SEQ ID NO: 1) | |

| Variant IgG1 Fc sequence | Chain | Mutations |
|---|---|---|
| 1 | A | L351Y_F405A_Y407V |
|   | B | T366L_K392M_T394W |
| 2 | A | L351Y_F405A_Y407V |
|   | B | T366L_K392L_T394W |
| 3 | A | T350V_L351Y_F405A_Y407V |
|   | B | T350V_T366L_K392L_T394W |
| 4 | A | T350V_L351Y_F405A_Y407V |
|   | B | T350V_T366L_K392M_T394W |
| 5 | A | T350V_L351Y_S400E_F405A_Y407V |
|   | B | T350V_T366L_N390R_K392M_T394W |

In certain embodiments, the anti-HER2 biparatopic antibody may comprise a heterodimeric Fc scaffold having a modified CH3 domain with a first CH3 sequence comprising one or more amino acid modifications selected from L351Y, F405A, and Y407V, and the second CH3 sequence comprising the amino acid modifications T366L or T366I; K392L or K392M, and T394W, and one or both of the first and second CH3 sequences may optionally further comprise the amino acid modification T350V.

In certain embodiments, the anti-HER2 biparatopic antibody may comprise a heterodimeric Fc scaffold having a modified CH3 domain comprising asymmetric amino acid modifications as described above that promote the formation of a heterodimeric Fc in which the heterodimeric CH3 domain has a stability that is comparable to a wild-type homodimeric CH3 domain. The stability of the CH3 domain may be assessed by measuring the melting temperature (Tm) of the CH3 domain, for example by differential scanning calorimetry (DSC). In some embodiments, the one or more asymmetric amino acid modifications promote the formation of a heterodimeric Fc domain in which the CH3 domain has a stability as observed via the melting temperature (Tm) in a differential scanning calorimetry study that is within about 8° C., for example, within about 7° C., about 6° C., about 5° C., or about 4° C., of that observed for the corresponding symmetric wild-type homodimeric CH3 domain.

A heterodimeric Fc comprising modified CH3 sequences may be formed with a purity of at least about 75% as compared to homodimeric Fc in the expressed product. In some embodiments, the anti-HER2 biparatopic antibody may comprise a heterodimeric Fc scaffold having a modified CH3 domain comprising asymmetric amino acid modifications that promote the formation of a heterodimeric Fc with a purity greater than about 80%, greater than about 85%, greater than about 90%, greater than about 95% or greater than about 97%.

Additional methods for modifying monomeric Fc polypeptides to promote heterodimeric Fc formation are known in the art and include, for example, those described in International Patent Application Publication No. WO 96/027011 (knobs into holes); Gunasekaran et al. J Biol Chem, 285, 19637-46 (2010) (electrostatic design to achieve selective heterodimerization); Davis et al., Prot Eng Des Sel, 23(4):195-202 (2010) (strand exchange engineered domain (SEED) technology), and Labrijn et al., Proc Natl Acad Sci USA, 110(13):5145-50 (2013) (Fab-arm exchange).

In some embodiments, in which the anti-HER2 biparatopic antibody comprises a heterodimeric Fc scaffold, the heterodimeric Fc also comprises a CH2 domain. In some embodiments, the CH2 domain is a modified CH2 domain. One example of a CH2 domain of an Fc is amino acids 231-340 of the sequence shown in Table 1. Several effector functions are mediated by Fc receptors (FcRs), which bind to the Fc of an antibody.

Fc receptors (FcRs) include receptors of the FcγRI, FcγRII, and FcγRIII subclasses, including allelic variants and alternatively spliced forms of these receptors. The term FcR may also include in certain embodiments the neonatal receptor, FcRn.

Modifications in the $CH_2$ domain can affect the binding of FcRs to the Fc. A number of amino acid modifications in the Fc region are known in the art for selectively altering the affinity of the Fc for different Fcγ receptors. In some embodiments, in which the anti-HER2 biparatopic antibody comprises a heterodimeric Fc scaffold having a modified $CH_2$ domain, the modified $CH_2$ domain may comprise one or more modifications to promote selective binding of Fcγ receptors.

Non-limiting examples of modifications that alter the binding of the Fc by FcRs include S298A/E333A/K334A and S298A/E333A/K334A/K326A (Lu, et al., J Immunol Methods, 365(1-2):132-41(2011)); F243L/R292P/Y300L/V305I/P396L and F243L/R292P/Y300L/L235V/P396L (Stavenhagen, et al., Cancer Res, 67(18):8882-90 (2007) and Nordstrom J L, et al., Breast Cancer Res, 13(6):R123 (2011)); F243L (Stewart, et al., Protein Eng Des Sel. 24(9): 671-8 (2011)); S298A/E333A/K334A (Shields, et al., J Biol Chem, 276(9):6591-604 (2001)); S239D/I332E/A330L and S239D/I332E (Lazar, et al., Proc Natl Acad Sci USA, 103(11):4005-10 (2006)); S239D/S267E and S267E/L328F (Chu, et al., Mol Immunol, 45(15):3926-33 (2008)). Additional modifications that affect Fc binding by FcRs are described in *Therapeutic Antibody Engineering* (Strohl & Strohl, Woodhead Publishing series in Biomedicine No 11, ISBN 1 907568 37 9, October 2012, page 283). Fc regions that comprise asymmetric modifications that affect binding by FcRs are described in International Patent Publication No. WO 2014/190441.

Additional modifications may be made to Fc regions to improve their ability to mediate effector function. Such modifications are known in the art and include afucosylation, or engineering of the affinity of the Fc towards an activating receptor, mainly FcγRIIIa for ADCC, and towards C1q for CDC. In certain embodiments, the anti-HER2 biparatopic antibody may comprise an Fc region modified to improve its ability to mediate effector function.

Methods of producing antibodies with little or no fucose on the Fc glycosylation site (Asn 297, EU numbering) without altering the amino acid sequence are well known in the art. For example, the GlymaX® technology (ProBioGen AG) (see von Horsten et al., Glycobiology, 20(12):1607-18 (2010) and U.S. Pat. No. 8,409,572). In certain embodiments, the anti-HER2 biparatopic antibody may comprise an Fc region that is aglycosylated. In this context, the anti-HER2 biparatopic antibody may be fully afucosylated (i.e. containing no detectable fucose) or partially afucosylated, such that the anti-HER2 biparatopic antibody contains less than 95%, less than 85%, less than 75%, less than 65%, less than 55%, less than 45%, less than 35%, less than 25%, less than 15% or less than 5%, or any amount therebetween, of the amount of fucose normally detected for a similar construct produced by a mammalian expression system.

Fc modifications reducing FcγR and/or complement binding and/or effector function are known in the art and include those described above. Various publications describe strategies that have been used to engineer antibodies with reduced or silenced effector activity (see, for example, Strohl, Curr Opin Biotech 20:685-691 (2009), and Strohl & Strohl, "*Antibody Fc engineering for optimal antibody performance*" In *Therapeutic Antibody Engineering*, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc (see also, U.S. Patent Publication No. 2011/0212087, International Patent Publication No. WO 2006/105338, U.S. Patent Publication No. 2012/0225058, U.S. Patent Publication No. 2012/0251531 and Strop et al., J. Mol. Biol. 420: 204-219 (2012)).

Specific, non-limiting examples of known amino acid modifications to reduce FcγR or complement binding to the Fc include those identified in Table 2.

TABLE 2

Modifications to reduce FcγR or complement binding to the Fc

| Company | Mutations |
| --- | --- |
| GSK | N297A |
| Ortho Biotech | L234A/L235A |
| Protein Design labs | IgG2 V234A/G237A |
| Wellcome Labs | IgG4 L235A/G237A/E318A |
| GSK | IgG4 S228P/L236E |
| Alexion | IgG2/IgG4combo |
| Merck | IgG2 H268Q/V309L/A330S/A331S |
| Bristol-Myers | C220S/C226S/C229S/P238S |
| Seattle Genetics | C226S/C229S/E3233P/L235V/L235A |
| Amgen | *E. coli* production, non-glycosylated |
| Medimmune | L234F/L235E/P331S |
| Trubion | Hinge mutant, possibly C226S/P230S |

In some embodiments, the anti-HER2 biparatopic antibody may comprise an Fc region that comprises a modified CH2 domain having one or more mutations identified in Table 2. In some embodiments, the anti-HER2 biparatopic antibody may comprise an Fc region comprising a modified CH2 domain having amino acid modifications at positions L234, L235 and/or D265. In some embodiments, the anti-HER2 biparatopic antibody may comprise an Fc region comprising a modified $CH_2$ domain having the amino acid modifications L234A, L235A and D265S.

HER2 Epitopes

The two antigen-binding polypeptide constructs comprised by the anti-HER2 biparatopic antibody each bind to a different epitope of HER2, that is, a first antigen-binding polypeptide construct binds to a first HER2 epitope and a second antigen-binding polypeptide construct binds to a second HER2 epitope. In the context of the present disclosure, each of the antigen-binding polypeptide constructs specifically binds to its target epitope.

"Specifically binds" or "specific binding" mean that the binding is selective for the antigen and can be discriminated from unwanted or non-specific interactions. The ability of an antigen-binding polypeptide construct to bind to a specific epitope can be measured, for example, through an enzyme-linked immunosorbent assay (ELISA), surface plasmon resonance (SPR) techniques (analyzed on a BIAcore instrument) (Liljeblad et al, Glyco J 17, 323-329 (2000)) or traditional binding assays (Heeley, Endocr Res 28, 217-229 (2002)). In some embodiments, the antigen-binding polypeptide construct is considered to specifically bind to its target epitope when the extent of binding of the antigen-binding polypeptide construct to an unrelated protein is less than about 10% of the binding of the antigen-binding polypeptide construct to its target epitope as measured, for example, by SPR.

"HER2" (also known as ErbB2) refers to human HER2 protein described, for example, in Semba et al., PNAS (USA), 82:6497-6501 (1985) and Yamamoto et al., Nature, 319:230-234 (1986) (GenBank accession number X03363). The terms "erbB2" and "neu" refer to the gene encoding human HER2 protein. The terms p185 or p185neu may also be used to refer to the protein product of the neu gene.

HER2 comprises an extracellular domain, which typically binds a HER ligand, a lipophilic transmembrane domain, a conserved intracellular tyrosine kinase domain and a carboxyl-terminal signaling domain harboring several tyrosine residues which can be phosphorylated. The extracellular (ecto) domain of HER2 comprises four domains, Domains I-IV. The sequence of HER2 is provided in Table 3 (SEQ ID NO:2). The Extracellular Domain (ECD) boundaries are: Domain I—approximately amino acids 1-165; Domain II— approximately amino acids 166-322; Domain III—approximately amino acids 323-488, and Domain IV—approximately amino acids 489-607.

TABLE 3

Amino Acid Sequence of Human HER2 (SEQ ID NO: 2)

| | |
|---|---|
| 1 | TQVCTGTDMKLRLPASPETHLDMLRHLYQGCQVVQGNLELTYLPTNASLSFLQDIQEVQG |
| 61 | YVLIAHNQVRQVPLQRLRIVRGTQLFEDNYALAVLDNGDPLNNTTPVTGASPGGLRELQL |
| 121 | RSLTEILKGGVLIQRNPQLCYQDTILWKDIFHKNNQLALTLIDTNRSRACHPCSPMCKGS |
| 181 | RCWGESSEDCQSLTRTVCAGGCARCKGPLPTDCCHEQCAAGCTGPKHSDCLACLHFNHSG |
| 241 | ICELHCPALVTYNTDTFESMPNPEGRYTFGASCVTACPYNYLSTDVGSCTLVCPLHNQEV |
| 301 | TAEDGTQRCEKCSKPCARVCYGLGMEHLREVRAVTSANIQEFAGCKKIFGSLAFLPESFD |
| 361 | GDPASNTAPLQPEQLQVFETLEEITGYLYISAWPDSLPDLSVFQNLQVIRGRILHNGAYS |
| 421 | LTLQGLGISWLGLRSLRELGSGLALIHHNTHLCFVHTVPWDQLFRNPHQALLHTANRPED |
| 481 | ECVGEGLACHQLCARGHCWGPGPTQCVNCSQFLRGQECVEECRVLQGLPREYVNARHCLP |
| 541 | CHPECQPQNGSVTCFGPEADQCVACAHYKDPPFCVARCPSGVKPDLSYMPIWKFPDEEGA |
| 601 | CQPCPIN |

"Epitope 2C4" is the region in the extracellular domain of HER2 to which the antibody 2C4 binds and comprises residues from Domain II in the extracellular domain of HER2 (also referred to as ECD2). 2C4 and Pertuzumab bind to the extracellular domain of HER2 at the junction of Domains I, II and III (Franklin et al. Cancer Cell 5:317-328 (2004)).

"Epitope 4D5" is the region in the extracellular domain of HER2 to which the antibody 4D5 (ATCC CRL 10463) and trastuzumab bind. This epitope is close to the transmembrane domain of HER2, and within Domain IV of HER2 (also referred to as ECD4).

In general, the anti-HER2 biparatopic antibody of the present disclosure will bind to epitopes within the extracellular domains of HER2. In some embodiments, the first and second HER2 epitopes bound by the first and second antigen-binding polypeptide constructs of the anti-HER2 biparatopic antibody are non-overlapping epitopes. In some embodiments, the first and second HER2 epitopes bound by the first and second antigen-binding polypeptide constructs of the anti-HER2 biparatopic antibody are on different extracellular domains of HER2. In some embodiments, the first antigen-binding polypeptide construct of the anti-HER2 biparatopic antibody binds to a first HER2 epitope on a first domain of HER2, and the second antigen-binding polypeptide construct binds to a second HER2 epitope on a second domain of HER2. In some embodiments, the first domain of HER2 is ECD2 and the second domain of HER2 is ECD4.

In some embodiments, one of the antigen-binding polypeptide constructs comprised by the anti-HER2 biparatopic antibody competes with trastuzumab for binding to HER2. In some embodiments, one of the antigen-binding polypeptide constructs comprised by the anti-HER2 biparatopic antibody competes with Pertuzumab for binding to HER2. In some embodiments, one of the antigen-binding polypeptide constructs comprised by the anti-HER2 biparatopic antibody competes with trastuzumab for binding to HER2, and the other antigen-binding polypeptide construct competes with Pertuzumab for binding to HER2.

In some embodiments, one of the antigen-binding polypeptide constructs comprised by the anti-HER2 biparatopic antibody is in a Fab or scFv format and competes with trastuzumab for binding to HER2, and the other antigen-binding polypeptide construct is in a Fab or scFv format and competes with Pertuzumab for binding to HER2. In some embodiments, one of the antigen-binding polypeptide constructs comprised by the anti-HER2 biparatopic antibody is in a Fab format and competes with trastuzumab for binding to HER2, and the other antigen-binding polypeptide construct is in an scFv format and competes with Pertuzumab for binding to HER2.

In some embodiments, one of the antigen-binding polypeptide constructs comprised by the anti-HER2 biparatopic antibody binds to the same epitope on HER2 as trastuzumab. In some embodiments, one of the antigen-binding polypeptide constructs comprised by the anti-HER2 biparatopic antibody binds to the same epitope on HER2 as Pertuzumab. In some embodiments, one of the antigen-binding polypeptide constructs comprised by the anti-HER2 biparatopic antibody binds to the same epitope on HER2 as trastuzumab, and the other antigen-binding polypeptide construct binds to the same epitope on HER2 as Pertuzumab.

In some embodiments, one of the antigen-binding polypeptide constructs comprised by the anti-HER2 biparatopic antibody comprises the CDR sequences of trastuzumab or a variant thereof comprising one or more mutations known to increase HER2 binding, and the other antigen-binding polypeptide construct comprises the CDRs of pertuzumab or a variant thereof comprising one or more mutations known to increase HER2 binding. Literature mutations known to enhance HER2 binding by trastuzumab or pertuzumab include those listed in Tables 4 and 5 below (HC=heavy chain; LC=light chain). Combinations of these mutations are also contemplated.

TABLE 4

Trastuzumab Mutations that Increase Binding to HER2

| Mutation | Reported Improvement |
|---|---|
| HC: D102W (HC: D98W) | 3.2X |
| HC: D102Y | 3.1X |

TABLE 4-continued

| Trastuzumab Mutations that Increase Binding to HER2 | |
|---|---|
| Mutation | Reported Improvement |
| HC: D102K | 2.3X |
| HC: D102T | 2.2X |
| HC: N55K | 2.0X |
| HC: N55T | 1.9X |
| LC: H91F | 2.1X |
| LC: D28R | 1.9X |

TABLE 5

| Pertuzumab Mutations that Increase Binding to HER2 | |
|---|---|
| Mutation | Reported Improvement |
| LC: I31A | 1.9X |
| LC: Y96A | 2.1X |
| LC: Y96F | 2.5X |
| HC: T30A | 2.1X |
| HC: G56A | 8.3X |
| HC: F63V | 1.9X |

Various anti-HER2 biparatopic antibodies are known in the art and may be suitable candidate antibodies for inclusion in the ADCs described herein. Examples include antibodies described in U.S. Patent Application Publication Nos. 2014/0170148; 2015/0284463; 2016/0289335; 2017/0029529; 2017/0291955 and 2018/0022820, and International Patent Application Publication No. WO 2016/179707.

In certain embodiments, the anti-HER2 biparatopic antibody is one of the biparatopic antibodies described in U.S. Patent Application Publication No. 2016/0289335. In some embodiments, the anti-HER2 biparatopic antibody is one of v5019, v5020, v7091, v10000, v6902, v6903 or v6717 (see Tables 6, 6A and 6B, and Sequence Tables). In some embodiments, one of the antigen-binding polypeptide constructs of the anti-HER2 biparatopic antibody comprises a VH sequence and a VL sequence from the ECD2-binding arm of one of v5019, v5020, v7091, v10000, v6902, v6903 or v6717. In some embodiments, one of the antigen-binding polypeptide constructs of the anti-HER2 biparatopic antibody comprises a VH sequence and a VL sequence from the ECD2-binding arm of one of v5019, v5020, v7091, v10000, v6902, v6903 or v6717, and the other antigen-binding polypeptide construct comprises a VH sequence and a VL sequence from the ECD4-binding arm of one of v5019, v5020, v7091, v10000, v6902, v6903 or v6717.

In some embodiments, one of the antigen-binding polypeptide constructs of the anti-HER2 biparatopic antibody comprises the CDR sequences from the ECD2-binding arm of one of v5019, v5020, v7091, v10000, v6902, v6903 or v6717. In some embodiments, one of the antigen-binding polypeptide constructs of the anti-HER2 biparatopic antibody comprises the CDR sequences from the ECD2-binding arm of one of v5019, v5020, v7091, v10000, v6902, v6903 or v6717, and the other antigen-binding polypeptide construct comprises the CDR sequences from the ECD4-binding arm of one of v5019, v5020, v7091, v10000, v6902, v6903 or v6717.

One skilled in the art will appreciate that a limited number of amino acid substitutions may be introduced into the CDR sequences or to the VH or VL sequences of known antibodies without the antibody losing its ability to bind its target. Candidate amino acid substitutions may be identified by computer modeling or by art-known techniques such as alanine scanning, with the resulting variants being tested for binding activity by standard techniques. Accordingly, in certain embodiments, one of the antigen-binding polypeptide constructs of the anti-HER2 biparatopic antibody comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD2-binding arm of one of v5019, v5020, v7091, v10000, v6902, v6903 or v6717, wherein the antigen-binding polypeptide construct retains the ability to bind ECD2. In certain embodiments, one of the antigen-binding polypeptide constructs of the anti-HER2 biparatopic antibody comprises a variant of these CDR sequences comprising between 1 and 10 amino acid substitutions across the six CDRs (that is, the CDRs may be modified by including up to 10 amino acid substitutions with any combination of CDRs being modified), for example, between 1 and 7 amino acid substitutions, between 1 and 5 amino acid substitutions, between 1 and 4 amino acid substitutions, between 1 and 3 amino acid substitutions, between 1 and 2 amino acid substitutions, or 1 amino acid substitution, across the CDRs, wherein the variant retains the ability to bind ECD2. Typically, such amino acid substitutions will be conservative amino acid substitutions. In certain embodiments, one of the antigen-binding polypeptide constructs of the anti-HER2 biparatopic antibody comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD2-binding arm of v10000, wherein the antigen-binding polypeptide construct retains the ability to bind ECD2.

In certain embodiments, one of the antigen-binding polypeptide constructs of the anti-HER2 biparatopic antibody comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD2-binding arm of one of v5019, v5020, v7091, v10000, v6902, v6903 or v6717, wherein the antigen-binding polypeptide construct retains the ability to bind ECD2. In some embodiments, one of the antigen-binding polypeptide constructs of the anti-HER2 biparatopic antibody comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD2-binding arm of one of v5019, v5020, v7091, v10000, v6902, v6903 or v6717, wherein the antigen-binding polypeptide construct retains the ability to bind ECD2.

In certain embodiments, one of the antigen-binding polypeptide constructs of the anti-HER2 biparatopic antibody comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD2-binding arm of v10000, wherein the antigen-binding polypeptide construct retains the ability to bind ECD2. In some embodiments, one of the antigen-binding polypeptide constructs of the anti-HER2 biparatopic antibody comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD2-binding arm of v10000, wherein the antigen-binding polypeptide construct retains the ability to bind ECD2.

In certain embodiments, one of the antigen-binding polypeptide constructs of the anti-HER2 biparatopic antibody comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD4-binding arm of one of v5019, v5020, v7091, v10000, v6902, v6903 or v6717, wherein the antigen-binding polypeptide construct retains the ability to bind ECD4. In certain embodiments, one of the antigen-binding polypeptide constructs of the anti-HER2 biparatopic antibody comprises a variant of these CDR sequences comprising between 1 and 10 amino acid substitutions across the six CDRs (that is, the CDRs may be modified by including up to 10 amino acid substitutions with any combination of CDRs being modified), for example, between 1 and 7 amino acid substitutions, between 1 and 5 amino acid substitutions, between 1 and 4 amino acid substitutions, between 1 and 3 amino acid substitutions, between 1 and 2 amino acid substitutions, or 1 amino acid substitution, across the CDRs, wherein the variant retains the ability to bind ECD4. Typically, such amino acid substitutions will be conservative amino acid substitutions. In certain embodiments, one of the antigen-binding polypeptide constructs of the anti-HER2 biparatopic antibody comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD4-binding arm of v10000, wherein the antigen-binding polypeptide construct retains the ability to bind ECD4.

In certain embodiments, one of the antigen-binding polypeptide constructs of the anti-HER2 biparatopic antibody comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD4-binding arm of one of v5019, v5020, v7091, v10000, v6902, v6903 or v6717, wherein the antigen-binding polypeptide construct retains the ability to bind ECD4. In some embodiments, one of the antigen-binding polypeptide constructs of the anti-HER2 biparatopic antibody comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD4-binding arm of one of v5019, v5020, v7091, v10000, v6902, v6903 or v6717, wherein the antigen-binding polypeptide construct retains the ability to bind ECD4.

In certain embodiments, one of the antigen-binding polypeptide constructs of the anti-HER2 biparatopic antibody comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD4-binding arm of v10000, wherein the antigen-binding polypeptide construct retains the ability to bind ECD4. In some embodiments, one of the antigen-binding polypeptide constructs of the anti-HER2 biparatopic antibody comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD4-binding arm of v10000, wherein the antigen-binding polypeptide construct retains the ability to bind ECD4.

TABLE 6

Exemplary Anti-HER2 Biparatopic Antibodies

| Variant | | Chain A | Chain B |
|---|---|---|---|
| 5019 | Domain containing target epitope | ECD2 | ECD4 |
| | Format | Fab | scFv |
| | Antibody name | Pertuzumab | Trastuzumab |
| | CH3 sequence substitutions§ | T350V_L351Y_F405A_Y407V | T366I_N390R_K392M_T394W |
| 5020 | Domain containing target epitope | ECD4 | ECD2 |
| | Format | scFv | Fab |
| | Antibody name | Trastuzumab | Pertuzumab |
| | CH3 sequence substitutions | L351Y_S400E_F405A_Y407V | T350V_T366L_K392L_T394W |
| 7091 | Domain containing target epitope | ECD2 | ECD4 |
| | Format | Fab | scFv |
| | Antibody name | Pertuzumab | Trastuzumab |
| | CH3 sequence substitutions | T350V_L351Y_F405A_Y407V | T350V_T366L_K392L_T394W |
| 10000 | Domain containing target epitope | ECD2 | ECD4 |
| | Format | Fab | scFv |
| | Antibody name | Pertuzumab | Trastuzumab |
| | Fab sequence substitutions* | HC: T30A_A49G_L69F<br>LC: Y96A | |
| | CH3 sequence substitutions | T350V_L351Y_F405A_Y407V | T350V_T366L_K392L_T394W |

TABLE 6-continued

Exemplary Anti-HER2 Biparatopic Antibodies

| Variant | | Chain A | Chain B |
|---|---|---|---|
| 6902 | Domain containing target epitope | ECD4 | ECD2 |
| | Format | Fab | Fab |
| | Antibody name | Trastuzumab | Pertuzumab |
| | Fab sequence substitutions | HC: L143E_K145T<br>LC: Q124R | HC: D146G_Q179K<br>LC: Q124E_Q160E_T180E |
| | CH3 sequence substitutions | T350V_L351Y_F405A_Y407V | T350V_T366L_K392L_T394W |
| 6903 | Domain containing target epitope | ECD4 | ECD2 |
| | Format | Fab | Fab |
| | Fab sequence substitutions | HC: L143E_K145T<br>LC: Q124R_Q1160K_T178R | HC: D146G_Q179K<br>LC: Q124E_Q160E_T180E |
| | Antibody name | Trastuzumab | Pertuzumab |
| | CH3 sequence substitutions | T350V_L351Y_F405A_Y407V | T350V_T366L_K392L_T394W |
| 6717 | Domain containing target epitope | ECD2 | ECD4 |
| | Format | scFv | scFv |
| | Antibody name | Pertuzumab | Trastuzumab |
| | CH3 sequence substitutions | T350V_L351Y_F405A_Y407V | T366I_N390R_K392M_T394W |

*Fab or variable domain numbering according to Kabat (Kabat et al., *Sequences of proteins of immunological interest*, 5th Edition, US Department of Health and Human Services, NIH Publication No. 91-3242, p.647, 1991)
§CH3 numbering according to EU index as in Kabat (Edelman et al., 1969, PNAS USA, 63: 78-85)

TABLE 6A

CDR Sequences of the ECD2-Binding Arm of Variants v5019, v5020, v7091, v10000, v6902, v6903 and v6717

| Variant | HC CDRs | SEQ ID NO | LC CDRs | SEQ ID NO |
|---|---|---|---|---|
| 5019, 5020, 7091, 6902, 6903 & 6717 | H1: GFTFTDYT<br>H2: VNPNSGGS<br>H3: ARNLGPSFYFDY | 6<br>8<br>7 | L1: QDVSIG<br>L2: SAS<br>L3: QQYYIYPYT | 12<br>14<br>13 |
| 10000 | H1: GFTFADYT<br>H2: VNPNSGGS<br>H3: ARNLGPSFYFDY | 39<br>41<br>40 | L1: QDVSIG<br>L2: SAS<br>L3: QQYYIYPAT | 27<br>29<br>28 |

TABLE 6B

CDR Sequences of the ECD4-Binding Arm of Variants v5019, v5020, v7091, v10000, v6902, v6903 and v6717

| HC CDRs | SEQ ID NO | LC CDRs | SEQ ID NO |
|---|---|---|---|
| H1: GFNIKDTY | 33 | L1: QDVNTA | 67 |
| H2: IYPTNGYT | 35 | L2: SAS | 68 |
| H3: SRWGGDGFYAMDY | 34 | L3: QQHYTTPPT | 69 |

In certain embodiments, the anti-HER2 biparatopic antibody is one of the biparatopic antibodies described in International Patent Application Publication No. WO 2016/179707. This application describes high-affinity variants of the anti-HER2 antibody pertuzumab, including biparatopic antibodies comprising sequences from a high-affinity variant as one antigen-binding domain. In some embodiments, the anti-HER2 biparatopic antibody is one of v7133, v15079, v15080, v15081, v15082, v15083, v15084 or v15085 (see Tables 7 and 7A, and Sequence Tables). In some embodiments, one of the antigen-binding polypeptide constructs of the anti-HER2 biparatopic antibody comprises a VH sequence and a VL sequence from the ECD2-binding arm of one of v7133, v15079, v15080, v15081, v15082, v15083, v15084 or v15085. In some embodiments, one of the antigen-binding polypeptide constructs of the anti-HER2 biparatopic antibody comprises the CDR sequences from the ECD2-binding arm of one of v7133, v15079, v15080, v15081, v15082, v15083, v15084 or v15085. In some embodiments, one of the antigen-binding polypeptide constructs of the anti-HER2 biparatopic antibody comprises a VH sequence and a VL sequence from the ECD2-binding arm of one of v7133, v15079, v15080, v15081, v15082, v15083, v15084 or v15085, and the other antigen-binding polypeptide construct comprises the VH sequence and VL sequence from trastuzumab. In some embodiments, one of the antigen-binding polypeptide constructs of the anti-HER2 biparatopic antibody comprises the CDR sequences from the ECD2-binding arm of one of v7133, v15079, v15080, v15081, v15082, v15083, v15084 or v15085, and the other antigen-binding polypeptide construct comprises the CDR sequences from trastuzumab.

TABLE 7

Additional Exemplary Anti-HER2 Biparatopic Antibodies

| Variant | | Chain A | Chain B |
|---|---|---|---|
| 7133 | Domain containing target epitope | ECD2 | ECD4 |
| | Format | Fab | scFv |
| | Antibody name | Pertuzumab | Trastuzumab |
| | Fab sequence substitutions* | HC: T30A<br>LC: Y96A | |
| | CH3 sequence substitutions§ | T350V_L351Y_F405A_Y407V | T350V_T366L_K392L_T394W |
| 15082 | Domain containing target epitope | ECD2 | ECD4 |
| | Format | Fab | scFv |
| | Antibody name | Pertuzumab | Trastuzumab |
| | Fab sequence substitutions | HC: G56Y_K75W | |
| | CH3 sequence substitutions | T350V_L351Y_F405A_Y407V | T350V_T366L_K392L_T394W |
| 15085 | Domain containing target epitope | ECD2 | ECD4 |
| | Format | Fab | scFv |
| | Antibody name | Pertuzumab | Trastuzumab |
| | Fab sequence substitutions | HC: T30Q_S99W | |
| | CH3 sequence substitutions | T350V_L351Y_F405A_Y407V | T350V_T366L_K392L_T394W |
| 15083 | Domain containing target epitope | ECD2 | ECD4 |
| | Format | Fab | scFv |
| | Antibody name | Pertuzumab | Trastuzumab |
| | Fab sequence substitutions | HC: T30Q<br>LC: Y49W_Y96G | |
| | CH3 sequence substitutions | T350V_L351Y_F405A_Y407V | T350V_T366L_K392L_T394W |
| 15080 | Domain containing target epitope | ECD2 | ECD4 |
| | Format | Fab | scFv |
| | Antibody name | Pertuzumab | Trastuzumab |
| | Fab sequence substitutions | HC: T30Q_K75W<br>LC: Y49W_Y96G | |
| | CH3 sequence substitutions | T350V_L351Y_F405A_Y407V | T350V_T366L_K392L_T394W |
| 15079 | Domain containing target epitope | ECD2 | ECD4 |
| | Format | Fab | scFv |
| | Antibody name | Pertuzumab | Trastuzumab |
| | Fab sequence substitutions | HC: T30Y_K75W<br>LC: Y49W_Y96G | |
| | CH3 sequence substitutions | T350V_L351Y_F405A_Y407V | T350V_T366L_K392L_T394W |
| 15084 | Domain containing target epitope | ECD2 | ECD4 |
| | Format | Fab | scFv |
| | Antibody name | Pertuzumab | Trastuzumab |
| | Fab sequence substitutions | HC: T30Q_G56Y_S99W<br>LC: Y49W | |
| | CH3 sequence substitutions | T350V_L351Y_F405A_Y407V | T350V_T366L_K392L_T394W |
| 15081 | Domain containing target epitope | ECD2 | ECD4 |
| | Format | Fab | scFv |
| | Antibody name | Pertuzumab | Trastuzumab |
| | Fab sequence substitutions | HC: T30Q_G56Y<br>LC: Y49W_Y96G | |
| | CH3 sequence substitutions | T350V_L351Y_F405A_Y407V | T350V_T366L_K392L_T394W |

*Fab or variable domain numbering according to Kabat (Kabat et al., *Sequences of proteins of immunological interest*, 5th Edition, US Department of Health and Human Services, NIH Publication No. 91-3242, p.647, 1991)
§CH3 numbering according to EU index as in Kabat (Edelman et al., 1969, PNAS USA, 63: 78-85)

TABLE 7A

CDR Sequences of the ECD2-Binding Arm of Variants v7133, v15079, v15080, v15081, v15082, v15083, v15084 and v15085

| Variant | HC CDRs | SEQ ID NO | LC CDRs | SEQ ID NO |
|---|---|---|---|---|
| 7133 | H1: GFTFADYT | 39 | L1: QDVSIG | 12 |
|  | H2: VNPNSGGS | 8 | L2: SAS | 14 |
|  | H3: ARNLGPSFYFDY | 7 | L3: QQYYIYPAT | 28 |
| 15082 | H1: GFTFTDYT | 6 | L1: QDVSIG | 12 |
|  | H2: VNPNSGYS | 73 | L2: SAS | 14 |
|  | H3: ARNLGPSFYFDY | 7 | L3: QQYYIYPYT | 13 |
| 15085 | H1: GFTFQDYT | 74 | L1: QDVSIG | 12 |
|  | H2: VNPNSGGS | 8 | L2: SAS | 14 |
|  | H3: ARNLGPWFYFDY | 75 | L3: QQYYIYPYT | 13 |
| 15083 & 15080 | H1: GFTFQDYT | 74 | L1: QDVSIG | 12 |
|  | H2: VNPNSGGS | 8 | L2: SAS | 14 |
|  | H3: ARNLGPSFYFDY | 7 | L3: QQYYIYPGT | 76 |
| 15079 | H1: GFTFYDYT | 77 | L1: QDVSIG | 12 |
|  | H2: VNPNSGGS | 8 | L2: SAS | 14 |
|  | H3: ARNLGPSFYFDY | 7 | L3: QQYYIYPGT | 76 |
| 15084 | H1: GFTFQDYT | 74 | L1: QDVSIG | 12 |
|  | H2: VNPNSGYS | 73 | L2: SAS | 14 |
|  | H3: ARNLGPWFYFDY | 75 | L3: QQYYIYPYT | 13 |
| 15081 | H1: GFTFQDYT | 74 | L1: QDVSIG | 12 |
|  | H2: VNPNSGYS | 73 | L2: SAS | 14 |
|  | H3: ARNLGPSFYFDY | 7 | L3: QQYYIYPGT | 76 |

Properties of Anti-HER2 Biparatopic Antibodies

Conjugation of toxin at low DAR is of particular benefit to anti-HER2 biparatopic antibodies that show an increased binding to HER2 and/or a higher internalization into HER2-expressing cells compared to a corresponding bivalent monospecific antibody. A corresponding bivalent monospecific antibody may comprise two of the first antigen-binding polypeptide constructs, or two of the second antigen-binding polypeptide constructs that are comprised by the biparatopic antibody.

In certain embodiments, the anti-HER2 biparatopic antibodies show an increased binding (i.e. bind with a higher affinity) to HER2 compared to a corresponding bivalent monospecific antibody. Increased binding may be shown, for example, by a decrease in dissociation constant and/or an increase in maximal binding.

A dissociation constant or ($K_D$) refers to the equilibrium dissociation constant of a particular ligand-protein interaction, such as antibody-antigen interactions. The $K_D$ measures the propensity of two proteins (e.g. AB) to dissociate reversibly into smaller components (A+B), and is defined as the ratio of the rate of dissociation (also called the "off-rate" or $k_{off}$) to the association rate (also called the "on-rate" or $k_{on}$). Thus, $K_D$ equals $k_{off}/k_{on}$ and is expressed as a molar concentration (M). It follows that the smaller the $K_D$, the stronger the affinity of binding. $K_D$ values for antibodies can be determined using methods well established in the art. Examples of such methods include surface plasmon resonance (SPR), typically using a biosensor system such as a Biacore® system, and isothermal titration calorimetry (ITC).

Apparent $K_D$, or apparent equilibrium dissociation constant, represents the antibody concentration at which half maximal cell binding is observed. The apparent $K_D$ is dependent on the conditions of the cell binding experiment, such as different receptor levels expressed on the cells and incubation conditions, and thus the apparent $K_D$ is generally different from the $K_D$ values determined from cell-free molecular experiments such as SPR and ITC. However, there is generally good agreement between the different methods.

Maximal binding (or "Bmax") refers to the maximum antibody binding level on the cells at saturating concentrations of antibody. This parameter can be reported in the arbitrary unit MFI for relative comparisons, or converted into an absolute value corresponding to the number of antibodies bound to the cell with the use of a standard curve.

Bmax and apparent $K_D$ can be determined by various techniques. One example is the measurement of binding to target antigen-expressing cells by flow cytometry. Typically, in such an experiment, the target antigen-expressing cells are incubated with antibodies at different concentrations, washed, incubated with a secondary agent for detecting the antibody, washed, and analyzed in the flow cytometer to measure the median fluorescent intensity (MFI) representing the strength of detection signal on the cells, which in turn is related to the number of antibodies bound to the cells. The antibody concentration vs. MFI data is then fitted into a saturation binding equation to yield Bmax and apparent $K_D$.

In certain embodiments, the anti-HER2 biparatopic antibody displays an increase in Bmax to a target cell displaying HER2 as compared to a corresponding reference antibody. For an anti-HER2 biparatopic antibody comprising a first antigen-binding polypeptide construct and a second antigen-binding polypeptide construct as described herein, a corresponding reference antibody would be a bivalent monospecific antibody that comprises two of the first antigen-binding polypeptide constructs, or two of the second antigen-binding polypeptide constructs. In certain embodiments, the Bmax determined for the anti-HER2 biparatopic antibody is at least about 110% of the Bmax of a corresponding reference antibody. In some embodiments, the Bmax determined for the anti-HER2 biparatopic antibody is at least about 125% of the Bmax for a corresponding reference antibody, for example, about 150% of the Bmax of the corresponding reference antibody, or at least about 200% of the Bmax of the corresponding reference antibody.

In some embodiments, the Bmax determined for the anti-HER2 biparatopic antibody is 1.1, 1.2, 1.3, 1.4, 1.5, 1.6, 1.7, 1.8, 1.9 or 2.0 times the Bmax of a reference antibody.

In certain embodiments, the anti-HER2 biparatopic antibodies show a higher internalization into HER2-expressing cells than a corresponding reference bivalent monospecific antibody. The anti-HER2 biparatopic antibodies are internalized in HER2+ cells through binding to the receptor HER2. The anti-HER2 biparatopic antibodies thus can be considered as being able to induce receptor internalization in HER2+ cells.

Antibody internalization may be measured using art-known methods, for example, by a direct internalization method according to the protocol detailed in Schmidt, M. et al., Cancer Immunol Immunother, 57:1879-1890 (2008). As is known in the art, cancer cells may express HER2 at various levels. One method of classifying HER2 expressing cells is as HER2 1+, 2+ or 3+ (low, medium and high, respectively). In certain embodiments, the anti-HER2 biparatopic antibody shows a higher internalization than a corresponding reference bivalent monospecific antibody in cells expressing HER2 at the 3+ level. In some embodiments, the anti-HER2 biparatopic antibody shows a higher internalization than a corresponding reference bivalent monospecific antibody in cells expressing HER2 at the 2+ level. In some embodiments, the anti-HER2 biparatopic antibody shows a higher internalization than a corresponding reference bivalent monospecific antibody in cells expressing HER2 at the 1+ level. Examples of cell lines expressing different levels of HER2 are described in more detail below.

In the context of the present disclosure, an anti-HER2 biparatopic antibody is considered to demonstrate a higher internalization into HER2-expressing cells than a corresponding reference bivalent monospecific antibody when the amount of anti-HER2 biparatopic antibody internalized into the HER2-expressing cells is at least 1.2 times greater than the amount of reference bivalent monospecific antibody internalized into the same HER2-expressing cells. In certain embodiments, the amount of internalized antibody is determined by the direct internalization method according to the protocol detailed in Schmidt, M. et al., Cancer Immunol Immunother, 57:1879-1890 (2008). In some embodiments, the amount of internalized antibody is determined in HER2-expressing cells that express HER2 at the 2+ level.

In some embodiments, an anti-HER2 biparatopic antibody is considered to demonstrate a higher internalization into HER2-expressing cells than a corresponding reference bivalent monospecific antibody when the amount of anti-HER2 biparatopic antibody internalized into the HER2-expressing cells is at least 1.3 times greater than the amount of reference bivalent monospecific antibody internalized into the same HER2-expressing cells. In some embodiments, an anti-HER2 biparatopic antibody is considered to demonstrate a higher internalization into HER2-expressing cells than a corresponding reference bivalent monospecific antibody when the amount of anti-HER2 biparatopic antibody internalized into the HER2-expressing cells is at least 1.4 times greater, for example, at least 1.5 times greater, 1.6 times greater, 1.7 times greater, 1.8 times greater, 1.9 times greater, or 2.0 times greater, than the amount of reference bivalent monospecific antibody internalized into the same HER2-expressing cells. In certain embodiments, the amount of internalized antibody is determined by the direct internalization method according to the protocol detailed in Schmidt, M. et al., Cancer Immunol Immunother, 57:1879-1890 (2008). In some embodiments, the amount of internalized antibody is determined in HER2-expressing cells that express HER2 at the 2+ level.

Auristatin Analogues

The ADCs described herein comprise an auristatin-based toxin (or "auristatin analogue"). Various auristatin analogues are known in the art. Examples include, but are not limited to, monomethylauristatin F (MMAF), monomethylauristatin E (MMAE), auristatin EB (AEB), auristatin EVB (AEVB) and auristatin F phenylenediamine (AFP). The synthesis and structure of various auristatin analogues are described in U.S. Pat. Nos. 6,884,869; 7,098,308; 7,256,257 and 7,498,298.

In certain embodiments, the auristatin analogue included in the ADCs described herein may be an auristatin analogue as described in International Patent Application Publication No. WO 2016/041082. In certain embodiments, the auristatin analogue included the ADCs described herein is a compound of general Formula (I):

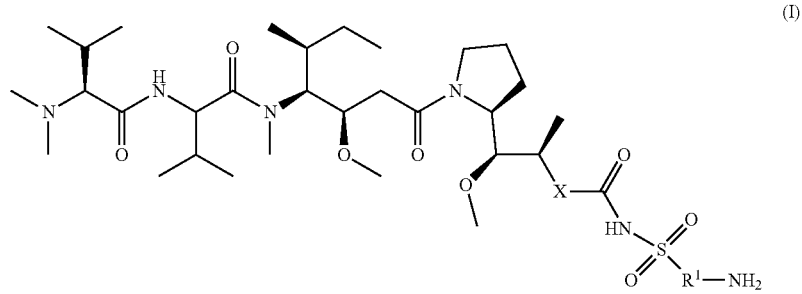

wherein:

X is —C(O)NHCH(CH$_2$R$^2$)—, or X is absent;

R$^1$ is selected from:

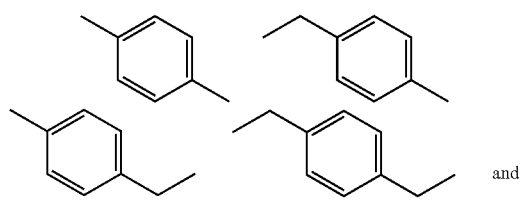

and

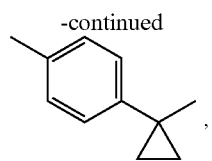

and
R² is phenyl.

In certain embodiments, in compounds of general Formula (I), R¹ is selected from:

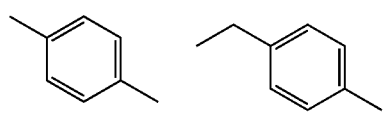 and

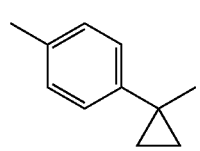

In certain embodiments, in compounds of general Formula (I), X is absent.

In certain embodiments, the compound of general Formula (I) has general Formula (IV):

(IV)

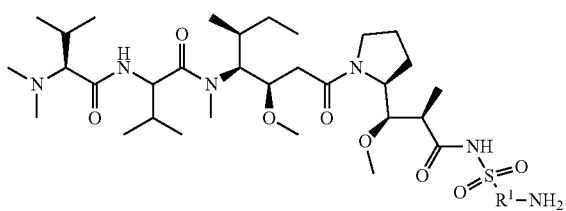

wherein R¹ is as defined for general Formula (I).

In certain embodiments, in compounds of Formula (IV), R¹ is selected from:

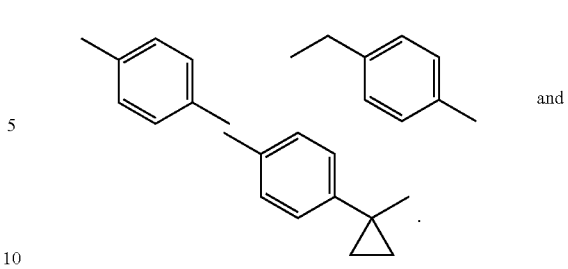

In certain embodiments, in compounds of Formula (IV), R¹ is:

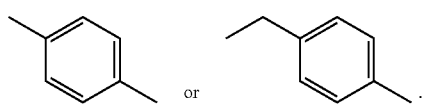 or

In certain embodiments, in compounds of Formula (IV), R¹ is:

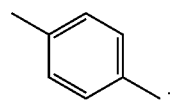

In certain embodiments, the compound of general Formula (I) has general Formula (V):

(V)

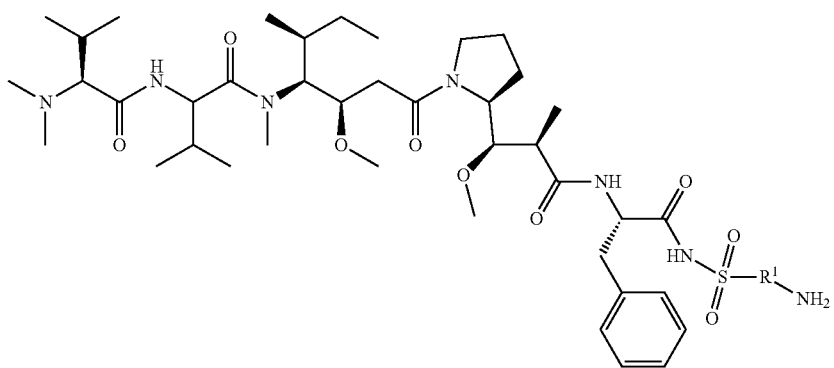

wherein R¹ is as defined for general Formula (I).

In certain embodiments, in compounds of Formula (V), R¹ is selected from:

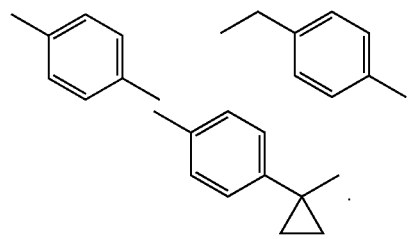 and

In certain embodiments, in compounds of Formula (V), R¹ is:

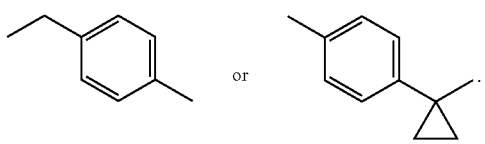 or

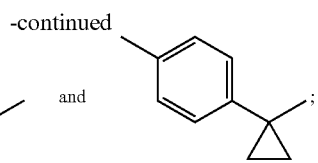 and ;

In certain embodiments, in compounds of Formula (V), $R^1$ is:

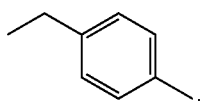

Compounds of general Formula (I) may be prepared by standard synthetic organic chemistry protocols from commercially available starting materials. Exemplary methods are provided in International Patent Application Publication No. WO 2016/041082 and in the Examples section below.

It is to be understood that reference to compounds of general Formula (I) throughout the remainder of this disclosure includes, in various embodiments, compounds of general Formula (IV) and (V), to the same extent as if embodiments reciting each of these formulae individually were specifically recited.

In certain embodiments, the ADC of the present disclosure comprises an anti-HER2 biparatopic antibody conjugated to an auristatin analogue (toxin) via a linker (L), in which the linker-toxin has general Formula (II):

$R^2$ is phenyl;
L is a linker, and
⁂ represents the point of attachment of the linker-toxin to the anti-HER2 biparatopic antibody.

In some embodiments, in the linker-toxin of general Formula (II), $R^1$ is selected from:

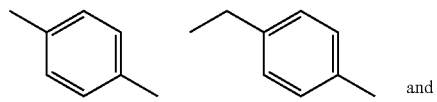

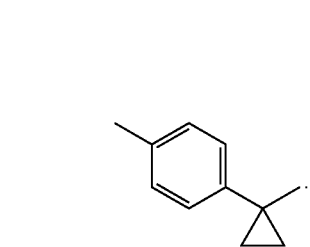

(II)

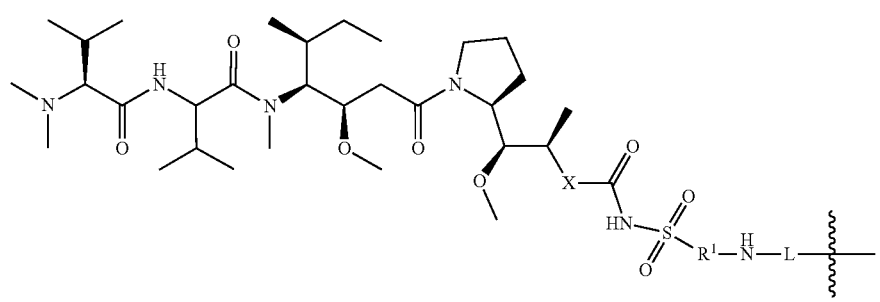

wherein:
X is —C(O)NHCH(CH$_2$R$^2$)—, or X is absent;
$R^1$ is selected from:

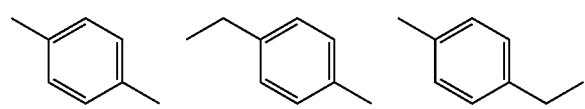

In some embodiments, in the linker-toxin of general Formula (II), X is absent.

In some embodiments, in the linker-toxin of general Formula (II), L is a cleavable linker.

In some embodiments, in the linker-toxin of general Formula (II), L is a peptide-containing linker.

In certain embodiments, the linker-toxin of general Formula (II) has general Formula (X):

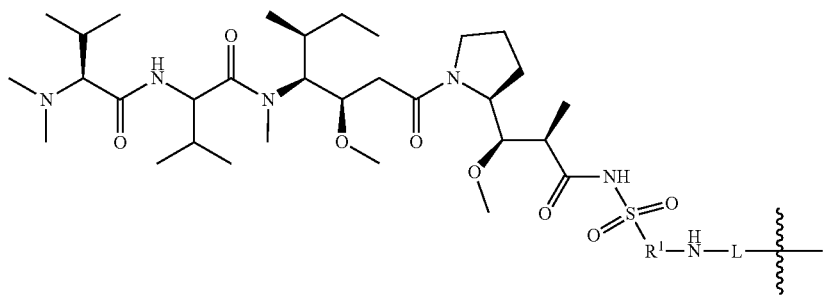

(X)

wherein R¹, L and ⸹ are as defined above for general Formula (II).

In some embodiments, in the linker-toxin of general Formula (X), R¹ is selected from:

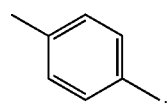

and

In some embodiments, in the linker-toxin of general Formula (X), L is a cleavable linker.

In some embodiments, in the linker-toxin of general Formula (X), L is a peptide-containing linker.

In some embodiments, in the linker-toxin of general Formula (X), L is a protease-cleavable linker.

In certain embodiments, the linker-toxin of general Formula (II) has general Formula (XI):

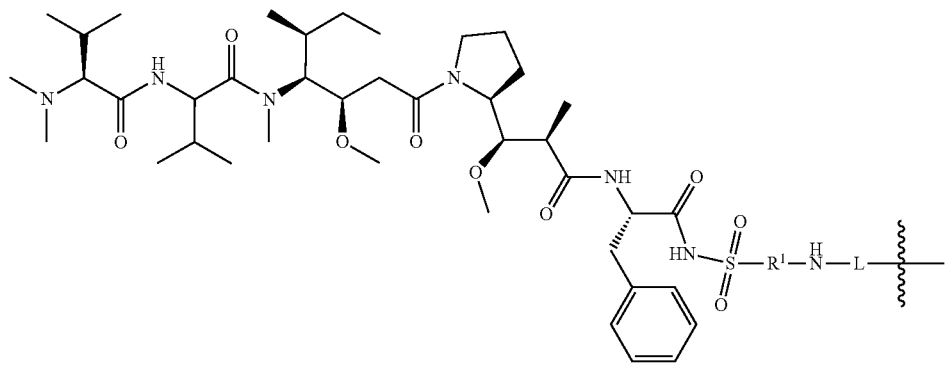

(XI)

wherein R¹, L and ⸹ are as defined above for general Formula (II).

In some embodiments, in the linker-toxin of general Formula (XI), R¹ is selected from:

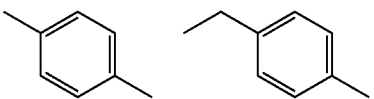

and

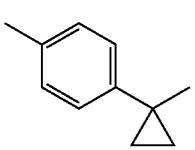

-continued

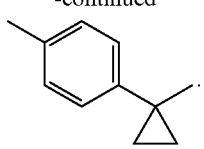

In some embodiments, in the linker-toxin of general Formula (X), R¹ is:

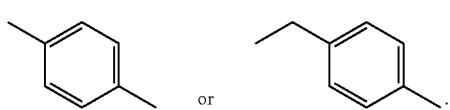

or

In some embodiments, in compounds of Formula (X), R¹ is:

In some embodiments, in the linker-toxin of general Formula (XI), R¹ is:

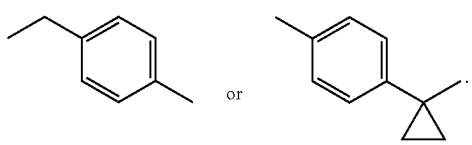

In some embodiments, in the linker-toxin of general Formula (XI), R¹ is:

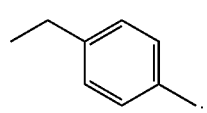

In some embodiments, in the linker-toxin of general Formula (XI), L is a cleavable linker.

In some embodiments, in the linker-toxin of general Formula (XI), L is a peptide-containing linker.

In some embodiments, in the linker-toxin of general Formula (XI), L is a protease-cleavable linker.

Also contemplated herein, are ADCs comprising an anti-HER2 biparatopic antibody conjugated to a linker-toxin of general Formula (II), Formula (X) or Formula (XI), in which the linker has general Formula (VIII) or (IX) as shown below.

In certain embodiments, the ADC comprises a linker-toxin having the structure:

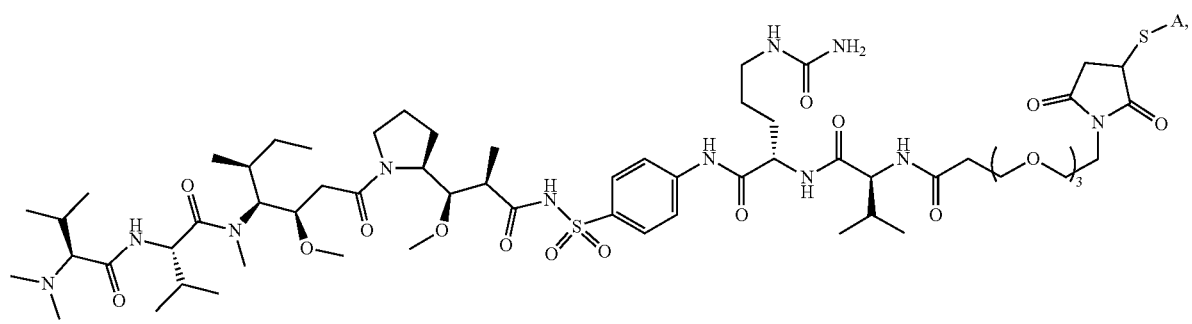

wherein A-S— is the point of attachment to the anti-HER2 biparatopic antibody.

In certain embodiments, the ADC of the present disclosure comprising an anti-HER2 biparatopic antibody conjugated to an auristatin analogue (toxin) via a linker (L) has general Formula (III):

wherein X and R¹ are as defined for general Formula (II);
L is a linker;
n is the average drug-to-antibody ratio (DAR) and is less than 3.9, and
Ab is an anti-HER2 biparatopic antibody.

In some embodiments, in the ADC of general Formula (III), R¹ is selected from:

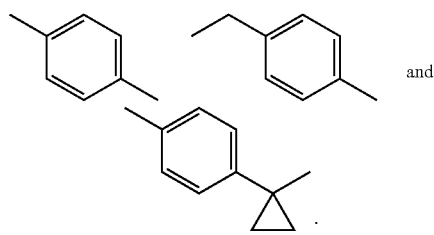

In some embodiments, in the ADC of general Formula (III), X is absent.

In some embodiments, in the ADC of general Formula (III), R¹ is:

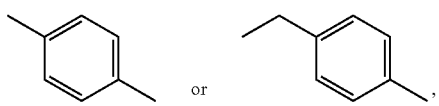

and

X is absent.

In some embodiments, in the ADC of general Formula (III), R¹ is:

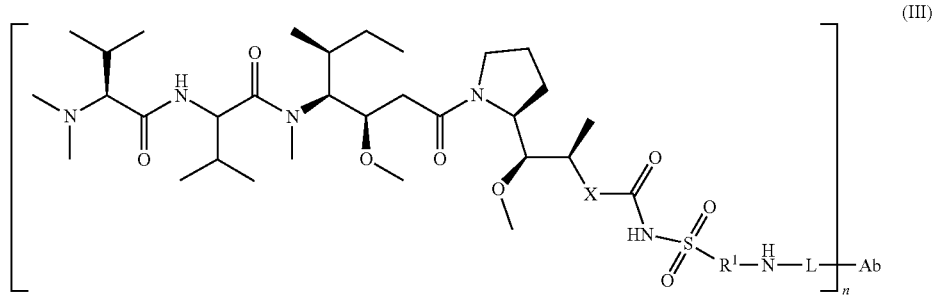

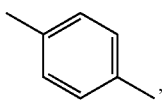

and
X is absent.

In some embodiments, in the ADC of general Formula (III), X is —C(O)NHCH(CH$_2$R$^2$)—

In some embodiments, in the ADC of general Formula (III), R$^1$ is:

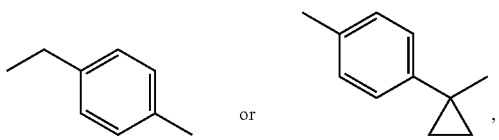

and
X is —C(O)NHCH(CH$_2$R$^2$)—.

In some embodiments, in the ADC of general Formula (III), R$^1$ is:

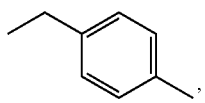

and
X is —C(O)NHCH(CH$_2$R$^2$)—.

In some embodiments, in the ADC of general Formula (III), L is a cleavable linker.

In some embodiments, in the ADC of general Formula (III), L is a peptide-containing linker.

In some embodiments, in the ADC of general Formula (III), L is a protease-cleavable linker.

In some embodiments, in the ADC of general Formula (III), n is between 0.5 and 3.8.

In some embodiments, in the ADC of general Formula (III), n is between 0.7 and 3.8, between 0.7 and 3.5, between 0.7 and 3.0, or between 0.7 and 2.5.

In some embodiments, in the ADC of general Formula (III), n is between 1.0 and 3.8, between 1.0 and 3.5, between 1.0 and 3.0, or between 1.0 and 2.5.

In some embodiments, in the ADC of general Formula (III), n is between 1.5 and 3.8, between 1.5 and 3.5, between 1.5 and 3.0, or between 1.5 and 2.5.

In some embodiments, in the ADC of general Formula (III), n is between 1.6 and 3.8, between 1.6 and 3.5, between 1.6 and 3.0, or between 1.6 and 2.5.

In some embodiments, in the ADC of general Formula (III), n is between 1.8 and 2.8, or between 1.8 and 2.5.

Combinations of any of the foregoing embodiments for compounds of general Formula (III) are also contemplated and each combination forms a separate embodiment for the purposes of the present disclosure.

Linkers

In the ADCs described herein, the anti-HER2 biparatopic antibody is linked to the auristatin analogue (toxin) by a linker. Linkers are bifunctional or multifunctional moieties capable of linking one or more toxin molecules to an antibody. A linker may be bifunctional (or monovalent) such that it links a single drug to a single site on the antibody, or it may be multifunctional (or polyvalent) such that it links more than one toxin molecule to a single site on the antibody. Linkers capable of linking one toxin molecule to more than one site on the antibody may also be considered to be multifunctional.

Attachment of a linker to an antibody can be accomplished in a variety of ways, such as through surface lysines on the antibody, reductive-coupling to oxidized carbohydrates on the antibody, or through cysteine residues on the antibody liberated by reducing interchain disulfide linkages. Alternatively, attachment of a linker to an antibody may be achieved by modification of the antibody to include additional cysteine residues (see, for example, U.S. Pat. Nos. 7,521,541; 8,455,622 and 9,000,130) or non-natural amino acids that provide reactive handles, such as selenomethionine, p-acetylphenylalanine, formylglycine or p-azidomethyl-L-phenylalanine (see, for example, Hofer et al., Biochemistry, 48:12047-12057 (2009); Axup et al., PNAS, 109:16101-16106 (2012); Wu et al., PNAS, 106:3000-3005 (2009); Zimmerman et al., Bioconj. Chem., 25:351-361 (2014)), to allow for site-specific conjugation.

Linkers include a functional group capable of reacting with the target group or groups on the antibody, and one or more functional groups capable of reacting with a target group on the toxin. Suitable functional groups are known in the art and include those described, for example, in *Bioconjugate Techniques* (G. T. Hermanson, 2013, Academic Press).

Non-limiting examples of functional groups for reacting with free cysteines or thiols include maleimide, haloacetamide, haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Also useful in this context are "self-stabilizing" maleimides as described in Lyon et al., Nat. Biotechnol., 32:1059-1062 (2014).

Non-limiting examples of functional groups for reacting with surface lysines on an antibody and free amines on a toxin include activated esters such as N-hydroxysuccinamide (NHS) esters, sulfo-NHS esters, imido esters such as Traut's reagent, isothiocyanates, aldehydes and acid anhydrides such as diethylenetriaminepentaacetic anhydride (DTPA). Other examples include succinimido-1,1,3,3-tetramethyluronium tetrafluoroborate (TSTU) and benzotriazol-1-yl-oxytripyrrolidinophosphonium hexafluorophosphate (PyBOP).

Non-limiting examples of functional groups capable of reacting with an electrophilic group on the antibody or toxin (such as an aldehyde or ketone carbonyl group) include hydrazide, oxime, amino, hydrazine, thiosemicarbazone, hydrazine carboxylate and arylhydrazide.

Other linkers include those having a functional group that allows for bridging of two interchain cysteines on the antibody, such as a ThioBridge™ linker (Badescu et al., Bioconjug. Chem., 25:1124-1136 (2014)), a dithiomaleimide (DTM) linker (Behrens et al., Mol. Pharm., 12:3986-3998 (2015)), a dithioaryl(TCEP)pyridazinedione based linker (Lee et al., Chem. Sci., 7:799-802 (2016)), a dibromopyridazinedione based linker (Maruani et al., Nat. Commun., 6:6645 (2015)) and others known in the art.

A linker may comprise one or more linker components. Typically, a linker will comprise two or more linker components. Exemplary linker components include functional groups for reaction with the antibody, functional groups for reaction with the toxin, stretchers, peptide components, self-immolative groups, self-elimination groups, hydrophilic moieties, and the like. Various linker components are known in the art, some of which are described below.

Certain useful linker components can be obtained from various commercial sources, such as Pierce Biotechnology, Inc. (now Thermo Fisher Scientific, Waltham, MA) and Molecular Biosciences Inc. (Boulder, Colo.), or may be synthesized in accordance with procedures described in the art (see, for example, Toki et al., J. Org. Chem., 67:1866-1872 (2002); Dubowchik, et al., Tetrahedron Letters, 38:5257-60 (1997); Walker, M. A., J. Org. Chem., 60:5352-5355 (1995); Frisch, et al., Bioconjugate Chem., 7:180-186 (1996); U.S. Pat. Nos. 6,214,345 and 7,553,816, and International Patent Application Publication No. WO 02/088172).

Examples of linker components include, but are not limited to, N-(β-maleimidopropyloxy)-N-hydroxy succinimide ester (B MPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl)aminobenzoate (STAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (S MCC), succinimidyl 4-(p-maleimidophenyl) butyrate (SMPB), succinimidyl 6-[(β-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, sulfo-SMPB and succinimidyl-(4-vinylsulfone)benzoate (SVSB).

Additional examples include bis-maleimide reagents such as dithiobismaleimidoethane (DTME), bis-maleimido-trioxyethylene glycol (BMPEO), 1,4-bismaleimidobutane (BMB), 1,4 bismaleimidyl-2,3-dihydroxybutane (BMDB), bismaleimidohexane (BMH), bismaleimidoethane (BMOE), $BM(PEG)_2$ and $BM(PEG)_3$; bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Suitable linkers typically are more chemically stable to conditions outside the cell than to conditions inside the cell, although less stable linkers may be contemplated in certain situations, such as when the toxin is selective or targeted and has a low toxicity to normal cells. Linkers may be "cleavable linkers" or "non-cleavable linkers." A cleavable linker is typically susceptible to cleavage under intracellular conditions, for example, through lysosomal processes. Examples include linkers that are protease-sensitive, acid-sensitive, reduction-sensitive or photolabile. Non-cleavable linkers by contrast, rely on the degradation of the antibody in the cell, which typically results in the release of an amino acid-linker-toxin moiety.

Suitable cleavable linkers include, for example, linkers comprising a peptide component that includes two or more amino acids and is cleavable by an intracellular protease, such as lysosomal protease or an endosomal protease. A peptide component may comprise amino acid residues that occur naturally and/or minor amino acids and/or non-naturally occurring amino acid analogues, such as citrulline. Peptide components may be designed and optimized for enzymatic cleavage by a particular enzyme, for example, a tumour-associated protease, cathepsin B, C or D, or a plasmin protease.

In certain embodiments, the linker included in the ADCs may be a dipeptide-containing linker, such as a linker containing valine-citrulline (Val-Cit) or phenylalanine-lysine (Phe-Lys). Other examples of suitable dipeptides for inclusion in linkers include Val-Lys, Ala-Lys, Me-Val-Cit, Phe-homoLys, Phe-Cit, Leu-Cit, Ile-Cit, Trp-Cit, Phe-Arg, Ala-Phe, Val-Ala, Met-Lys, Asn-Lys, Ile-Pro, Ile-Val, Asp-Val, His-Val, Met-(D)Lys, Asn-(D)Lys, Val-(D)Asp, NorVal-(D)Asp, Ala-(D)Asp, Me₃Lys-Pro, PhenylGly-(D)Lys, Met-(D)Lys, Asn-(D)Lys, Pro-(D)Lys and Met-(D)Lys. Cleavable linkers may also include longer peptide components such as tripeptides, tetrapeptides or pentapeptides. Examples include, but are not limited to, the tripeptides Met-Cit-Val, Gly-Cit-Val, (D)Phe-Phe-Lys and (D)Ala-Phe-Lys, and the tetrapeptides Gly-Phe-Leu-Gly and Ala-Leu-Ala-Leu.

Additional examples of cleavable linkers include disulfide-containing linkers, such as, for example, N-succinimydyl-4-(2-pyridyldithio) butanoate (SPBD) and N-succinimydyl-4-(2-pyridyldithio)-2-sulfo butanoate (sulfo-SPBD). Disulfide-containing linkers may optionally include additional groups to provide steric hindrance adjacent to the disulfide bond in order to improve the extracellular stability of the linker, for example, inclusion of a geminal dimethyl group. Other suitable linkers include linkers hydrolyzable at a specific pH or within a pH range, such as hydrazone linkers. Linkers comprising combinations of these functionalities may also be useful, for example, linkers comprising both a hydrazone and a disulfide are known in the art.

A further example of a cleavable linker is a linker comprising a β-glucuronide, which is cleavable by β-glucuronidase, an enzyme present in lysosomes and tumour interstitium (see, for example, De Graaf et al., Curr. Pharm. Des., 8:1391-1403 (2002)).

Cleavable linkers may optionally further comprise one or more additional components such as self-immolative and self-elimination groups, stretchers or hydrophilic moieties.

Self-immolative and self-elimination groups that find use in linkers include, for example, p-aminobenzyloxycarbonyl (PABC) and p-aminobenzyl ether (PABE) groups, and methylated ethylene diamine (MED). Other examples of self-immolative groups include, but are not limited to, aromatic compounds that are electronically similar to the PABC or PABE group such as heterocyclic derivatives, for example 2-aminoimidazol-5-methanol derivatives as described in U.S. Pat. No. 7,375,078. Other examples include groups that undergo cyclization upon amide bond hydrolysis, such as substituted and unsubstituted 4-aminobutyric acid amides (Rodrigues et al., Chemistry Biology, 2:223-227 (1995)) and 2-aminophenylpropionic acid amides (Amsberry, et al., J. Org. Chem., 55:5867-5877 (1990)).

Stretchers that find use in linkers for ADCs include, for example, alkylene groups and stretchers based on aliphatic acids, diacids, amines or diamines, such as diglycolate, malonate, caproate and caproamide. Other stretchers include, for example, glycine-based stretchers, polyethylene glycol (PEG) stretchers and monomethoxy polyethylene glycol (mPEG) stretchers. PEG and mPEG stretchers also function as hydrophilic moieties.

Examples of components commonly found in cleavable linkers that may find use in the ADCs of the present disclosure in some embodiments include, but are not limited to, SPBD, sulfo-SPBD, hydrazone, Val-Cit, maleidocaproyl (MC or mc), mc-Val-Cit, mc-Val-Cit-PABC, Phe-Lys, mc-Phe-Lys, mc-Phe-Lys-PABC, maleimido triethylene glycolate (MT), MT-Val-Cit, MT-Phe-Lys and adipate (AD).

In certain embodiments, the linker included in the ADCs of the present disclosure are peptide-based linkers having general Formula (VI):

$$Z-[\text{Str}]_s-AA_1-[AA_2]_m-[X]_o-D \qquad (VI)$$

wherein:
Z is a functional group capable of reacting with the target group on the antibody;
Str is a stretcher;
$AA_1$ and $AA_2$ are each independently an amino acid, wherein $AA_1$-$[AA_2]_m$ forms a protease cleavage site;
X is a self-immolative group;
D is the point of attachment to the auristatin analogue;
s is 0 or 1;
m is an integer between 1 and 4, and
is 0, 1 or 2.

In some embodiments, in general Formula (VI), Z is:

[maleimide structure]

In some embodiments, in general Formula (VI), Str is selected from:

$$-(CH_2)_p-\overset{O}{\underset{\|}{C}}-; \quad -(CH_2CH_2O)_q-\overset{O}{\underset{\|}{C}}-;$$

$$-(CH_2)_p-(CH_2CH_2O)_q-\overset{O}{\underset{\|}{C}}-;$$

$$-(CH_2CH_2O)_q-(CH_2)_p-\overset{O}{\underset{\|}{C}}-;$$

$$-(CH_2)_p-\overset{O}{\underset{\|}{C}}-\overset{R}{\underset{|}{N}}-(CH_2)_p-\overset{O}{\underset{\|}{C}}- \quad \text{and}$$

$$-(CH_2)_p-\overset{O}{\underset{\|}{C}}-\overset{R}{\underset{|}{N}}-(CH_2CH_2O)_q-\overset{O}{\underset{\|}{C}}-,$$

wherein:
R is H or $C_1$-$C_6$ alkyl;
p is an integer between 2 and 10, and
q is an integer between 1 and 10.

In some embodiments, in general Formula (VI), Str is:

$$-(CH_2)_p-\overset{O}{\underset{\|}{C}}-; \quad -(CH_2)_p-(CH_2CH_2O)_q-\overset{O}{\underset{\|}{C}}- \quad \text{or}$$

$$-(CH_2CH_2O)_q-(CH_2)_p-\overset{O}{\underset{\|}{C}}-,$$

wherein p and q are as defined above.

In some embodiments, in general Formula (VI), Str is:

$$-(CH_2)_p-\overset{O}{\underset{\|}{C}}- \quad \text{or} \quad -(CH_2CH_2O)_q-(CH_2)_p-\overset{O}{\underset{\|}{C}}-,$$

wherein p is an integer between 2 and 6, and
q is an integer between 2 and 8.

In some embodiments, in general Formula (VI), $AA_1$-$[AA_2]_m$ is selected from Val-Lys, Ala-Lys, Phe-Lys, Val-Cit, Phe-Cit, Leu-Cit, Ile-Cit, Trp-Cit, Phe-Arg, Ala-Phe, Val-Ala, Met-Lys, Asn-Lys, Ile-Pro, Ile-Val, Asp-Val, His-Val, Met-(D)Lys, Asn-(D)Lys, Val-(D)Asp, NorVal-(D)Asp, Ala-(D)Asp, Me₃Lys-Pro, PhenylGly-(D)Lys, Met-(D)Lys, Asn-(D)Lys, Pro-(D)Lys, Met-(D)Lys, Met-Cit-Val, Gly-Cit-Val, (D)Phe-Phe-Lys, (D)Ala-Phe-Lys, Gly-Phe-Leu-Gly and Ala-Leu-Ala-Leu.

In some embodiments, in general Formula (VI), m is 1 (i.e. $AA_1$-$[AA_2]_m$ is a dipeptide).

In some embodiments, in general Formula (VI), $AA_1$-$[AA_2]_m$ is a dipeptide selected from Val-Lys, Ala-Lys, Phe-Lys, Val-Cit, Phe-Cit, Leu-Cit, Ile-Cit and Trp-Cit.

In some embodiments, in general Formula (VI), each X is independently selected from p-aminobenzyloxycarbonyl (PABC), p-aminobenzyl ether (PABE) and methylated ethylene diamine (MED).

In some embodiments, in general Formula (VI), m is 1, 2 or 3.

In some embodiments, in general Formula (VI), s is 1.
In some embodiments, in general Formula (VI), o is 0.
In some embodiments, in general Formula (VI):
Z is

[maleimide structure];

Str is $$-(CH_2)_p-\overset{O}{\underset{\|}{C}}- \quad \text{or} \quad -(CH_2CH_2O)_q-(CH_2)_p-\overset{O}{\underset{\|}{C}}-,$$

wherein p is an integer between 2 and 6, and q is an integer between 2 and 8;
m is 1 and $AA_1$-$[AA_2]_m$ is a dipeptide selected from Val-Lys, Ala-Lys, Phe-Lys, Val-Cit, Phe-Cit, Leu-Cit, Ile-Cit and Trp-Cit;
s is 1, and
is 0.

In some embodiments, the linker is a disulfide-containing linker and the ADC has general Formula (VII):

$$A-\overset{H}{\underset{}{N}}-\overset{O}{\underset{\|}{C}}-Y-\underset{R}{\overset{R}{C}}-S-S-\underset{R}{\overset{R}{C}}(CH_2)_r-D \qquad (VII)$$

wherein:
A is the antibody;
D is the auristatin analogue;
Y is —(CH$_2$)$_p$— or —(CH$_2$CH$_2$O)$_q$—, wherein p and q are each independently an integer between 1 and 10;
each R is independently H or C$_1$-C$_6$ alkyl;
r is 1, 2 or 3, and
wherein

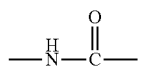

represents an amide bond formed between the linker and the s-amino group of a surface lysine on the antibody.

In some embodiments in general Formula (VII), p and q are each independently an integer between 1 and 4.

In some embodiments in general Formula (VII), Y is —(CH$_2$)$_p$— and p is an integer between 1 and 4.

In some embodiments in general Formula (VII), each R is independently H or Me.

In some embodiments in general Formula (VII), r is 1 or 2.

Various non-cleavable linkers are known in the art for linking drugs to antibodies and may be useful in the ADCs of the present disclosure in certain embodiments. Examples of non-cleavable linkers include linkers having an N-succinimidyl ester or N-sulfosuccinimidyl ester moiety for reaction with the antibody, as well as a maleimido- or haloacetyl-based moiety for reaction with the toxin, or vice versa. An example of such a non-cleavable linker is based on sulfosuccinimidyl-4-[N-maleimidomethyl]cyclohexane-1-carboxylate (sulfo-SMCC). Other non-limiting examples of such linkers include those based on N-succinimidyl 4-(maleimidomethyl)cyclohexanecarboxylate (SMCC), N-succinimidyl-4-(N-maleimidomethyl)-cyclohexane-1-carboxy-(6-amidocaproate) ("long chain" SMCC or LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MB S), N-(α-maleimidoacetoxy)-succinimide ester (AMAS), succinimidyl-6-(β-maleimidopropionamido) hexanoate (S MPH), N-succinimidyl 4-(p-maleimidophenyl)-butyrate (SMPB), and N-(p-maleimidophenyl)isocyanate (PMPI). Other examples include those comprising a haloacetyl-based functional group such as N-succinimidyl-4-(iodoacetyl)-aminobenzoate (STAB), N-succinimidyl iodoacetate (SIA), N-succinimidyl bromoacetate (SBA) and N-succinimidyl 3-(bromoacetamido)propionate (SBAP).

Other examples of non-cleavable linkers include maleimidocarboxylic acids, such as maleimidocaproyl (MC).

Selection of an appropriate linker for a given ADC may be readily made by the skilled person having knowledge of the art and taking into account relevant factors, such as the site of attachment to the antibody, any structural constraints of the toxin and the hydrophobicity of the toxin (see, for example, review in Nolting, Chapter 5, *Antibody-Drug Conjugates: Methods in Molecular Biology*, 2013, Ducry (Ed.), Springer).

In certain embodiments, the linker included in the ADCs of the present disclosure has general Formula (VIII):

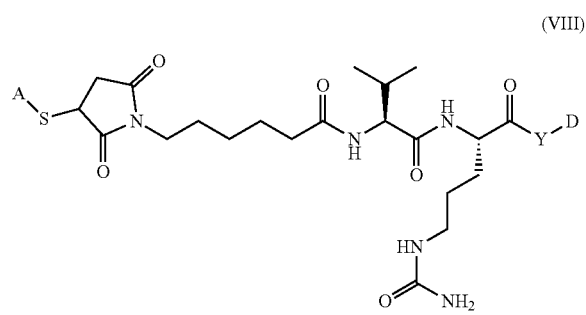

(VIII)

wherein:
A-S— is the point of attachment to anti-HER2 biparatopic antibody;
Y is one or more additional linker components, or is absent, and
D is the point of attachment to the auristatin analogue.

In certain embodiments, the linker included in the ADCs of the present disclosure has general Formula (IX):

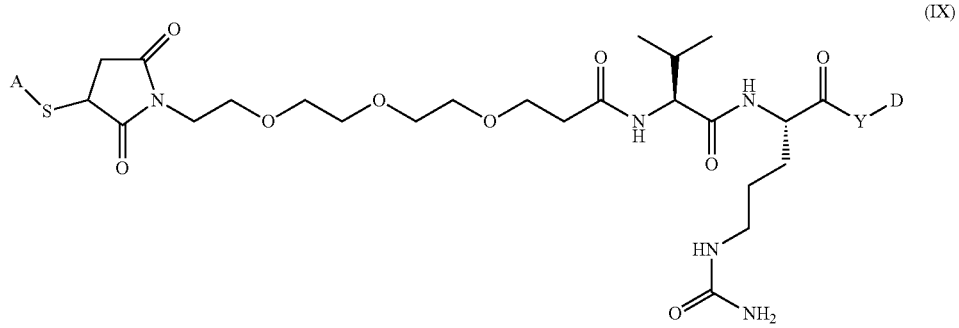

(IX)

wherein:
A-S— is the point of attachment to anti-HER2 biparatopic antibody;
Y is one or more additional linker components, or is absent, and
D is the point of attachment to the auristatin analogue.

Preparation of Antibody Drug Conjugates

The ADCs of the present disclosure may be prepared by one of several routes known in the art, employing organic chemistry reactions, conditions, and reagents known to those skilled in the art (see, for example, *Bioconjugate Techniques* (G. T. Hermanson, 2013, Academic Press, and the Examples provided herein). For example, conjugation may be achieved by (1) reaction of a nucleophilic group or an electrophilic group of an antibody with a bifunctional linker to form an antibody-linker intermediate Ab-L, via a covalent bond, followed by reaction with an activated auristatin analogue (D), or (2) reaction of a nucleophilic group or an electrophilic group of an auristatin analogue with a linker to form linker-toxin D-L, via a covalent bond, followed by reaction with the nucleophilic group or an electrophilic group of an antibody. Conjugation methods (1) and (2) may be employed with a variety of antibodies, auristatin analogues, and linkers to prepare the ADCs described herein.

As described above, the auristatin analogue may be conjugated via an appropriate linker to various groups on the antibody to provide the ADC. For example, conjugation may be through surface lysines, through oxidized carbohydrates or through cysteine residues that have been liberated by reducing one or more interchain disulfide linkages. Alternatively, the antibody may be modified to include additional cysteine residues or non-natural amino acids that provide reactive handles, such as selenomethionine, p-acetylphenylalanine, formylglycine or p-azidomethyl-L-phenylalanine. Such modifications are well-known in the art (see, for example, U.S. Pat. Nos. 7,521,541; 8,455,622 and 9,000,130; Hofer et al., Biochemistry, 48:12047-12057 (2009); Axup et al., PNAS, 109:16101-16106 (2012); Wu et al., PNAS, 106:3000-3005 (2009); Zimmerman et al., Bioconj. Chem., 25:351-361 (2014)).

In certain embodiments, the ADCs of the present disclosure comprise an auristatin analogue conjugated via an appropriate linker to cysteine residues that have been liberated by reducing one or more interchain disulfide linkages.

In the ADCs described herein, the anti-HER2 biparatopic antibody is conjugated to the toxin via a linker at a low average drug-to-antibody ratio (DAR), specifically an average DAR of less than 3.9 but more than 0.5, for example, between about 1.5 and about 2.5 in certain embodiments.

Various methods are known in the art to prepare ADCs with a low average DAR (see, for example, review by McCombs and Owen, The AAPS Journal, 17(2):339-351 (2015) and references therein; Boutureira & Bernardes, Chem. Rev., 115:2174-2195 (2015)).

For example, for conjugation to cysteine residues, a partial reduction of the antibody interchain disulfide bonds may be conducted followed by conjugation to linker-toxin. Partial reduction can be achieved by limiting the amount of reducing agent used in the reduction reaction (see, for example, Lyon et al., Methods in Enzymology, 502:123-138 (2012), and examples therein, and the Examples provided herein). Suitable reducing agents are known in the art and include, for example, dithiothreitol (DTT), tris(2-carboxyethyl)phosphine (TCEP), 2-mercaptoethanol, cysteamine and a number of water soluble phosphines. Alternatively, or in addition, fewer equivalents of linker-toxin may be employed in order to obtain a low average DAR.

Alternatively, an engineered antibody may be employed in which one or more of the cysteine residues that make up the interchain disulfide bonds is replaced with a serine residue resulting in fewer available cysteine residues for conjugation (see McDonagh et al., Protein Eng. Des. Sel. PEDS, 19(7):299-307). The engineered antibody can then be treated with reducing agent and conjugated to linker-toxin.

Another approach is to employ a bis-thiol linker that bridges two cysteines that normally make up an interchain disulfide bond. Use of a bis-thiol linker that carries only one toxin molecule would produce an ADC with a maximum DAR4 for a full-size antibody, if all four interchain disulfide bonds are reduced and replaced with the bis-thiol linker. Partial reduction of the interchain disulfide bonds and/or fewer equivalents of linker may be used in conjunction with a bis-thiol linker in order to further reduce the DAR. Various bis-thiol linkers are known in the art (see, for example, Badescu et al., Bioconjug. Chem., 25(6):1124-1136 (2014); Behrens et al., Mol. Pharm., 12:3986-3998 (2015); Lee et al., Chem. Sci., 7:799-802 (2016); Maruani et al., Nat. Commun., 6:6645 (2015)).

Cysteine engineering approaches may also be employed in order to generate ADCs with a low average DAR. Such approaches involve engineering solvent-accessible cysteines into the antibody in order to provide a site-specific handle for conjugation. A number of appropriate sites for introduction of a cysteine residue have been identified with the IgG structure, and include those described in Junutula, et al., J. Immunol Methods, 332(1-2):41-52 (2008); Junutula, et al., Nat. Biotechnol., 26(8), 925-932 (2008), and U.S. Pat. Nos. 9,315,581; 9,000,130; 8,455,622; 8,507,654 and 7,521,541.

Low average DAR ADCs may also be prepared by lysine conjugation employing limiting amounts of activated linker-toxin. Selective reaction at the antibody N-terminal amino acids may also be employed. For example, N-terminal serine may be oxidized to an aldehyde with periodate, then reacted with linker-toxin (see, for example, Thompson, et al., Bioconjug. Chem., 26(10):2085-2096 (2015)). Similarly, N-terminal cysteine residues can be selectively reacted with aldehydes to give thiazolidinones (see, for example, Bernardes, et al., Nature Protocols, 8:2079-2089).

Additional approaches include engineering the antibody to include one or more unnatural amino acids, such as p-acetylphenylalanine (pAcPhe) or selenocysteine (Sec). The keto group in pAcPhe can be reacted with a linker-toxin comprising a terminal alkoxyamine or hydrazide to form an oxime or hydrazone bond (see, for example, Axup, et al., PNAS USA, 109:16101-16106 (2012)). Sec-containing antibodies can be reacted with maleimide- or iodoacetamide containing linker-toxins to form a selenoether conjugate (see, for example, Hofer, et al., Biochemistry, 48:12047-12057 (2009)).

Antibodies may also be engineered to include peptide tags recognized by certain enzymes to allow for enzyme-catalyzed conjugation. For example, Sortase-A (SortA) recognizes the sequence LPXTG. This pentapeptide may be engineered into the N- or C-terminus of the antibody to allow for SortA-mediated conjugation (see, for example, U.S. Patent Application Publication No. 2016/0136298; Kornberger and Skerra, mAbs, 6(2):354-366 (2014)). Transglutaminases have also been employed to generate DAR2 ADCs by using antibodies that have been deglycosylated at position N297 (which exposes Q295 for enzymatic conjugation) or by engineering antibodies to include a "glutamine tag" (LLQG) (Jeger, et al., Angew. Chem., 49:9995-9997 (2010); Strop, et al., Chem. Biol., 20(2):161-167 (2013)). In another approach, a formylglycine residue can be introduced into an antibody by engineering an appropriate consensus sequence into the antibody and co-expressing the engineered antibody with formylglycine-generating enzyme (FGE). The aldehyde functionality of the introduced formylglycine may then be used as a handle for conjugation of toxin (see, for example, Drake, et al., Bioconjug. Chem., 25(7):1331-1341 (2014)).

Another approach used to generate DAR2 ADCs is by conjugation of linker-toxin to the native sugars found on glycosylated antibodies. Conjugation to glycosylated antibodies may be achieved, for example, by periodate oxidation of terminal sugar residues to yield aldehydes, which may then be conjugated to an appropriate linker-toxin, or by glycoengineering approaches in which native sugars are modified with terminal sialic acid residues, which can then be oxidized to yield aldehydes for conjugation to linker-toxin (Zhou, et al., Bioconjug. Chem., 25(3):510-520 (2014)).

The use of UV cross-linking for conjugation of active moieties to antibodies has also been reported. This method uses the nucleotide binding site (NBS) for site-specific covalent functionalization of antibodies with reactive thiol moieties. An indole-3-butyric acid (IBA) conjugated version of cysteine was used to site-specifically photo-cross-link a reactive thiol moiety to antibodies at the NBS. The thiol moiety may then be used to conjugate linker-toxin having a thiol reactive group (Alves, et al., Bioconjug. Chem., 25(7): 1198-1202 (2014)).

Alternatively, ADCs with a low average DAR may be isolated from an ADC preparation containing a mixture of DAR species using chromatographic separation techniques, such as hydrophobic interaction chromatography (see, for example, Hamblett, et al., Clin. Cancer Res., 10:7063-7070 (2004); Sun, et al., Bioconj Chem., 28:1371-81 (2017); U.S. Patent Application Publication No. 2014/0286968).

ADC preparations with a low average DAR may also be generated by adding unconjugated (i.e. DAR0) antibody to preparations of ADC having an average DAR ≥3.9. As is known in the art, the majority of conjugation methods yield an ADC preparation that includes various DAR species, with the reported DAR being the average of the individual DAR species. In certain embodiments, ADC preparations that include a proportion of DAR0 species may be advantageous. In some embodiments, the ADC preparation having an average DAR of less than 3.9 may include at least 5% DAR0 species. In some embodiments, the ADC preparation may include at least 10% DAR0 species, for example, at least 15% DAR0 species or at least 20% DAR0 species. In some embodiments, the ADC preparation may include between about 5% and about 50% DAR0 species. In some embodiments, the ADC preparation may include between about 10% and about 50% DAR0 species, for example, between about 10% and about 40%, or between about 10% and about 30% DAR0 species.

The average DAR for the ADCs may be determined by standard techniques such as UV/VIS spectroscopic analysis, ELISA-based techniques, chromatography techniques such as hydrophobic interaction chromatography (HIC), UV-MALDI mass spectrometry (MS) and MALDI-TOF MS. In addition, distribution of drug-linked forms (for example, the fraction of DAR0, DAR1, DAR2, etc. species) may also be analyzed by various techniques known in the art, including MS (with or without an accompanying chromatographic separation step), hydrophobic interaction chromatography, reverse-phase HPLC or iso-electric focusing gel electrophoresis (IEF) (see, for example, Sun et al., Bioconj Chem., 28:1371-81 (2017); Wakankar et al., mAbs, 3:161-172 (2011)).

In certain embodiments, the average DAR of the ADCs is determined by hydrophobic interaction chromatography (HIC) techniques.

Following conjugation, the ADCs may be purified and separated from unconjugated reactants and/or any conjugate aggregates by purification methods known in the art. Such methods include, but are not limited to, size exclusion chromatography (SEC), hydrophobic interaction chromatography (HIC), ion exchange chromatography, chromatofocusing, ultrafiltration, centrifugal ultrafiltration, and combinations thereof.

Testing

The anti-cancer activity of the ADCs in HER2-expressing cancer cells may be tested in vitro and/or in vivo using standard techniques.

For example, the cytotoxic activity of the ADCs may be measured by exposing HER2-expressing cancer cells to the ADC in a cell culture medium, culturing the cells for an appropriate period of time (for example, about 6 hrs to about 7 days), then measuring cell viability. Non-HER2 expressing cells may be included as a control.

A variety of cancer cell lines expressing HER2 at varying levels, which may be used to test the ADCs are known in the art and many are commercially available (for example, from the American Type Culture Collection, Manassas, VA; Addexbio Technologies, San Diego, CA; DSMZ, Braunschweig, Germany). Examples include the BT-474 (3+), SK-BR-3 (3+), HCC1954 (3+), JIMT-1 (2+) and ZR-75-1 (1+) cell lines. These and other examples are summarized in Table 8.

TABLE 8

Relative Expression Levels of HER2 in Cell Lines of Interest

| Cell Line | Description | IHC scoring | HER2 receptors/cell |
|---|---|---|---|
| NCI-N87 | Human gastric carcinoma | 3+ | Not assessed |
| A549 | Human lung alveolar carcinoma (non-small cell lung cancer) | 0/1+ | Not assessed |
| BxPC-3 | Human pancreatic adenocarcinoma | 1+ | Not assessed |
| MIA PaCa-2 | Human pancreatic ductal adenocarcinoma | 2+ | Not assessed |
| FaDu | Human pharyngeal squamous cell carcinoma | 2+ | Not assessed |
| HCT-116 | Human colorectal epithelial carcinoma | 1+ | Not assessed |
| MDA-MB-231 | Human triple negative breast epithelial adenocarcinoma | 0/1+ | $1.7 \times 10E4$-$2.3 \times 10E4$ |
| MCF-7 | Human estrogen receptor positive breast epithelial adenocarcinoma | 1+ | $4 \times 10E4$-$7 \times 10E4$ |
| JIMT-1 | Trastuzumab-resistant breast epithelial carcinoma, amplified HER2 oncogene | 2+ | $2 \times 10E5$-$8 \times 10E5$ |
| ZR-75-1 | Estrogen receptor positive breast ductal carcinoma | 2+ | $3 \times 10E5$ |
| SKOV-3 | Human ovarian epithelial adenocarcinoma, HER2 gene amplified | 2/3+ | $5 \times 10E5$-$1 \times 10E6$ |
| SK-BR-3 | Human breast epithelial adenocarcinoma | 3+ | $>1 \times 10E6$ |
| BT-474 | Human breast epithelial ductal carcinoma | 3+ | $>1 \times 10E6$ |

TABLE 8-continued

Relative Expression Levels of HER2 in Cell Lines of Interest

| Cell Line | Description | IHC scoring | HER2 receptors/cell |
|---|---|---|---|
| MDA-MB-468 | Human breast adenocarcinoma, derived from metastatic site: pleural effusion | 0 | Undetectable (≤1000) |

The ability of the ADCs to inhibit tumour growth in vivo can be determined in an appropriate animal model using standard techniques known in the art (see, for example, Enna, et al., Current Protocols in Pharmacology, J. Wiley & Sons, Inc., New York, NY). In general, current animal models for screening anti-tumour compounds are xenograft models, in which a human tumour has been implanted into an animal, typically a rodent.

For example, the ADCs may be tested in vivo on HER2-expressing tumours using mice that are subcutaneously grafted with tumour fragment, or implanted with an appropriate number of cancer cells, on day 0. The tumours are allowed to develop to the desired size, with animals having insufficiently developed tumours being eliminated. ADC treatment generally begins from 3 to 22 days after grafting, depending on the type of tumour. The ADC may be administered to the animals, for example, by intravenous (i.v.) injection. Tumours are measured either after a pre-determined time period or continuously (for example, 2 or 3 times a week) until a pre-determined endpoint for the study, for example, when the tumour reaches a pre-determined size or weight. Tumours expressing HER2 at various levels may be used in the xenograft models. Patient-derived xenografts (PDX) are particularly useful.

In vivo toxic effects of the ADCs may initially be evaluated in rodents, for example mice or rats, by measuring their effect on animal body weight during treatment. Hematological profiles and liver enzyme analysis may also be performed on blood samples taken from the animals.

In vivo toxicity and pharmacokinetics may be further analyzed in appropriate animal models, for example, rats or non-human primates, following standard protocols. Cynomolgus monkeys are particularly useful in this regard as human and cynomolgus monkey HER2 share 98% sequence homology.

The ADCs described herein have improved tolerability and lower toxicity as compared to a corresponding ADC having a DAR ≥3.9 when administered at the same toxin dose. In certain embodiments, the ADCs show an improvement in tolerability of greater than 2× that of a corresponding ADC having a DAR ≥3.9 when administered at the same toxin dose. In some embodiments, the ADCs show an improvement in tolerability of greater than 2.2×, for example, 2.3×, 2.4× or 2.5×, that of a corresponding ADC having a DAR ≥3.9 when administered at the same toxin dose. Improvement in tolerability may be determined, for example, by comparison of maximal tolerated dose (MTD), no observed adverse event level (NOAEL) or highest non-severely toxic dose (HNSTD) for the ADC of the present disclosure and the corresponding ADC having a DAR ≥3.9. MTD, NOAEL and/or HNSTD may be measured by standard techniques in an appropriate animal model, for example, a rodent or non-human primate.

Pharmaceutical Compositions

For therapeutic use, the ADCs may be provided in the form of compositions comprising the ADC and a pharmaceutically acceptable carrier or diluent. The compositions may be prepared by known procedures using well-known and readily available ingredients.

Pharmaceutical compositions may be formulated for administration to a subject by, for example, oral (including, for example, buccal or sublingual), topical, parenteral, rectal or vaginal routes, or by inhalation or spray. The term "parenteral" as used herein includes subcutaneous injection, and intradermal, intra-articular, intravenous, intramuscular, intravascular, intrasternal, intrathecal injection or infusion. The pharmaceutical composition will typically be formulated in a format suitable for administration to the subject, for example, as a syrup, elixir, tablet, troche, lozenge, hard or soft capsule, pill, suppository, oily or aqueous suspension, dispersible powder or granule, emulsion, injectable or solution. Pharmaceutical compositions may be provided as unit dosage formulations.

In certain embodiments, the pharmaceutical compositions comprising the ADCs are formulated for parenteral administration in a unit dosage injectable form, for example as lyophilized formulations or aqueous solutions.

Pharmaceutically acceptable carriers are generally non-toxic to recipients at the dosages and concentrations employed. Examples of such carriers include, but are not limited to, buffers such as phosphate, citrate, and other organic acids; antioxidants such as ascorbic acid and methionine; preservatives such as octadecyldimethylbenzyl ammonium chloride, hexamethonium chloride, benzalkonium chloride, benzethonium chloride, phenol, butyl alcohol, benzyl alcohol, alkyl parabens (such as methyl or propyl paraben), catechol, resorcinol, cyclohexanol, 3-pentanol and m-cresol; low molecular weight (less than about 10 residues) polypeptides; proteins such as serum albumin or gelatin; hydrophilic polymers such as polyvinylpyrrolidone; amino acids such as glycine, glutamine, asparagine, histidine, arginine or lysine; monosaccharides, disaccharides, and other carbohydrates such as glucose, mannose or dextrins; chelating agents such as EDTA; sugars such as sucrose, mannitol, trehalose or sorbitol; salt-forming counter-ions such as sodium; metal complexes such as Zn-protein complexes, and non-ionic surfactants such as polyethylene glycol (PEG).

In certain embodiments, the compositions comprising the ADCs may be in the form of a sterile injectable aqueous or oleaginous solution or suspension. Such suspensions may be formulated using suitable dispersing or wetting agents and/or suspending agent that are known in the art. The sterile injectable solution or suspension may comprise the ADC in a non-toxic parentally acceptable diluent or carrier. Acceptable diluents and carriers that may be employed include, for example, 1,3-butanediol, water, Ringer's solution or isotonic sodium chloride solution. In addition, sterile, fixed oils may be employed as a carrier. For this purpose, various bland fixed oils may be employed, including synthetic mono- or diglycerides. In addition, fatty acids such as oleic acid find use in the preparation of injectables. Adjuvants such as local anesthetics, preservatives, and/or buffering agents may also be included in the injectable solution or suspension.

In certain embodiments, the composition comprising the ADC may be formulated for intravenous administration to humans. Typically, compositions for intravenous administration are solutions in sterile isotonic aqueous buffer. Where necessary, the composition may also include a solubilizing agent and/or a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, PA (2000).

Methods of Use

The ADCs described herein may be used in methods of inhibiting the growth of HER2-expressing tumour cells. The cells may be in vitro or in vivo. In certain embodiments, the ADCs may be used in methods of treating a HER2-expressing cancer or tumour in a subject.

Treatment of a HER2-expressing cancer may result in one or more of alleviation of symptoms, shrinking the size of the tumour, inhibiting growth of the tumour, diminishing one or more direct or indirect pathological consequences of the disease, preventing metastasis, decreasing the rate of disease progression, amelioration or palliation of the disease state, improving survival, increasing progression-free survival, remission and/or improving prognosis.

In certain embodiments, treatment of a HER2-expressing cancer with an ADC as described herein slows the progression of the disease. In some embodiments, treatment of a HER2-expressing cancer with an ADC as described herein results in tumour regression. In some embodiments, treatment of a HER2-expressing cancer with an ADC as described herein results in inhibition of tumour growth.

HER2-expressing cancers are typically solid tumours. Examples of HER2-expressing solid tumours include, but are not limited to, breast cancer, ovarian cancer, lung cancer, gastric cancer, esophageal cancer, colorectal cancer, urothelial cancer, pancreatic cancer, salivary gland cancer and brain cancer. HER2-expressing breast cancer include estrogen receptor negative (ER−) and/or progesterone receptor negative (PR−) breast cancers and triple negative (ER−, PR−, low HER2) breast cancers. HER2-expressing lung cancers include non-small cell lung cancer (NSCLC) and small cell lung cancer.

In certain embodiments, the ADCs described herein may be used in the treatment of HER2-expressing breast cancer, ovarian cancer, lung cancer or gastric cancer. In some embodiments, the ADCs described herein may be used in the treatment of HER2-expressing breast cancer. In some embodiments, the ADCs described herein may be used in the treatment of HER2-expressing breast cancer that is also estrogen receptor and progesterone receptor negative. In some embodiments, the ADCs described herein may be used in the treatment of HER2-expressing triple negative breast cancer (TNBC). In some embodiments, the ADCs described herein may be used in the treatment of HER2-expressing breast cancer that has metastasized to the brain. In some embodiments, the ADCs described herein may be used in the treatment of HER2-expressing ovarian cancer.

As is known in the art, HER2-expressing cancers may be characterized by the level of HER2 they express (i.e. by "HER2 status"). HER2 status can be assessed, for example, by immunohistochemistry (IHC), fluorescent in situ hybridization (FISH) and chromogenic in situ hybridization (CISH).

IHC identifies HER2 protein expression on the cell membrane. Paraffin-embedded tissue sections from a tumour biopsy may be subjected to the IHC assay and accorded a HER2 staining intensity criteria as follows:

Score 0: no staining observed or membrane staining is observed in less than 10% of tumour cells; typically <20,000 receptors/cell.

Score 1+: a faint/barely perceptible membrane staining is detected in more than 10% of the tumour cells. The cells are only stained in part of their membrane. Typically about 100,000 receptors/cell.

Score 2+: a weak to moderate complete membrane staining is observed in more than 10% of the tumour cells; typically about 500,000 receptors/cell.

Score 3+: a moderate to strong complete membrane staining is observed in more than 10% of the tumour cells; typically about 2,000,000 receptors/cell.

Tumours with 0 or 1+ scores for HER2 expression are characterized as HER2 negative, whereas those tumours with 2+ or 3+ scores are characterized as HER2 positive.

Examples of FDA-approved commercial kits available for HER2 detection using IHC include HercepTest™ (Dako Denmark A/S); PATHWAY (Ventana Medical Systems, Inc.); InSite™HER2/NEU kit (Biogenex Laboratories, Inc.) and Bond Oracle HER2 IHC System (Leica Biosystems.

ADCs as described herein may be useful in the treatment of cancers that express HER2 at various levels. In certain embodiments, the ADCs may be used in the treatment of cancers that express high levels of HER2 (IHC 3+). In some embodiments, the ADCs may be used in the treatment of cancers that express high levels of HER2 (3+ IHC) or moderate levels of HER2 (2+ IHC or 2+/3+ IHC). In some embodiments, the ADCs may be used in the treatment of cancers that express high levels of HER2 (3+ IHC), moderate levels of HER2 (2+ IHC or 2+/3+ IHC), or low levels of HER2 (1+ IHC or 1+/2+ IHC). In some embodiments, the ADCs described herein may be used in the treatment of cancers that are scored as HER2 negative by IHC.

In certain embodiments, HER2 levels of the cancer to be treated with the ADCs are determined by IHC. In some embodiments, HER2 levels of the cancer to be treated with the ADCs are determined by IHC performed using the Herceptest™ assay.

HER2-expressing cancers may be homogeneous in nature (i.e. the majority of tumour cells express a similar amount of HER2) or they may be heterogeneous in nature (i.e. comprise different tumour cell populations expressing different levels of HER2). It is contemplated that the ADCs may be used to treat HER2-expressing cancers that are either homogeneous or heterogeneous with respect to HER2 levels.

In certain embodiments, the ADCs find use in methods for treating a subject having a HER2-expressing cancer that is resistant or becoming resistant to other standard-of-care therapies. In some embodiments, the ADCs find use in methods for treating a subject having a HER2-expressing cancer who is unresponsive to one or more current therapies, such as trastuzumab (Herceptin®), pertuzumab (Perjeta®), T-DM1 (Kadcyla® or trastuzumab emtansine) or taxanes (such as such as paclitaxel, docetaxel, cabazitaxel, and the like). In some embodiments, the ADCs find use in methods for treating a subject having a HER2-expressing cancer that is resistant to trastuzumab. In some embodiments, the ADCs find use in methods for treating a subject having a HER2-expressing cancer that is resistant to pertuzumab. In some embodiments, the ADCs find use in methods for treating a subject having a HER2-expressing cancer that is resistant to T-DM1. In some embodiments, the ADCs find use in the treatment of metastatic cancer when the patient has progressed on previous anti-HER2 therapy.

When the ADCs are used in the treatment of subjects having a HER2-expressing cancer that is resistant to, refractory to and/or relapsed from treatment with another therapeutic agent, the ADCs may be part of a second-line therapy, or a third- or fourth-line therapy, depending on the number of prior treatments undergone by the subject.

In certain embodiments, the ADCs described herein may be used in conjunction with an additional anti-tumour agent in the treatment of subjects having a HER2-expressing cancer. The additional anti-tumour agent may be a therapeutic antibody such as those noted above, or a chemotherapeutic agent. Chemotherapeutic agents commonly used for the treatment of HER2-expressing cancers include, for example, cisplatin, carboplatin, paclitaxel, albumin-bound paclitaxel Abraxane®), docetaxel, gemcitabine, vinorelbine, irinotecan, etoposide, vinblastine, pemetrexed, 5-fluorouracil (with or without folinic acid), capecitabine, carboplatin, epirubicin, oxaliplatin, folfirinox, cyclophosphamide, and various combinations of these agents as is known in the art. The additional agent(s) may be administered to the subject concurrently with the ADCs or sequentially.

In certain embodiments, it is contemplated that the ADCs described herein may be used to treat a subject having a HER2-expressing cancer who has not undergone any prior anti-cancer treatments (i.e. the ADCs may be used as a first line therapy).

In certain embodiments, the subject being treated with the ADC in the above methods may be a human, a non-human primate or other mammal. In some embodiments, the subject being treated with the ADC in the above methods is a human subject.

The amount of the ADC to be administered to a subject will vary in the light of the relevant circumstances, including the condition to be treated, the chosen route of administration, the actual compound administered, the age, weight, and response of the individual subject and the severity of the subject's symptoms, but is a therapeutically effective amount.

The term "therapeutically effective amount" as used herein refers to the amount of ADC required to be administered in order to accomplish the goal of the recited method, for example, amelioration of one or more of the symptoms of the disease being treated. The amount of the ADC described herein that will be effective in the treatment of a HER2-expressing cancer can be determined by standard clinical techniques. In addition, in vitro assays may optionally be employed to help identify optimal dosage ranges. Effective doses are extrapolated from dose-response curves derived from in vitro or animal model test systems.

Pharmaceutical Kits

Certain embodiments provide for pharmaceutical kits comprising an ADC as described herein.

The kit typically will comprise a container and a label and/or package insert on or associated with the container. The label or package insert contains instructions customarily included in commercial packages of therapeutic products, providing information about the indications, usage, dosage, administration, contraindications and/or warnings concerning the use of such therapeutic products. The label or package insert may further include a notice in the form prescribed by a governmental agency regulating the manufacture, use or sale of pharmaceuticals or biological products, which notice reflects approval by the agency of manufacture, for use or sale for human or animal administration. The label or package insert also indicates that the ADC is for use to treat a HER2-expressing cancer. The container holds a composition comprising the ADC and may in some embodiments have a sterile access port (for example, the container may be an intravenous solution bag or a vial having a stopper that may be pierced by a hypodermic injection needle).

In addition to the container containing the composition comprising the ADC, the kit may comprise one or more additional containers comprising other components of the kit. For example, a pharmaceutically-acceptable buffer, such as bacteriostatic water for injection (BWFI), phosphate-buffered saline, Ringer's solution or dextrose solution; other buffers or diluents.

Suitable containers include, for example, bottles, vials, syringes, intravenous solution bags, and the like. The containers may be formed from a variety of materials such as glass or plastic. If appropriate, one or more components of the kit may be lyophilized or provided in a dry form, such as a powder or granules, and the kit can additionally contain a suitable solvent for reconstitution of the lyophilized or dried component(s).

The kit may further include other materials desirable from a commercial or user standpoint, such as filters, needles, and syringes.

The following Examples are provided for illustrative purposes and are not intended to limit the scope of the invention in any way.

EXAMPLES

Example 1: Synthesis of Linker-Toxin

The following example describes the preparation of an exemplary linker-toxin (Linker-Toxin 001) that comprises the following auristatin analogue (Compound 9):

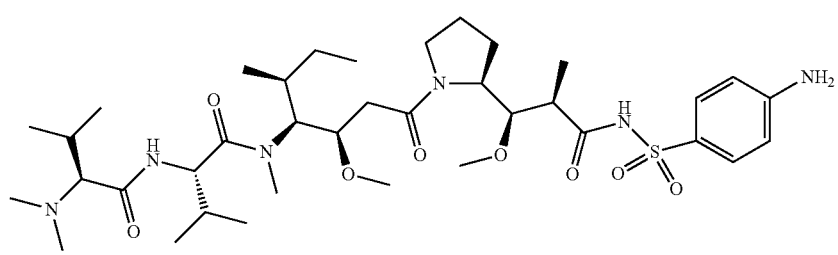

Similar protocols may be employed to prepare linker-toxins comprising other auristatin analogues including the following exemplary compounds (see also International Patent Application Publication No. WO 2016/041082):
16
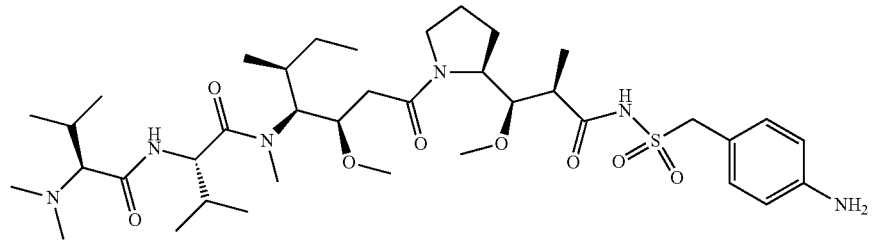
17
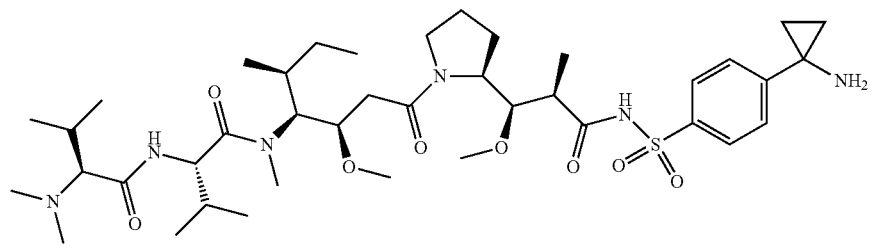
18
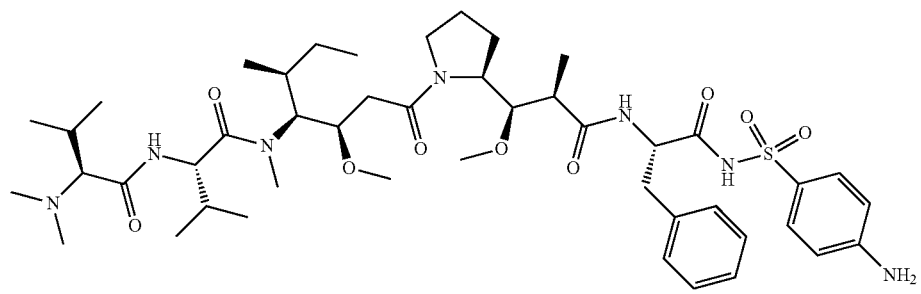
19
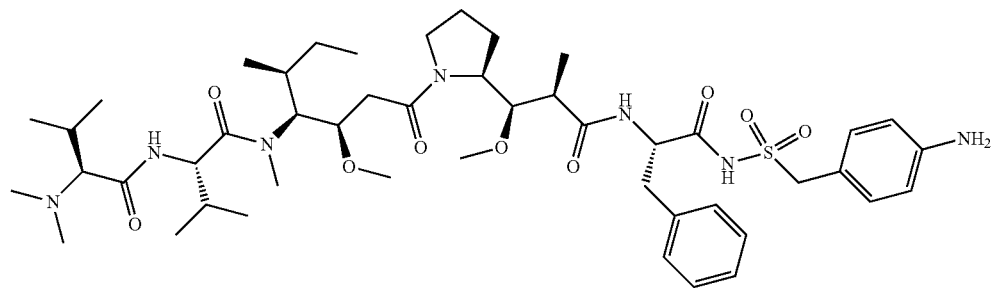
20
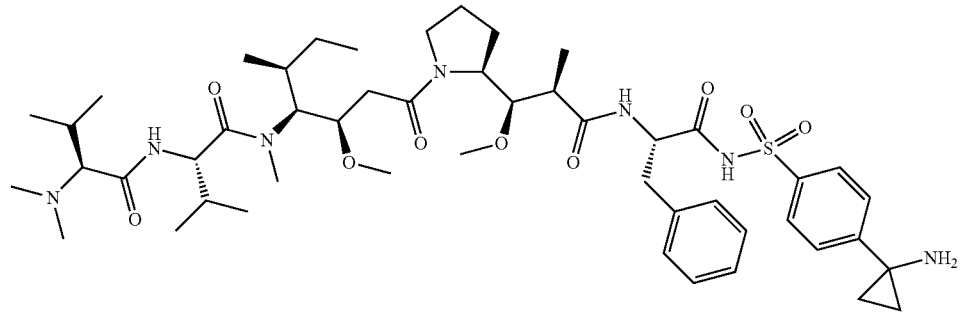

1.1 Ethyl (2R,3R)-3-methoxy-2-methyl-3-((S)-pyrrolidin-2-yl)propanoate (Compound 1)

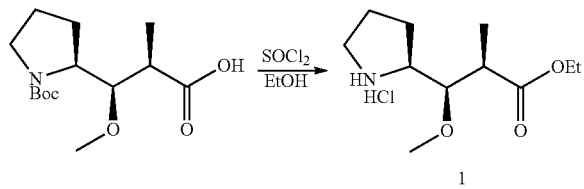

To a stirred solution of (2R,3R)-3-((S)-1-(tert-butoxycarbonyl)pyrrolidin-2-yl)-3-methoxy-2-methylpropanoic acid (Boc-Dap-OH, 4.31 g, 15.0 mmol) in absolute ethanol (27.0 mL) at 0° C. was added thionyl chloride (3.0 mL) in a dropwise fashion. The resulting solution was allowed to warm to room temperature and progress was monitored by HPLC-MS. After 18 h, no remaining starting material was detected and the solution was concentrated to dryness under reduced pressure. The resulting oil was suspended in toluene (10 mL) and concentrated under reduced pressure two times, then suspended in diethyl ether (5 mL) and concentrated under reduced pressure two times to afford a white solid foam (3.78 g, quant yield %). MS m/z obs.=216.5 (M+1).

1.2 (3R,4S,5S)-4-((S)-2-(((benzyloxy)carbonyl)amino)-N,3-dimethylbutanamido)-3-methoxy-5-methylheptanoic Acid (Compound 3)

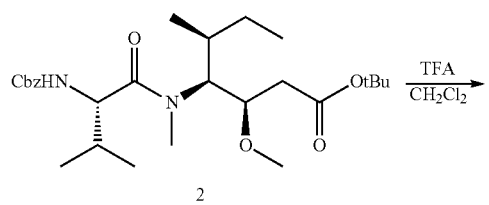

Compound 2 was prepared as described in International Patent Application Publication No. WO 2016/041082.

To a stirred solution of Compound 2 (6.965 g, 14.14 mmol) in dichloromethane (20 mL) was added trifluoroacetic acid (5.0 mL). The reaction was monitored for completion by HPLC-MS and after 40 h no starting material remained. The reaction was concentrated under reduced pressure, co-evaporated with toluene (2×10 mL) and dichloromethane (2×10 mL) to obtain a foamy white solid (6.2 g, quant yield with residual TFA). This material was dissolved in 200 mL of hot 1:3 EtOAc:hexanes and allowed to cool to room temperature. During cooling, a precipitate formed as well as some small crystals. 5 mL EtOAc was added and the suspension was heated once again to fully dissolve the precipitate. More crystals formed on cooling to room temperature and the flask was placed at −30° C. overnight. The following morning the mother liquor was decanted and the crystals rinsed with 2×50 mL hexanes and dried under high vacuum. Recovered 5.67 g of crystalline product. MS m/z obs.=405.7 (M+1).

1.3 Ethyl (2R,3R)-3-((S)-1-((3R,4S,5S)-4-((S)-2-(((benzyloxy)carbonyl)amino)-N,3-dimethylbutanamido)-3-methoxy-5-methylheptanoyl)pyrrolidin-2-yl)-3-methoxy-2-methylpropanoate (Compound 4)

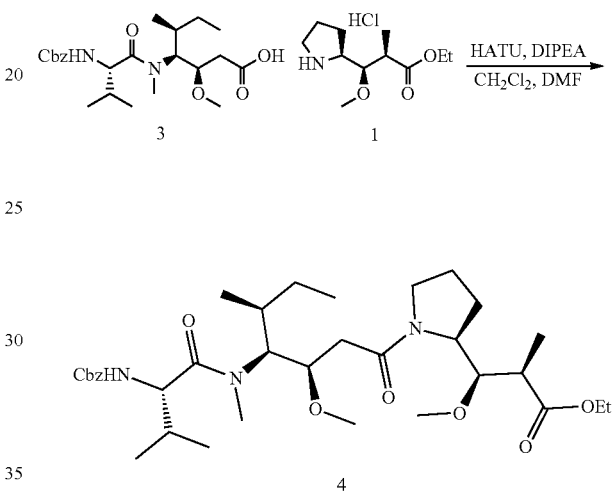

To a stirred solution of Compound 3 (6.711 g, 15.37 mmol, 1.025 equiv) in a mixture of dichloromethane (5.0 mL) and N,N-dimethylformamide (5.0 mL) at room temperature was added HATU (5.732 g, 15.07 mmol, 1.005 equiv) and N,N-diisopropylethylamine (7.84 mL, 3 equiv). After stirring for 30 minutes at room temperature, a solution of Compound 1 (3.776 g, 15.00 mmol, 1.0 equiv) in a mixture of dichloromethane (1.0 mL) and N,N-dimethylformamide (1.0 mL) was added dropwise, rinsed in residual Compound 1 with an additional 3 mL of 1:1 dichloromethane:N,N-dimethylformamide. The reaction was monitored by HPLC-MS and no remaining Compound 1 was observed after 15 minutes. The reaction was concentrated under reduced pressure, diluted with ethyl acetate (~125 mL) and the organic phase was extracted with 1 M HCl (2×50 mL), 1×dH$_2$O (1×50 mL), saturated NaHCO$_3$(3×50 mL), brine (25 mL). Acidic and basic aqueous layers were both washed with 25 mL EtOAc. All organics were then pooled and dried over MgSO$_4$, filtered and concentrated to give a red oil. The residue was dissolved in a minimal amount of dichloromethane (~10 mL), loaded on to a Biotage® SNAP Ultra 360 g silica gel column (Isolera™ Flash System; Biotage AB, Sweden) for purification (20-100% EtOAc in hexanes over 10 column volumes). Fractions containing pure product were pooled to recover 7.9 g of foamy white solid. Impure fractions were subjected to a second purification on a Biotage® SNAP Ultra 100 g silica gel column and pooled with pure product to recover a white foam solid (8.390 g, 88.3%). MS m/z obs.=634.7 (M+1).

1.4 (2R,3R)-3-((S)-1-((3R,4S,5S)-4-((S)-2-(((benzyloxy)carbonyl)amino)-N,3-dimethyl butanamido)-3-methoxy-5-methylheptanoyl)pyrrolidin-2-yl)-3-methoxy-2-methylpropanoic Acid (Compound 5)

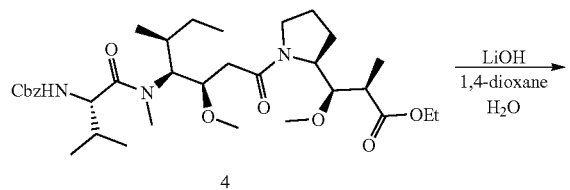

$MgSO_4$, filtered and concentrated under reduced pressure to yield a light coloured oil. The oil was re-dissolved in diethyl ether (~50 mL) and concentrated under reduced pressure (3×) to facilitate the removal of residual dioxane, affording the title product as a stiff oil (7.81 g 97% yield with some residual dioxane and Compound 4). MS m/z obs.=606.7 (M+1).

1.5 Benzyl ((S)-1-(((3R,4S,5S)-3-methoxy-14(S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl)carbamate (Compound 7)

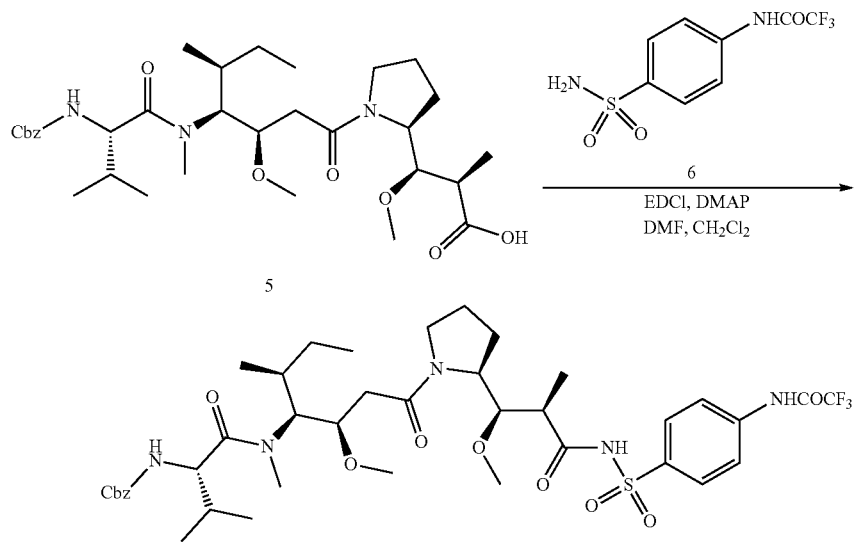

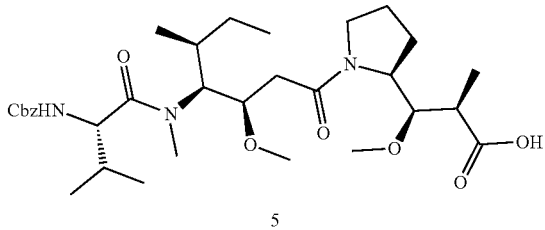

To a stirred solution of Compound 4 (8.390 g, 13.24 mmol) in 1,4-dioxane (158 mL) was added $dH_2O$ (39.7 ml) and lithium hydroxide monohydrate (1 M in $H_2O$, 39.7 mL, 3 equiv). The reaction was stirred at 4° C. and monitored by HPLC-MS for consumption of starting material, which took 3 days until only trace Compound 4 remained. During the course of the reaction, a new product, corresponding to loss of methanol (β-elimination, <2%) formed in small percentages in addition to the desired material. The reaction was acidified with the addition of 1 M aqueous HCl (50 mL) and concentrated under reduced pressure to remove the dioxane. The remaining reaction mixture was extracted with ethyl acetate (4×50 mL) and the organic phase was pooled, washed with brine (15 mL+2 mL 2 M HCl), dried over Compound 6 was prepared as described in International Patent Application Publication No. WO 2016/041082).

To a stirred solution of Compound 5 (7.12 g, 11.754 mmol) in dichloromethane (20 mL) was added 2,2,2-trifluoro-N-(4-sulfamoylphenyl)acetamide (Compound 6, 4.095 g, 1.3 equiv, dissolved in 3 mL DMF), N,N-dimethylpyridine (1.867 g, 1.3 equiv) and N,N-dimethylformamide (1.5 mL) to generate a light yellow suspension. Further addition of 5 mL of DMF did not clarify solution. N-(3-Dimethylaminopropyl)-N'-ethylcarbodiimide hydrochloride (EDCI) (2.817 g, 1.25 equiv) was added in a single portion and the reaction was monitored by HPLC-MS. After 48 hr, reaction was no longer progressing and an additional 400 mg of EDCI was added. After 18 hr, no remaining starting material was observed and the reaction was concentrated under reduced pressure to give a yellow oil. The oil was dissolved in ethyl acetate (~150 mL) and 1 M HCl (20 mL), and the organic phase was washed with cold 2 M HCl (2×10 mL), saturated $NaHCO_3$ (1×10 mL), brine (20 mL+5 mL 2 M HCl). Acidic and basic aqueous fractions were extracted with EtOAc (1×20 mL), all organic fractions were pooled, dried over $MgSO_4$ and concentrated under reduced pressure to yield an oily crude solid (13 g). The residue was dissolved in dichloromethane (~10 mL), loaded on to a Biotage® SNAP Ultra 360 g silica gel column and purified under a 10-100% EtOAc (2% AcOH) in hexanes gradient over 12 column volumes with a 3-column volume plateau at 50% EtOAc. Fractions containing the pure product were pooled, concentrated under reduced pressure, dissolved and concentrated from toluene (2×10 mL) and diethyl ether (2×10 mL) to afford the desired product, 7.1 g of white foam solid. Impure fractions were subjected to repeat purification under shallower gradient conditions using a Biotage® SNAP Ultra 100 g silica gel column on an Isolera™ instrument. All pure fractions were pooled to recover pure product as a white foam solid (8.60 g, 86%). MS m/z obs.=856.7 (M+1).

1.6 (S)-2-amino-N-((3R,4S,5S)-3-methoxy-14(S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)-N,3-dimethylbutanamide (Compound 7a)

single portion, the 3-way adapter was fitted to the flask, a hydrogen balloon was fitted to the adapter and the vessel twice evacuated under reduced pressure and charged with hydrogen. The reaction was allowed to stir for 2 days, over which time the hydrogen balloon was occasionally recharged. After approximately 48 h, HPLC-MS analysis indicated that no starting material remained. The reaction was diluted with methanol (20 mL) and filtered through a plug of celite. The celite was washed with methanol (2×50 mL). All filtrates were pooled and concentrated under reduced pressure and the resulting oil dissolved and concentrated from dichloromethane. After drying under reduced pressure, the title compound was isolated as a colourless powder (3.10 g, 99%). MS m/z obs.=722.6 (M+1).

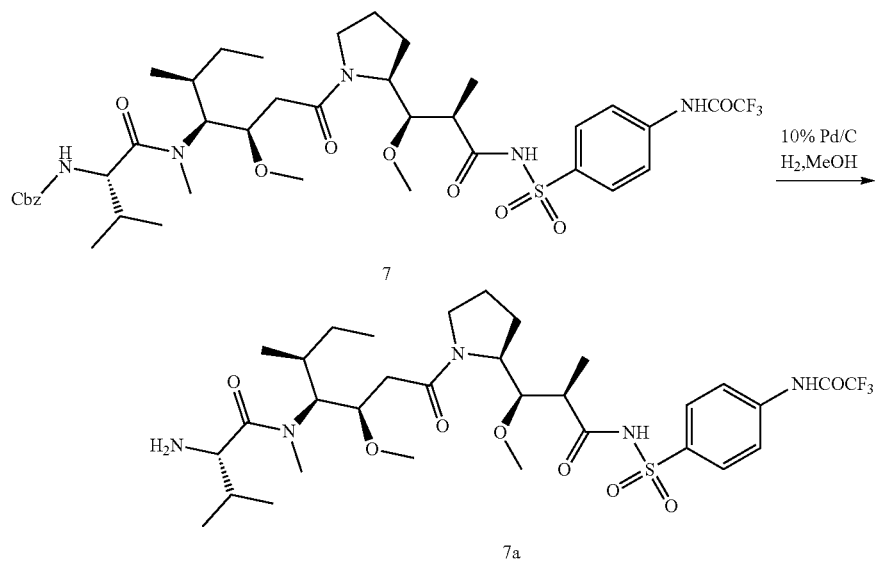

Compound 7 (3.71 g, 4.33 mmol) was dissolved in 10% N,N-dimethylformamide in ethyl acetate (30 mL) in a round bottom flask containing a magnetic stirrer and fitted with a 3-way gas line adapter. The vessel was twice evacuated under reduced pressure and charged with nitrogen gas. 10% palladium on carbon (0.461 g, 0.1 equiv) was added in a 1.7 (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((4-(2,2,2-trifluoroacetamido)phenyl)sulfonamido) propyl)pyrrolidin-1-yl)-5-methyl-1-oxoheptan-4-yl)-N,3-dimethylbutanamide (Compound 8)

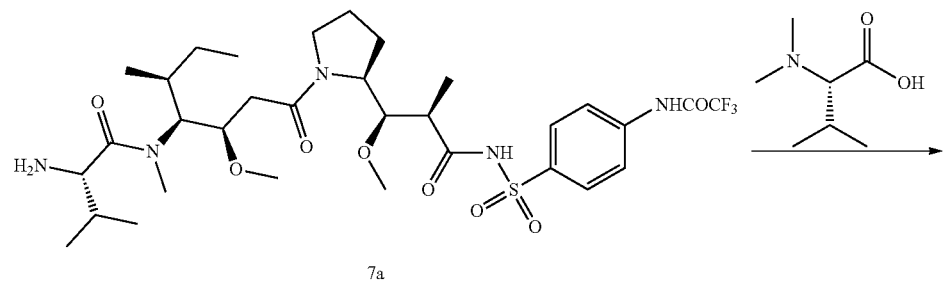

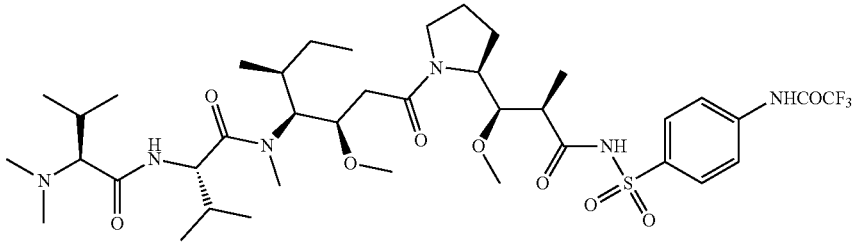

8

To a stirred solution of N,N-(L)-dimethylvaline (1.696 g, 9.35 mmol) in N,N-dimethylformamide (10 mL) was added HATU (3.216 g, 8.46 mmol) and di-isopropylethylamine (3.10 mL, 17.8 mmol). A clear yellow solution resulted after 5 minutes. Stirring was continued for an additional 10 minutes, then Compound 7a (3.213 g, 4.45 mmol) was added in a single portion. After an additional 1 h of stirring, HPLC-MS indicated that trace amounts of Compound 7a remained and the reaction was for 16 h. The reaction was then concentrated under reduced pressure, diluted with ethyl acetate (120 mL) and 40 mL 1:1 NaHCO₃(sat.): 5% LiCl and transferred to a separating funnel. The aqueous layer was removed and the organic phase was washed with LiCl (1×20 mL), NaHCO₃(sat., 2×20 mL). Aqueous layers were pooled and extracted with EtOAc (3×50 mL). Organic layers were pooled and washed with brine (1×20 mL), dried over sodium sulfate, filtered and concentrated to give a DMF-laden oil which was concentrated via rotary evaporator to remove residual DMF, yielding 7 g of crude straw coloured oil. The oil was dissolved in a minimal amount of 10% methanol in dichloromethane (~11 mL) and loaded onto a Biotage® SNAP Ultra 360 g silica gel column for purification (2-20% MeOH in CH₂Cl₂ over 15 column volumes, product eluting around 10-13%). The fractions containing the desired product were pooled and concentrated under reduced pressure to afford the title compound as a colourless foam. Impure fractions were combined, evaporated and subjected to repeat purification on a Biotage® SNAP Ultra 100 g silica gel column on an Isolera™ instrument and combined with the pure product from the first column to yield a colourless foam solid (3.78 g). MS m/z obs.=850.6 (M+1).

1.8 (S)—N-((3R,4S,5R)-1-((S)-2-((1R,2R)-3-((4-aminophenyl)sulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 9)

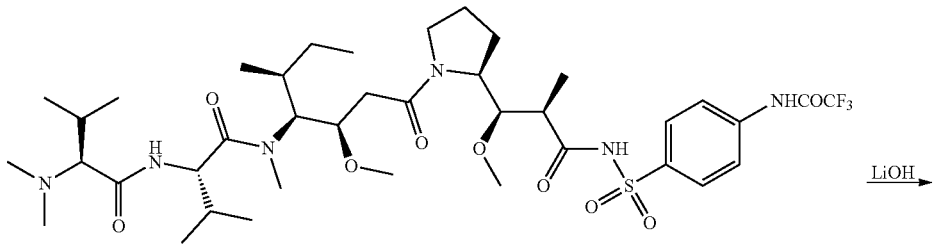

8

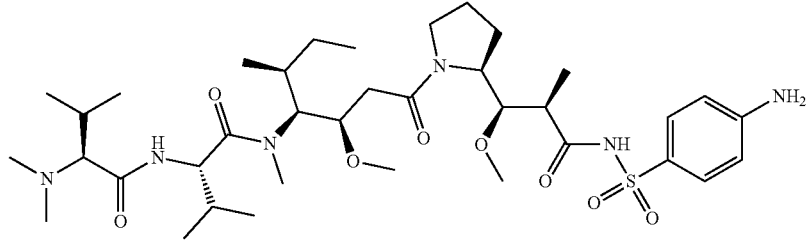

9

To a stirred solution of Compound 8 (0.980 g, 1.154 mmol) in 1,4-dioxanes (15 mL) was added water (3.5 mL) and 1 M lithium hydroxide monohydrate (3 equiv., 3.46 mL). The resulting light suspension was allowed to stir at 4° C. and was monitored by HPLC-MS for consumption of the starting material. When the conversion was complete (~5 days), the reaction was neutralized with 3.46 mL of 1 M HCl and concentrated under reduced pressure to remove dioxane. The resulting aqueous phase was diluted with 60 mL EtOAc and 5 mL brine, then extracted with ethyl acetate (2×30 mL). The organic fractions were pooled, dried over Na₂SO₄, filtered and evaporated to yield the title compound as a tan solid (0.930 g). $R_f$=0.5 (8% MeOH in CH₂Cl₂). MS m/z obs.=753.7 (M+1).

1.9 2,3,5,6-tetrafluorophenyl 3-(2-(2-(2-(2,5-dioxo-2,5-dihydro-1H-pyrrol-1-yl)ethoxy)ethoxy)ethoxy)propanoate (Compound 15)

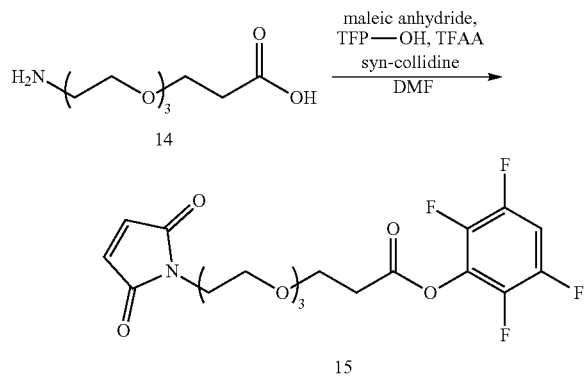

In a dried 50 mL conical flask, 3-(2-(2-(2-aminoethoxy)ethoxy)ethoxy)propanoic acid (Compound 14, 1.000 g, 4.52 mmol) and maleic anhydride (0.443 g, 4.52 mmol) were dissolved in anhydrous N,N-dimethylformamide (5 mL). The reaction was stirred at room temperature for 6 hr under N2, at which point it was cooled to 0° C. and syn-collidine (1.263 mL, 2.1 eq) was added dropwise. In a separate dried 50 mL conical flask, tetrafluorophenol (3.002 g, 4 eq) was dissolved in anhydrous N,N-dimethylformamide (10 mL). The flask was cooled to 0° C. in an ice bath and trifluoroacetic anhydride (2.548 mL, 4 eq) was added dropwise. This flask was stirred for 15 minutes, at which point syn-collidine (2.407 mL, 4 eq) was added dropwise. The flask was allowed to stir for another 15 minutes, and then the contents were added to the first flask dropwise, via syringe. The reaction was allowed to warm to room temperature and stirring was continued under N2. The reaction was monitored by HPLC-MS for the consumption of starting materials. After 6 days, the reaction was complete with the total consumption of Compound 14, leaving only Compound 15 and a small amount (~5%) of the bis-TFP maleic amide intermediate. The reaction was transferred to a separating funnel, diluted with diethyl ether (75 ml) and washed with 5% LiCl (1×20 mL), 1 M HCl (2×20 mL), sat. NaHCO$_3$ (5×20 mL) and brine (1×20 mL). The organic layer was dried over Na$_2$SO$_4$, filtered and evaporated to give brown crude oil with residual DMF. Crude oil was dissolved in 8 mL of 1:1 DMF:H$_2$O+ 0.1% TFA, loaded onto a 60 g Biotage® SNAP Ultra C18 column (Biotage AB, Uppsala, Sweden) and purified under a linear 30-100% gradient of ACN/H$_2$O+0.1% TFA over 8 column volumes. Pure fractions were pooled and diluted with brine (20 mL), then extracted 3×50 mL Et$_2$O. Pooled organics were dried over MgSO$_4$, filtered and evaporated to recover a light-yellow oil (1.34 g, 66% yield).

1.10 Tert-butyl ((S)-1-(((S)-1-((4-(N-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)amino)-1-oxo-5-ureidopentan-2-yl)amino)-3-methyl-1-oxobutan-2-yl)carbamate (Compound 12)

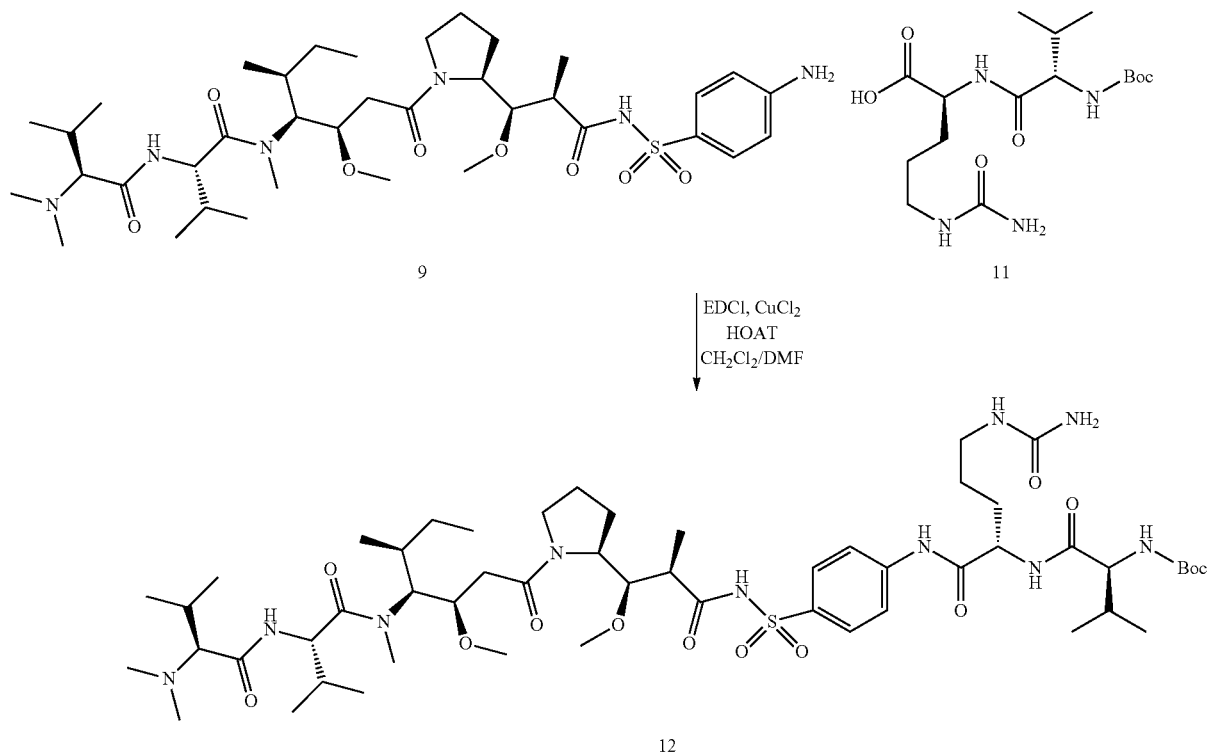

Compound 11 was prepared as described in International Patent Application Publication No. WO 2016/041082.

To an empty 25 mL pear shaped flask, was added Compound 11 (1.342 g, 3.58 mmol, 3.0 equiv), 1-ethyl-3-(3-dimethylaminopropyl)carbodiimide hydrochloride (0.664 g, 3.46 mmol, 2.9 equiv) and 7-hydroxy-azabenzotriazole (HOAT) (0.472 g, 3.46 mmol, 2.9 equiv). These solids were dissolved in a mixture of N,N-dimethylformamide (0.5 mL) and dichloromethane (4.5 mL) with stirring at room temperature over 30 minutes. Separately, Compound 9 (0.900 g, 1.20 mmol) was dissolved in a mixture of N,N-dimethylformamide (0.2 mL) and dichloromethane (1.8 mL) and added to the pear shaped flask, rinsing with dichloromethane (1.0 mL). Stirring rate was increased to 1000 rpm, producing a vortex. Within 2 minutes of adding Compound 9, copper (II) chloride (0.514 g, 3.83 mmol, 3.2 equiv) was added in one portion directly into the center of the vortex through a narrow powder funnel. The initially light-yellow solution turned to a dark-brown suspension which changed over 10 minutes to a dark-green suspension. The reaction was monitored for completion by HPLC-MS and no change to reaction progress was observed between the samples taken at 30 minutes and 1 h (~95% complete). The reaction was allowed to stir overnight at room temperature, then 2-(2-aminoethylamino)ethanol (0.483 mL, 4.781 mmol, 4 equiv), EtOAc (10 mL) and dH$_2$O (5 mL) were added to the stirred suspension, which underwent a colour change to deep blue. The suspension was stirred vigorously for 4 hr as the suspended solids gradually dissolved into the biphasic mixture. This mixture was transferred to a separating funnel and diluted with EtOAc (100 mL) and brine (10 mL), and the aqueous layer was extracted 10% IpOH/EtOAc (4×50 mL). The organic layers were pooled and washed with brine (10 mL), dried over Na$_2$SO$_4$, and evaporated to yield a faintly blue crude solid. This crude solid was dissolved in a mixture of methanol (0.5 mL) and dichloromethane (6 mL) and purified on a Biotage® SNAP Ultra 100 g silica gel column (2-20% MeOH in CH$_2$Cl$_2$ over 10 column volumes, followed by an 8-column volume plateau at 20% MeOH). The product eluted as a broad peak after 1-2 column volumes at ~20% MeOH in CH$_2$Cl$_2$. Fractions containing the desired material were pooled and concentrated under reduced pressure to give the title compound as a white solid (1.105 g, 83%). MS m/z obs.=555.9 ((M+2)/2), 1109.8 (M+1).

1.11 (S)-2-((S)-2-amino-3-methylbutanamido)-N-(4-(N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)-5-ureidopentanamide (Compound 13)

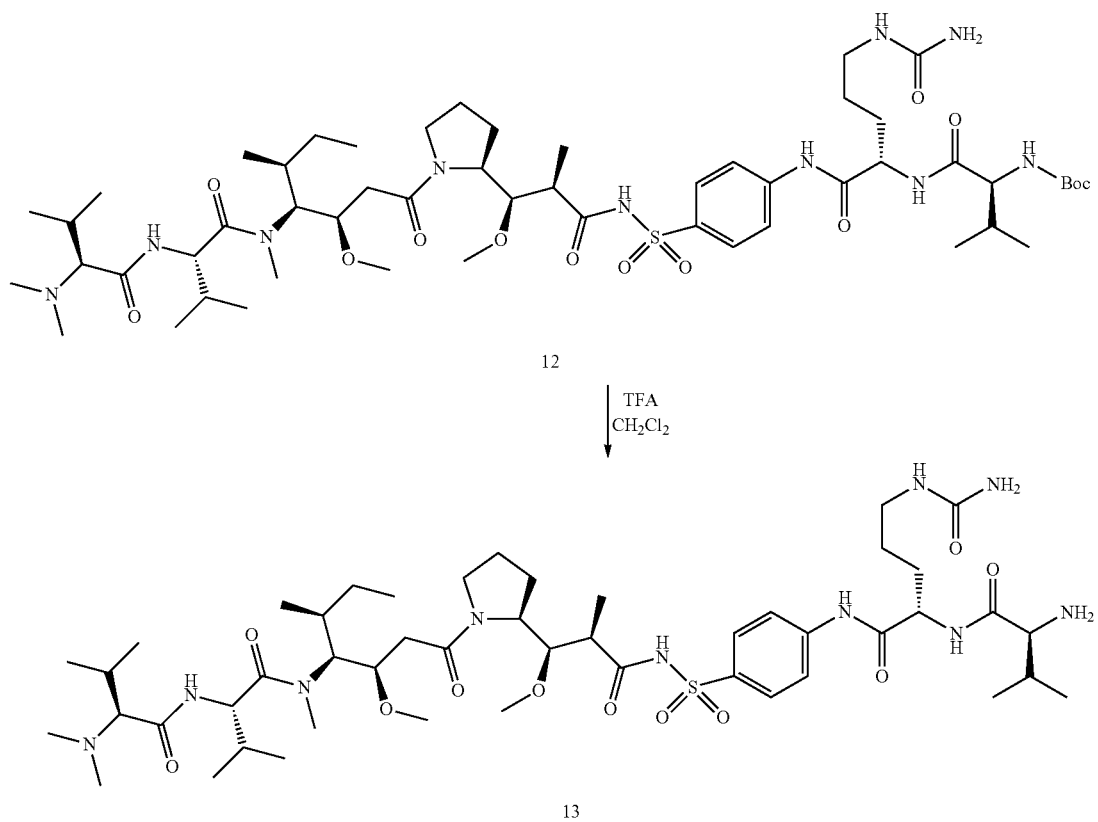

To a solution of Compound 12 (0.926 g, 0.834 mmol) was added a mixture of dichloromethane (10 mL) and trifluoroacetic acid (2.0 mL). The reaction was monitored by HPLC-MS for consumption of starting material (~45 minutes). The reaction was co-evaporated with acetonitrile (2×10 mL) and dichloromethane (2×10 mL) under reduced pressure to remove excess trifluoroacetic acid. The resulting residue was dissolved in a minimal amount of dichloromethane and methanol (3:1, v/v, ~2 mL), and added to a stirred solution of diethyl ether (200 mL) and hexanes (100 mL) dropwise via pipette, producing a suspension of light white solids. The solids were filtered and dried under vacuum to afford the title compound in the form of a white powder, as the trifluoroacetate salt (1.04 g, quantitative yield with some residual solvents). MS m/z obs.=505.8 ((M+2)/2).

1.12 (S)—N-(4-(N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide (Linker-Toxin 001)

lyophilizer. The lyophilization was repeated at higher concentration (approx. 50 mg/mL in 2:1 $H_2O$/ACN) into a vial to produce a denser, less flocculant lyophilized solid (754.2 mg, 91%). MS m/z obs.=647.4 ((M+2)/2), 1292.8 (M+1).

Example 2: Conjugation of Linker-Toxin to Biparatopic Antibody

Antibody-drug conjugates (ADCs) of the biparatopic anti-HER2 mAb, v10000, and Linker-Toxin 001 were generated by partial reduction of the antibody interchain disulfide bonds, followed by capping of the free cysteine residues by

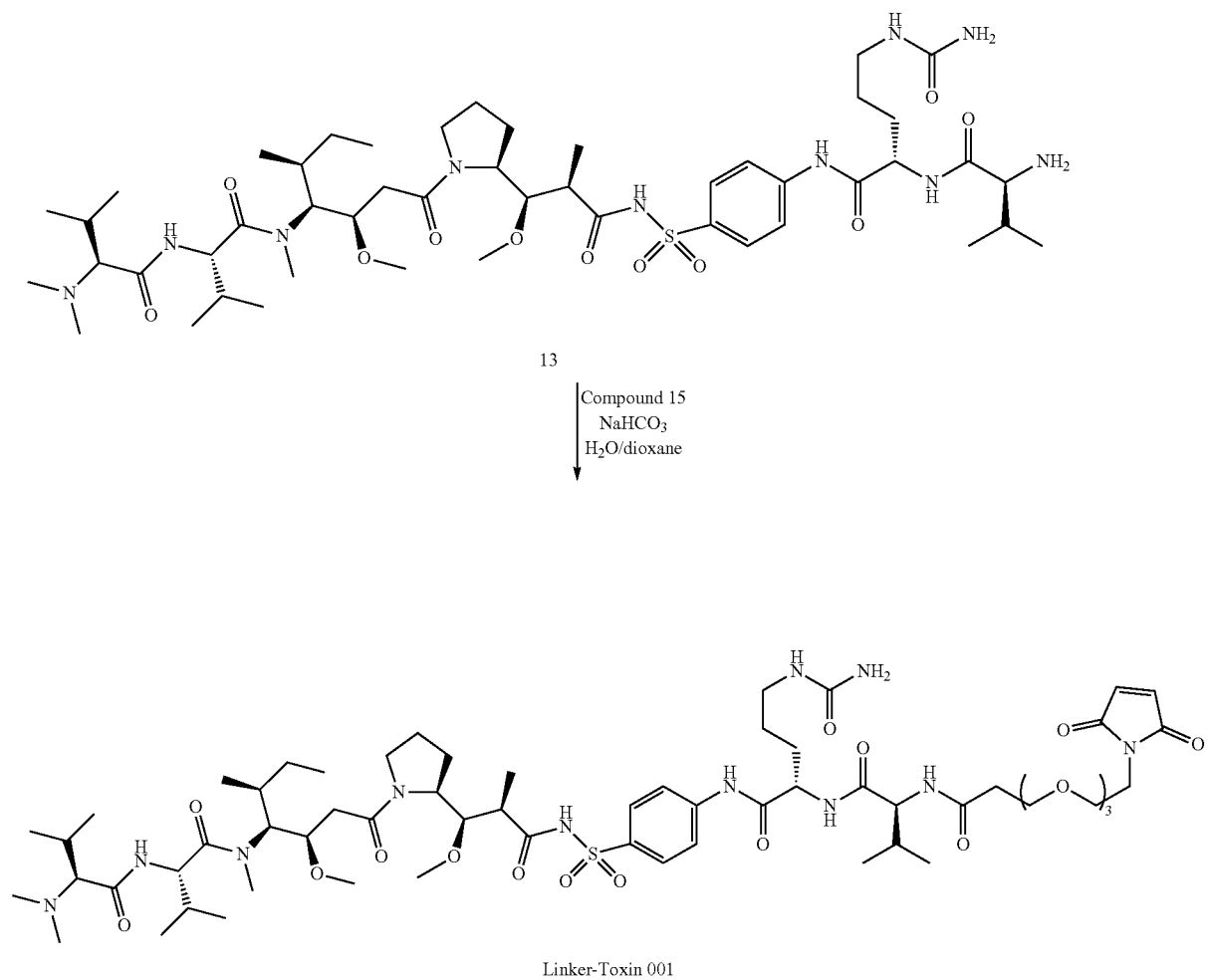

To a stirred solution of Compound 13 (0.722 g, 0.584 mmol) in N,N-dimethylformamide (4 mL) was added Compound 15 (0.314 g, 1.2 equiv) and diisopropylethylamine (0.305 mL, 3.0 equiv). HPLC-MS analysis at 2 h indicated no remaining starting material. The reaction was acidified with TFA (300 μL) and then diluted with di$H_2O$+0.1% TFA (9 mL). The resultant solution was loaded onto a 120 g Biotage® SNAP Ultra C18 column (Biotage, Uppsala, Sweden) and purified under an ACN/$H_2O$+0.1% TFA gradient: 20-60% ACN over 10 column volumes, 60-100% ACN over 5 column volumes. Product eluted near 40% ACN. Pure fractions as identified by LCMS were pooled and lyophilized. A white powder solid was recovered from the reaction with the maleimide component of the Linker-Toxin. Through variation of the amount of TCEP used to reduce the antibody, ADCs with average drug-to-antibody ratios of between 0 and 6 may be obtained. ADCs were purified to remove contaminant small molecules and characterized to demonstrate DAR, purity, monomeric content, endotoxin levels, and binding to antigen positive tumour cells.

Preparation of v10000 is described in International Patent Application Publication No. WO 2015/077891. Details of this antibody are provided in Table 9 below. Sequences are provided in the Sequence Tables.

TABLE 9

| Variant | | Chain A | Chain B |
|---|---|---|---|
| 10000 | Domain containing the epitope | ECD2 | ECD4 |
| | Format | Fab | scFv |
| | Antibody name | Pertuzumab - with Y96A in VL region*, and T30A/A49G/L69F in VH region | Trastuzumab |
| | CH3 sequence substitutions§ | T350V/L351Y/F405A/Y407V | T350V/T366L/K392L/T394W |

*Fab or variable domain numbering according to Kabat (Kabat et al., *Sequences of proteins of immunological interest*, 5th Edition, US Department of Health and Human Services, NIH Publication No. 91-3242, p.647, 1991)
§CH3 numbering according to EU index as in Kabat (Edelman et al., 1969, PNAS USA, 63: 78-85)

2.1 Conjugation of Anti-HER2 Antibody by Partial Reduction of Interchain Disulfide Bonds (v17597; DAR 3.9)

A solution (138.9 mL) of the antibody v10000 (2.0 g) in 10 mM sodium acetate, 9% (w/v) sucrose, pH 4.5 was reduced by addition of a freshly prepared mixture of 200 mM $Na_2HPO_4$, pH 8.9 (15.4 mL), 5 mM DTPA solution (39.5 mL in PBS, pH 7.4), and 10 mM TCEP solution (3.68 mL, 2.3 eq.). After 90 minutes at 37° C., the reaction was cooled on ice before addition of an excess of Linker-Toxin 001 (6.41 mL; 8 eq) from a 20 mM DMSO stock solution. The conjugation reaction was quenched after 90 minutes by addition of an excess of a 20 mM N-acetyl cysteine solution (4.81 mL; 6 eq.).

2.2 Conjugation of Anti-HER2 Antibody by Partial Reduction of Interchain Disulfide Bonds (v21252; DAR 2.1)

A solution (138.9 mL) of the antibody v10000 (2.0 g) in 10 mM sodium acetate, 9% (w/v) sucrose, pH 4.5 was pH-adjusted by addition of 200 mM $Na_2HPO_4$, pH 8.9 (15.4 mL). After addition of a DTPA solution (44 mL in PBS, pH 7.4, final concentration 1.0 mM), reduction of the interchain disulfides was initiated by addition of an aqueous 10 mM TCEP solution (1.68 mL, 1.05 eq.). After 90 minutes at 37° C., the reaction was cooled on ice before addition of an excess of Linker-Toxin 001 (4.81 mL; 6 eq) from a 20 mM DMSO stock solution. The conjugation reaction was quenched after 90 minutes by addition of an excess of a 20 mM N-acetyl cysteine solution (4.81 mL; 6 eq.).

2.3 Purification of Antibody Drug Conjugates v17597 and v21252

Quenched antibody drug conjugate (ADC) solutions were purified with 9-15 diavolumes of 10 mM sodium acetate, 9% (w/v) sucrose, pH 4.5 on a Millipore Labscale™ Tangential Flow Filtration instrument using a Pellicon® XL Ultrafiltration Module (Ultracel® 30 kDa 0.005 $m^2$; Millipore Sigma). The eluted ADC was sterile filtered (0.22 um). ADCs produced on small scale were purified over 40 KDa MWCO Zeba™ columns (ThermoFisher Scientific, Waltham, MA) preconditioned with either PBS or 10 mM sodium acetate, 9% (w/v) sucrose, pH 4.5.

Following purification, the concentration of the ADC was determined by a BCA assay with reference to a standard curve generated from v10000. Alternatively, concentrations were estimated by measurement of absorption at 280 nm ($\epsilon$=195065 $M^{-1}$ $cm^{-1}$).

Samples of the ADCs were assessed by non-reducing and reducing SDS-PAGE (see FIGS. 1A-1B). No extraneous bands were observed.

2.4 Hydrophobic Interaction Chromatography

Antibody and ADCs were analyzed by hydrophobic interaction chromatography (HIC) to estimate the drug-to-antibody ratio (DAR). Chromatography was on a Proteomix® HIC Ethyl column (7.8×50 mm, 5 μm) (Sepax Technologies Inc., Newark, DE) employing a gradient of 80% MPA/20% MPB to 35% MPA/65% MPB over a period of 13.5 minutes at a flow rate of 1 mL/min (MPA=1.5 M $(NH_4)_2SO_4$, 25 mM $Na_xPO_4$, and MPB=75% 25 mM $Na_xPO_4$, 25% isopropanol).

The average drug to antibody ratio (DAR) of an ADC can vary depending on the number of disulphide bonds liberated during the reduction of the antibody. A single conjugation reaction that yields an ADC with a particular average DAR comprises a mixture of species. For v17597 and v21252, a mixture of four species was generated: unconjugated antibody, ADC with a DAR of 2, ADC with a DAR of 4 and ADC with a DAR of 6.

The results of the HIC are shown in FIGS. 2A-2E and show that v17597 has an average DAR of 3.92 (FIG. 2A), and v21252 has an average DAR of 2.07 (FIG. 2B).

The individual contributions of the DAR0, DAR2, DAR4 and DAR6 species to the average DAR of the purified ADCs were assessed by the integration of the HPLC-HIC chromatogram. Each peak in the HIC chromatogram was isolated by preparative chromatography and the identity of the peak was verified by LC-MS. The % content of individual DAR species for each variant (as determined by HIC) is shown in Table 10 and in FIG. 2D. As can be seen from Table 10 and FIG. 2D, v17597 contains significantly more DAR6 species than v21252, and v21252 contains significantly more DAR0 species than v17597.

FIG. 2E illustrates the change in the relative amounts of DAR 0, 2, 4, and 6 species within v10000-Linker Toxin 001 for a series of ADC preparations having average DAR values ranging from 0.5 to 6.

TABLE 10

DAR Distribution for v17597 and v21252

| | Area % | |
|---|---|---|
| DAR | v17597 | v21252 |
| 0 | 2 | 23 |
| 2 | 35 | 56 |

TABLE 10-continued DAR Distribution for v17597 and v21252

| | Area % | |
|---|---|---|
| DAR | v17597 | v21252 |
| 4 | 26 | 17 |
| 6 | 36 | 4 |

2.5 Size Exclusion Chromatography

The extent of aggregation of the antibody and ADCs (~15 ug, 5 uL injection volume) was assessed by size exclusion chromatography (SEC) on an ACQUITY UPLC® Protein BEH SEC column (200 angstrom, 1.7 4.6×150 mm) (Waters Corporation, Milford, MA) using a mobile phase consisting of 150 mM phosphate, pH 6.8 and a flow rate of 400 uL/min. Detection was by absorbance at 280 nm.

Figure 3A:
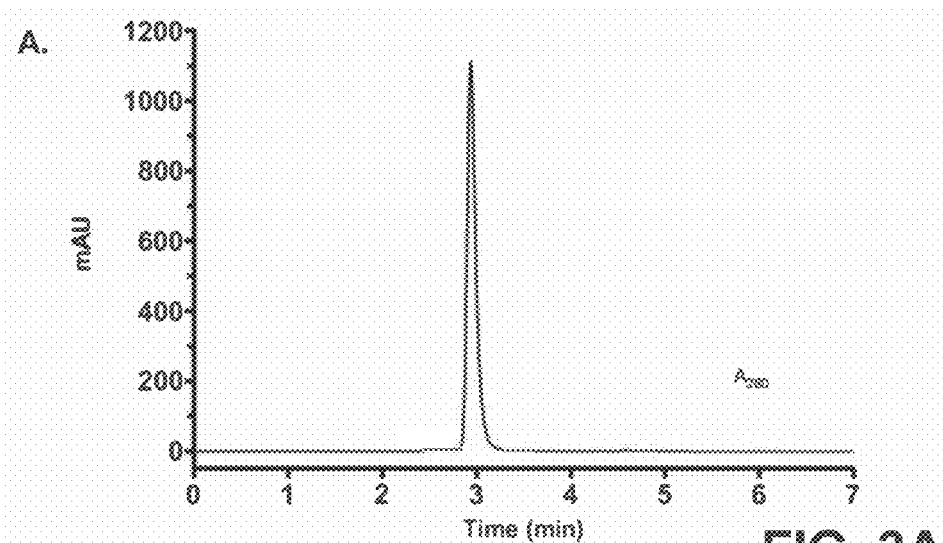
FIGS. 3A-3C show size-exclusion chromatography (SEC) traces for (FIG. 3A) parent anti-HER2 biparatopic antibody v10000, (FIG. 3B) v17597 (anti-HER2 biparatopic antibody conjugated to Linker-Toxin 001 at DAR4), and (FIG. 3C) v21252 (anti-HER2 biparatopic antibody conjugated to Linker-Toxin 001 at DAR2).
Figure 3B:
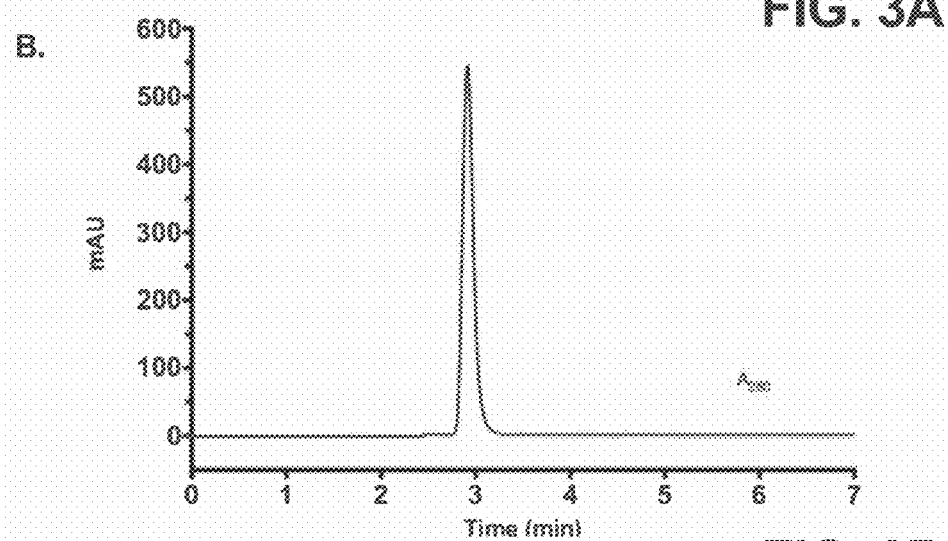
Figure 3C:
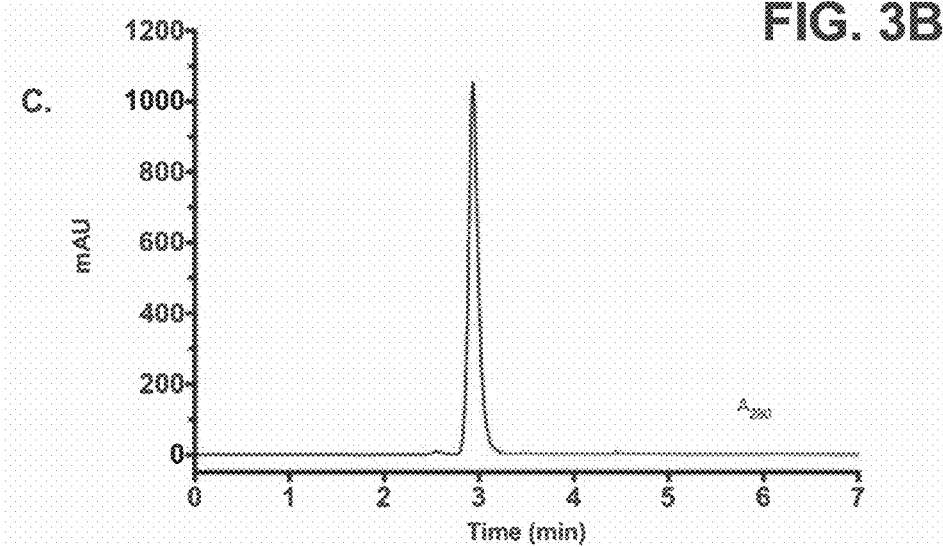

The results are shown in FIGS. 3A-3C and summarized in Table 11. The mAb v10000 is highly monomeric by SEC analysis. No significant increase in aggregation was observed upon conjugation to Linker-Toxin 001. A comparison of v21252 and v17597 indicates that the extent of aggregation is unaffected by increasing the DAR from 2 to 4.

TABLE 11

Summary of SEC Results

| Variant | Peak # | Ret Time (min) | Width (min) | Area (mAU*s) | Area % |
|---|---|---|---|---|---|
| v10000 | 1 | 2.557 | 0.1243 | 86.8 | 1.16 |
| | 2 | 2.938 | 0.1101 | 7387.6 | 98.40 |
| | 3 | 3.516 | 0.1452 | 3.8 | 0.44 |
| v17597 | 1 | 2.532 | 0.1343 | 31.0 | 0.68 |
| | 2 | 2.914 | 0.1370 | 4491.3 | 98.69 |
| | 3 | 3.477 | 0.1370 | 28.6 | 0.63 |
| v21252 | 1 | 2.549 | 0.1376 | 76.4 | 0.98 |
| | 2 | 2.936 | 0.1212 | 7685.8 | 98.47 |
| | 3 | 3.477 | 0.1456 | 43.4 | 0.56 |

2.6 Quantitation of Free Toxin and Linker-Toxin by LC-MS-MS

The residual concentrations of free toxin (Compound 9), Linker-Toxin 001, and quenched drug linker N-acetyl cysteine-Linker-Toxin 001 in the ADC formulations were assessed by liquid chromatography (LC) separation and mass detection, with reference to standard curves for each analyte. Separations were performed on a PolymerX™ RP-1 column (3 µm, 100 angstrom, 50×4 mm) (Phenomenex Inc., Torrance, CA) employing a flow rate of 0.4 mL/min, column temperature of 30° C., and a gradient of 75% MPA/25% MPB to 60% MPA/40% MPB over 7.8 minutes (MPA=0.1% aqueous formic acid, and MPB=0.1% formic acid in acetonitrile). Positive mode ESI-MRM mass detection was achieved on an Agilent 6470 Triple Quadrupole mass spectrometer (Agilent Technologies, Santa Clara, CA).

All samples contained <0.1 mol % analyte relative to total conjugated payload.

2.7 Flow Cytometry Binding Assay on Antigen-Positive Cells

The binding of ADCs to antigen-positive tumour cell lines JIMT-1 (breast carcinoma, Addexbio Technologies, San Diego, CA) and RT-112/84 (bladder carcinoma, Sigma-Aldrich, St. Louis, MO) was compared to parental antibody (v10000) binding by flow cytometry. Cells were cultured as per vendor instructions. Briefly, cells (50,000 cells/well) were incubated with antibody or ADC serial dilutions for 90 minutes on ice. Following this incubation, cells were washed twice and then incubated with an AlexaFluor® 647 conjugated anti-hIgG (Jackson ImmunoResearch Inc., Westgrove, PA) secondary reagent for 60 minutes on ice. Cells were then washed twice and fluorescence was analyzed by flow cytometry (LSRFortessa™ X-20 flow cytometer, BD, San Jose, CA).

Figure 4A:
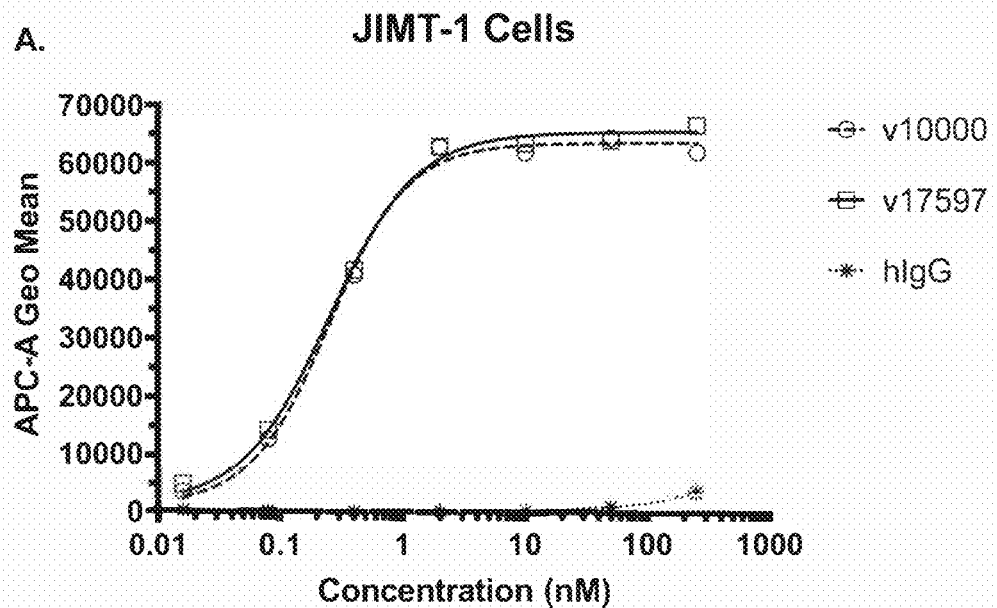
FIGS. 4A-4C show the results of flow cytometry binding assays on antigen-positive cells, comparison of v17597 (anti-HER2 biparatopic antibody conjugated to Linker-Toxin 001 at DAR4) and v10000 (parent biparatopic anti-HER2 antibody) binding to (FIG. 4A) JIMT-1 breast carcinoma cells, and (FIG. 4B) RT-112 bladder carcinoma cells, and (FIG. 4C) comparison of v21252 (anti-HER2 biparatopic antibody conjugated to Linker-Toxin 001 at DAR2) and v10000 (parent anti-HER2 biparatopic antibody) binding to JIMT-1 breast carcinoma cells.
Figure 4B:
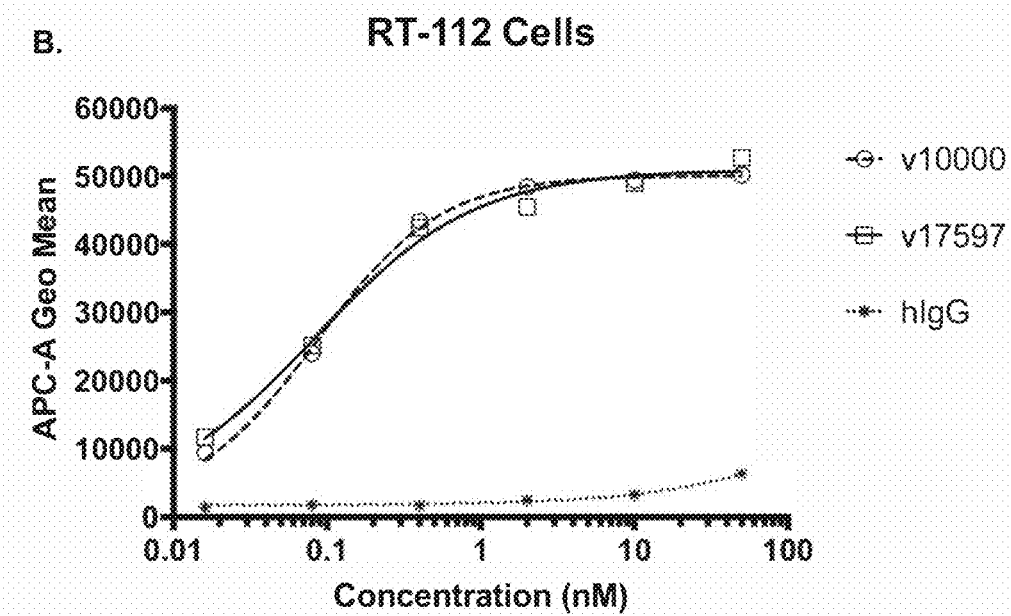
Figure 4C:
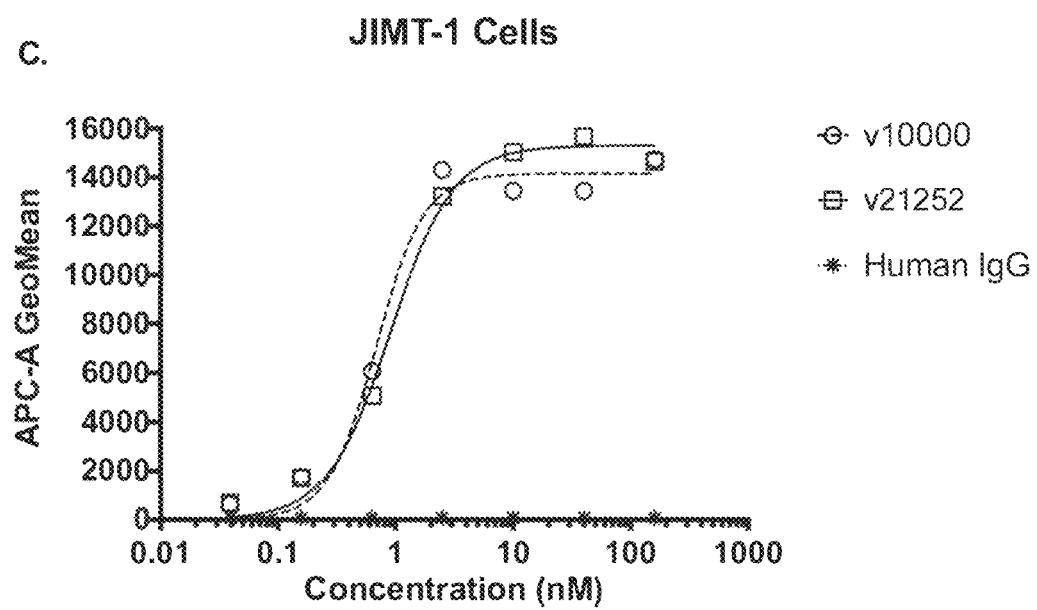
Figure 5A:
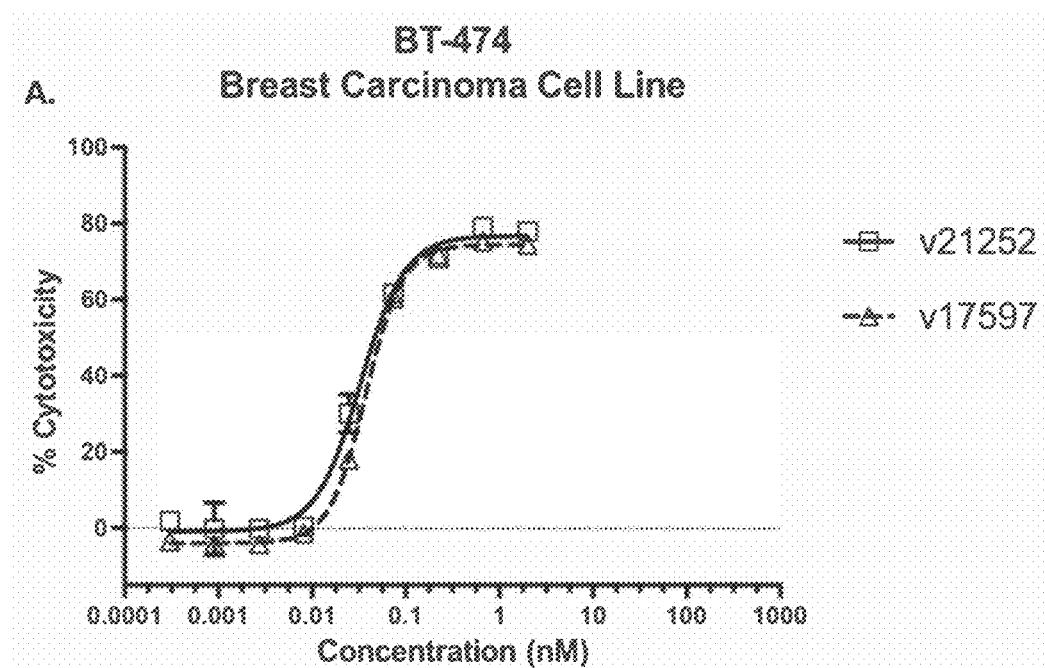
FIGS. 5A-5F show the results of treating the HER2-expressing breast carcinoma cell lines BT-474 (FIG. 5A), SK-BR-3 (FIG. 5B), HCC1954 (FIG. 5C), JIMT-1 (FIG. 5D) and ZR-75-1 (FIG. 5E), and the HER2 negative cell line MDA-MB-468 (FIG. 5F) with v17597 (anti-HER2 biparatopic antibody conjugated to Linker-Toxin 001 at DAR4) and v21252 (anti-HER2 biparatopic antibody conjugated to Linker-Toxin 001 at DAR2).
Figure 5B:
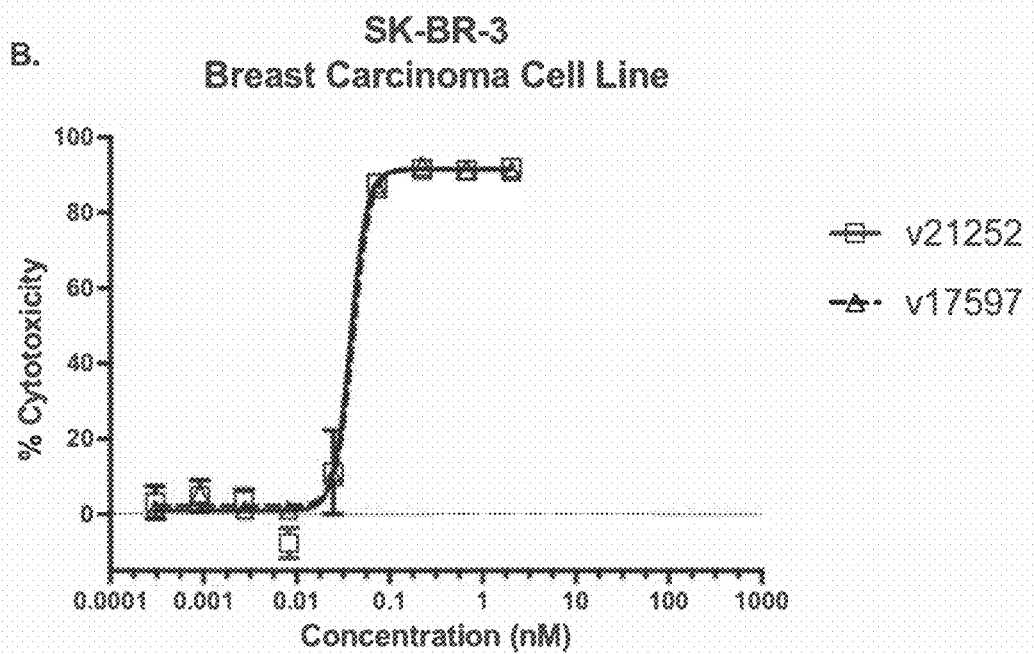
Figure 5C:
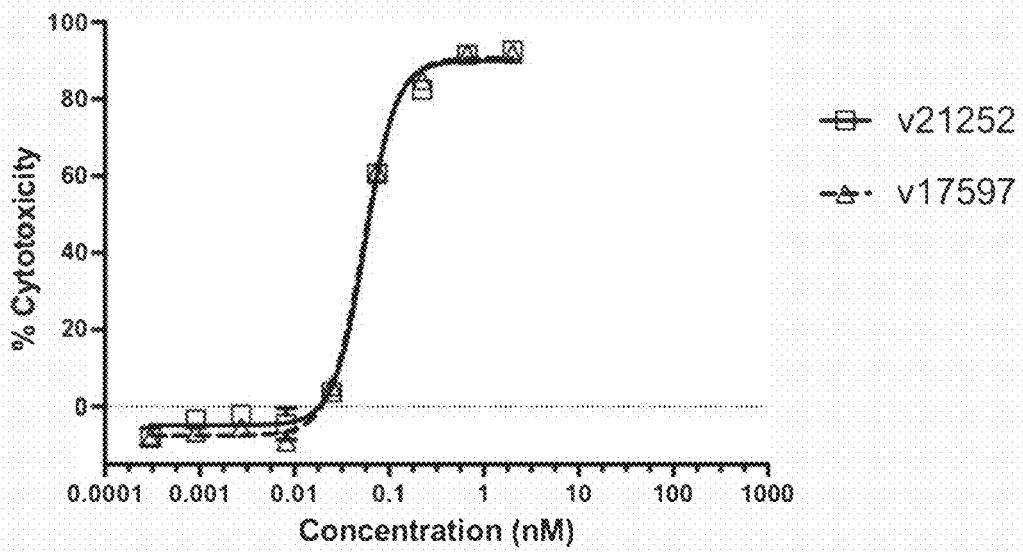
Figure 5D:
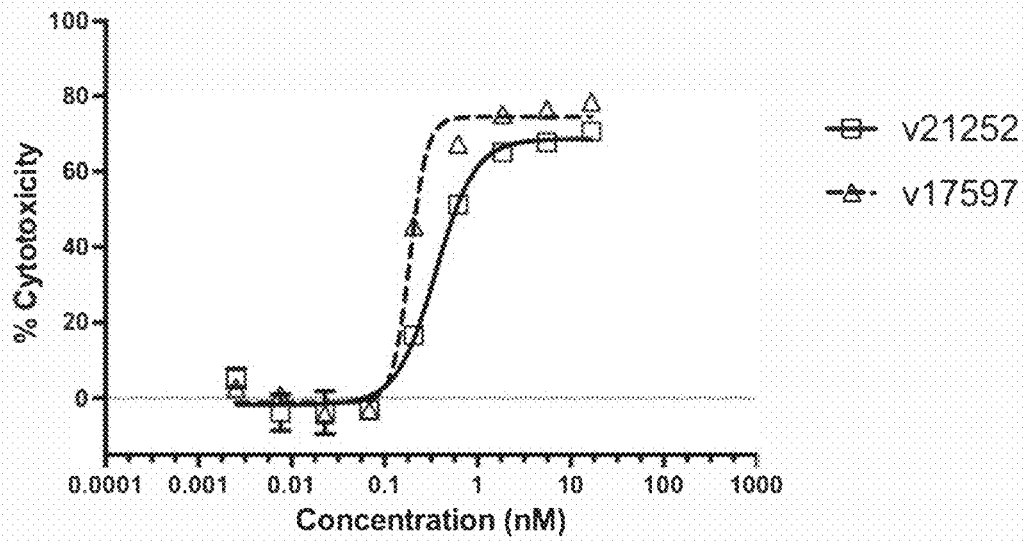
Figure 5E:
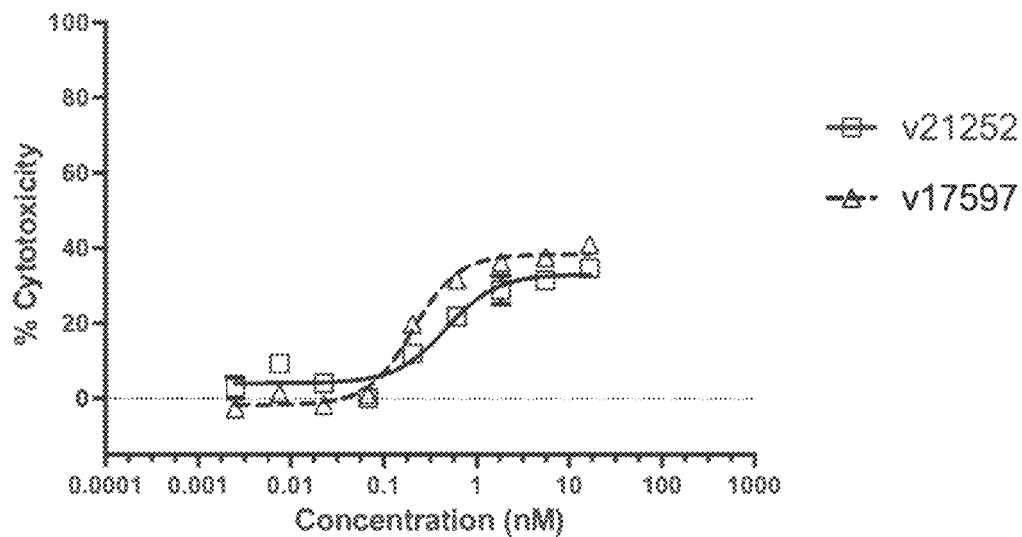
Figure 5F:
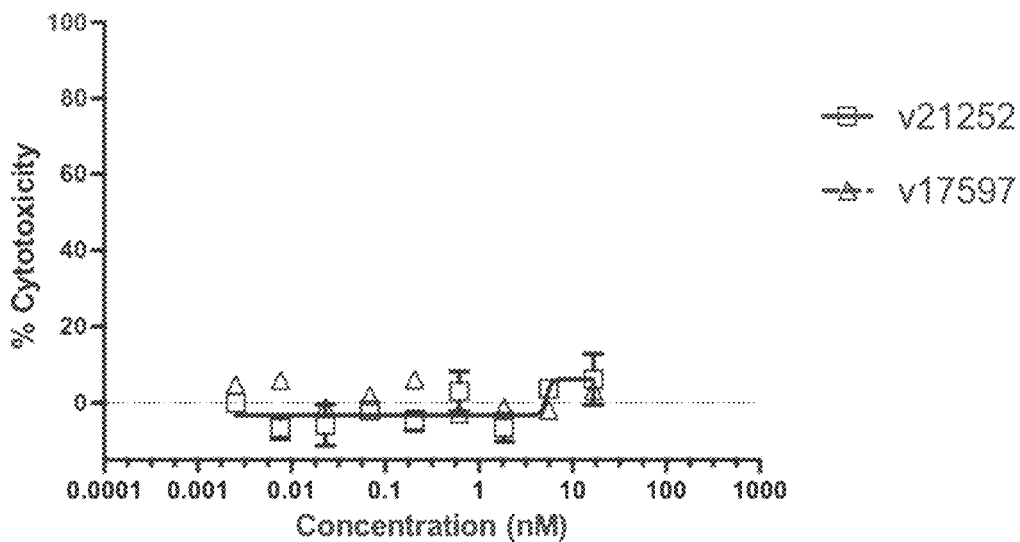
Figure 6A:
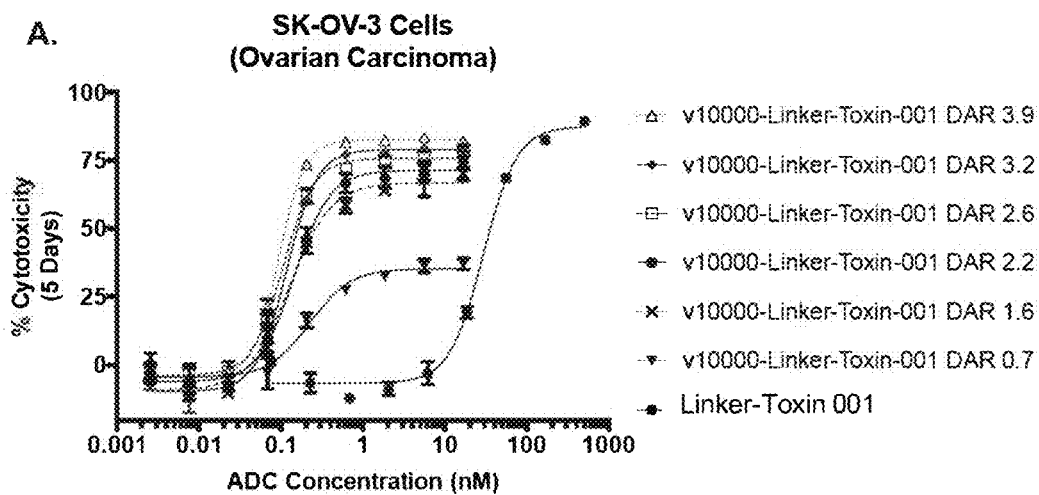
FIGS. 6A-6D show the results of treating the HER2-expressing ovarian carcinoma cell line SK-OV-3 (FIG. 6A), and the breast carcinoma cell lines ZR-75-1 (FIG. 6B) and JIMT-1 (FIG. 6C) with antibody-drug conjugates comprising v10000 conjugated to Linker-Toxin 001 at various average DAR. The individual contributions of the DAR0, DAR2, DAR4 and DAR6 species to the average DAR of the ADCs having an average DAR of 0.7, 2.2 and 3.9 is shown in (FIG. 6D).
Figure 6B:
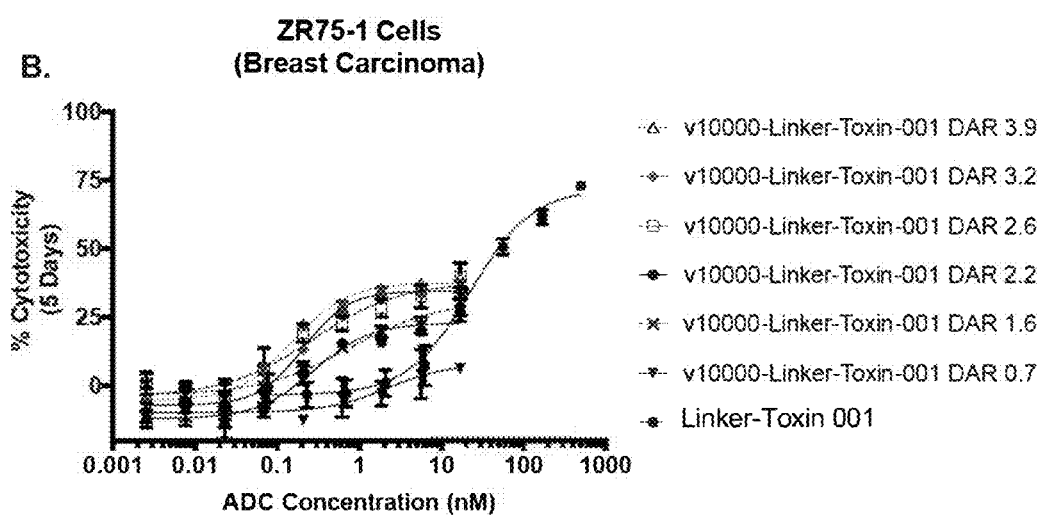
Figure 6C:
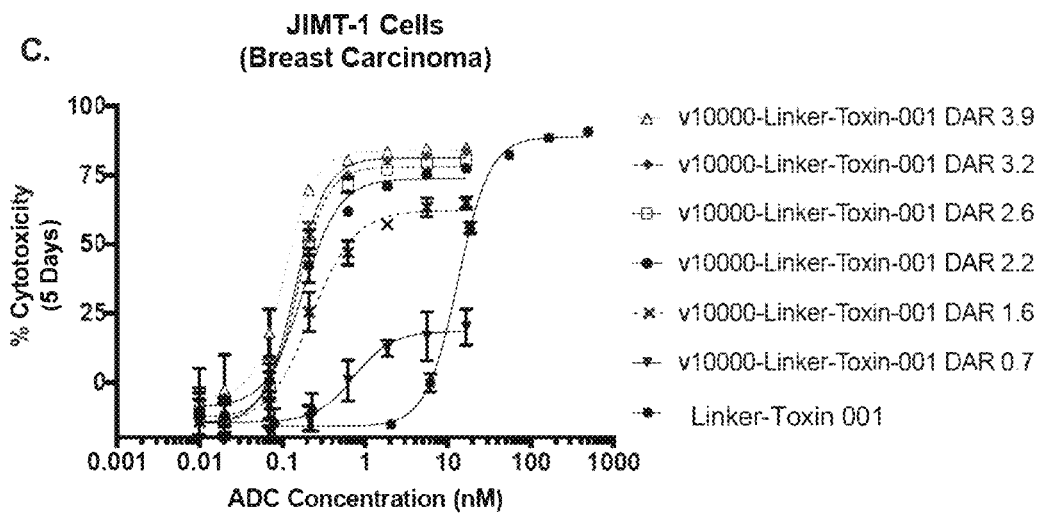
Figure 6D:
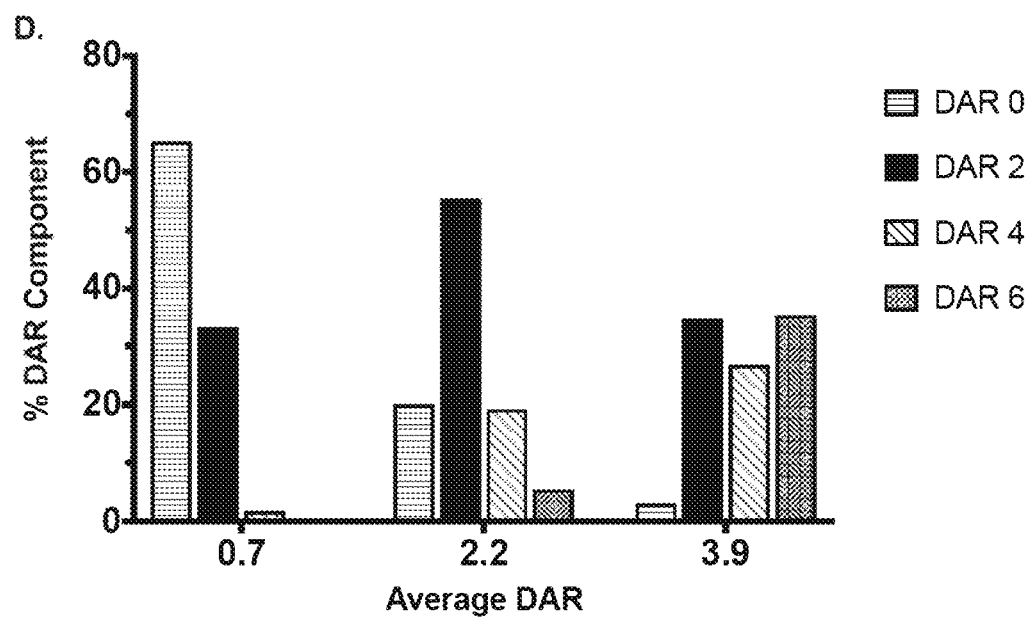

The results are shown in FIGS. 4A-4C and demonstrate that the binding of v17597 and v21252 to antigen-positive cells is not affected by conjugation to toxin, with both ADCs showing similar binding to the parent antibody v10000.

2.8 Endotoxin Testing

The endotoxin level of formulated ADCs was assessed using a Limulus Amebocyte Lysate (LAL) gelation end point assay (Genscript ToxinSensor™ Single Test Kit; GenScript, Piscataway, NJ) with a 0.125 EU/mL threshold. All ADCs employed in in vivo experiments (below) were dosed below 5 endotoxin units per kilogram body mass.

Example 3: In Vitro Activity of Biparatopic ADCS

The in vitro potency of v17597 and v21252 was measured by a cell proliferation assay on antigen-positive tumour cells BT-474 (ductal carcinoma, ATCC, Manassas, VA (HTB-20)), SK-BR-3 (breast carcinoma, ATCC, Manassas, VA (HTB-30)), HCC-1954 (breast carcinoma, ATCC (CRL-2338)), JIMT-1 (breast carcinoma, Addexbio Technologies, San Diego, CA, (C0006005)), ZR-75-1 (breast carcinoma, ATCC (CRL-1500)) and antigen-negative tumour cells MDA-MB-468 (breast carcinoma, Addexbio Technologies (C0006003)). Cells were cultured as per vendor instructions. Briefly, on the day prior to adding the ADC, cells (50 uL/well, 1000 cells/well) were added to sterile, tissue culture (TC) treated, 384-well plates (ThermoFisher Scientific, Waltham, MA) and incubated overnight at 37° C./5% $CO_2$ to allow the cells to adhere to the plate surface. In a sterile, U-bottom, 96-well plate, ADCs were diluted in complete growth medium at 4.3-times the desired final maximum concentration and were titrated 1:3 in the same medium, creating a 10-point dose response titration. Control wells with no ADC (growth medium alone) were included on each microtiter 96-well plate. 15 uL from the 10-point dose response titration were added into each well of the 384-well plate containing the seeded cells, in triplicate, and plates were incubated at 37° C./5% $CO_2$ for 5 nights. After 5-night incubation, cell viability was quantified by the addition of 20 uL/well of CellTiter-Glo® (Promega, Madison, WI) and incubation at room temperature for 30 min. Luminescence was measured using a microplate luminometer. The collected relative light units (RLU) were converted to % cytotoxicity using the growth medium alone control mentioned above (% Cytotoxicity=1−[Well RLU/average medium alone control RLU]). Data were fit to curves using non-linear regression methods available with Prism® software (GraphPad Software, La Jolla, CA).

The results are shown in FIGS. 5A-5F and summarized in Table 12. The results show that both v17597 and v21252 demonstrate selective cell killing. HER2 expressing cell lines BT-474, SK-BR-3, HCC1954, JIMT-1, and ZR-75-1 (FIGS. 5A-5E) were sensitive to both v17597 and v21252.

Both v17597 and v21252 were ineffective against MDA-MB-468 cells (FIG. 5F), which are from a HER2 negative breast carcinoma cell line.

TABLE 12

In Vitro Activity of v17597 and v21252

$EC_{50}$ (nM)

| Variant | BT-474 | SK-BR-3 | HCC1954 | JIMT-1 | ZR-75-1 | MDA-MB-468 |
|---|---|---|---|---|---|---|
| v17597 | 0.04 | 0.04 | 0.05 | 0.19 | 0.21 | NA |
| v21252 | 0.03 | 0.04 | 0.06 | 0.36 | 0.47 | NA |

Example 4: In Vitro Proliferation Assay of v10000-Linker-Toxin 001 at Different Average DARs ADCs comprised of v10000 conjugated to Linker-Toxin 001 with an average DAR ranging from 0.7 to 3.9 were prepared by varying the amount of TCEP (0.5 to 10 molar equivalents) utilized in the reduction reaction. The conjugation reaction was conducted in accordance with the procedures outlined in Example 2 and the resulting ADCs were purified using a 40 kDa Zeba™ column, pre-equilibrated with PBS pH 7.4.

The in vitro potency of the ADCs was measured by a cell proliferation assay on antigen-positive tumour cells SK-OV-3 (ovarian carcinoma, ATCC, Manassas, VA (HTB-77)), JIMT-1 (breast carcinoma, DSMZ, Braunschweig, Germany (ACC 589)) and ZR-75-1 (breast carcinoma, ATCC (CRL-1500)). Cells were cultured as per vendor instructions. Briefly, on the day prior to adding ADC, cells (100 uL/well, 2500 cells/well) were added to sterile, TC treated, 96-well opaque-walled plates (Corning 3904) and incubated overnight at 37° C./5% $CO_2$ to allow the cells to adhere to the plate surface. On the following day, ADCs were diluted in complete growth medium (96-well U bottom plate) at 5-times the desired final maximum concentration and were titrated 1:3 in the same medium, eight steps (9 compound titration points in total). A control titration point containing growth medium alone was also included, creating a 10-point dose response titration in total. 25 uL from the 10-point dose response titration were added into each well of the 96-well plate containing the seeded cells, in triplicate, and plates were incubated at 37° C./5% $CO_2$ for 5 nights. Following incubation, cell viability was quantified by the addition of 25 uL/well of CellTiter-Glo® (Promega Corporation, Madison, WI) and incubation at room temperature for 30 min. Luminescence was then measured using a microplate luminometer and the collected relative light units (RLU) were converted to % cytotoxicity as described in Example 3.

The results are shown in FIGS. 6A-6D. The ADCs having average DARs between 3.9 and 1.6 showed comparable potency across the three cell-lines, however, the ADC with average DAR0.7 showed a significant decrease in potency. The approximate amounts of individual DAR species making up the DAR0.7, DAR2.2 and DAR3.9 ADCs are shown in Table 13 and FIG. 6D. It can be seen that the DAR0.7 ADC contains approximately three times as much DAR0 species (approx. 65% vs. approx. 20%) as the DAR1.9 ADC. The DAR2.2 ADC in turn contains significantly more DAR0 species than the DAR3.9 species (approx. 20% vs. <3%), however, the DAR2.2 ADC showed comparable in vitro potency to the DAR3.9 ADC. These results suggest that there may be a threshold for the proportion of DAR0 species an ADC preparation may contain before the potency of the ADC is impacted.

TABLE 13

Approximate DAR Distribution for ADCs

| Average DAR of ADC | DAR Distribution (%) | | | |
|---|---|---|---|---|
| | DAR 0 | DAR 2 | DAR 4 | DAR 6 |
| 0.7 | 65 | 33 | 2 | 0 |
| 1.6 | 33 | 54 | 11 | 2 |
| 2.2 | 20 | 55 | 19 | 5 |
| 2.6 | 13 | 55 | 22 | 10 |
| 3.2 | 7 | 47 | 26 | 21 |
| 3.9 | 3 | 35 | 27 | 35 |

Example 5: Internalization of Biparatopic ADCS into HER2-Expressing Cells

To determine internalization of v21252, pHAb Dye (Promega Corporation, Madison, WI) was coupled to amine residues of v21252, trastuzumab-Linker-Toxin 001 and a negative control ADC according to manufacturer's recommended protocols. The negative control ADC was an anti-RSV Protein F antibody conjugated to Linker-Toxin 001.

pHAb-conjugated antibodies can be used to monitor receptor-mediated antibody internalization. Antibody conjugated with pHAb Dye bound to antigen on the cell membrane exhibits minimal fluorescence, but after receptor-mediated internalization and traffic through the endosome and lysosomal system, the antibody-pHAb conjugate is exposed to more acidic pH, causing the antibody-pHAb conjugate to fluoresce.

pHAb conjugated v21252, pHAb conjugated trastuzumab-Linker-Toxin 001 and pHAb conjugated control were incubated with the HER2 expressing cell lines SKBR3 and JIMT-1. Briefly, SKBR3 and JIMT-1 HER2+ tumour cells were seeded into a 384-well black optical bottom plate (ThermoFisher Scientific, Waltham, MA) at 5,000 cells/well in assay media. The plate was incubated overnight at 37° C.+5% $CO_2$. The following day, pHAb-conjugated antibodies were added to plates at 10 ug/ml and 1 ug/mL final in assay media. Media containing Vybrant® DyeCycle™ Violet stain (ThermoFisher Scientific, Waltham, MA) was added at 2 uM final concentration to visualize nuclei. The plate was incubated at 37° C.+5% CO2 between time points. Sample wells were scanned at various time points on the CellInsight™ CX5 High Content Screening (HCS) Platform (ThermoFisher Scientific, Waltham, MA). The plate was scanned using a 20× objective on the SpotAnalysis Bioapplication with 2 channels. Channel 1 (385 nm, Vybrant Dye Cycle Violet) was used as the focus channel and Channel 2 (560 nm, pHAb) was used to obtain internalization data. Fluorescence of internalized pHAb-conjugated antibodies was measured using the parameter "Mean Total Spot Intensity."

The results are shown in FIGS. 13A-14B, and show that v21252 internalizes and traffics to lysosomes in HER2 expressing cells to a greater level than the monospecific trastuzumab-Linker-Toxin 001.

Figure 7A:
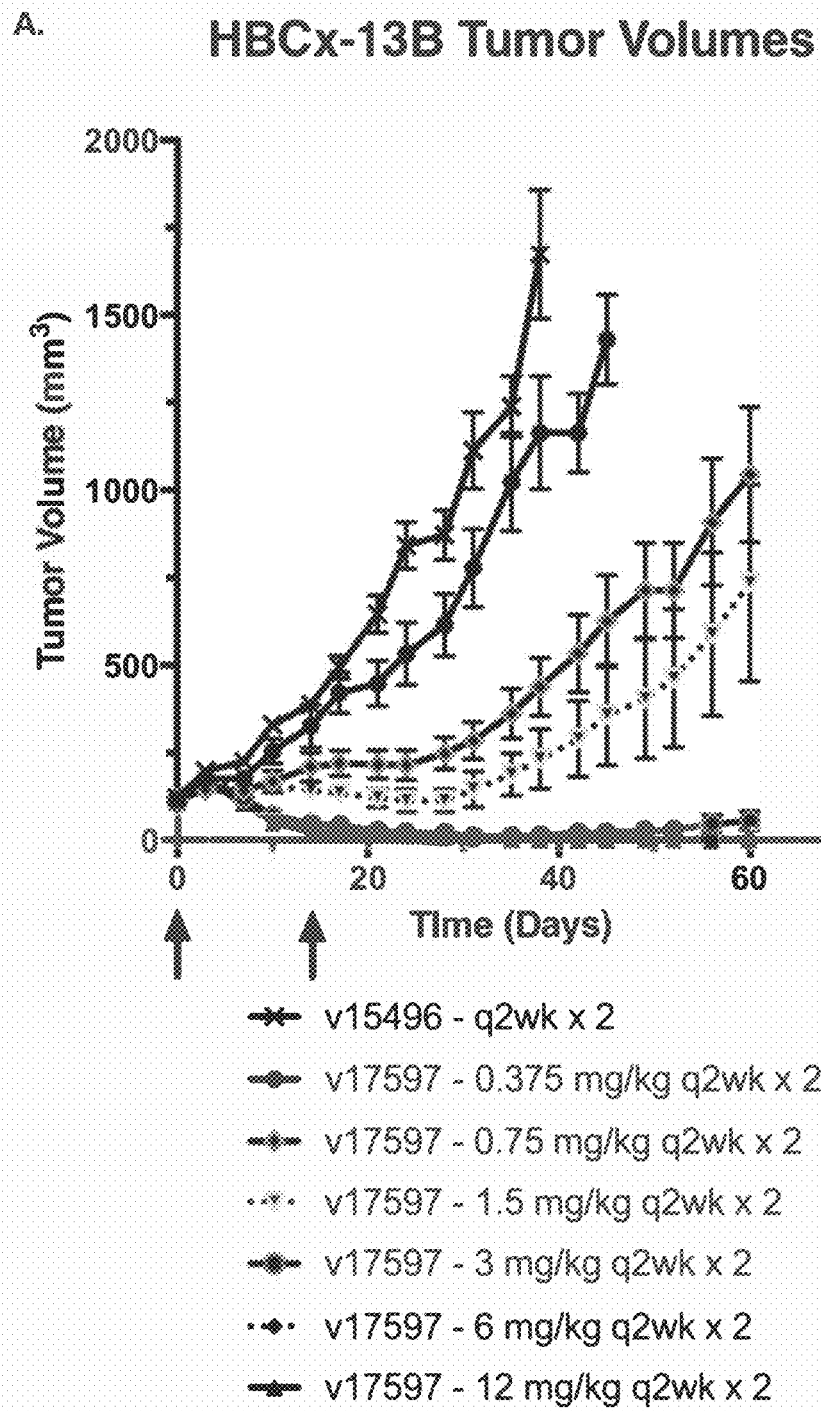
FIGS. 7A-7B show the results of treating HBCx-13b breast cancer patient derived xenograft mice q14d×2 with the noted doses of (FIG. 7A) v17597 (anti-HER2 biparatopic antibody conjugated to Linker-Toxin 001 at DAR4) and (FIG. 7B) v21252 (anti-HER2 biparatopic antibody conjugated to Linker-Toxin 001 at DAR2). v15496=vehicle.
Figure 7B:
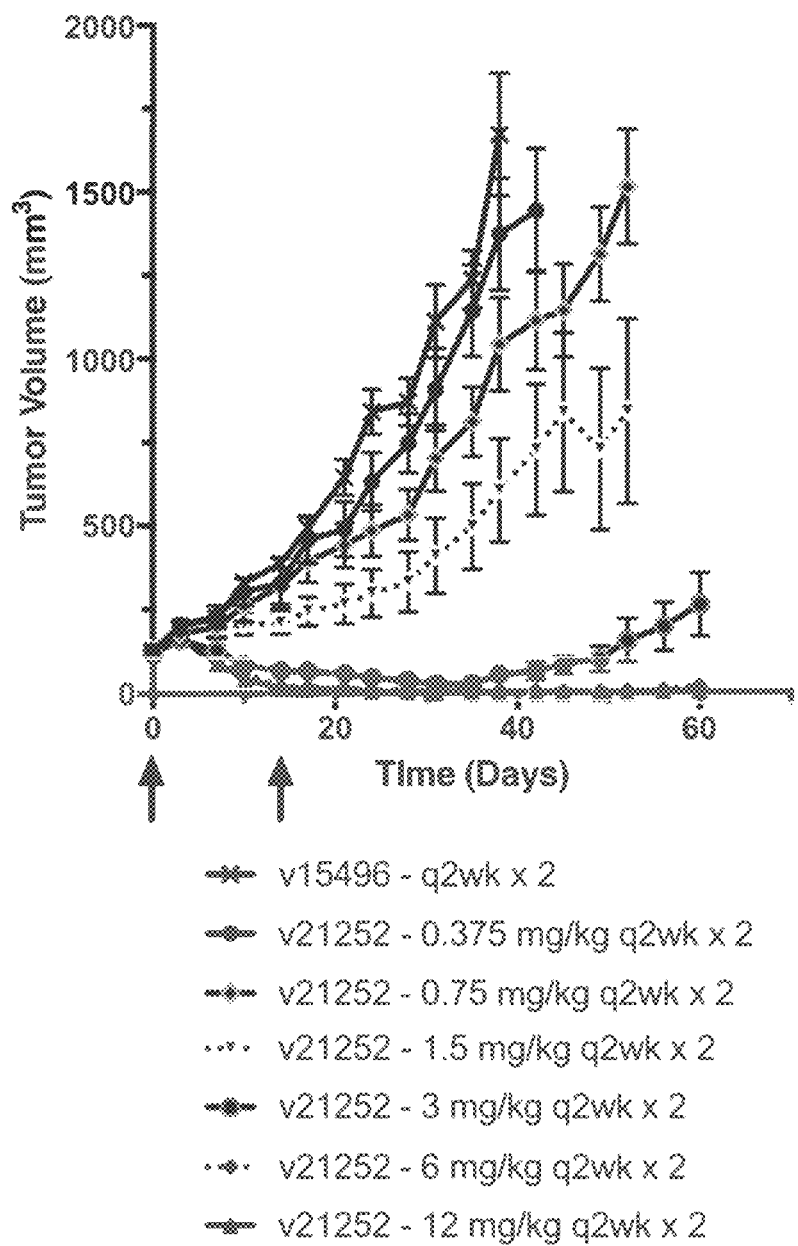

Example 6: In Vivo Activity of Biparatopic ADCS 6.1 ADCs v17597 and v21252 Inhibit HBCx-13b Breast Cancer Patient Derived Xenograft Growth Female athymic mice (Envigo, Huntingdon, UK) were subcutaneously implanted with a 20 $mm^3$ tumour fragment (n=7 per group). Once tumours reached 75 to 200 mm³ in size, animals were assigned to treatment groups and v17597, v21252 or vehicle were dosed by intravenous injection for a total of 2 doses on day 1 and day 15 (q14d×2) as indicated in FIGS. 7A-7B. Tumour measurements were performed with a caliper biweekly. Mice were ethically sacrificed when tumours reached a size of 1764 mm³. Tumour volumes are reported as the mean±SEM for each group.

FIG. 7A provides the results for the tumour response in mice subcutaneously implanted with HBCx-13b tumour fragments after i.v. administration of vehicle or v17597. FIG. 7B provides the results for the tumour response in mice subcutaneously implanted with HBCx-13b tumour fragments after i.v. administration of vehicle or v21252. These results show that treatment of HBCx-13b engrafted mice with either v17597 or v21252 results in a tumour volume reduction in a dose-dependent manner.

Figure 8A:
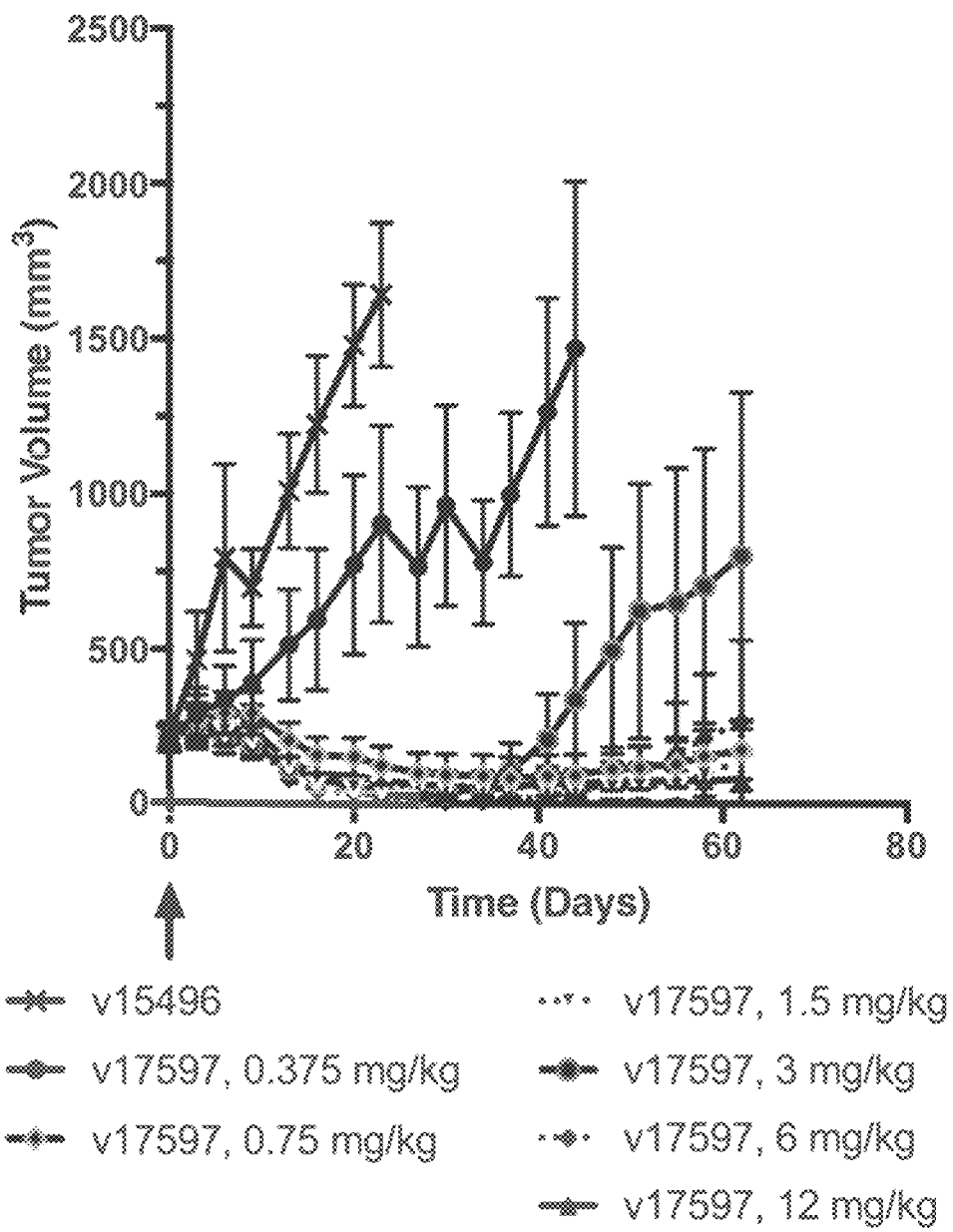
FIGS. 8A-8B show the results of treating ST-910 breast cancer patient derived xenograft mice qd×1 with the noted doses of (FIG. 8A) v17597 (anti-HER2 biparatopic antibody conjugated to Linker-Toxin 001 at DAR4) and (FIG. 8B) v21252 (anti-HER2 biparatopic antibody conjugated to Linker-Toxin 001 at DAR2). v15496=vehicle.
Figure 8B:
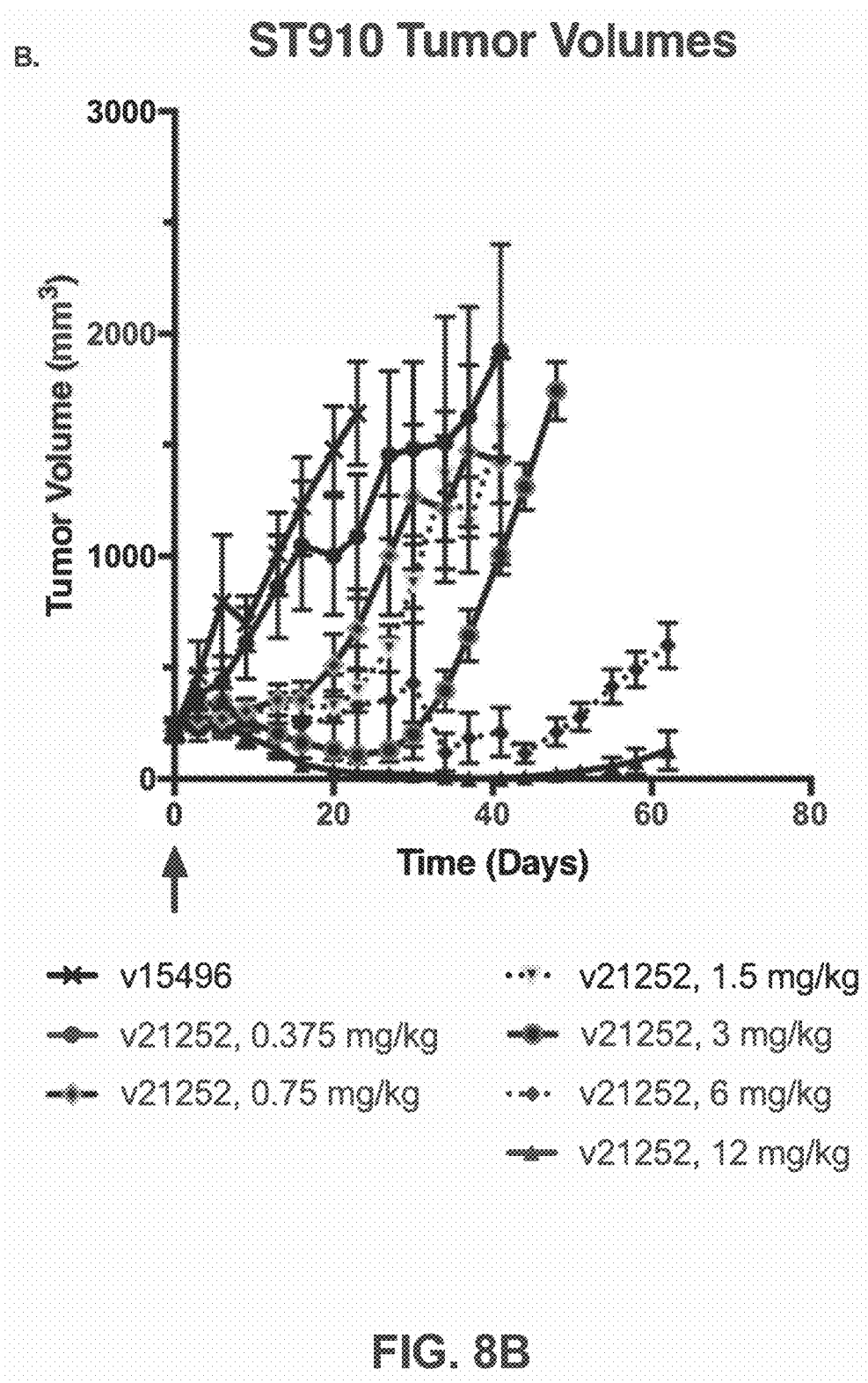

6.2 ADCs v17597 and v21252 Inhibit ST-910 Breast Cancer Patient Derived Xenograft Growth Female athymic nude mice (Charles Rivers Laboratories, Wilmington, MA) were subcutaneously implanted with a ~70 mg tumour fragment (n=6 per group). Once tumours reached 125 to 250 mm³ in size, animals were assigned to treatment groups and v17597, v21252 or vehicle were dosed by intravenous single injection as indicated in FIGS. 8A-8B. Tumour measurements were performed with a digital caliper biweekly. Mice were ethically sacrificed when tumours reached a size of 2000 mm³. Tumour volumes are reported as the mean±SEM for each group.

FIG. 8A provides the results for the tumour response in mice subcutaneously implanted with ST-910 tumour fragments after i.v. administration of vehicle or v17597. FIG. 8B provides the results for the tumour response in mice subcutaneously implanted with ST-910 tumour fragments after i.v. administration of vehicle or v21252. These results show that treatment of ST-910 engrafted mice with either v17597 or v21252 results in a tumour volume reduction in a dose-dependent manner.

ST-910 is a patient derived xenograft (PDX) that represents HER2 1+ breast cancer while HBCx-13b (used in Example 6.1) is a PDX that represents HER2 3+ breast cancer. Examples 6.1 and 6.2 thus demonstrate that both v17597 and v21252 are active in both HER2 3+ and HER2 1+ tumours.

6.3 Pharmacokinetic Analysis

Figure 15A:
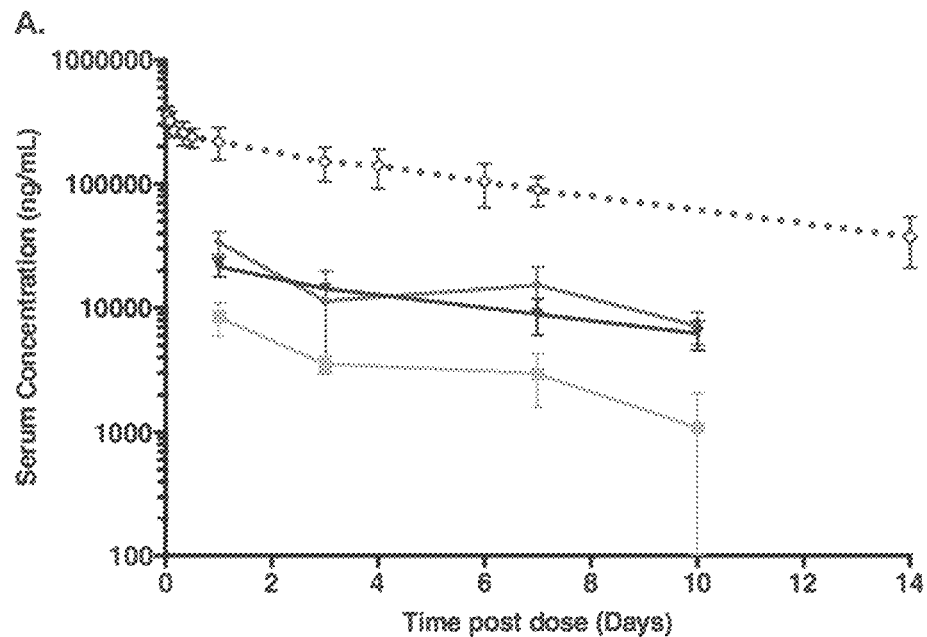
FIGS. 15A-15B show comparative exposure in cynomolgus monkeys and mice treated with v21252 at the indicated doses.
Figure 15B:
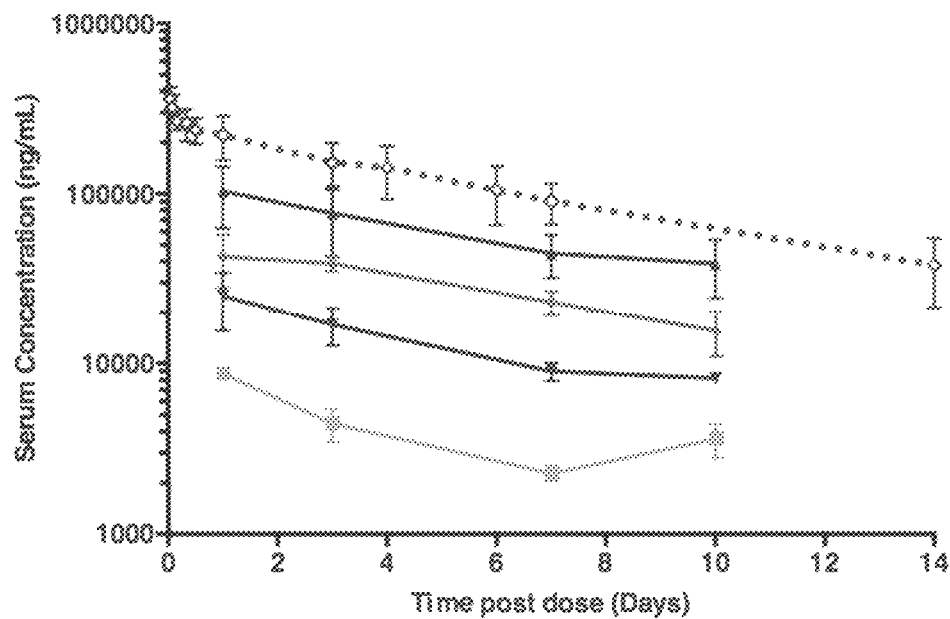

For the patient derived xenografts, HBCx-13b and ST-910, pharmacokinetic samples for total antibody (unconjugated and conjugated antibody) were collected at pre-specified time points and were evaluated using an ELISA-based assay for total antibody quantification. Serum concentrations for total antibody for either v21252 or v17597 were analyzed by first coating 384-well ELISA plates with goat anti-human IgG Fc antibody (Jackson ImmunoResearch, West Grove, PA) in PBS pH 7.4 and incubating at 4° C. overnight. The following day, plates were washed and blocked using assay diluent and incubated at RT for 1 hr. After blocking, standard curve samples, controls, and diluted serum samples were added to the plates and incubated at RT for 1 hr. Detection antibody, HRP-goat anti-human IgG F(ab')₂ conjugate (Jackson ImmunoResearch), was then added to the plates and after 1-hr incubation at RT, HRP substrate, 3,3',5,5'-tetramethylbenzidine (TMB), was added to plates. TMB was quenched using HCl and absorbance was measured at 450 nm using a plate reader. FIGS. 15A-15B show the total antibody serum concentration-time profile for HBCx-13b (FIG. 15A) and ST-910 (FIG. 15B).

Example 7: Single-Dose Pharmacokinetics/Tolerability Study of v17597 and v21252 in Cynomolgus Monkeys The objective of this study was to characterize the pharmacokinetics (PK) and tolerability of v17597 and v21252 in cynomolgus monkeys following a single intravenous (IV) infusion administration. The cynomolgus monkey was selected for the nonclinical safety assessment of both v17597 and v21252 based on sequence homology and binding affinity. Human and cynomolgus monkey HER2 share 98% sequence homology, whereas the sequence homology for dog and mouse/rat HER2 is 93% and 88%, respectively. In addition, v17597 and v21252 bind to cynomolgus monkey HER2 with similar affinity to human HER2 (monkey $K_D=0.55\times10^{-9}$; human $K_D=0.83\times10^{-9}$) and do not bind to dog, mouse or rat HER2.

The study demonstrates that a single-dose of v17597 at doses of 3, 6 or 9 mg/kg was well tolerated, and that a single-dose of v21252 at doses of 9 or 12 mg/kg was well tolerated.

Materials and Methods

Tolerability

A single dose of v17597 (3, 6 or 9 mg/kg) or v21252 (9 mg/kg or 12 mg/kg) was administered by IV infusion over 60 minutes in female cynomolgus monkeys (N=3). General tolerability was assessed with clinical observations, body weight, food consumption, and clinical pathology (hematology and clinical chemistry). Blood was collected throughout the study for bioanalytical analysis of v17597 or v21252, total antibody, and free toxin (Compound 9). The study design is summarized in Table 14.

TABLE 14

Design of Single-Dose Pharmacokinetic and General Tolerability Study in Cynomolgus Monkeys

| Group | v17597 Dose (mg/kg) | v21252 Dose (mg/kg) | Number of Females |
|---|---|---|---|
| 1 | 0 | 0 | 3 |
| 2 | 3 | — | 3 |
| 3 | 6 | — | 3 |
| 4 | 9 | — | 3 |
| 5 | — | 9 | 3 |
| 6 | — | 12 | 3 |

Bioanalytical Methods v17597 and v21252: Serum concentrations of v17597 or v21252 (DAR of 1 or greater) were analyzed using an Electrochemiluminescence assay with Meso Scale Discovery platform (ECL/MSD) (Meso Scale Diagnostics, LLC, Rockville, MD) with anti-toxin mouse IgG as the capture agent and anti-pertuzumab sulfo-TAG as the detection agent.

Total Antibody: The total antibody bioanalytical assay measured the antibody component of v17597 or v21252 regardless of whether the antibody component was conjugated with toxin (at all DARs) or not. Serum concentrations of total antibody were analyzed using an Electrochemiluminescence assay with Meso Scale Discovery platform (ECL/MSD) with anti-pertuzumab antibody as the capture agent and anti-trastuzumab sulfo-TAG as the detection agent.

Toxin (Compound 9): Serum concentrations of toxin were analyzed using a LC-MS/MS method. Serum samples were precipitated with acetonitrile/methanol (50:50, v/v) and supernatants were analyzed. The liquid chromatography system used was a reverse phase column with a gradient flow consisting of water/acetic acid (100/0.05, v/v) and acetonitrile. Toxin and the internal standard (toxin-d4; deuterated Compound 9) were detected using a triple quadrupole mass spectrometer system equipped with an electrospray ionization (ESI) source operated in the positive ion mode.

Pharmacokinetic Analysis

Non-compartmental analysis of the serum sample bioanalytical results was used to derive PK parameters (maximum serum concentration [$C_{max}$], terminal half-life [$T_{1/2}$], clearance [CL] and apparent volume of distribution [$V_{ss}$]).

Results

Figure 9A:
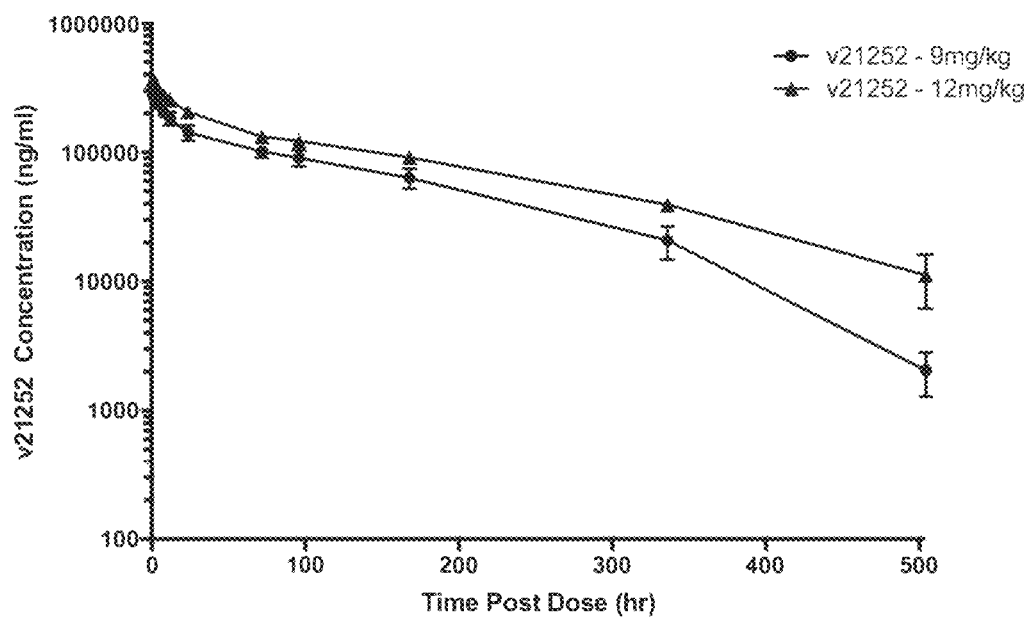
FIGS. 9A-9B show (FIG. 9A) the mean (±SD) v21252 serum concentration-time profiles, and (FIG. 9B) the mean (±SD) total antibody serum concentration-time profiles, following administration of a single dose of v21252 to female cynomolgus monkeys (n=3) at 9 mg/kg or 12 mg/kg.

Pharmacokinetics v17597: v17597 exposure was generally dose proportional between 3 to 9 mg/kg. $C_{max}$ was achieved at the end of the 60-minute infusion (median Tmax) and increased in a dose-proportional manner. Systemic exposure ($AUC_{0-\infty}$) increased in a slightly greater than dose-proportional manner. Preliminary mean terminal half-life ($T_{1/2}$) generally appeared to increase with increasing dose, clearance (CL) generally appeared to decease with increasing dose and apparent volume of distribution (Vss) generally did not appear to change with dose.

v21252: v21252 exposure was generally dose proportional between 9 to 12 mg/kg. $C_{max}$ was achieved at the end of the 60-minute infusion (median Tmax) and increased in a dose-proportional manner. The v21252 serum concentration-time profile is shown in FIG. 9A. Systemic exposure ($AUC_{0-\infty}$) increased in a slightly greater than dose-proportional manner. Preliminary mean terminal half-life ($T_{1/2}$), clearance (CL) and apparent volume of distribution (Vss) generally did not appear to change with dose.

Figure 9B:
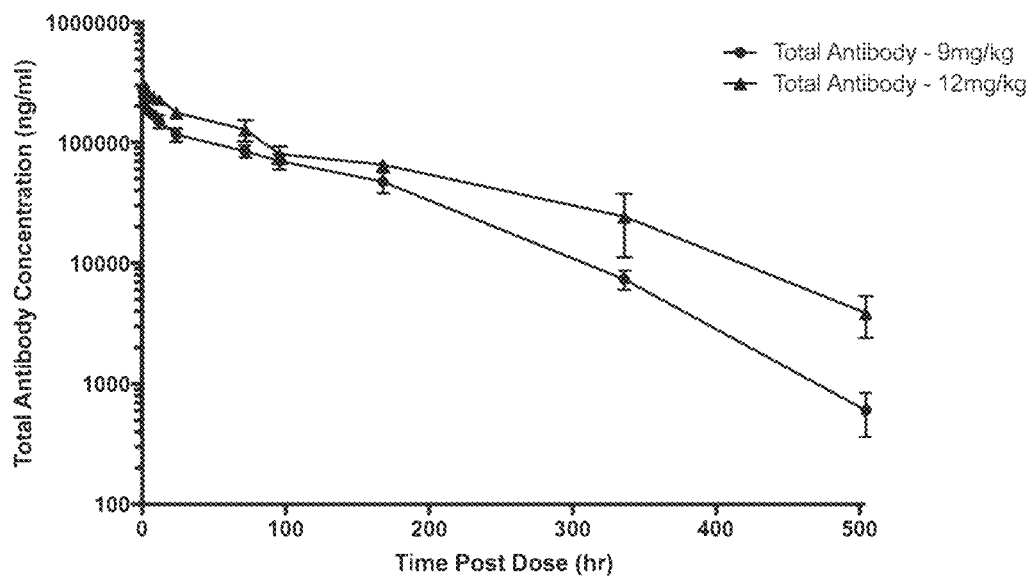

Total Antibody (conjugated and non-conjugated): Maximum serum concentration of total antibody ($C_{max}$) was achieved at the end of the 60-minute infusion (median $T_{max}$). The total antibody serum concentration-time profile of v21252 is shown in FIG. 9B. A non-compartment model was used to derive PK parameters. $C_{max}$ increased in a dose-proportional manner, while $AUC_{0-\infty}$ increased in a slightly greater than dose-proportional manner for both v17597 and v21252. The mean terminal half-life of v17597 increased with increasing dose, while serum clearance (CL) and total apparent volume of distribution (Vss) of total antibody decreased with increasing dose. The mean terminal half-life and total apparent volume of distribution (Vss) of v21252 increased with increasing dose, while serum clearance (CL) of total antibody decreased with increasing dose.

Toxin (Compound 9): Following administration of a single dose of v17597 (3, 6 or 9 mg/kg) or v21252 (9 mg/kg or 12 mg/kg), all toxin serum concentrations were below the lower limit of quantitation (LLOQ, <5.00 ng/mL).

Tolerability

A single-dose of v17597 (3, 6 or 9 mg/kg) or v21252 at doses of 9 or 12 mg/kg was well tolerated. There was no mortality during the course of the study. No treatment-related effects were noted in clinical observations, food consumption, or body weight.

Minimal to mild changes in clinical pathology parameters that were considered treatment-related were observed in some animals. There were no test article-related effects among hematology endpoints in any treatment group. All fluctuations were considered within expected ranges for biological and/or procedure-related fluctuation despite any apparent differences among individual values.

Example 8: Non-GLP Toxicity Study of v17597 in Cynomolgus Monkeys

A non-GLP toxicity study was conducted to investigate the toxicokinetics and toxicity of v17597 in cynomolgus monkeys. The study was designed based on results from the single-dose pharmacokinetic/tolerability study in female cynomolgus monkeys (Example 6).

The study demonstrated that administration of v17597 weekly at doses of 2.25 and 4.5 mg/kg, and bi-weekly at doses of 4.5 and 9 mg/kg was not well tolerated in male and female cynomolgus monkeys. The no adverse effect level (NOAEL) and the highest non-severely toxic dose (HNSTD) for v17597 following weekly or bi-weekly administration for up to 6 weeks was considered to be less than 2.25 mg/kg administered weekly or 4.5 mg/kg administered bi-weekly.

Materials and Methods

Vehicle or v17597 was administered by a 1-hr IV infusion weekly on Days 1, 8, 15, 22, 29 and 36 at doses 0, 2.25 and 4.5 mg/kg, and once every other week on Days 1, 15 and 29 at doses of 4.5 and 9 mg/kg. All animals were evaluated for changes in clinical signs, food consumption, body weight, blood pressure, ECGs, respiration rates (visual), clinical pathology (hematology, clinical chemistry, coagulation, urinalysis), organ weights, and macroscopic/microscopic examination of tissues. Blood was collected for toxicokinetic analysis and anti-drug antibody (ADA) analysis. Animals dosed weekly were terminated on Day 42 and animals dosed every other week were terminated on Day 36. The study design is presented in Table 15.

TABLE 15

Study Design

| Group | Dose (mg/kg) | Dose Regimen | No. of Animals |
|---|---|---|---|
| 1 | 0 | Weekly | 3M/3F |
| 2 | 2.25 | Weekly | 3M/3F |
| 3 | 4.5 | Weekly | 3M/3F |
| 4 | 4.5 | Every other week | 3M/3F |
| 5 | 9 | Every other week | 3M/3F |

Results

Based on body weight, clinical observations, and clinical pathology findings, v17597 was considered to be adverse at all doses tested in this study. Animals at 9 mg/kg/dose (bi-weekly) and one female at 4.5 mg/kg/dose (bi-weekly) were terminated early and only received doses on Days 1 and 15.

Based on the results of this study, the no adverse effect level (NOAEL) and the highest non-severely toxic dose (HNSTD) for v17597 following weekly or bi-weekly administration for up to 6 weeks was considered to be less than 2.25 mg/kg administered weekly or 4.5 mg/kg administered bi-weekly.

Example 9: Non-GLP Toxicity Study of v21252 in Cynomolgus Monkeys

The objective of this study was to further characterize the toxicokinetics and toxicity of v21252.

The study demonstrated that administration of v21252 on Days 1, 15 and 29 at doses up to 12 mg/kg was clinically well tolerated in male and female cynomolgus monkeys. The no observed adverse event level (NOAEL) was 12 mg/kg and the highest non-severely toxic dose (HNSTD) was greater than 12 mg/kg.

Materials and Methods

In this study, vehicle or v21252 was administered to male and female cynomolgus monkeys by a 1-hr IV infusion once every other week on Days 1, 15 and 29 at doses of 0, 9 and 12 mg/kg (3 animals per sex at each dose level). All animals were evaluated for changes in clinical signs, food consumption, body weight, blood pressure, ECGs, respiration rates (visual), clinical pathology (hematology, clinical chemistry, coagulation, urinalysis), organ weights, and macroscopic/microscopic examination of tissues. Blood was collected for toxicokinetic (TK) analysis (v21252, total antibody, and free toxin (Compound 9)) and anti-drug antibody (ADA) analysis, and the animals were terminated on Day 36. Another group of animals was administered a single dose of 12 mg/kg v21252 on Day 1 and terminated 4, 8 and 15 days post dose (n=2 per timepoint). The study design is presented in Table 16.

TABLE 16

Non-GLP Toxicity Study Design

| Group | v21252 Dose (mg/kg) | Day Animals Terminated (Male/Female) | | | |
|---|---|---|---|---|---|
| | | 4 | 8 | 15 | 36 |
| 1 | 0 | — | — | — | 3/3 |
| 2 | 12 | 1/1 | 1/1 | 1/1 | — |
| 3 | 9 | — | — | — | 3/3 |
| 4 | 12 | — | — | — | 3/3 |

Results

Figure 10A:
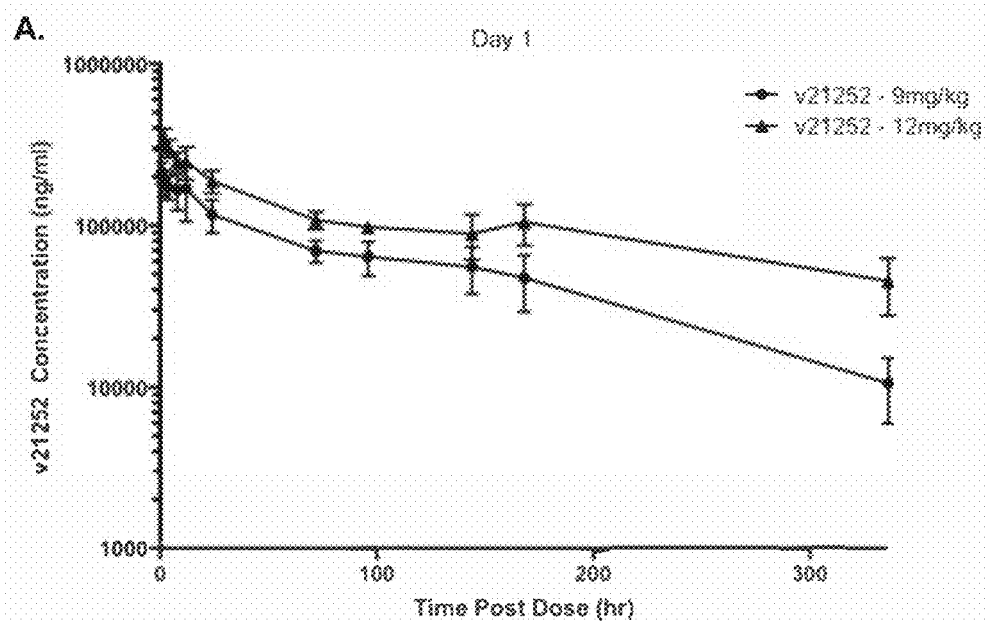
FIGS. 10A-10B show the mean (±SD) v21252 serum concentration-time profiles on Day 1 (FIG. 10A) and Day 29 (FIG. 10B) following a bi-weekly infusion of v21252 to cynomolgus monkeys (n=6) at either 12 mg/kg or 9 mg/kg.
Figure 10B:
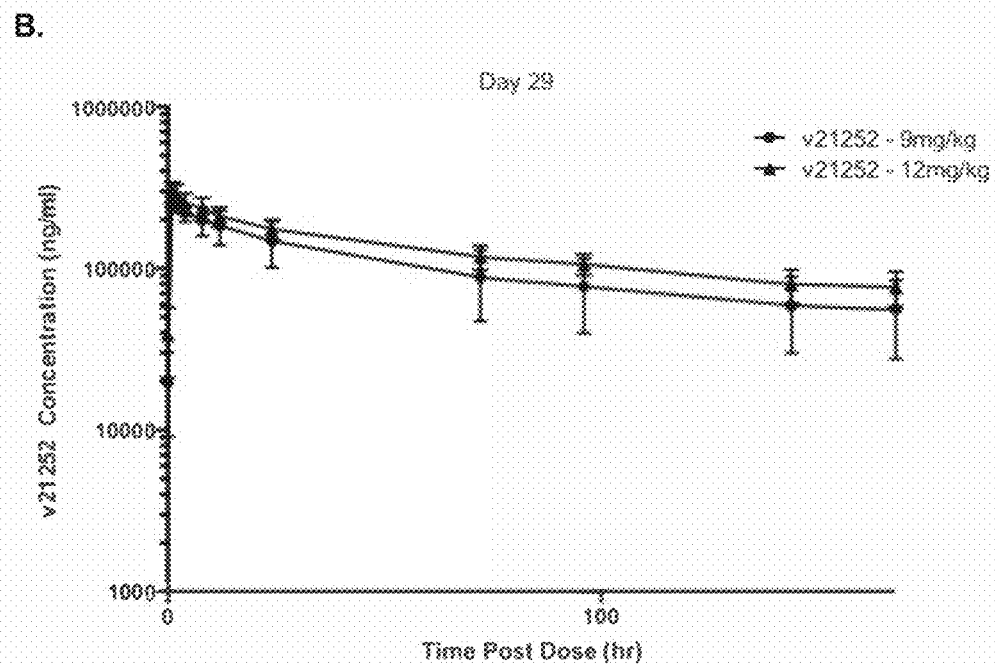

Pharmacokinetics v21252: Pharmacokinetics were calculated after repeat administration of v21252. $C_{max}$ was achieved either at the end of the 60-minute infusion or 60 minutes after the end of infusion (median $T_{max}$). The v21252 serum concentration-time profile is shown in FIGS. 10A-10B. On Day 1, $C_{max}$ and systemic exposure ($AUC_{0-168h}$) increased in a slightly greater than dose-proportional manner. On Day 29, $C_{max}$ and $AUC_{0-168h}$ increased in an approximately dose-proportional manner. Systemic exposure and $AUC_{0-168h}$ did not appear to change and showed no accumulation following repeated administration. Mean elimination half-lives ($T_{1/2}$) increased from the 9 mg/kg group to the 12 mg/kg group. A saturable clearance mechanism for v21252 may account for the difference in $T_{1/2}$ and clearance between the low (9 mg/kg) and high (12 mg/kg) dose groups.

Figure 11A:
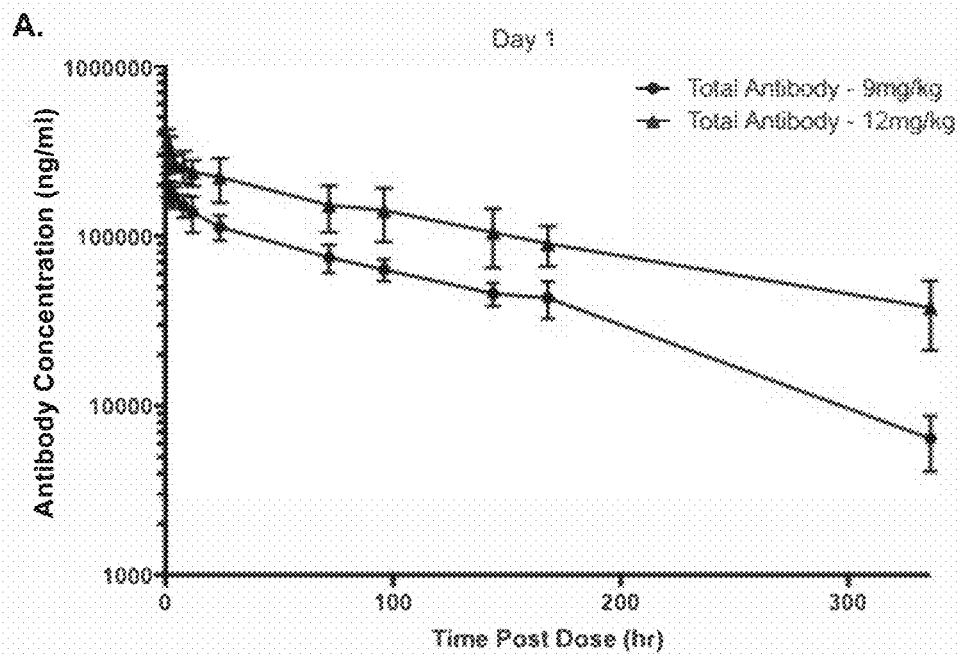
FIGS. 11A-11B show the mean (±SD) total antibody serum concentration-time profiles on Day 1 (FIG. 11A) and Day 29 (FIG. 11B) following a bi-weekly infusion of v21252 to cynomolgus monkeys (n=6) at either 12 mg/kg or 9 mg/kg.
Figure 11B:
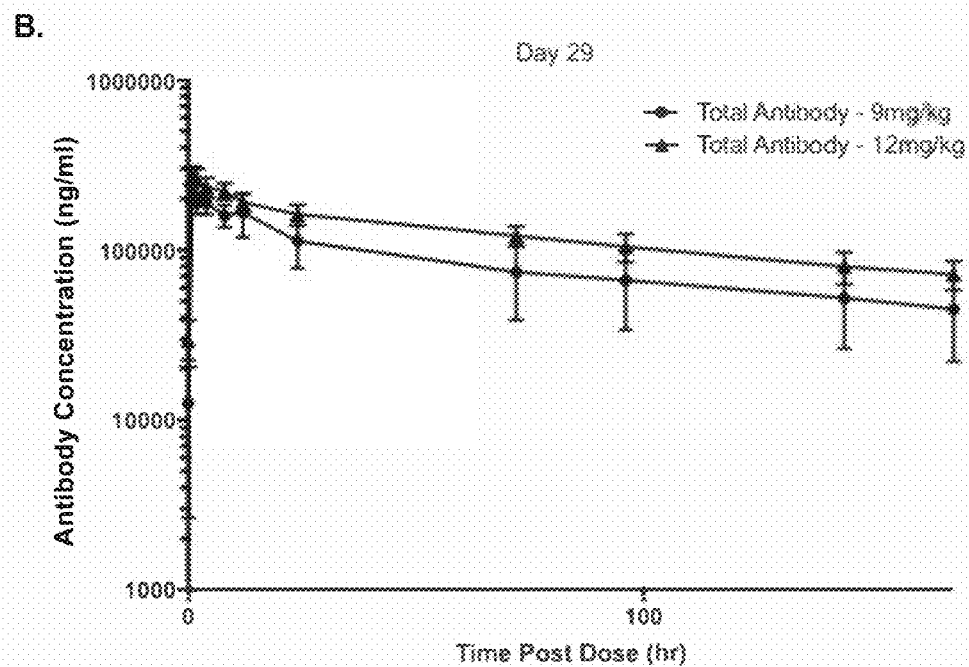

Total Antibody (conjugated and unconjugated): Total antibody was measured in cynomolgus monkeys after the repeat administrations of v21252. The $C_{max}$ for total antibody was achieved at the end of the 60-minute infusion (median $T_{max}$). The total antibody serum concentration-time profile is shown in FIGS. 11A-11B. On Day 1, $C_{max}$ and systemic exposure ($AUC_{0-168h}$) increased in a slightly greater than dose-proportional manner. On Day 29, $C_{max}$ and $AUC_{0-168h}$ increased in an approximately dose-proportional manner. Systemic exposure $AUC_{0-168h}$ was unchanged and showed no accumulation following repeated administrations. Similar to v21252, mean elimination half-lives ($T_{1/2}$) for total antibody increased from the 9 mg/kg group to the 12 mg/kg group.

Figure 12:
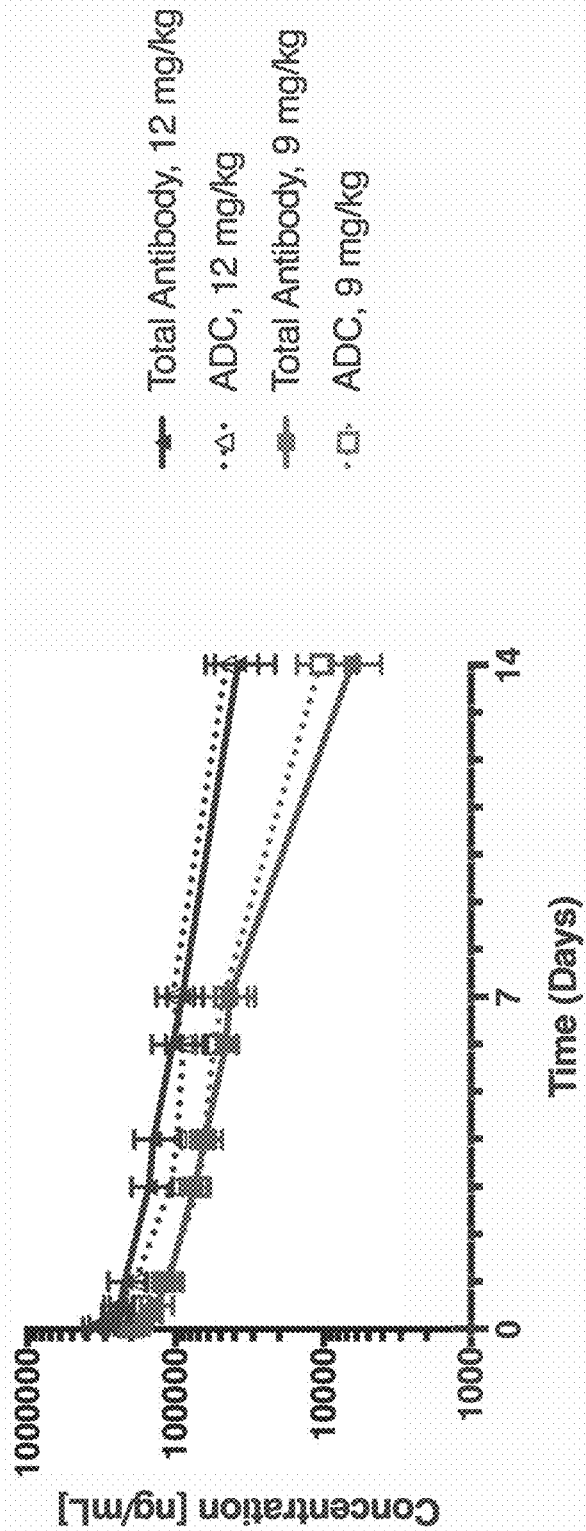
FIG. 12 shows the mean (±SD) serum concentration-time profiles for both v21252 and total antibody (conjugated and unconjugated) following a bi-weekly infusion of v21252 to cynomolgus monkeys (n=6) at either 12 mg/kg or 9 mg/kg.
Figure 13A:
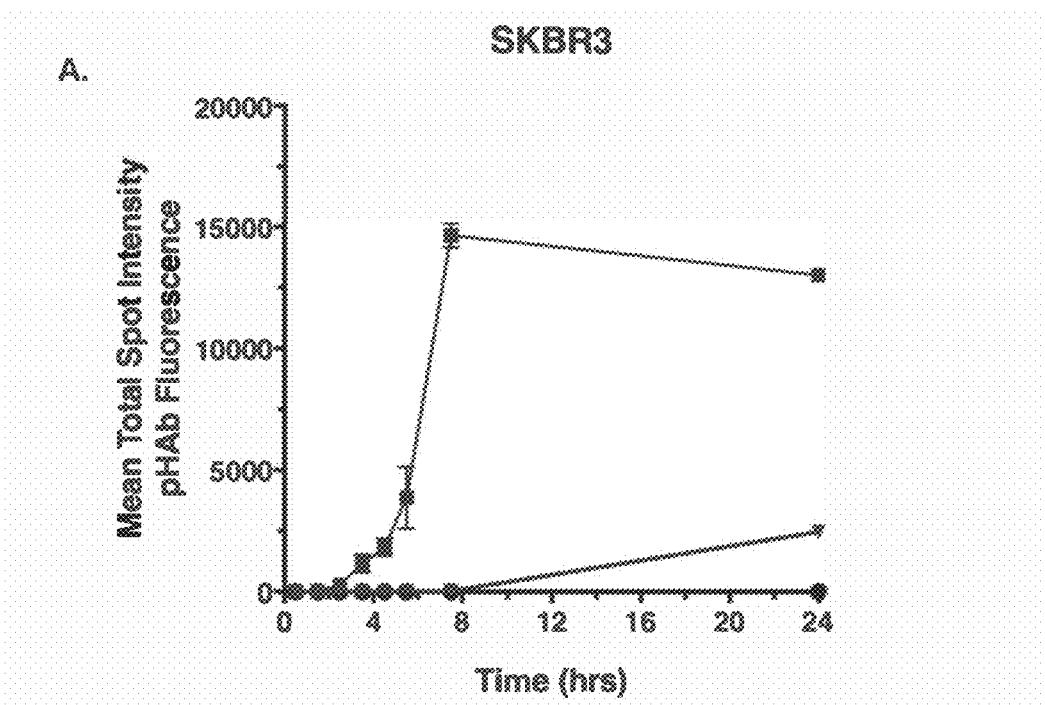
FIGS. 13A-13B show internalization of pHAb-conjugated v21252 compared to pHAb-conjugated Trastuzumab-Linker-Toxin 001 and negative control into (FIG. 13A) SKBR3 cells, and (FIG. 13B) JIMT-1 cells.
Figure 13B:
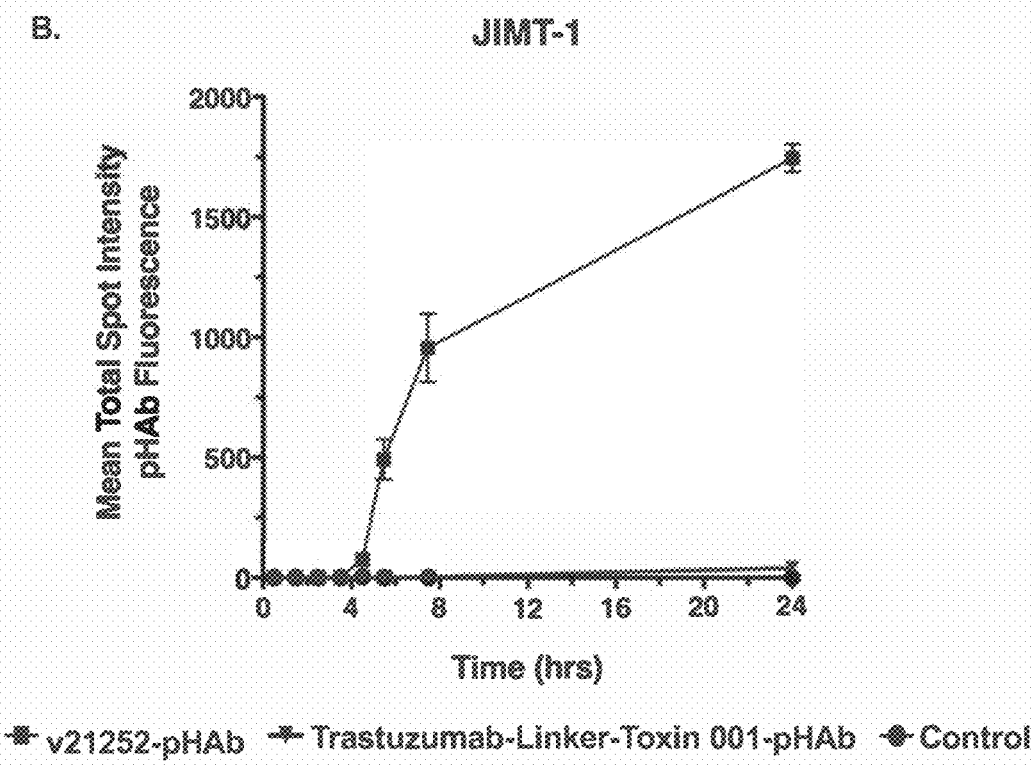

The pharmacokinetics of v21252 as indicated by the serum concentration-time profiles of v21252 and Total Antibody are indicative of minimal linker-toxin loss from v21252 in vivo (see FIG. 12).

Toxin (Compound 9): Free toxin was measured in cynomolgus monkeys after the repeat administrations of v21252. All payload (Compound 9) serum concentrations were below the limit of quantitation (<0.500 ng/mL) with the exception of one female at 12 mg/kg on Day 1, one female at 9 mg/kg on Day 29, and one male at 12 mg/kg on Day 29.

Anti-drug Antibodies (ADA): Anti-v21252 antibodies were screened in cynomolgus monkeys following the repeat administrations of v21252. ADA were detected in serum of a single female in the 9 mg/kg dosing cohort.

Toxicity

Overall, administration of v21252 was clinically well tolerated at all doses tested. No treatment related changes in urinalysis, ECG parameters, or respiratory rates were observed.

Sporadic, minimal effects on individual body weights were noted in animals receiving repeat administrations of v21252 at 12 mg/kg/dose. These animals all partially or fully recovered by Day 35. All other animals either maintained or gained weight throughout the study.

Minimal to mild changes in clinical signs, clinical pathology, organ weight or macroscopic/microscopic examination of tissues were observed in some animals. Macroscopic observations considered related to v21252 were limited to red discoloration observed at the infusion site in all animals, including controls. Test article-related organ weight changes were limited to the spleen. In animals terminated on Day 36 following 3 bi-weekly doses, microscopic treatment-related effects included changes in the gastrointestinal tract, liver, spleen, lymph nodes, pancreas, skin and the IV infusion sites. All were classified as minimal or mild. In animals terminated at various times after a single dose of 12 mg/kg, similar minimal to mild test article-related effects were observed.

The PK analysis confirmed systemic exposure in the v21252-treated animals and mean systemic exposure increased with increasing dose in a dose proportional manner for v21252 and total antibody, while exposure to free toxin (Compound 9) was only seen at low levels in a few animals.

Tables 17-20 show a comparison of the results from the PK/tolerability studies and the non-GLP repeat dose studies for v17597 and v21252.

TABLE 17

Comparison of Mortality Observed in Single-Dose and Repeat-Dose Studies for v17597 and v21252 in Cynomolgus Monkeys

| | v17597 | | | v21252 | |
|---|---|---|---|---|---|
| Dose | PK/Tolerability | Repeat-Dose Weekly | Every Other week | PK/Tolerability | Repeat-Dose |
| 12 mg/kg | — | — | — | 0/3 | 0/6 |
| 9 mg/kg | 0/3 | — | 3/6 | 0/3 | 0/6 |

TABLE 17-continued

Comparison of Mortality Observed in Single-Dose and Repeat-Dose Studies for v17597 and v21252 in Cynomolgus Monkeys

| | v17597 | | | v21252 | |
|---|---|---|---|---|---|
| Dose | PK/Toler-ability | Repeat-Dose Weekly | Every Other week | PK/Toler-ability | Repeat-Dose |
| 6 mg/kg | 0/3 | — | — | — | — |
| 4.5 mg/kg | — | 0/6 | 1/6 | — | — |
| 3 mg/kg | 0/3 | — | — | — | — |
| 2.25 mg/kg | — | 0/6 | — | — | — |

TABLE 18

Comparison of NOAEL and HNSTD Determined in Repeat-Dose Studies for v17597 and v21252 in Cynomolgus Monkeys

| | v17597 | | v21252 |
|---|---|---|---|
| | Weekly | Every Other week | |
| NOAEL | Could not be determined (<2.25 mg/kg) | Could not be determined (<4.5 mg/kg) | 12 mg/kg |
| HNSTD | Could not be determined (<2.25 mg/kg) | Could not be determined (<4.5 mg/kg) | >12 mg/kg |

TABLE 19

ADC Bioanalytical Analysis

| Drug and Dose | $AUC_{0-336hr}$ First Dose (hr*ug/mL) | $AUC_{0-336hr}$ First Dose Fold Difference[#] | $AUC_{0-168hr}$ Last Dose (hr*ug/mL) | $AUC_{0-168hr}$ Last Dose Fold Difference[#] |
|---|---|---|---|---|
| v17597 4.5 mg/kg | 9,920 | 1 | 7,180 | 1 |
| v17597 9 mg/kg | 24,600 | 2.2 | N/A | N/A |
| v21252 9 mg/kg | 18,800 | 1.9 | 18,700 | 2.60 |
| v21252 12 mg/kg | 34,900 | 3.5 | 17,700 | 2.47 |

[#]compared to v17597 @ 4.5 mg/kg

TABLE 20

Total Antibody Bioanalytical Analysis

| Drug and Dose | $AUC_{0-336}$ First Dose (hr*ug/mL) | $AUC_{0-336hr}$ First Dose Fold Difference | $AUC_{0-168}$ Last Dose (hr*ug/mL) | $AUC_{0-168hr}$ Last Dose Fold Difference |
|---|---|---|---|---|
| v17597 4.5 mg/kg | 8,090 | 1 | 7,530 | 1 |
| v17597 9 mg/kg | 18,700 | 2.3 | N/A | N/A |
| v21252 9 mg/kg | 17,400 | 2.2 | 13,900 | 1.8 |
| v21252 12 mg/kg | 37,400 | 4.6 | 20,600 | 2.7 |

[#]compared to v17597 @ 4.5 mg/kg

CONCLUSIONS

Auristatin analogues of general Formula (I) have been shown to have good in vivo tolerability when administered to mice. Conjugation of Compound 9 to the monospecific anti-HER2 antibody trastuzumab at an average DAR4 produced an ADC that showed excellent tolerability in cynomolgus monkeys with a highest non-severely toxic dose (HNSTD) of 18 mg/kg. In contrast, the ADC comprising Compound 9 conjugated to an anti-HER2 biparatopic antibody, v10000, at an average DAR4 (v17597) showed greatly decreased tolerability with a HNSTD of less than 4.5 mg/kg (Example 8). Without being limited to any particular theory, it is proposed that the decreased tolerability observed for v17597 may be due in part to the increased on-target binding and internalization of the biparatopic antibody compared to the monospecific trastuzumab, leading to increased on-target toxicity, and/or a decreased proportion of DAR0 or naked species in average DAR4 (v17597) compared to average DAR2 (v21252) that increases the toxicity associated with higher DAR species (DAR2, DAR4 and DAR6), and/or increased proportion of DAR6 species in average DAR4 compared to average DAR2 increasing the toxicity associated with the highest DAR species.

Surprisingly, however, the ADC comprising Compound 9 conjugated to v10000 at an average DAR2 (v21252) showed much improved tolerability with a HNSTD of 12 mg/kg (Example 9). This result is unexpected as it has previously been shown that the toxicity of ADCs comprising either monomethyl auristatin E (MMAE) or a maytansinoid directly correlates with the total amount of drug attached to the antibody, i.e. the relationship between DAR and the maximum tolerated dose is linear for ADCs (Hamblett, et al., Clin. Cancer Res., 10:7063-7070 (2004); Sun, et al., Bioconj Chem., 28:1371-81 (2017)). Specifically, the maximum tolerated dose of an ADC with 8 drug molecules per antibody was 50 mg/kg, and the maximum tolerated dose of an ADC with 4 drug molecules per antibody (i.e. half the amount of toxin) was 100 mg/kg (Hamblett, et al., ibid.). That is, an ADC with half the amount of toxin of the DAR8 ADC, when administered at the same antibody dose, showed an MTD that was twice that of the DAR8 ADC.

v21252 has a DAR of 2 and thus half the amount of toxin as v17597 when administered at the same antibody dose. Based on previous studies with v17597, therefore, the amount of v21252 that would be tolerated was expected to be less than 9 mg/kg (i.e. 2× the maximum dose tolerated for v17597). However, as shown in Example 9, v21252 administered to cynomolgus monkeys at doses of either 9 or 12 mg/kg every two weeks for three doses was tolerated and 12 mg/kg was designated as a no observed adverse event level (NOAEL).

Importantly, it should be noted that v21252 has less toxicity and more tolerability compared to v17597 when dosed bi-weekly, even though it has greater exposure. Based on the non-GLP toxicology study in the cynomolgus monkeys (Example 8), v17597 was considered to have adverse findings at both bi-weekly doses of 4.5 and 9 mg/kg. However, in a similar non-GLP study (Example 9), v21252 was not considered to have adverse findings at bi-weekly doses of both 9 mg/kg and 12 mg/kg, despite having approximately 1.8 to 4.6 fold increases in exposure ($AUC_{0-336hr}$ after first dose or $AUC_{0-168hr}$ last dose) compared to 4.5 mg/kg of v17597 (summarized in Tables 19 and 20).

In addition, v21252 demonstrated in vivo efficacy at exposure levels shown to be tolerated in cynomolgus monkeys. Specifically, complete responses were achieved in patient derived xenograft models of both high HER2 and low HER2 tumours at exposures tolerated in cynomolgus monkeys, as summarized in FIGS. 15A-15B (see also, Example 6).

Example 10: GLP Toxicity Study of v21252 in Cynomolgus Monkeys

In a subsequent GLP toxicity study, v21252 was administered to cynomolgus monkeys every two weeks at 0, 6, 12 and 18 mg/kg for 4 doses, with a 6 week recovery period. The highest non-severely toxic dose (HNSTD) was determined to be 18 mg/kg. v21252 was well tolerated at all doses. No clinical observations were considered adverse and no mortality was observed in this GLP study. The only consistent clinical observation was increased diarrhea. No change in body weight was observed at all doses and no clinical pathology findings (liver function—aspartate transaminase and alanine transaminase and hematology—neutrophils, platelets, hemoglobin, and lymphocytes) were considered adverse. The exposure ($C_{max}$ and $AUC_{0-168hr}$) of v21252 was virtually identical to that of v10000 (antibody alone). Details of the study are provided below.

The objective of this GLP study was to further characterize the toxicokinetics and toxicity of v21252 administered 4 times intravenously to cynomolgus monkeys.

In the GLP toxicity study, v21252 was administered to male and female cynomolgus monkeys on Days 1, 15, 29 and 43 at doses of 0, 6, 12 and 18 mg/kg, with a 6 week recovery period. The no observed adverse event level (NOAEL) was 12 mg/kg and the highest non-severely toxic dose (HNSTD) was 18 mg/kg.

Materials and Methods

In this study, vehicle or v21252 was administered to male and female cynomolgus monkeys by a 1-hr IV infusion once every other week on Days 1, 15, 29 and 43 at doses of 0, 6, 12 and 18 mg/kg (4 animals per sex at each dose level and an additional 2 animals per sex at 0, 12 and 18 mg/kg for recovery evaluation). All animals were evaluated for changes in clinical signs, food consumption, body weight, blood pressure, ECGs, respiration rates (visual), clinical pathology (hematology, clinical chemistry, coagulation, urinalysis), organ weights, and macroscopic/microscopic examination of tissues. Blood was collected for toxicokinetic (TK) analysis (v21252, total antibody, and free toxin (Compound 9)) and anti-drug antibody (ADA) analysis, and the animals were terminated on Day 50 and after 6 weeks recovery at Day 92. The study design is presented in Table 21.

TABLE 21

GLP Toxicity Study Design

| Group | v21252 Dose (mg/kg) | Animals Terminated on Day (Male/Female) | |
|---|---|---|---|
| | | D 50 | D 92 |
| 1 | 0 | 4/4 | 2/2 |
| 2 | 6 | 4/4 | — |
| 3 | 12 | 4/4 | 2/2 |
| 4 | 18 | 4/4 | 2/2 |

Results
Pharmacokinetics v21252: Median peak v21252 serum concentrations were observed by 1 hr following the start of infusion (SOI) on Days 1 and 43. Following bi-weekly administration of v21252, mean $C_{max}$ and AUC values for v21252 increased with increasing dose. Increases in $C_{max}$ were approximately proportional to dose on Day 1. On Day 1, a 1:2:3 fold increase in v21252 dose resulted in an approximate 1:2.3:3.3 fold increase in $C_{max}$ values, an approximate 1:2.6:3.8 fold increase in mean $AUC_{0-168hr}$ values, and an approximate 1:2.9:4.5 fold increase in $AUC_{0-336hr}$ values. On Day 43, $C_{max}$ and $AUC_{0-168hr}$ were approximately dose proportional. On Day 43, a 1:2:3 fold increase in v21252 dose resulted in an approximate 1:2.5:3.5 fold increase in $C_{max}$ values and an approximate 1:3.2:4.7 fold increase in $AUC_{0-168hr}$ values. Systemic exposure to v21252 did not appear to change following repeated bi-weekly IV infusion at 6 mg/kg, however, the exposure generally appeared to increase following repeated bi-weekly IV infusion at 12 and 18 mg/kg. The mean $AUC_{0-168hr}$ accumulation ratios were 1.20, 1.47 and 1.50 at 6, 12 and 18 mg/kg, respectively. Individual $AUC_{0-168hr}$ accumulation ratios ranged from 1.01 to 1.64 at 6 mg/kg, from 1.17 to 1.95 at 12 mg/kg, and from 0.983 to 2.08 at 18 mg/kg.

Total Antibody (conjugated and unconjugated): Median peak Total Antibody serum concentrations were observed by 1 hr following the SOI of v21252 on Days 1 and 43. Following bi-weekly administration of v21252, mean $C_{max}$ and $AUC_{0-168hr}$ values for Total Antibody increased with increasing dose. On Day 1, a 1:2:3 fold increase in v21252 dose resulted in an approximate 1:2.1:3.3 fold increase in C. values, an approximate 1:2.4:3.8 fold increase in $AUC_{0-168hr}$ values, and an approximate 1:2.8:4.5 fold increase in mean $AUC_{0-336hr}$ values. On Day 43, a 1:2:3 fold increase in v21252 dose resulted in an approximate 1:2.6:3.9 fold increase in $C_{max}$ values and in an approximate 1:3.1:4.8 fold increase in $AUC_{0-168hr}$ values. Systemic exposure to Total Antibody did not appear to change following repeated bi-weekly IV infusion of v21252 at 6 mg/kg, however, but did appear to increase following repeated bi-weekly IV infusion of v21252 at 12 and 18 mg/kg. The mean $AUC_{0-168hr}$ accumulation ratios were 1.20, 1.47 and 1.50 at 6, 12 and 18 mg/kg, respectively.

Toxin (Compound 9): Free toxin was measured after the repeat administrations of v21252. Most toxin (Compound 9) serum concentrations were below the limit of quantitation (<0.500 ng/mL). The following exceptions were noted: one female at 12 mg/kg on Day 43 had a single quantifiable toxin (Compound 9) concentration (0.513 ng/ml at 72 hr post dose); one male at 18 mg/kg on Day 29 had a single quantifiable toxin (Compound 9) concentration (0.532 ng/mL at 1 hr following the SOI); two males and two females at 18 mg/kg on Day 43 each had a single quantifiable toxin (Compound 9) concentration (0.555, 0.505, 0.556 and 0.653 ng/mL, respectively, at 24 hr following the SOI); and one male at 18 mg/kg on Day 43 had four consecutive quantifiable toxin (Compound 9) concentrations with an $AUC_{0-168hr}$ value of 125 hr*ng/mL.

Anti-drug Antibodies (ADA): A total of 144 samples from all dosing cohorts were screened for ADA. Seven samples were confirmed positive in the confirmatory/immunodepletion assay, including one control animal and a pretest sample from a treated animal. These latter two samples were deemed to be due to pre-existing reactive antibodies and not related to v21252 exposure. For the five remaining positive samples, one female dosed at 18 mg/kg had a detectable titer on Day 43, and the remaining 4 animals (2 females dosed at 12 mg/kg and one male and one female dosed at 18 mg/kg) had detectable titers at the Day 92 recovery point. Although the actual anti-v21252 antibody results do not suggest a strong immunogenic response in most animals, circulating v21252 could be binding with anti-v21252 antibodies, limiting the detection of the antibodies within this assay format. However, it is unlikely that ADA significantly impacted the PK of v21252 as no changes in the serum concentration time data were observed on dosing Day 43 in comparison with dosing Day 1.

Toxicity

Repeat-dose administration of v21252 (every other week×4) was generally well tolerated. There were no v21252-related deaths and no effects noted in ophthalmic and electrocardiographic evaluations, visual respiration rates, urinalysis, or troponin I assessments. There were no v21252-related changes in body weight parameters noted during the treatment or recovery periods following administration of v21252.

Increased incidence of soft/watery faeces was noted in animals administered repeated doses of v21252 at ≥6 mg/kg. In addition, sporadic inappetence was noted in male and female animals at 18 mg/kg and hunched posture was sporadically noted in female animals at 18 mg/kg. Following the recovery period, inappetence and hunched posture were absent while the incidence of soft/watery faeces decreased or resolved, suggesting reversal of v21252-related effects. During the study, animals were provided with fluid/nutritional supplementation (frozen Gatorade and PeptoPro® diet) due to repeated observations of soft/liquid faeces. Females receiving repeated administration of v21252 received fluid and/or nutritional supplementation from Day 4 (6 and 18 mg/kg) or Day 8 (12 mg/kg) until the end of the treatment period. Similarly, males receiving repeated administration of v21252 received fluid and/or nutritional supplementation from Day 8 (12 mg/kg) or Day 7 (18 mg/kg) until the end of the treatment period. No fluids or supplementation were provided during the recovery.

The clinical pathological findings were not considered to be adverse because of the limited severity and the reversibility of the findings. Test article-related hematology changes included: increases in monocyte counts, morphologic alterations in neutrophils, decreases in reticulocyte counts and red cell mass (RBC, hemoglobin and hematocrit) with concomitant increase in red blood cell distribution width. There were minimal to mild increases in mean fibrinogen concentrations relative to baseline means at Days 8 through 50 in males at 18 mg/kg and in females at ≥12 mg/kg. These changes were test article-related and indicative of an immune or inflammatory stimulus. These changes had resolved at Day 92. Treatment-related changes were observed in AST, phosphorus, total protein, albumin, globulin and citrulline.

Tables 22-25 show a comparison of the results from the non-GLP repeat dose studies for v17597 and v21252 and the GLP study for v21252.

TABLE 22

Comparison of Mortality Observed in Every Other Week Repeat-Dose Studies for v17597 and v21252 in Cynomolgus Monkeys

| | v17597 - DAR 4 | | v21252 - DAR 2 | |
|---|---|---|---|---|
| Dose | Mortality/ Total Animals | Cumulative Toxin Dose Prior to Mortality | Mortality/ Total animals | Cumulative Toxin Dose |
| 18 mg/kg | — | — | 0/12 | 1.44 mg/kg |
| 12 mg/kg | — | — | 0/6 | 0.72 mg/kg |
| | | | 0/12 | 0.96 mg/kg |
| 9 mg/kg | 3/6 | 0.36 mg/kg | 0/6 | 0.54 mg/kg |
| 6 mg/kg | — | — | 0/12 | 0.48 mg/kg |
| 4.5 mg/kg | 1/6 | 0.36 mg/kg | — | — |

TABLE 23

Comparison of NOAEL and HNSTD Determined in Every Other Week Repeat-Dose Studies for v17597 and v21252 in Cynomolgus Monkeys

| | v17597 - DAR 4 (Cumulative Toxin Dose) | v21252 - DAR 2 (Cumulative Toxin Dose) |
|---|---|---|
| NOAEL | Could not be determined <4.5 mg/kg (<0.54 mg/kg) | 12 mg/kg (0.96 mg/kg) |
| HNSTD | Could not be determined <4.5 mg/kg (<0.54 mg/kg) | 18 mg/kg (1.44 mg/kg) |

TABLE 24

Comparison of ADC PK Parameters for v17597 DAR4 and v21252 DAR2 (Toxin Dose Matched)

| Toxin Dose | Drug (Dose) | $AUC_{0-336hr}$ First Dose (hr*ug/mL) | Fold Difference[#] | Half life First Dose (Hours) | Fold Difference[#] |
|---|---|---|---|---|---|
| 0.18 mg/kg | v17597 DAR4 (4.5 mg/kg) | 9,920 | 1 | 39 | 1 |
| | v21252 DAR2 (9 mg/kg) | 18,800 | 1.9 | 85.6 | 2.2 |
| 0.36 mg/kg | v17597 DAR4 (9 mg/kg) | 24,600 | 1 | 103 | 1 |
| | v21252 DAR2 (18 mg/kg) | 49,800 | 2.0 | 179 | 1.7 |

[#]compared to v17597 DAR4 @ 4.5 and 9 mg/kg

TABLE 25

Comparison of Total Antibody PK Parameters for v17597
DAR4 and v21252 DAR2 (Toxin Dose Matched)

| Toxin Dose | Drug (Dose) | $AUC_{0-336}$ First Dose (hr*ug/mL) | Dose Fold Difference | Half life First Dose (Hours) | Fold Difference[#] |
|---|---|---|---|---|---|
| 0.18 mg/kg | v17597 DAR 4 (4.5 mg/kg) | 8,090 | 1 | 37.3 | 1 |
|  | v21252 DAR 2 (9 mg/kg) | 17,400 | 2.2 | 67.4 | 1.8 |
| 0.36 mg/kg | v17597 DAR 4 (9 mg/kg) | 18,700 | 1 | 81.9 | 1 |
|  | v21252 DAR2 (18 mg/kg) | 50,300 | 2.7 | 155 | 1.9 |

[#]compared to v17597 @ 4.5 and 9 mg/kg

CONCLUSIONS

The highest non-severely toxic dose (HNSTD) of v21252 was determined to be 18 mg/kg. v21252 was well tolerated at all doses. No clinical observations were considered adverse and no mortality was observed in this GLP study. The only consistent clinical observation was increased diarrhea. No change in body weight was observed at all doses and no clinical pathology findings (liver function—aspartate transaminase and alanine transaminase and hematology—neutrophils, platelets, hemoglobin, and lymphocytes) were considered adverse. These GLP toxicology results support clinical dosing above predicted efficacious doses in humans.

Surprisingly, the ADC comprising Compound 9 conjugated to v10000 at an average DAR2 (v21252) showed improved tolerability compared to an ADC with an average DAR4 (v17597) with a HNSTD of 18 mg/kg. This result is unexpected as it has previously been shown that toxin Compound 9 conjugated to v10000 at an average DAR4 (v17597) when administered at a toxin dose of 0.36 mg/kg was associated with mortality either when dosed acutely (with a single dose of 9 mg/kg) or sub-chronically (with two doses of 4.5 mg/kg separated by two weeks) (Example 8). In contrast, when v21252 (DAR2) was administered at 0.36 mg/kg dose of toxin (Compound 9) for four doses (a cumulative toxin dose of 1.44 mg/kg), there was no mortality and substantially reduced toxicity compared to v17597. For instance, v21252 administered at a cumulative dose of 0.96 mg/kg of toxin (Compound 9) was associated with no adverse findings and was designated as a no observed adverse event level (NOAEL). Furthermore, 1.44 mg/kg cumulative dose of toxin (Compound 9) was administered with 18 mg/kg of v21252 over 4 doses and was tolerated. This is a four-fold higher dose than the dose of v17597 that was associated with mortality (0.36 mg/kg).

Importantly, v21252 has less toxicity and more tolerability compared to v17597 when dosed every two every weeks, even though it has approximately two times greater exposure ($AUC_{0-336hr}$ after first dose) and two times longer half-life after first dose when compared at toxin-matched doses (4.5 mg/kg of v17597 v. 9 mg/kg of v21252 and 9 mg/kg of v17597 v. 18 mg/kg of v21252) (summarized in Tables 24 and 25).

Example 11: v21252 Inhibits Low HER2 Patient Derived Xenograft Growth In Vivo LTL-654 was derived from an ovarian serous carcinoma patient metastasis and was scored by immunohistochemistry (IHC) as HER2 negative. An earlier biopsy was scored by IHC as HER2 equivocal.

Female NOD Rag gamma (NRG) mice were subcutaneously implanted via the renal capsule with two LTL-654 tumour fragments, approximately 15 mm³ each. Animals were randomly assigned to one of two blinded treatment groups of six animals each when mean tumour volumes reached 70.3-77.8 mm³.

Animals were treated with either vehicle or 3 mg/kg of v21252 administered intravenously once weekly for four total injections (qw×4) (Table 21). Tumour size was measured using a Vevo®3100 imaging system (FUJIFILM VisualSonics, Inc., Toronto, Canada) using three-dimensional (3D)-mode. Multiple images (70 to 100 per tumour) throughout the whole tumour were recorded and analyzed using Vevo® LAB software v2.1.0 (FUJIFILM VisualSonics, Inc.). Tumour size was measured once weekly after randomization up to Day 24. Mice were ethically sacrificed when individual tumours reached a size of 1500 mm³. Tumour volumes are reported as the mean±SEM for each group.

Figure 16:
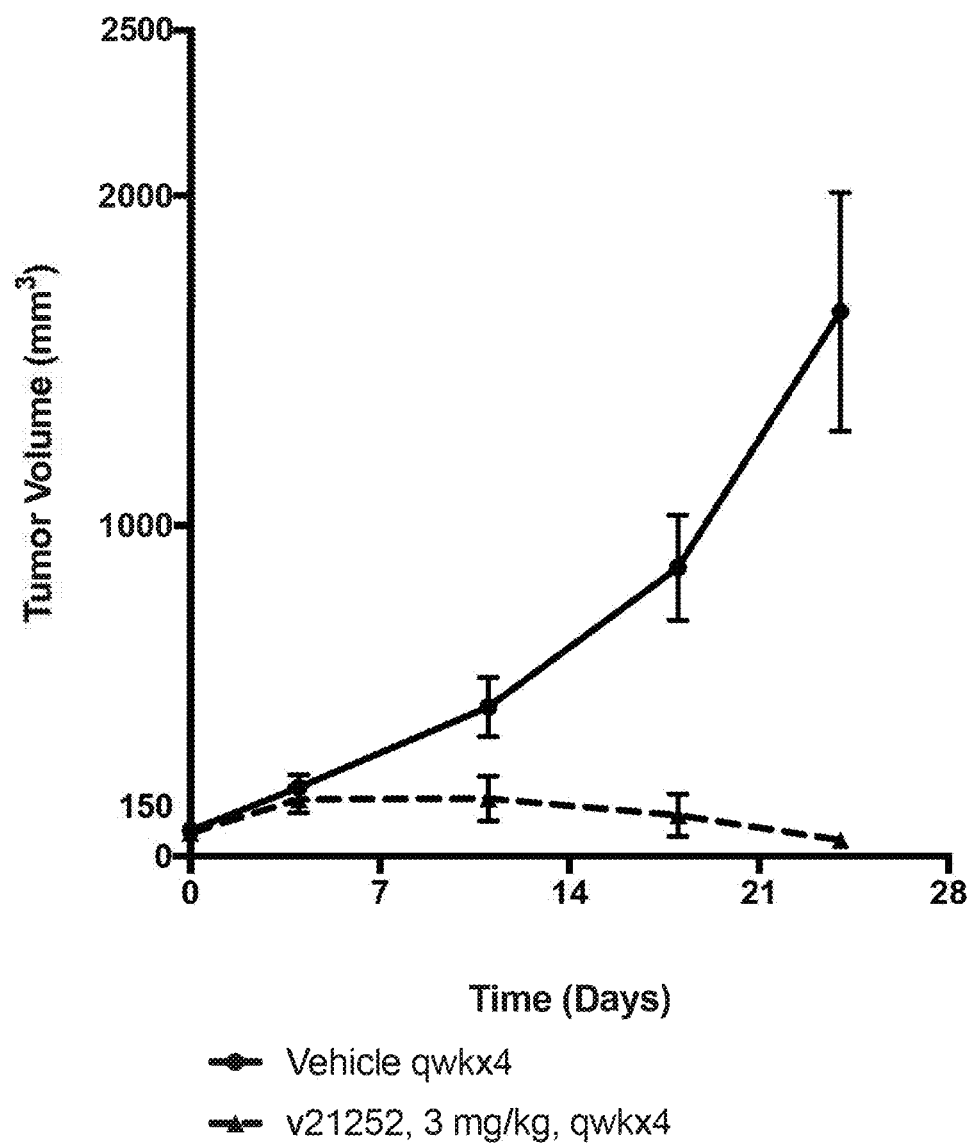
FIG. 16 shows the results of treating LTL-654 ovarian cancer patient derived xenograft mice qwk×4 with 3 mg/kg of vehicle or v21252.

FIG. 16 provides the results for the tumour response in mice subcutaneously implanted with LTL-654 tumour fragments after i.v. administration of vehicle or v21252, which demonstrate that treatment of LTL-654 engrafted mice with v21252 inhibited the growth rate of the LTL-654 tumour xenografts.

This example demonstrates that v21252 is effective in a patient derived xenograft in which HER2 expression is sufficiently low to be scored by IHC as HER2 negative.

TABLE 21

LTL-654 Ovarian Cancer PDX Model Study Design

| Test Article | Dose (mg/kg) | Route of Administration | Days of Administration | Animals per group |
|---|---|---|---|---|
| Vehicle | N/A | IV | 0, 7, 14, 21 | 6 |
| v21252 | 3 | IV | 0, 7, 14, 21 | 6 |

N/A = Not applicable

Example 12: v21252 Prolongs Survival of Mice Bearing Intracranially Implanted Human Breast Tumours In Vivo The constructs used in this example were: control conjugate (humanized antibody against respiratory syncytial virus conjugated to Linker-Toxin 001), v21252, v7155 (T-DM1, DAR3.5) and v24029 (trastuzumab conjugated at DAR8 to an exatecan-derivative topoisomerase I inhibitor (DXd)). The intracranially implanted BT-474 human breast tumours utilized in this example serve as a HER2 positive breast cancer brain metastasis model.

Female Balb/c Nude mice (CByJ.Cg-Foxn1nu/J) mice were irradiated with a 7-source (2 Gy, $^{60}$Co, BioMep, Bretenières, France). Anesthetized mice were stereotactically injected with $1×10^5$ BT-474 cells in 2 microliters of RPMI 1640 medium without phenol red. Animals were randomized into treatment groups and, starting on day 8, were administered intravenously with vehicle, control conjugate, v21252, v7155 or v24029 at 6 mg/kg every week for twelve total injections (Table 26). Body weights were recorded twice weekly until day 18 and then daily thereafter. Mice were ethically sacrificed when bodyweight loss met or exceeded 20% for 3 consecutive days.

Figure 17:
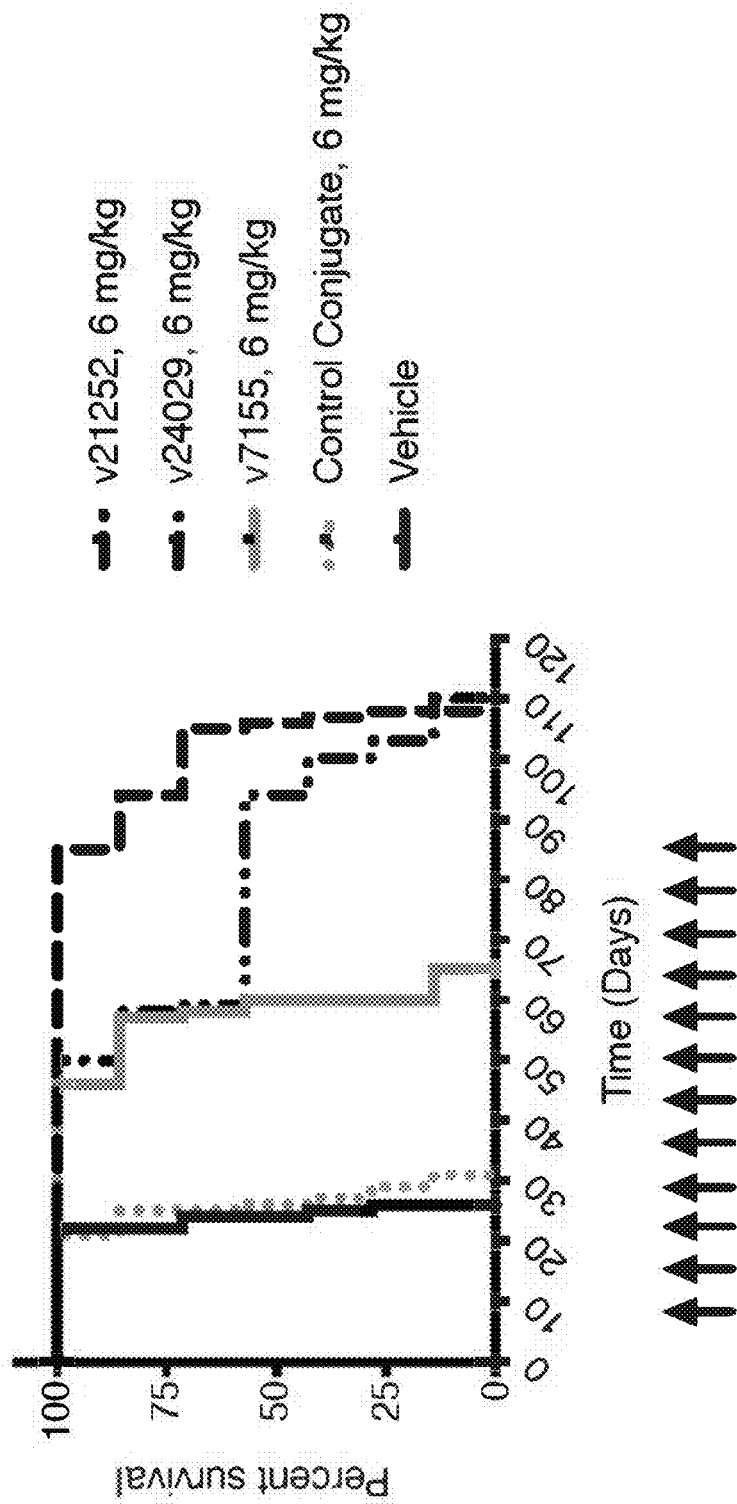
FIG. 17 provides the survival results for mice intracranially implanted with BT-474 breast tumour cells after weekly i.v. administration of vehicle, control conjugate (humanized antibody against respiratory syncytial virus conjugated to Linker-Toxin 001), v21252, v7155 (T-DM1, DAR3.5) and v24029 (trastuzumab conjugated at DAR8 to an exatecan-derivative topoisomerase I inhibitor (DXd)), each at 6 mg/kg weekly for 12 total injections.

FIG. 17 provides the survival results for mice intracranially implanted with BT-474 tumour cells after i.v. administration of vehicle, control conjugate, v21252, v7155, or v24029.

Two additional cohorts of animals intracranially implanted with BT-474 cells were also randomized into treatment groups and, starting on day 8, were administered intravenously with either v21252 or v24029 at 6 mg/kg every two weeks for six total injections. Body weights were recorded twice weekly until day 18 and then daily thereafter. Mice were ethically sacrificed when bodyweight loss met or exceeded 20% for 3 consecutive days.

Figure 18:
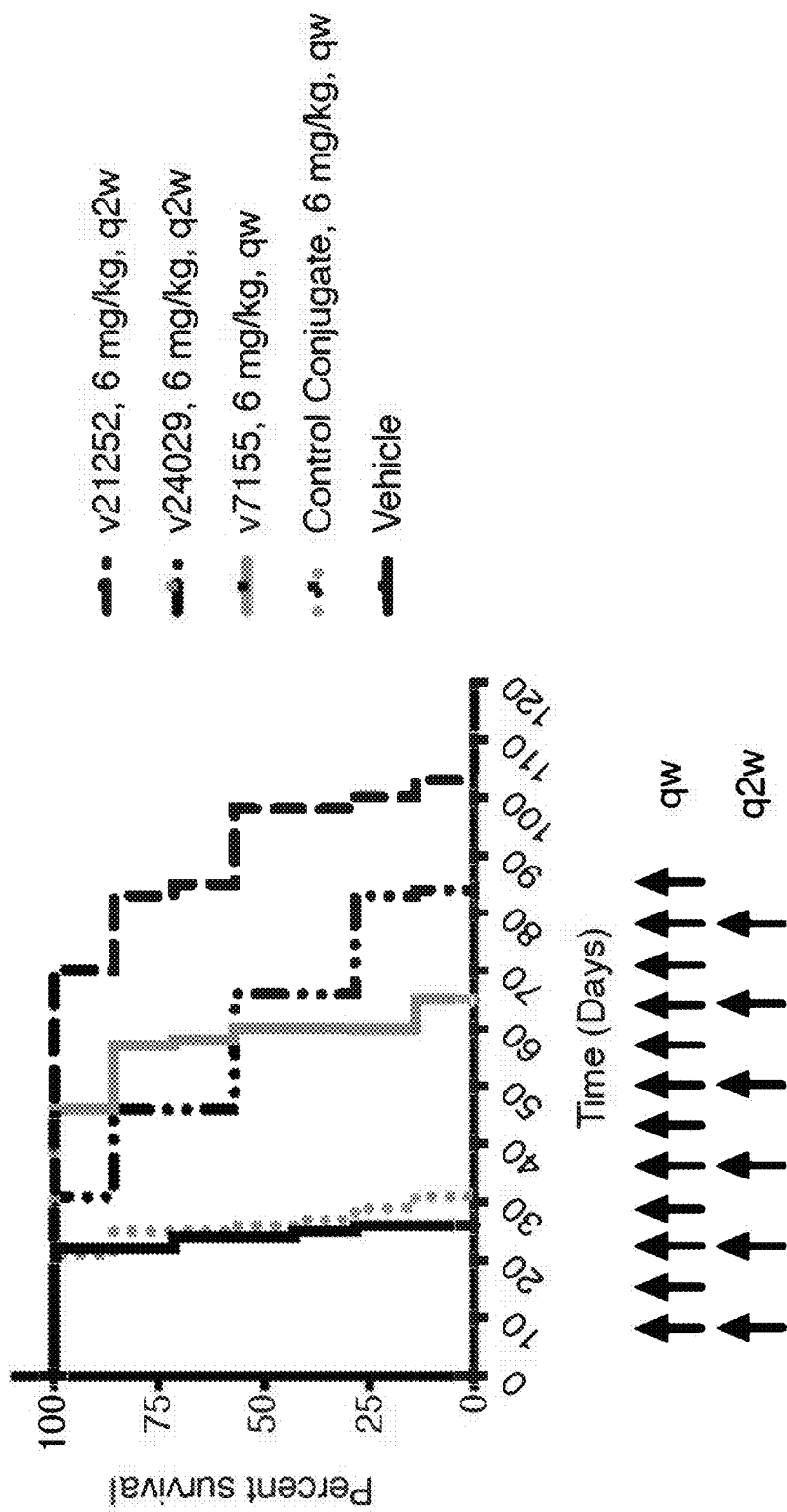
FIG. 18 provides the survival results for mice intracranially implanted with BT-474 breast tumour cells after i.v. administration of vehicle, control conjugate (humanized antibody against respiratory syncytial virus conjugated to Linker-Toxin 001), or v7155 (T-DM1, DAR3.5) at 6 mg/kg weekly for 12 total injections or v21252 or v24029 (trastuzumab conjugated at DAR8 to an exatecan-derivative topoisomerase I inhibitor (DXd)), each at 6 mg/kg every two weeks for 6 total injections.

FIG. 18 provides the survival results for mice intracranially implanted with BT-474 tumour cells after weekly (qw) i.v. administration of vehicle, control conjugate or v7155, or i.v. administration every two weeks (q2w) of either v21252 or v24029.

This example demonstrates that v21252 is effective in prolonging the survival of mice intracranially implanted with BT-474 breast tumour cells.

TABLE 26

Intracranially Implanted BT-474 Human Breast Cancer Model Study Design

| Test Article | Dose (mg/kg) | Route of Administration | Days of Administration | Animals per group |
|---|---|---|---|---|
| Vehicle | N/A | IV | 8, 15, 22, 29, 36, 43, 50, 57, 64, 71, 78, 85 | 7 |
| v21252 | 6 | IV | 8, 15, 22, 29, 36, 43, 50, 57, 64, 71, 78, 85 | 7 |
| v7155 | 6 | IV | 8, 15, 22, 29, 36, 43, 50, 57, 64, 71, 78, 85 | 7 |
| v24029 | 6 | IV | 8, 15,22, 29, 36, 43, 50, 57, 64, 71, 78, 85 | 7 |
| Control conjugate | 6 | IV | 8, 15, 22, 29, 36, 43, 50, 57, 64, 71, 78, 85 | 7 |

N/A = Not applicable

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Modifications of the specific embodiments described herein that would be apparent to those skilled in the art are intended to be included within the scope of the following claims.

SEQUENCE TABLES

TABLE A

Clone Numbers for Variants v5019, v5020, v7091, v10000, v6903, v6902 and v6717

| Variant | H1 clone # | H2 clone # | L1 clone # | L2 clone # |
|---|---|---|---|---|
| 5019 | 3057 | 720 | 1811 | — |
| 5020 | 719 | 3041 | — | 1811 |
| 7091 | 3057 | 5244 | 1811 | — |
| 10000 | 6586 | 5244 | 3382 | — |
| 6903 | 5065 | 3468 | 5037 | 3904 |
| 6902 | 5065 | 3468 | 5034 | 3904 |
| 6717 | 3317 | 720 | — | — |

TABLE B

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 3 | 3468 | Full | EVQLVESGGGLVQPGGSLRLSCAASGFTFTDYTMDWVRQAPGKGL EWVADVNPNSGGSIYNQRFKGRFTLSVDRSKNTLYLQMNSLRAED TAVYYCARNLGPSFYFDYWGQGTLVTVSSASTKGPSVFPLAPSSKS TSGGTAALGCLVKGYFPEPVTVSWNSGALTSGVHTFPAVLKSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYVLPPSRDELTKNQVSLL CLVKGFYPSDIAVEWESNGQPENNYLTWPPVLDSDGSFFLYSKLTV DKSRWQQGNVFSCSVMHEALHNHYTQKSLSLSPG |
| 4 | 3468 | Full | GAAGTGCAGCTGGTCGAATCTGGAGGAGGACTGGTGCAGCCAGG AGGGTCCCTGCGCCTGTCTTGCGCCGCTAGTGGCTTCACTTTTAC CGACTACACCATGGATTGGGTGCGACAGGCACCTGGAAAGGGCC TGGAGTGGGTCGCCGATGTGAACCCAAATAGCGGAGGCTCCATC |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | TACAACCAGCGGTTCAAGGGCCGGTTCACCCTGTCAGTGGACCG |
| | | | GAGCAAAAACACCCTGTATCTGCAGATGAATAGCCTGCGAGCCG |
| | | | AAGATACTGCTGTGTACTATTGCGCCCGGAATCTGGGGCCCTCCT |
| | | | TCTACTTTGACTATTGGGGGCAGGGAACTCTGGTCACCGTGAGCT |
| | | | CCGCCTCCACCAAGGGACCTTCTGTGTTCCCACTGGCTCCCTCTA |
| | | | GTAAATCCACATCTGGGGAACTGCAGCCCTGGGCTGTCTGGTG |
| | | | AAGGGCTACTTCCCAGAGCCCGTCACAGTGTCTTGGAACAGTGG |
| | | | CGCTCTGACTTCTGGGGTCCACACCTTTCCTGCAGTGCTGAAGTC |
| | | | AAGCGGGCTGTACAGCCTGTCCTCTGTGGTCACCGTGCCAAGTTC |
| | | | AAGCCTGGGAACACAGACTTATATCTGCAACGTGAATCACAAGC |
| | | | CATCCAATACAAAAGTCGACAAGAAAGTGGAACCCAAGTCTTGT |
| | | | GATAAAACCCATACATGCCCCCCTTGTCCTGCACCAGAGCTGCTG |
| | | | GGAGGACCAAGCGTGTTCCTGTTTCCACCCAAGCCTAAAGATAC |
| | | | ACTGATGATTAGTAGGACCCCAGAAGTCACATGCGTGGTCGTGG |
| | | | ACGTGAGCCACGAGGACCCCGAAGTCAAGTTTAACTGGTACGTG |
| | | | GACGGCGTCGAGGTGCATAATGCCAAGACTAAACCCAGGGAGG |
| | | | AACAGTACAACAGTACCTATCGCGTCGTGTCAGTCCTGACAGTG |
| | | | CTGCATCAGGATTGGCTGAACGGGAAAGAGTATAAGTGCAAAGT |
| | | | GAGCAATAAGGCTCTGCCCGCACCTATCGAGAAAACAATTTCCA |
| | | | AGGCAAAAGGACAGCCTAGAGAACCACAGGTGTACGTGCTGCCT |
| | | | CCATCAAGGGATGAGCTGACAAAGAACCAGGTCAGCCTGCTGTG |
| | | | TCTGGTGAAAGGATTCTATCCCTCTGACATTGCTGTGGAGTGGGA |
| | | | AAGTAATGGCCAGCCTGAGAACAATTACCTGACCTGGCCCCCTG |
| | | | TGCTGGACTCAGATGGCAGCTTCTTTCTGTATAGCAAGCTGACCG |
| | | | TCGACAAATCCCGGTGGCAGCAGGGGAATGTGTTTAGTTGTTCA |
| | | | GTCATGCACGAGGCACTGCACAACCATTACACCCAGAAGTCACT |
| | | | GTCACTGTCACCAGGG |
| 5 | 3468 | VH | EVQLVESGGGLVQPGGSLRLSCAASGFTFTDYTMDWVRQAPGKGL EWVADVNPNSGGSIYNQRFKGRFTLSVDRSKNTLYLQMNSLRAED TAVYYCARNLGPSFYFDYWGQGTLVTVSS |
| 6 | 3468, 3057, 3041, 3317 | H1 | GFTFTDYT |
| 7 | 3468, 3057, 3041, 3317 | H3 | ARNLGPSFYFDY |
| 8 | 3468, 3057, 3041, 3317 | H2 | VNPNSGGS |
| 9 | 1811 | Full | DIQMTQSPSSLSASVGDRVTITCKASQDVSIGVAWYQQKPGKAPKL LIYSASYRYTGVPSRFSGSGSGTDFTLTISSLQPEDFATYYCQQYYIY PYTFGQGTKVEIKRTVAAPSVFIFPPSDEQLKSGTASVVCLLNNFYPR EAKVQWKVDNALQSGNSQESVTEQDSKDSTYSLSSTLTLSKADYE KHKVYACEVTHQGLSSPVTKSFNRGEC |
| 10 | 1811 | Full | GATATTCAGATGACCCAGTCCCCAAGCTCCCTGAGTGCCTCAGTG GGCGACCGAGTCACCATCACATGCAAGGCTTCCCAGGATGTGTC TATTGGAGTCGCATGGTACCAGCAGAAGCCAGGCAAAGCACCCA AGCTGCTGATCTATAGCGCCTCCTACCGGTATACCGGCGTGCCCT CTAGATTCTCTGGCAGTGGGTCAGGAACAGACTTTACTCTGACCA TCTCTAGTCTGCAGCCTGAGGATTTCGCTACCTACTATTGCCAGC AGTACTATATCTACCCATATACCTTTGGCCAGGGGACAAAAGTG GAGATCAAGAGGACTGTGGCCGCTCCCTCCGTCTTCATTTTTCCC CCTTCTGACGAACAGCTGAAAAGTGGCACAGCCAGCGTGGTCTG TCTGCTGAACAATTTCTACCCTCGCGAAGCCAAAGTGCAGTGGA AGGTCGATAACGCTCTGCAGAGCGGCAACAGCCAGGAGTCTGTG ACTGAACAGGACAGTAAAGATTCAACCTATAGCCTGTCAAGCAC ACTGACTCTGAGCAAGGCAGACTACGAGAAGCACAAAGTGTATG CCTGCGAAGTCACACATCAGGGCGTGCCTCTCCTGTGACTAAG AGCTTTAACAGAGGAGAGTGT |
| 11 | 1811 | VL | DIQMTQSPSSLSASVGDRVTITCKASQDVSIGVAWYQQKPGKAPKL LIYSASYRYTGVPSRFSGSGSGTDFTLTISSLQPEDFATYYCQQYYIY PYTFGQGTKVEIK |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 12 | 1811, 3904, 3317 | L1 | QDVSIG |
| 13 | 1811, 3904, 3317 | L3 | QQYYIYPYT |
| 14 | 1811, 3904, 3317 | L2 | SAS |
| 15 | 5034 | Full | DYKDDDDKDIQMTQSPSSLSASVGDRVTITCRASQDVNTAVAWYQ QKPGKAPKLLIYSASFLYSGVPSRFSGSRSGTDFTLTISSLQPEDFATY YCQQHYTTPPTFGQGTKVEIKRTVAAPSVFIFPPSDERLKSGTASVV CLLNNFYPREAKVQWKVDNALQSGNSQESVTEQDSKDSTYSLSSTL TLSKADYEKHKVYACEVTHQGLSSPVTKSFNRGEC |
| 16 | 5034 | Full | GACTACAAAGACGACGATGACAAAGATATCCAGATGACCCAGTC CCCTAGCTCCCTGTCCGCTTCTGTGGGCGATAGGGTCACTATTAC CTGCCGCGCATCTCAGGACGTGAACACCGCAGTCGCCTGGTACC AGCAGAAGCCTGGGAAAGCTCCAAAGCTGCTGATCTACAGTGCA TCATTCCTGTATTCAGGAGTGCCCAGCCGGTTTAGCGGCAGCAG ATCTGGCACCGATTTCACACTGACTATTTCTAGTCTGCAGCCTGA GGACTTTGCCACATACTATTGCCAGCAGCACTATACCACACCCCC TACTTTCGGCCAGGGGACCAAAGTGGAGATCAAGCGAACTGTGG CCGCTCCAAGTGTCTTCATTTTTCCACCCAGCGATGAAAGACTGA AGTCCGGCACAGCTTCTGTGGTCTGTCTGCTGAACAATTTTTACC CCAGAGAGGCCAAAGTGCAGTGGAAGGTCGACAACGCTCTGCA GAGTGGCAACAGCCAGGAGAGCGTGACAGAACAGGATTCCAAA GACTCTACTTATAGTCTGTCAAGCACCCTGACACTGAGCAAGGC AGACTACGAAAAGCATAAAGTGTATGCCTGTGAGGTCACACATC AGGGGCTGTCATCACCAGTCACCAAATCATTCAATCGGGGGGAG TGC |
| 17 | 5034 | VL | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIK |
| 18 | 5037 | Full | DYKDDDDKDIQMTQSPSSLSASVGDRVTITCRASQDVNTAVAWYQ QKPGKAPKLLIYSASFLYSGVPSRFSGSRSGTDFTLTISSLQPEDFATY YCQQHYTTPPTFGQGTKVEIKRTVAAPSVFIFPPSDERLKSGTASVV CLLNNFYPREAKVQWKVDNALQSGNSKESVTEQDSKDSTYSLSSRL TLSKADYEKHKVYACEVTHQGLSSPVTKSFNRGEC |
| 19 | 5037 | Full | GACTACAAAGACGACGATGACAAAGATATCCAGATGACCCAGTC CCCTAGCTCCCTGTCCGCTTCTGTGGGCGATAGGGTCACTATTAC CTGCCGCGCATCTCAGGACGTGAACACCGCAGTCGCCTGGTACC AGCAGAAGCCTGGGAAAGCTCCAAAGCTGCTGATCTACAGTGCA TCATTCCTGTATTCAGGAGTGCCCAGCCGGTTTAGCGGCAGCAG ATCTGGCACCGATTTCACACTGACTATTTCTAGTCTGCAGCCTGA GGACTTTGCCACATACTATTGCCAGCAGCACTATACCACACCCCC TACTTTCGGCCAGGGGACCAAAGTGGAGATCAAGCGAACTGTGG CCGCTCCAAGTGTCTTCATTTTTCCACCCAGCGATGAAAGACTGA AGTCCGGCACAGCTTCTGTGGTCTGTCTGCTGAACAATTTTTACC CCAGAGAGGCCAAAGTGCAGTGGAAGGTCGACAACGCTCTGCA GAGTGGCAACAGCAAGGAGAGCGTGACAGAACAGGATTCCAAA GACTCTACTTATAGTCTGTCAAGCAGACTGACACTGAGCAAGGC AGACTACGAAAAGCATAAAGTGTATGCCTGTGAGGTCACACATC AGGGGCTGTCATCACCAGTCACCAAATCATTCAATCGGGGGGAG TGC |
| 20 | 5037 | VL | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIK |
| 21 | 5037 | L1 | QDVNTA |
| 22 | 5037 | L3 | QQHYTTPPT |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 23 | 5037 | L2 | SAS |
| 24 | 3382 | Full | DIQMTQSPSSLSASVGDRVTITCKASQDVSIGVAWYQQKPGKAPKL<br>LIYSASYRYTGVPSRFSGSGSGTDFTLTISSLQPEDFATYYCQQYYIY<br>PATFGQGTKVEIKRTVAAPSVFIFPPSDEQLKSGTASVVCLLNNFYPR<br>EAKVQWKVDNALQSGNSQESVTEQDSKDSTYSLSSTLTLSKADYE<br>KHKVYACEVTHQGLSSPVTKSFNRGEC |
| 25 | 3382 | Full | GATATTCAGATGACCCAGTCCCCAAGCTCCCTGAGTGCCTCAGTG<br>GGCGACCGAGTCACCATCACATGCAAGGCTTCCCAGGATGTGTC<br>TATTGGAGTCGCATGGTACCAGCAGAAGCCAGGCAAAGCACCCA<br>AGCTGCTGATCTATAGCGCCTCCTACCGGTATACCGGCGTGCCCT<br>CTAGATTCTCTGGCAGTGGGTCAGGAACAGACTTTACTCTGACCA<br>TCTCTAGTCTGCAGCCTGAGGATTTCGCTACCTACTATTGCCAGC<br>AGTACTATATCTACCCAGCCACCTTTGGCCAGGGGACAAAAGTG<br>GAGATCAAGAGGACTGTGGCCGCTCCCTCCGTCTTCATTTTTCCC<br>CCTTCTGACGAACAGCTGAAAAGTGGCACAGCCAGCGTGGTCTG<br>TCTGCTGAACAATTTCTACCCTCGCGAAGCCAAAGTGCAGTGGA<br>AGGTCGATAACGCTCTGCAGAGCGGCAACAGCCAGGAGTCTGTG<br>ACTGAACAGGACAGTAAAGATTCAACCTATAGCCTGTCAAGCAC<br>ACTGACTCTGAGCAAGGCAGACTACGAGAAGCACAAAGTGTATG<br>CCTGCGAAGTCACACATCAGGGGCTGTCCTCTCCTGTGACTAAG<br>AGCTTTAACAGAGGAGAGTGT |
| 26 | 3382 | VL | DIQMTQSPSSLSASVGDRVTITCKASQDVSIGVAWYQQKPGKAPKL<br>LIYSASYRYTGVPSRFSGSGSGTDFTLTISSLQPEDFATYYCQQYYIY<br>PATFGQGTKVEIK |
| 27 | 3382 | L1 | QDVSIG |
| 28 | 3382 | L3 | QQYYIYPAT |
| 29 | 3382 | L2 | SAS |
| 30 | 5065 | Full | EVQLVESGGGLVQPGGSLRLSCAASGFNIKDTYIHWVRQAPGKGLE<br>WVARIYPTNGYTRYADSVKGRFTISADTSKNTAYLQMNSLRAEDT<br>AVYYCSRWGGDGFYAMDYWGQGTLVTVSSASTKGPSVFPLAPSSK<br>STSGGTAALGCEVTDYFPEPVTVSWNSGALTSGVHTFPAVLQSSGL<br>YSLSSVVTVPSSSLGTQTYICNVNHKPSNTKVDKKVEPKSCDKTHTC<br>PPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKE<br>YKCKVSNKALPAPIEKTISKAKGQPREPQVYVYPPSRDELTKNQVSL<br>TCLVKGFYPSDIAVEWESNGQPENNYKTTPPVLDSDGSFALVSKLT<br>VDKSRWQQGNVFSCSVMHEALHNHYTQKSLSLSPG |
| 31 | 5065 | Full | GAGGTGCAGCTGGTCGAAAGCGGAGGAGGACTGGTGCAGCCAG<br>GAGGGTCACTGCGACTGAGCTGCGCAGCTTCCGGCTTCAACATC<br>AAGGACACCTACATTCACTGGGTCCGCCAGGCTCCTGGAAAAGG<br>CCTGGAGTGGGTGGCACGAATCTATCCAACTAATGGATACACCC<br>GGTATGCCGACTCCGTGAAGGGCCGGTTCACCATTTCTGCAGAT<br>ACAAGTAAAAACACTGCCTACCTGCAGATGAACAGCCTGCGAGC<br>CGAAGATACAGCCGTGTACTATTGCAGCCGATGGGGAGGCGACG<br>GCTTCTACGCTATGGATTATTGGGGGCAGGGAACCCTGGTCACA<br>GTGAGCTCCGCATCAACAAAGGGGCCTAGCGTGTTTCCACTGGC<br>CCCCTCTAGTAAATCCACCTCTGGGGGAACAGCAGCCCTGGGAT<br>GTGAGGTGACCGACTACTTCCCAGAGCCCGTCACTGTGAGCTGG<br>AACTCCGGCGCCCTGACATCTGGGGTCCATACTTTTCCTGCTGTG<br>CTGCAGTCAAGCGGCCTGTACAGCCTGTCCTCTGTGGTCACTGTG<br>CCAAGTTCAAGCCTGGGGACTCAGACCTATATCTGCAACGTGAA<br>TCACAAGCCATCCAATACCAAAGTCGACAAGAAAGTGGAACCCA<br>AGTCTTGTGATAAAACACATACTTGCCCCCCTTGTCCTGCACCAG<br>AGCTGCTGGAGGACCAAGCGTGTTCCTGTTTCCACCCAAGCCT<br>AAAGACACCCTGATGATTAGTAGGACTCCAGAAGTCACCTGCGT<br>GGTCGTGGACGTGAGCCACGAGGACCCCGAAGTCAAGTTCAACT<br>GGTACGTGGATGGCGTCGAGGTGCATAATGCCAAGACAAAACCC<br>AGGGAGGAACAGTACAACTCCACTTATCGCGTCGTGTCTGTCCT<br>GACCGTGCTGCACCAGGACTGGCTGAACGGCAAGGAGTATAAGT<br>GCAAAGTGAGCAATAAGGCTCTGCCCGCACCTATCGAGAAAACA<br>ATTTCCAAGGCTAAAGGGCAGCCTAGAGAACCACAGGTGTACGT<br>GTACCCTCCATCTAGGGACGAGCTGACCAAGAACCAGGTCAGTC<br>TGACATGTCTGGTGAAAGGGTTCTATCCCAGCGATATCGCAGTG<br>GAGTGGGAATCAAATGGACAGCCTGAGAACAATTACAAGACCAC<br>ACCCCCTGTGCTGGACTCTGATGGAAGTTTCGCCCTGGTGAGTAA |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | GCTGACCGTCGATAAATCACGGTGGCAGCAGGGCAACGTGTTCA GCTGTTCAGTGATGCACGAAGCACTGCACAACCACTACACCCAG AAAAGCCTGTCCCTGTCCCCCGGC |
| 32 | 5065 | VH | EVQLVESGGGLVQPGGSLRLSCAASGFNIKDTYIHWVRQAPGKGLE WVARIYPTNGYTRYADSVKGRFTISADTSKNTAYLQMNSLRAEDT AVYYCSRWGGDGFYAMDYWGQGTLVTVSS |
| 33 | 5065, 720, 719 | H1 | GFNIKDTY |
| 34 | 5065, 720, 719 | H3 | SRWGGDGFYAMDY |
| 35 | 5065, 720, 719 | H2 | IYPTNGYT |
| 36 | 6586 | Full | EVQLVESGGGLVQPGGSLRLSCAASGFTFADYTMDWVRQAPGKGL EWVGDVNPNSGGSIYNQRFKGRFTFSVDRSKNTLYLQMNSLRAED TAVYYCARNLGPSFYFDYWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYVYPPSRDELTKNQVSLT CLVKGFYPSDIAVEWESNGQPENNYKTTPPVLDSDGSFALVSKLTV DKSRWQQGNVFSCSVMHEALHNHYTQKSLSLSPG |
| 37 | 6586 | Full | GAGGTGCAGCTGGTGGAATCAGGAGGGGGCCTGGTGCAGCCCG GAGGGTCTCTGCGACTGTCATGTGCCGCTTCTGGGTTCACTTTCG CAGACTACACAATGGATTGGGTGCGACAGGCCCCCGGAAAGGG ACTGGAGTGGGTGGGCGATGTCAACCCTAATTCTGGCGGGAGTA TCTACAACCAGCGGTTCAAGGGGAGATTCACTTTTTCAGTGGAC AGAAGCAAAAACACCCTGTATCTGCAGATGAACAGCCTGAGGGC CGAAGATACCGCTGTCTACTATTGCGCTCGCAATCTGGGCCCCAG TTTCTACTTTGACTATTGGGGGCAGGGAACCCTGGTGACAGTCAG CTCCGCTAGCACTAAGGGGCCTTCCGTGTTTCCACTGGCTCCCTC TAGTAAATCCACCTCTGGAGGCACAGCTGCACTGGGATGTCTGG TGAAGGATTACTTTCCCTGAACCAGTCACAGTGAGTTGGAACTCA GGGGCTCTGACAAGTGGAGTCCATACTTTTCCCGCAGTGCTGCA GTCAAGCGGACTGTACTCCCTGTCCTCTGTGGTCACCGTGCCTAG TTCAAGCCTGGGCACCCAGACATATATCTGCAACGTGAATCACA AGCCATCAAATACAAAAGTCGACAAGAAAGTGGAGCCCAAGAG CTGTGATAAAACTCATACCTGCCCACCTTGTCCGGCGCCAGAACT GCTGGGAGGACCAAGCGTGTTCCTGTTTCCACCCAAGCCTAAAG ACACCCTGATGATTTCCCGGACTCCTGAGGTCACCTGCGTGGTCG TGGACGTGTCTCACGAGGACCCCGAAGTCAAGTTCAACTGGTAC GTGGATGGCGTCGAAGTGCATAATGCCAAGACCAAACCCCGGGA GGAACAGTACAACTCTACCTATAGAGTCGTGAGTGTCCTGACAG TGCTGCACCAGGACTGGCTGAATGGGAAGGAGTATAAGTGTAAA GTGAGCAACAAAGCCCTGCCCGCCCCAATCGAAAAAACAATCTC TAAAGCAAAAGGACAGCCTCGCGAACCACAGGTCTACGTCTACC CCCCATCAAGAGATGAACTGACAAAAAATCAGGTCTCTCTGACA TGCCTGGTCAAAGGATTCTACCCTTCCGACATCGCCGTGGAGTGG GAAAGTAACGGCCAGCCCGAGAACAATTACAAGACCACACCCCC TGTCCTGGACTCTGATGGGAGTTTCGCTCTGGTGTCAAAGCTGAC CGTCGATAAAAGCCGGTGGCAGCAGGGCAATGTGTTTAGCTGCT CCGTCATGCACGAAGCCCTGCACAATCACTACACACGAAGTCC CTGAGCCTGAGCCCTGGC |
| 38 | 6586 | VH | EVQLVESGGGLVQPGGSLRLSCAASGFTFADYTMDWVRQAPGKGL EWVGDVNPNSGGSIYNQRFKGRFTFSVDRSKNTLYLQMNSLRAED TAVYYCARNLGPSFYFDYWGQGTLVTVSS |
| 39 | 6586 | H1 | GFTFADYT |
| 40 | 6586 | H3 | ARNLGPSFYFDY |
| 41 | 6586 | H2 | VNPNSGGS |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 42 | 3904 | Full | YPYDVPDYATGSDIQMTQSPSSLSASVGDRVTITCKASQDVSIGVA WYQQKPGKAPKLLIYSASYRYTGVPSRFSGSGSGTDFTLTISSLQPE DFATYYCQQYYIYPYTFGQGTKVEIKRTVAAPSVFIFPPSDEELKSGT ASVVCLLNNFYPREAKVQWKVDNALQSGNSEESVTEQDSKDSTYS LSSTLELSKADYEKHKVYACEVTHQGLSSPVTKSFNRGEC |
| 43 | 3904 | Full | TATCCCTACGATGTGCCTGACTACGCTACTGGCTCCGATATCCAG ATGACCCAGTCTCCAAGCTCCCTGAGTGCATCAGTGGGGGACCG AGTCACCATCACATGCAAGGCTTCCCAGGATGTGTCTATTGGAGT CGCATGGTACCAGCAGAAGCCAGGCAAAGCACCCAAGCTGCTGA TCTACAGCGCCTCCTACCGGTATACTGGGGTGCCTTCCAGATTCT CTGGCAGTGGGTCAGGAACCGACTTTACTCTGACCATCTCTAGTC TGCAGCCCGAGGATTTCGCCACCTACTATTGCCAGCAGTACTATA TCTACCCTTATACCTTTGGCCAGGGGACAAAAGTGGAGATCAAG AGGACAGTGGCCGCTCCAAGTGTCTTCATTTTTCCCCCTTCCGAC GAAGAGCTGAAAAGTGGAACTGCTTCAGTGGTCTGTCTGCTGAA CAATTTCTACCCCGCGAAGCCAAAGTGCAGTGGAAGGTCGATA ACGCTCTGCAGAGCGGCAATTCCGAGGAGTCTGTGACAGAACAG GACAGTAAAGATTCAACTTATAGCCTGTCAAGCACACTGGAGCT GTCTAAGGCAGACTACGAGAAGCACAAAGTGTATGCCTGCGAAG TCACCCATCAGGGGCTGTCCTCTCCCGTGACAAAGAGCTTTAACA GAGGAGAGTGT |
| 44 | 3904 | VL | DIQMTQSPSSLSASVGDRVTITCKASQDVSIGVAWYQQKPGKAPKL LIYSASYRYTGVPSRFSGSGSGTDFTLTISSLQPEDFATYYCQQYYIY PYTFGQGTKVEIK |
| 45 | 719 | Full | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIKGGSGGGSGGGSGGGSGGGSGEVQLVESGGGLVQP GGSLRLSCAASGFNIKDTYIHWVRQAPGKGLEWVARIYPTNGYTRY ADSVKGRFTISADTSKNTAYLQMNSLRAEDTAVYYCSRWGGDGFY AMDYWGQGTLVTVSSAAEPKSSDKTHTCPPCPAPELLGGPSVFLFP PKPKDTLMISRTPEVTCVVVDVSHEDPEVKFNWYVDGVEVHNAKT KPREEQYNSTYRVVSVLTVLHQDWLNGKEYKCKVSNKALPAPIEK TISKAKGQPREPQVYTYPPSRDELTKNQVSLTCLVKGFYPSDIAVEW ESNGQPENNYKTTPPVLDEDGSFALVSKLTVDKSRWQQGNVFSCSV MHEALHNHYTQKSLSLSPGK |
| 46 | 719 | Full | GACATCCAGATGACCCAGTCTCCATCCTCCCTGTCTGCATCTGTA GGAGACAGAGTCACCATCACTTGCCGGGCAAGTCAGGACGTTAA CACCGCTGTAGCTTGGTATCAGCAGAAACCAGGGAAAGCCCCTA AGCTCCTGATCTATTCTGCATCCTTTTTGTACAGTGGGGTCCCAT CAAGGTTCAGTGGCAGTCGATCTGGGACAGATTTCACTCTCACC ATCAGCAGTCTGCAACCTGAAGATTTTGCAACTTACTACTGTCAA CAGCATTACACTACCCCACCCACTTTCGGCCAAGGGACCAAAGT GGAGATCAAAGGTGGTTCTGGTGGTGGTTCTGGTGGTGGTTCTG GTGGTGGTTCTGGTGGTGGTTCTGGTGAAGTGCAGCTGGTGGAG TCTGGGGGAGGCTTGGTACAGCCTGGCGGGTCCCTGAGACTCTC CTGTGCAGCCTCTGGATTCAACATTAAAGATACTTATATCCACTG GGTCCGGCAAGCTCCAGGGAAGGGCCTGGAGTGGGTCGCACGTA TTTATCCCACAAATGGTTACACACGGTATGCGGACTCTGTGAAG GGCCGATTCACCATCTCCGCAGACACTTCCAAGAACACCGCGTA TCTGCAAATGAACAGTCTGAGAGCTGAGGACACGGCCGTTTATT ACTGTTCAAGATGGGGCGGAGACGGTTTCTACGCTATGGACTAC TGGGGCCAAGGGACCCTGGTCACCGTCTCCTCAGCCGCCGAGCC CAAGAGCAGCGATAAGACCCACACCTGCCCTCCCTGTCCAGCTC CAGAACTGCTGGGAGGACCTAGCGTGTTCCTGTTTCCCCCTAAGC CAAAAGACACTCTGATGATTTCCAGGACTCCCGAGGTGACCTGC GTGGTGGTGGACGTGTCTCACGAGGACCCCGAAGTGAAGTTCAA CTGGTACGTGGATGGCGTGGAAGTGCATAATGCTAAGACAAAAC CAAGAGAGGAACAGTACAACTCCACTTATCGCGTCGTGAGCGTG CTGACCGTGCTGCACCAGGACTGGCTGAACGGGAAGGAGTATAA GTGCAAAGTCAGTAATAAGGCCCTGCCTGCTCCAATCGAAAAAA CCATCTCTAAGGCCAAAGGCCAGCCAAGGGAGCCCCAGGTGTAC ACATACCCACCCAGCAGAGACGAACTGACCAAGAACCAGGTGTC CCTGACATGTCTGGTGAAAGGCTTCTATCCTAGTGATATTGCTGT GGAGTGGGAATCAAATGGACAGCCAGAGAACAATTACAAGACC ACACCTCCAGTGCTGGACGAGGATGGCAGCTTCGCCCTGGTGTC CAAGCTGACAGTGGATAAATCTCGATGGCAGCAGGGGAACGTGT TTAGTTGTTCAGTGATGCATGAAGCCCTGCACAATCATTACACTC AGAAGAGCCTGTCCCTGTCTCCCGGCAAA |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 47 | 719 | VL | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIK |
| 48 | 719 | VH | EVQLVESGGGLVQPGGSLRLSCAASGFNIKDTYIHWVRQAPGKGLE WVARIYPTNGYTRYADSVKGRFTISADTSKNTAYLQMNSLRAEDT AVYYCSRWGGDGFYAMDYWGQGTLVTVSS |
| 49 | 720 | Full | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIKGGSGGGSGGGSGGGSGGGSGEVQLVESGGGLVQP GGSLRLSCAASGFNIKDTYIHWVRQAPGKGLEWVARIYPTNGYTRY ADSVKGRFTISADTSKNTAYLQMNSLRAEDTAVYYCSRWGGDGFY AMDYWGQGTLVTVSSAAEPKSSDKTHTCPPCPAPELLGGPSVFLFP PKPKDTLMISRTPEVTCVVVDVSHEDPEVKFNWYVDGVEVHNAKT KPREEQYNSTYRVVSVLTVLHQDWLNGKEYKCKVSNKALPAPIEK TISKAKGQPREPQVYTLPPSRDELTKNQVSLICLVKGFYPSDIAVEW ESNGQPENRYMTWPPVLDSDGSFFLYSKLTVDKSRWQQGNVFSCS VMHEALHNHYTQKSLSLSPGK |
| 50 | 720 | Full | GACATCCAGATGACCCAGTCTCCATCCTCCCTGTCTGCATCTGTA GGAGACAGAGTCACCATCACTTGCCGGGCAAGTCAGGACGTTAA CACCGCTGTAGCTTGGTATCAGCAGAAACCAGGGAAAGCCCCTA AGCTCCTGATCTATTCTGCATCCTTTTTGTACAGTGGGGTCCCAT CAAGGTTCAGTGGCAGTCGATCTGGGACAGATTTCACTCTCACC ATCAGCAGTCTGCAACCTGAAGATTTTGCAACTTACTACTGTCAA CAGCATTACACTACCCCACCCACTTTCGGCCAAGGGACCAAAGT GGAGATCAAAGGTGGTTCTGGTGGTGGTTCTGGTGGTGGTTCTG GTGGTGGTTCTGGTGGTGGTTCTGGTGAAGTGCAGCTGGTGGAG TCTGGGGGAGGCTTGGTACAGCCTGGCGGGTCCCTGAGACTCTC CTGTGCAGCCTCTGGATTCAACATTAAAGATACTTATATCCACTG GGTCCGGCAAGCTCCAGGGAAGGGCCTGGAGTGGGTCGCACGTA TTTATCCCACAAATGGTTACACACGGTATGCGGACTCTGTGAAG GGCCGATTCACCATCTCCGCAGACACTTCCAAGAACACCGCGTA TCTGCAAATGAACAGTCTGAGAGCTGAGGACACGGCCGTTTATT ACTGTTCAAGATGGGGCGGAGACGGTTTCTACGCTATGGACTAC TGGGGCCAAGGGACCCTGGTCACCGTCTCCTCAGCCGCCGAGCC CAAGAGCAGCGATAAGACCCACACCTGCCCTCCTGTCCAGCTC CAGAACTGCTGGGAGGACCTAGCGTGTTCCTGTTTCCCCCTAAGC CAAAAGACACTCTGATGATTTCCAGGACTCCCGAGGTGACCTGC GTGGTGGTGGACGTGTCTCACGAGGACCCCGAAGTGAAGTTCAA CTGGTACGTGGATGGCGTGGAAGTGCATAATGCTAAGACAAAAC CAAGAGAGGAACAGTACAACTCCACTTATCGCGTCGTGAGCGTG CTGACCGTGCTGCACCAGGACTGGCTGAACGGGAAGGAGTATAA GTGCAAAGTCAGTAATAAGGCCCTGCCTGCTCCAATCGAAAAAA CCATCTCTAAGGCCAAAGGCCAGCCAAGGGAGCCCCAGGTGTAC ACACTGCCACCCAGCAGAGACGAACTGACCAAGAACCAGGTGTC CCTGATCTGTCTGGTGAAAGGCTTCTATCCTAGTGATATTGCTGT GGAGTGGGAATCAAATGGACAGCCAGAGAACAGATACATGACC TGGCCTCCAGTGCTGGACAGCGATGGCAGCTTCTTCCTGTATTCC AAGCTGACAGTGGATAAATCTCGATGGCAGCAGGGGAACGTGTT TAGTTGTTCAGTGATGCATGAAGCCCTGCACAATCATTACACTCA GAAGAGCCTGTCCCTGTCTCCCGGCAAA |
| 51 | 720 | VL | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIK |
| 52 | 720 | VH | EVQLVESGGGLVQPGGSLRLSCAASGFNIKDTYIHWVRQAPGKGLE WVARIYPTNGYTRYADSVKGRFTISADTSKNTAYLQMNSLRAEDT AVYYCSRWGGDGFYAMDYWGQGTLVTVSS |
| 53 | 3041 | Full | EVQLVESGGGLVQPGGSLRLSCAASGFTFTDYTMDWVRQAPGKGL EWVADVNPNSGGSIYNQRFKGRFTLSVDRSKNTLYLQMNSLRAED TAVYYCARNLGPSFYFDYWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYVLPPSRDELTKNQVSLL CLVKGFYPSDIAVEWESNGQPENNYLTWPPVLDSDGSFFLYSKLTV DKSRWQQGNVFSCSVMHEALHNHYTQKSLSLSPG |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 54 | 3041 | Full | GAAGTGCAGCTGGTCGAATCTGGAGGAGGACTGGTGCAGCCAGG<br>AGGGTCCCTGCGCCTGTCTTGCGCCGCTAGTGGCTTCACTTTTAC<br>CGACTACACCATGGATTGGGTGCGACAGGCACCTGGAAAGGGCC<br>TGGAGTGGGTCGCCGATGTGAACCCAAATAGCGGAGGCTCCATC<br>TACAACCAGCGGTTCAAGGGCCGGTTCACCCTGTCAGTGGACCG<br>GAGCAAAAACACCCTGTATCTGCAGATGAATAGCCTGCGAGCCG<br>AAGATACTGCTGTGTACTATTGCGCCCGGAATCTGGGGCCCTCCT<br>TCTACTTTGACTATTGGGGGCAGGGAACTCTGGTCACCGTGAGCT<br>CCGCCTCCACCAAGGGACCTTCTGTGTTCCCACTGGCTCCCTCTA<br>GTAAATCCACATCTGGGGAACTGCAGCCCTGGGCTGTCTGGTG<br>AAGGACTACTTCCCAGAGCCCGTCACAGTGTCTTGGAACAGTGG<br>CGCTCTGACTTCTGGGGTCCACACCTTTCCTGCAGTGCTGCAGTC<br>AAGCGGGCTGTACAGCCTGTCCTCTGTGGTCACCGTGCCAAGTTC<br>AAGCCTGGGAACACAGACTTATATCTGCAACGTGAATCACAAGC<br>CATCCAATACAAAAGTCGACAAGAAAGTGGAACCCAAGTCTTGT<br>GATAAAACCCATACATGCCCCCCTTGTCCTGCACCAGAGCTGCTG<br>GGAGGACCAAGCGTGTTCCTGTTTCCACCCAAGCCTAAAGATAC<br>ACTGATGATTAGTAGGACCCCAGAAGTCACATGCGTGGTCGTGG<br>ACGTGAGCCACGAGGACCCCGAAGTCAAGTTTAACTGGTACGTG<br>GACGGCGTCGAGGTGCATAATGCCAAGACTAAACCCAGGGAGG<br>AACAGTACAACAGTACCTATCGCGTCGTGTCAGTCCTGACAGTG<br>CTGCATCAGGATTGGCTGAACGGGAAAGAGTATAAGTGCAAAGT<br>GAGCAATAAGGCTCTGCCCGCACCTATCGAGAAAACAATTTCCA<br>AGGCAAAAGGACAGCCTAGAGAACCACAGGTGTACGTGCTGCCT<br>CCATCAAGGGATGAGCTGACAAAGAACCAGGTCAGCCTGCTGTG<br>TCTGGTGAAAGGATTCTATCCCTCTGACATTGCTGTGGAGTGGGA<br>AAGTAATGGCCAGCCTGAGAACAATTACCTGACCTGGCCCCCTG<br>TGCTGGACTCAGATGGCAGCTTCTTTCTGTATAGCAAGCTGACCG<br>TCGACAAATCCCGGTGGCAGCAGGGGAATGTGTTTAGTTGTTCA<br>GTCATGCACGAGGCACTGCACAACCATTACACCCAGAAGTCACT<br>GTCACTGTCACCAGGG |
| 55 | 3041 | VH | EVQLVESGGGLVQPGGSLRLSCAASGFTFTDYTMDWVRQAPGKGL<br>EWVADVNPNSGGSIYNQRFKGRFTLSVDRSKNTLYLQMNSLRAED<br>TAVYYCARNLGPSFYFDYWGQGTLVTVSS |
| 56 | 3057 | Full | EVQLVESGGGLVQPGGSLRLSCAASGFTFTDYTMDWVRQAPGKGL<br>EWVADVNPNSGGSIYNQRFKGRFTLSVDRSKNTLYLQMNSLRAED<br>TAVYYCARNLGPSFYFDYWGQGTLVTVSSASTKGPSVFPLAPSSKS<br>TSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCP<br>PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYVYPPSRDELTKNQVSLT<br>CLVKGFYPSDIAVEWESNGQPENNYKTTPPVLDSDGSFALVSKLTV<br>DKSRWQQGNVFSCSVMHEALHNHYTQKSLSLSPG |
| 57 | 3057 | Full | GAAGTGCAGCTGGTCGAATCTGGAGGAGGACTGGTGCAGCCAGG<br>AGGGTCCCTGCGCCTGTCTTGCGCCGCTAGTGGCTTCACTTTTAC<br>CGACTACACCATGGATTGGGTGCGACAGGCACCTGGAAAGGGCC<br>TGGAGTGGGTCGCCGATGTGAACCCAAATAGCGGAGGCTCCATC<br>TACAACCAGCGGTTCAAGGGCCGGTTCACCCTGTCAGTGGACCG<br>GAGCAAAAACACCCTGTATCTGCAGATGAATAGCCTGCGAGCCG<br>AAGATACTGCTGTGTACTATTGCGCCCGGAATCTGGGGCCCTCCT<br>TCTACTTTGACTATTGGGGGCAGGGAACTCTGGTCACCGTGAGCT<br>CCGCCTCCACCAAGGGACCTTCTGTGTTCCCACTGGCTCCCTCTA<br>GTAAATCCACATCTGGGGAACTGCAGCCCTGGGCTGTCTGGTG<br>AAGGACTACTTCCCAGAGCCCGTCACAGTGTCTTGGAACAGTGG<br>CGCTCTGACTTCTGGGGTCCACACCTTTCCTGCAGTGCTGCAGTC<br>AAGCGGGCTGTACAGCCTGTCCTCTGTGGTCACCGTGCCAAGTTC<br>AAGCCTGGGAACACAGACTTATATCTGCAACGTGAATCACAAGC<br>CATCCAATACAAAAGTCGACAAGAAAGTGGAACCCAAGTCTTGT<br>GATAAAACCCATACATGCCCCCCTTGTCCTGCACCAGAGCTGCTG<br>GGAGGACCAAGCGTGTTCCTGTTTCCACCCAAGCCTAAAGATAC<br>ACTGATGATTAGTAGGACCCCAGAAGTCACATGCGTGGTCGTGG<br>ACGTGAGCCACGAGGACCCCGAAGTCAAGTTTAACTGGTACGTG<br>GACGGCGTCGAGGTGCATAATGCCAAGACTAAACCCAGGGAGG<br>AACAGTACAACAGTACCTATCGCGTCGTGTCAGTCCTGACAGTG<br>CTGCATCAGGATTGGCTGAACGGGAAAGAGTATAAGTGCAAAGT<br>GAGCAATAAGGCTCTGCCCGCACCTATCGAGAAAACAATTTCCA<br>AGGCAAAAGGACAGCCTAGAGAACCACAGGTGTACGTGTATCCT<br>CCATCAAGGGATGAGCTGACAAAGAACCAGGTCAGCCTGACTTG<br>TCTGGTGAAAGGATTCTATCCCTCTGACATTGCTGTGGAGTGGGA |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | AAGTAATGGCCAGCCTGAGAACAATTACAAGACCACACCCCCTG TGCTGGACTCAGATGGCAGCTTCGCGCTGGTGAGCAAGCTGACC GTCGACAAATCCCGGTGGCAGCAGGGGAATGTGTTTAGTTGTTC AGTCATGCACGAGGCACTGCACAACCATTACACCCAGAAGTCAC TGTCACTGTCACCAGGG |
| 58 | 3057 | VH | EVQLVESGGGLVQPGGSLRLSCAASGFTFTDYTMDWVRQAPGKGL EWVADVNPNSGGSIYNQRFKGRFTLSVDRSKNTLYLQMNSLRAED TAVYYCARNLGPSFYFDYWGQGTLVTVSS |
| 59 | 3317 | Full | DIQMTQSPSSLSASVGDRVTITCKASQDVSIGVAWYQQKPGKAPKL LIYSASYRYTGVPSRFSGSGSGTDFTLTISSLQPEDFATYYCQQYYIY PYTFGQGTKVEIKGGGGSGGGGSGGGGSEVQLVESGGGLVQPGGS LRLSCAASGFTFTDYTMDWVRQAPGKGLEWVADVNPNSGGSIYNQ RFKGRFTLSVDRSKNTLYLQMNSLRAEDTAVYYCARNLGPSFYFDY WGQGTLVTVSSAAEPKSSDKTHTCPPCPAPELLGGPSVFLFPPKPKD TLMISRTPEVTCVVVDVSHEDPEVKFNWYVDGVEVHNAKTKPREE QYNSTYRVVSVLTVLHQDWLNGKEYKCKVSNKALPAPIEKTISKAK GQPREPQVYVYPPSRDELTKNQVSLTCLVKGFYPSDIAVEWESNGQ PENNYKTTPPVLDSDGSFALVSKLTVDKSRWQQGNVFSCSVMHEA LHNHYTQKSLSLSPGK |
| 60 | 3317 | Full | GACATTCAGATGACCCAGAGCCCTAGCTCCCTGAGTGCCTCAGT CGGGGACAGGGTGACTATCACCTGCAAGGCTTCACAGGATGTCA GCATTGGCGTGGCATGGTACCAGCAGAAGCCAGGGAAAGCACCC AAGCTGCTGATCTATAGCGCCTCCTACAGGTATACAGGCGTGCC ATCCCGCTTCTCTGGCAGTGGGTCAGGAACTGACTTTACACTGAC TATTTCTAGTCTGCAGCCCGAAGATTTCGCCACATACTATTGCCA GCAGTACTATATCTACCCTTATACTTTTGGCCAGGGGACCAAAGT GGAGATTAAGGGCGGAGGAGGCTCCGGAGGAGGAGGGTCTGGA GGAGGAGGAAGTGAGGTCCAGCTGGTGGAATCTGGAGGAGGAC TGGTGCAGCCAGGAGGGTCCCTGAGGCTGTCTTGTGCCGCTAGT GGCTTCACCTTTACAGACTACACAATGGATTGGGTGCGCCAGGC ACCAGGAAAGGGACTGGAATGGGTCGCTGATGTGAACCCTAATA GCGGAGGCTCCATCTACAACCAGCGGTTCAAAGGACGGTTCACC CTGTCAGTGGACCGGAGCAAGAACACCCTGTATCTGCAGATGAA CAGCCTGAGAGCCGAGGATACTGCTGTGTACTATTGCGCCAGGA ATCTGGGCCCAAGCTTCTACTTTGACTATTGGGGCAGGGAACA CTGGTCACTGTGTCAAGCGCAGCCGAACCCAAATCCTCTGATAA GACTCACACCTGCCCCACCTTGTCCAGCTCCAGAGCTGCTGGGAG GACCTAGCGTGTTCCTGTTTCCACCCAAGCCAAAAGACACTCTGA TGATTTCTAGAACCCCTGAAGTGACATGTGTGGTCGTGGACGTCA GTCACGAGGACCCCGAAGTCAAATTCAACTGGTACGTGGATGGC GTCGAGGTGCATAATGCCAAGACCAAACCCCGAGAGGAACAGT ACAACTCAACCTATCGGGTCGTGAGCGTCCTGACAGTGCTGCAT CAGGACTGGCTGAACGGCAAGGAGTATAAGTGCAAAGTGAGCA ACAAGGCTCTGCCTGCACCAATCGAGAAGACCATTTCCAAGGCT AAAGGGCAGCCCCGCGAACCTCAGGTCTACGTGTATCCTCCAAG CCCAGAGATGAGCTGACAAAAAACCAGGTCTCCCTGACTTGTCTGG TGAAGGGATTTTACCCAAGTGACATCGCAGTGGAGTGGGAATCA AATGGCCAGCCCGAAAACAATTATAAGACCACACCCCCTGTGCT GGACTCTGATGGGAGTTTCGCACTGGTCTCCAAACTGACCGTGG ACAAGTCTCGGTGGCAGCAGGGGAAACGTCTTTAGCTGTTCCGTG ATGCACGAGGCCCTGCACAATCATTACACACAGAAATCTCTGAG TCTGTCACCTGGCAAG |
| 61 | 3317 | VL | DIQMTQSPSSLSASVGDRVTITCKASQDVSIGVAWYQQKPGKAPKL LIYSASYRYTGVPSRFSGSGSGTDFTLTISSLQPEDFATYYCQQYYIY PYTFGQGTKVEIK |
| 62 | 3317 | VH | EVQLVESGGGLVQPGGSLRLSCAASGFTFTDYTMDWVRQAPGKGL EWVADVNPNSGGSIYNQRFKGRFTLSVDRSKNTLYLQMNSLRAED TAVYYCARNLGPSFYFDYWGQGTLVTVSS |
| 63 | 5244 | Full | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIKGGSGGGSGGGSGGGSEVQLVESGGGLVQP GGSLRLSCAASGFNIKDTYIHWVRQAPGKGLEWVARIYPTNGYTRY ADSVKGRFTISADTSKNTAYLQMNSLRAEDTAVYYCSRWGGDGFY AMDYWGQGTLVTVSSAAEPKSSDKTHTCPPCPAPELLGGPSVFLFP PKPKDTLMISRTPEVTCVVVDVSHEDPEVKFNWYVDGVEVHNAKT KPREEQYNSTYRVVSVLTVLHQDWLNGKEYKCKVSNKALPAPIEK TISKAKGQPREPQVYVLPPSRDELTKNQVSLLCLVKGFYPSDIAVEW |

TABLE B-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | ESNGQPENNYLTWPPVLDSDGSFFLYSKLTVDKSRWQQGNVFSCSV MHEALHNHYTQKSLSLSPG |
| 64 | 5244 | Full | GACATTCAGATGACACAGAGCCCCAGCTCCCTGAGTGCTTCAGT CGGCGACAGGGTGACTATCACCTGCCGCGCATCCCAGGATGTCA ACACCGCTGTGGCATGGTACCAGCAGAAGCCTGGAAAAGCCCCA AAGCTGCTGATCTACAGCGCTTCCTTCCTGTATTCTGGCGTGCCA AGTCGGTTTTCTGGAAGTAGATCAGGCACTGACTTCACACTGACT ATCTCTAGTCTGCAGCCCGAAGATTTTGCCACCTACTATTGCCAG CAGCACTATACCACACCCCTACATTCGGACAGGGCACTAAAGT GGAGATTAAGGGCGGGTCAGGCGGAGGGAGCGGAGGAGGGTCC GGAGGAGGGTCTGGAGGAGGGAGTGGAGAGGTCCAGCTGGTGG AATCTGGAGGAGGACTGGTGCAGCCTGGAGGCTCACTGCGACTG AGCTGTGCCGCTTCCGGCTTTAACATCAAAGACATACATTCAT TGGGTCAGGCAGGCACCAGGGAAGGGACTGGAATGGGTGGCCC GCATCTATCCCACAAATGGGTACACTCGATATGCCGACAGCGTG AAAGGACGGTTTACCATTTCTGCTGATACCAGTAAGAACACAGC ATACCTGCAGATGAACAGCCTGCGCGCAGAGGATACAGCCGTGT ACTATTGCAGTCGATGGGGGGGAGACGGCTTCTACGCCATGGAT TATTGGGGCCAGGGGACTCTGGTCACCGTGTCAAGCGCAGCCGA ACCTAAATCCTCTGACAAGACCCACACATGCCCACCCTGTCCTGC TCCAGAGCTGCTGGGAGGACCATCCGTGTTCCTGTTTCCTCCAAA GCCTAAAGATACACTGATGATTAGCCGCACTCCCGAAGTCACCT GTGTGGTCGTGGACGTGTCCCACGAGGACCCCGAAGTCAAGTTC AACTGGTACGTGGACGGCGTCGAGGTGCATAATGCCAAGACTAA ACCAAGAGAGGAACAGTACAATTCAACCTATAGGGTCGTGAGCG TCCTGACAGTGCTGCATCAGGATTGGCTGAACGGCAAGGAGTAT AAGTGCAAAGTGTCTAACAAGGCCCTGCCCGCTCCTATCGAGAA GACTATTAGCAAGGCAAAAGGGCAGCCACGGGAACCCCAGGTCT ACGTGCTGCCCCCTAGCAGAGACGAGCTGACCAAAAACCAGGTC TCCCTGCTGTGTCTGGTGAAGGGCTTTTATCCTAGTGATATCGCT GTGGAGTGGGAATCAAATGGGCAGCCAGAAAACAATTACCTGAC ATGGCCACCCGTGCTGGACAGCGATGGGTCCTTCTTTCTGTATTC CAAACTGACTGTGGACAAGTCTAGATGGCAGCAGGGAAACGTCT TCAGCTGTTCCGTGATGCACGAGGCCCTGCACAATCATTACACCC AGAAGTCTCTGAGTCTGTCACCCGGC |
| 65 | 5244 | VL | DIQMTQSPSSLSASVGDRVTITCRASQDVNTAVAWYQQKPGKAPKL LIYSASFLYSGVPSRFSGSRSGTDFTLTISSLQPEDFATYYCQQHYTTP PTFGQGTKVEIK |
| 66 | 5244 | VH | EVQLVESGGGLVQPGGSLRLSCAASGFNIKDTYIHWVRQAPGKGLE WVARIYPTNGYTRYADSVKGRFTISADTSKNTAYLQMNSLRAEDT AVYYCSRWGGDGFYAMDYWGQGTLVTVSS |
| 67 | 5244, 5034, 719, 720 | L1 | QDVNTA |
| 68 | 5244, 5034, 719, 720 | L2 | SAS |
| 69 | 5244, 5034, 719, 720 | L3 | QQHYTTPPT |
| 70 | 5244 | H1 | GFNIKDTY |
| 71 | 5244 | H2 | IYPTNGYT |
| 72 | 5244 | H3 | SRWGGDGFYAMDY |

TABLE C

Sequences for VH and VL Regions of Variants v7133, v15082, v15085, v15083, v15080, v15079, v15084 and v15081

| SEQ ID NO | Variant | Desc. | Sequence |
|---|---|---|---|
| 78 | 7133 | VH | EVQLVESGGGLVQPGGSLRLSCAASGFTFADYTMDWVRQAPGKGL EWVADVNPNSGGSIYNQRFKGRFTLSVDRSKNTLYLQMNSLRAED TAVYYCARNLGPSFYFDYWGQGTLVTVSS |
| 79 | 7133 | VL | DIQMTQSPSSLSASVGDRVTITCKASQDVSIGVAWYQQKPGKAPKL LIYSASYRYTGVPSRFSGSGSGTDFTLTISSLQPEDFATYYCQQYYIY PATFGQGTKVEIK |
| 80 | 15082 | VH | EVQLVESGGGLVQPGGSLRLSCAASGFTFTDYTMDWVRQAPGKGL EWVADVNPNSGYSIYNQRFKGRFTLSVDRSWNTLYLQMNSLRAED TAVYYCARNLGPSFYFDYWGQGTLVTVSS |
| 81 | 15082 & 15085 | VL | DIQMTQSPSSLSASVGDRVTITCKASQDVSIGVAWYQQKPGKAPKL LIYSASYRYTGVPSRFSGSGSGTDFTLTISSLQPEDFATYYCQQYYIY PYTFGQGTKVEIK |
| 82 | 15085 | VH | EVQLVESGGGLVQPGGSLRLSCAASGFTFQDYTMDWVRQAPGKGL EWVADVNPNSGGSIYNQRFKGRFTLSVDRSKNTLYLQMNSLRAED TAVYYCARNLGPWFYFDYWGQGTLVTVSS |
| 83 | 15083 | VH | EVQLVESGGGLVQPGGSLRLSCAASGFTFQDYTMDWVRQAPGKGL EWVADVNPNSGGSIYNQRFKGRFTLSVDRSKNTLYLQMNSLRAED TAVYYCARNLGPSFYFDYWGQGTLVTVSS |
| 84 | 15083, 15080, 15079 & 15081 | VL | DIQMTQSPSSLSASVGDRVTITCKASQDVSIGVAWYQQKPGKAPKL LIWSASYRYTGVPSRFSGSGSGTDFTLTISSLQPEDFATYYCQQYYIY PGTFGQGTKVEIK |
| 85 | 15080 | VH | EVQLVESGGGLVQPGGSLRLSCAASGFTFQDYTMDWVRQAPGKGL EWVADVNPNSGGSIYNQRFKGRFTLSVDRSWNTLYLQMNSLRAED TAVYYCARNLGPSFYFDYWGQGTLVTVSS |
| 86 | 15079 | VH | EVQLVESGGGLVQPGGSLRLSCAASGFTFYDYTMDWVRQAPGKGL EWVADVNPNSGGSIYNQRFKGRFTLSVDRSWNTLYLQMNSLRAED TAVYYCARNLGPSFYFDYWGQGTLVTVSS |
| 87 | 15084 | VH | EVQLVESGGGLVQPGGSLRLSCAASGFTFQDYTMDWVRQAPGKGL EWVADVNPNSGYSIYNQRFKGRFTLSVDRSKNTLYLQMNSLRAED TAVYYCARNLGPWFYFDYWGQGTLVTVSS |
| 88 | 15084 | VL | DIQMTQSPSSLSASVGDRVTITCKASQDVSIGVAWYQQKPGKAPKL LIWSASYRYTGVPSRFSGSGSGTDFTLTISSLQPEDFATYYCQQYYIY PYTFGQGTKVEIK |
| 89 | 15081 | VH | EVQLVESGGGLVQPGGSLRLSCAASGFTFQDYTMDWVRQAPGKGL EWVADVNPNSGYSIYNQRFKGRFTLSVDRSKNTLYLQMNSLRAED TAVYYCARNLGPSFYFDYWGQGTLVTVSS |

We claim:

1. A method of treating a HER2-expressing cancer comprising administering to a subject having a HER2-expressing cancer an effective amount of an antibody-drug conjugate comprising an anti-HER2 biparatopic antibody conjugated to an auristatin analogue via a linker (L) at a low average drug-to-antibody ratio (DAR), wherein the anti-HER2 biparatopic antibody comprises a first antigen-binding polypeptide construct comprising the CDR sequences set forth in SEQ ID NOs: 67, 68, 69, 70, 71 and 72, and a second antigen-binding polypeptide construct comprising the CDR sequences set forth in SEQ ID NOs: 27, 28, 29, 39, 40 and 41, wherein the auristatin analogue and linker have general Formula (X):

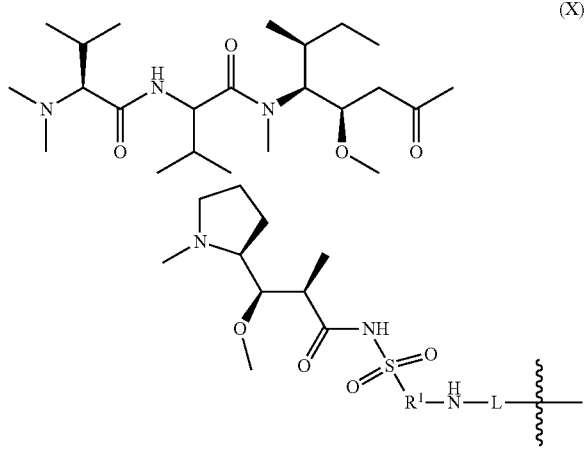

wherein:
$R^1$ is

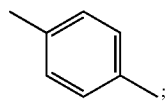

L is a protease-cleavable linker, and
⌇ represents the point of attachment of the linker to the anti-HER2 biparatopic antibody, and
wherein the low average DAR is an average DAR of between 1.5 and 2.5.

2. The method according to claim 1, wherein the HER2-expressing cancer is a breast cancer, ovarian cancer, lung cancer or gastric cancer.

3. The method according to claim 1, wherein the HER2-expressing cancer is scored as HER2 negative by immunohistochemistry.

4. The method according to claim 1, wherein the HER2-expressing cancer is scored as HER2 3+ by immunohistochemistry.

5. The method according to claim 1, wherein the HER2-expressing cancer is scored as HER2 1+ or HER2 1+/2+ by immunohistochemistry.

6. The method according to claim 1, wherein the average DAR is between 1.8 and 2.5.

7. The method according to claim 1, wherein the conjugate comprises between about 10% and about 30% DAR0 species.

8. The method according to claim 1, wherein the conjugate comprises between about 10% and about 25% DAR0 species.

9. The method according to claim 1, wherein the conjugate comprises between about 15% and about 25% DAR0 species.

10. The method according to claim 1, wherein the conjugate comprises between 0% and about 15% DAR6 or greater species.

11. The method according to claim 1, wherein the conjugate comprises between about 0% and about 10% DAR6 or greater species.

12. The method according to claim 6, wherein L has general Formula (VI):

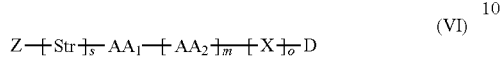

(VI)

wherein:
Z is a functional group capable of reacting with the target group on the anti-HER2 biparatopic antibody;
Str is a stretcher;
$AA_1$ and $AA_2$ are each independently an amino acid, wherein $AA_1$-$[AA_2]_m$ forms a protease cleavage site;
X is a self-immolative group;
D is the point of attachment to the auristatin analogue;
s is 0 or 1;
m is an integer between 1 and 4, and
o is 0, 1 or 2.

13. The method according to claim 1, wherein L has general Formula (VIII) or general Formula (IX):

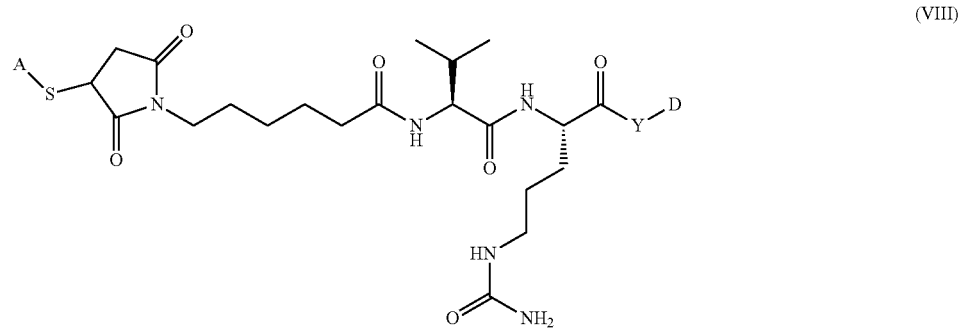

(VIII)

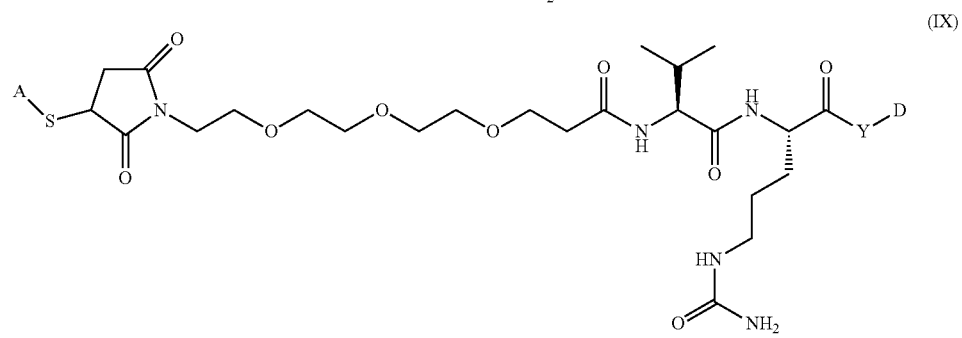

(IX)

wherein:
A-S- is the point of attachment to the anti-HER2 biparatopic antibody;
Y is one or more additional linker components, or is absent, and
D is the point of attachment to the auristatin analogue.

14. The method according to claim 1, wherein the auristatin analogue and linker have the structure:

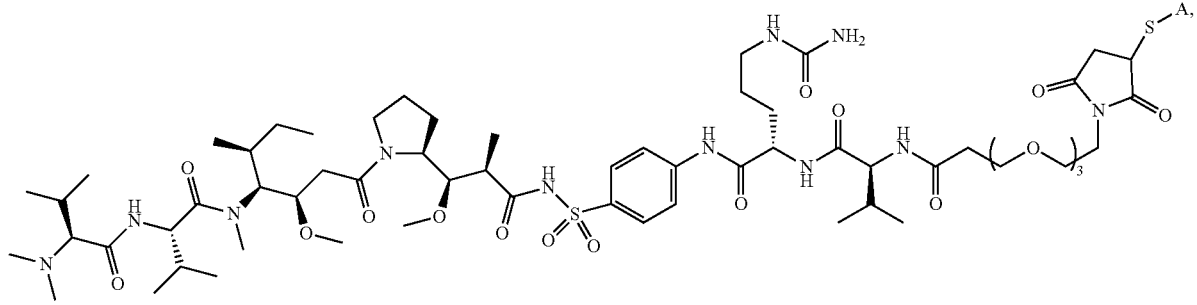

wherein A-S- is the point of attachment to the anti-HER2 biparatopic antibody.

15. The method according to claim 14, wherein the conjugate comprises between about 10% and about 30% DAR0 species.

16. The method according to claim 14, wherein the conjugate comprises between 0% and about 15% DAR6 or greater species.

17. The method according to claim 1, wherein the first and second antigen-binding polypeptide constructs are each independently an scFv or a Fab.

18. The method according to claim 1, wherein the first antigen-binding polypeptide construct is an scFv, and the second antigen-binding polypeptide construct is a Fab.

19. The method according to claim 1, wherein the anti-HER2 biparatopic antibody comprises an IgG Fc region that is a heterodimeric Fc region comprising a modified CH3 domain.

20. The method according to claim 19, wherein the modified CH3 domain comprises a first polypeptide sequence and a second polypeptide sequence, and wherein:
  (a) the first polypeptide sequence of the modified CH3 domain comprises the amino acid modifications L351Y, F405A and Y407V, and the second polypeptide sequence of the modified CH3 domain comprises the amino acid modifications T366L, K392M and T394W; or
  (b) the first polypeptide sequence of the modified CH3 domain comprises the amino acid modifications L351Y, F405A and Y407V, and the second polypeptide sequence of the modified CH3 domain comprises the amino acid modifications T366L, K392L and T394W; or
  (c) the first polypeptide sequence of the modified CH3 domain comprises the amino acid modifications T350V, L351Y, F405A and Y407V, and the second polypeptide sequence of the modified CH3 domain comprises the amino acid modifications T350V, T366L, K392M and T394W; or
  (d) the first polypeptide sequence of the modified CH3 domain comprises the amino acid modifications T350V, L351Y, F405A and Y407V, and the second polypeptide sequence of the modified CH3 domain comprises the amino acid modifications T350V, T366L, K392L and T394W; or
  (e) the first polypeptide sequence of the modified CH3 domain comprises the amino acid modifications T350V, L351Y, S400E, F405A and Y407V, and the second polypeptide sequence of the modified CH3 domain comprises the amino acid modifications T350V, T366L, N390R, K392M and T394W.

21. The method according to claim 19, wherein the first polypeptide sequence of the modified CH3 domain comprises the amino acid modifications T350V, L351Y, F405A and Y407V, and the second polypeptide sequence of the modified CH3 domain comprises the amino acid modifications T350V, T366L, K392L and T394W.

22. The method according to claim 1, wherein the anti-HER2 biparatopic antibody comprises:
  (i) a first heavy chain (H1) comprising the CDR sequences as set forth in SEQ ID NOs: 39, 40 and 41,
  (ii) a second heavy chain (H2) comprising the CDR sequences as set forth in SEQ ID NOs: 67, 68, 69, 70, 71 and 72, and
  (iii) a light chain (L1) comprising the CDR sequences as set forth in SEQ ID NOs: 27, 28 and 29, and the auristatin analogue and linker have the structure:

wherein A-S- is the point of attachment to the anti-HER2 biparatopic antibody;
wherein the low average DAR is an average DAR of between 1.8 and 2.5, and
wherein the conjugate comprises between about 10% and about 25% DAR0 species.

23. The method according to claim 22, wherein the average DAR is about 2.0.

24. The method according to claim 22, wherein:
  (i) the H1 comprises the VH sequence as set forth in SEQ ID NO: 38,
  (ii) the H2 comprises the VH sequence as set forth in SEQ ID NO: 66 and the VL sequence as set forth in SEQ ID NO: 65, and
  (iii) the L1 comprises the VL sequence as set forth in SEQ ID NO: 26.

25. The method according to claim 22, wherein the H1 comprises the sequence as set forth in SEQ ID NO: 36, the H2 comprises the sequence as set forth in SEQ ID NO: 63, and the L1 comprises the sequence as set forth in SEQ ID NO: 24.

26. The method according to claim 22, wherein the H1 consists of the sequence as set forth in SEQ ID NO: 36, the H2 consists of the sequence as set forth in SEQ ID NO: 63, and the L1 consists of the sequence as set forth in SEQ ID NO: 24.

27. The method according to claim 22, wherein the HER2-expressing cancer is a breast cancer, ovarian cancer, lung cancer or gastric cancer.

28. The method according to claim 22, wherein the HER2-expressing cancer is a breast cancer.

29. The method according to claim 22, wherein the HER2-expressing cancer is an ovarian cancer.

30. The method according to claim 22, wherein the HER2-expressing cancer is a HER2 high cancer.

31. The method according to claim 22, wherein the HER2-expressing cancer is a HER2 low cancer.

32. The method according to claim 22, wherein the subject has relapsed from prior therapy.

33. The method according to claim 6, wherein:
the first antigen-binding polypeptide construct comprises the VH sequence as set forth in SEQ ID NO: 66 and the VL sequence as set forth in SEQ ID NO: 65, and
the second antigen-binding polypeptide construct comprises the VH sequence as set forth in SEQ ID NO: 38 and the VL sequence as set forth in SEQ ID NO: 26.

* * * * *

SEQUENCE LISTING

<160> NUMBER OF SEQ ID NOS: 89

<210> SEQ ID NO 1
<211> LENGTH: 217
<212> TYPE: PRT
<213> ORGANISM: Artificial Sequence
<220> FEATURE:
<223> OTHER INFORMATION: Human IgG1 Fc

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 2
<211> LENGTH: 607
<212> TYPE: PRT
<213> ORGANISM: Homo sapiens

<400> SEQUENCE: 2

Thr Gln Val Cys Thr Gly Thr Asp Met Lys Leu Arg Leu Pro Ala Ser
 1               5                  10                  15

Pro Glu Thr His Leu Asp Met Leu Arg His Leu Tyr Gln Gly Cys Gln
             20                  25                  30

Val Val Gln Gly Asn Leu Glu Leu Thr Tyr Leu Pro Thr Asn Ala Ser
         35                  40                  45

Leu Ser Phe Leu Gln Asp Ile Gln Glu Val Gln Gly Tyr Val Leu Ile
     50                  55                  60

Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

```
Leu Thr Arg Thr Val Cys Ala Gly Gly Cys Ala Arg Cys Lys Gly Pro
    195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn
        595                 600                 605
```

<210> SEQ ID NO 3
<211> LENGTH: 448
<212> TYPE: PRT
<213> ORGANISM: Artificial Sequence
<220> FEATURE:
<223> OTHER INFORMATION: H2 clone 3468 Full

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Gly Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Lys Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Leu Pro Pro Ser Arg Asp Glu Leu Thr Lys Asn Gln Val Ser Leu Leu
        355                 360                 365
```

Cys Leu Val Lys Gly Phe Tyr Pro Ser Asp Ile Ala Val Glu Trp Glu
    370                 375                 380

Ser Asn Gly Gln Pro Glu Asn Asn Tyr Leu Thr Trp Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 4
<211> LENGTH: 1344
<212> TYPE: DNA
<213> ORGANISM: Artificial Sequence
<220> FEATURE:
<223> OTHER INFORMATION: H2 clone 3468 Full

<400> SEQUENCE: 4

```
gaagtgcagc tggtcgaatc tggaggagga ctggtgcagc caggagggtc cctgcgcctg      60
tcttgcgccg ctagtggctt cacttttacc gactacacca tggattgggt cgacaggca     120
cctggaaagg gcctggagtg ggtcgccgat gtgaacccaa atagcggagg ctccatctac    180
aaccagcggt tcaagggccg gttcaccctg tcagtggacc ggagcaaaaa cacccctgtat   240
ctgcagatga atagcctgcg agccgaagat actgctgtgt actattgcgc ccggaatctg    300
gggccctcct tctactttga ctattggggg cagggaactc tggtcaccgt gagctccgcc    360
tccaccaagg gaccttctgt gttcccactg gctccctcta gtaaatccac atctggggga    420
actgcagccc tgggctgtct ggtgaagggc tacttcccag agcccgtcac agtgtcttgg    480
aacagtggcg ctctgacttc tggggtccac acctttcctg cagtgctgaa gtcaagcggg    540
ctgtacagcc tgtcctctgt ggtcaccgtg ccaagttcaa gcctgggaac acagacttat    600
atctgcaacg tgaatcacaa gccatccaat acaaaagtcg acaagaaagt ggaacccaag    660
tcttgtgata aaacccatac atgccccct tgtcctgcac cagagctgct gggaggacca    720
agcgtgttcc tgtttccacc caagcctaaa gatacactga tgattagtag gaccccagaa    780
gtcacatgcg tggtcgtgga cgtgagccac gaggacccg aagtcaagtt taactggtac    840
gtggacggcg tcgaggtgca taatgccaag actaaaccca gggaggaaca gtacaacagt    900
acctatcgcg tcgtgtcagt cctgacagtg ctgcatcagg attggctgaa cgggaaagag    960
tataagtgca agtgagcaa taaggctctg cccgcaccta tcgagaaaac aatttccaag   1020
gcaaaaggac agcctagaga accacaggtg tacgtgctgc ctccatcaag ggatgagctg   1080
acaaagaacc aggtcagcct gctgtgtctg gtgaaaggat tctatccctc tgacattgct   1140
gtggagtggg aaagtaatgg ccagcctgag aacaattacc tgacctggcc ccctgtgctg   1200
gactcagatg gcagcttctt tctgtatagc aagctgaccg tcgacaaatc ccggtggcag   1260
caggggaatg tgtttagttg ttcagtcatg cacgaggcac tgcacaacca ttacacccag   1320
aagtcactgt cactgtcacc aggg                                          1344
```

<210> SEQ ID NO 5
<211> LENGTH: 119
<212> TYPE: PRT
<213> ORGANISM: Artificial Sequence
<220> FEATURE:
<223> OTHER INFORMATION: H2 clone 3468 VH

```
<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 6
<211> LENGTH: 8
<212> TYPE: PRT
<213> ORGANISM: Artificial Sequence
<220> FEATURE:
<223> OTHER INFORMATION: H1 clone 3057,3317 CDRH1, H2 clone 3468,3041
      CDRH1

<400> SEQUENCE: 6

Gly Phe Thr Phe Thr Asp Tyr Thr
1               5

<210> SEQ ID NO 7
<211> LENGTH: 12
<212> TYPE: PRT
<213> ORGANISM: Artificial Sequence
<220> FEATURE:
<223> OTHER INFORMATION: H1 clone 3057,3317 CDRH3, H2 clone 3468,3041
      CDRH3

<400> SEQUENCE: 7

Ala Arg Asn Leu Gly Pro Ser Phe Tyr Phe Asp Tyr
1               5                   10

<210> SEQ ID NO 8
<211> LENGTH: 8
<212> TYPE: PRT
<213> ORGANISM: Artificial Sequence
<220> FEATURE:
<223> OTHER INFORMATION: H1 clone 3057,3317 CDRH2, H2 clone 3468,3041
      CDRH2

<400> SEQUENCE: 8

Val Asn Pro Asn Ser Gly Gly Ser
1               5

<210> SEQ ID NO 9
<211> LENGTH: 214
<212> TYPE: PRT
<213> ORGANISM: Artificial Sequence
<220> FEATURE:
<223> OTHER INFORMATION: L2 clone 1811 Full

<400> SEQUENCE: 9

Asp Ile Gln Met Thr Gln Ser Pro Ser Ser Leu Ser Ala Ser Val Gly
```

```
  1               5                  10                 15
Asp Arg Val Thr Ile Thr Cys Lys Ala Ser Gln Asp Val Ser Ile Gly
                20                 25                 30

Val Ala Trp Tyr Gln Gln Lys Pro Gly Lys Ala Pro Lys Leu Leu Ile
            35                 40                 45

Tyr Ser Ala Ser Tyr Arg Tyr Thr Gly Val Pro Ser Arg Phe Ser Gly
        50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Tyr Tyr Ile Tyr Pro Tyr
                85                 90                 95

Thr Phe Gly Gln Gly Thr Lys Val Glu Ile Lys Arg Thr Val Ala Ala
            100                105                110

Pro Ser Val Phe Ile Phe Pro Pro Ser Asp Glu Gln Leu Lys Ser Gly
        115                120                125

Thr Ala Ser Val Val Cys Leu Leu Asn Asn Phe Tyr Pro Arg Glu Ala
    130                135                140

Lys Val Gln Trp Lys Val Asp Asn Ala Leu Gln Ser Gly Asn Ser Gln
145                 150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
            180                185                190

Ala Cys Glu Val Thr His Gln Gly Leu Ser Ser Pro Val Thr Lys Ser
        195                200                205

Phe Asn Arg Gly Glu Cys
    210

<210> SEQ ID NO 10
<211> LENGTH: 642
<212> TYPE: DNA
<213> ORGANISM: Artificial Sequence
<220> FEATURE:
<223> OTHER INFORMATION: L2 clone 1811 Full

<400> SEQUENCE: 10
gatattcaga tgacccagtc cccaagctcc ctgagtgcct cagtgggcga ccgagtcacc      60
atcacatgca aggcttccca ggatgtgtct attggagtcg catggtacca gcagaagcca     120
ggcaaagcac ccaagctgct gatctatagc gcctcctacc ggtataccgg cgtgccctct     180
agattctctg gcagtgggtc aggaacagac tttactctga ccatctctag tctgcagcct     240
gaggatttcg ctacctacta ttgccagcag tactatatct acccatatac ctttggccag     300
gggacaaaag tggagatcaa gaggactgtg gccgctccct ccgtcttcat tttteccect     360 tctgacgaac agctgaaaag tggcacagcc agcgtggtct gtctgctgaa caatttctac     420
cctcgcgaag ccaaagtgca gtggaaggtc gataacgctc tgcagagcgg caacagccag     480
gagtctgtga ctgaacagga cagtaaagat tcaacctata gcctgtcaag cacactgact     540
ctgagcaagg cagactacga gaagcacaaa gtgtatgcct gcgaagtcac acatcagggg     600
ctgtcctctc ctgtgactaa gagctttaac agaggagagt gt                        642

<210> SEQ ID NO 11
<211> LENGTH: 107
<212> TYPE: PRT
<213> ORGANISM: Artificial Sequence
<220> FEATURE:
```

<223> OTHER INFORMATION: L2 clone 1811 VL

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 12
<211> LENGTH: 6
<212> TYPE: PRT
<213> ORGANISM: Artificial sequence
<220> FEATURE:
<223> OTHER INFORMATION: L2 clones 1811, 3904 CDRL1 and H1 clone 3317
      CDRL1

<400> SEQUENCE: 12

```
Gln Asp Val Ser Ile Gly
1               5
```

<210> SEQ ID NO 13
<211> LENGTH: 9
<212> TYPE: PRT
<213> ORGANISM: Artificial Sequence
<220> FEATURE:
<223> OTHER INFORMATION: L3 clones 1811, 3904 CDRL3 and H1 clone 3317
      CDRL3

<400> SEQUENCE: 13

```
Gln Gln Tyr Tyr Ile Tyr Pro Tyr Thr
1               5
```

<210> SEQ ID NO 14
<211> LENGTH: 3
<212> TYPE: PRT
<213> ORGANISM: Artificial Sequence
<220> FEATURE:
<223> OTHER INFORMATION: L2 clones 1811, 3904 CDRL2 and H1 clone 3317
      CDRL2

<400> SEQUENCE: 14

```
Ser Ala Ser
1
```

<210> SEQ ID NO 15
<211> LENGTH: 222
<212> TYPE: PRT
<213> ORGANISM: Artificial Sequence
<220> FEATURE:
<223> OTHER INFORMATION: L1 clone 5034 Full

<400> SEQUENCE: 15

```
Asp Tyr Lys Asp Asp Asp Lys Asp Ile Gln Met Thr Gln Ser Pro
1               5                   10                  15
```

```
Ser Ser Leu Ser Ala Ser Val Gly Asp Arg Val Thr Ile Thr Cys Arg
            20                  25                  30

Ala Ser Gln Asp Val Asn Thr Ala Val Ala Trp Tyr Gln Gln Lys Pro
        35                  40                  45

Gly Lys Ala Pro Lys Leu Leu Ile Tyr Ser Ala Ser Phe Leu Tyr Ser
    50                  55                  60

Gly Val Pro Ser Arg Phe Ser Gly Ser Arg Ser Gly Thr Asp Phe Thr
65                  70                  75                  80

Leu Thr Ile Ser Ser Leu Gln Pro Glu Asp Phe Ala Thr Tyr Tyr Cys
                85                  90                  95

Gln Gln His Tyr Thr Thr Pro Pro Thr Phe Gly Gln Gly Thr Lys Val
            100                 105                 110

Glu Ile Lys Arg Thr Val Ala Ala Pro Ser Val Phe Ile Phe Pro Pro
        115                 120                 125

Ser Asp Glu Arg Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
            165                 170                 175

Lys Asp Ser Thr Tyr Ser Leu Ser Ser Thr Leu Thr Leu Ser Lys Ala
        180                 185                 190

Asp Tyr Glu Lys His Lys Val Tyr Ala Cys Glu Val Thr His Gln Gly
    195                 200                 205

Leu Ser Ser Pro Val Thr Lys Ser Phe Asn Arg Gly Glu Cys
    210                 215                 220

<210> SEQ ID NO 16
<211> LENGTH: 666
<212> TYPE: DNA
<213> ORGANISM: Artificial Sequence
<220> FEATURE:
<223> OTHER INFORMATION: L1 clone 5034 Full

<400> SEQUENCE: 16
gactacaaag acgacgatga caaagatatc cagatgaccc agtcccctag ctccctgtcc    60
gcttctgtgg gcgatagggt cactattacc tgccgcgcat ctcaggacgt gaacaccgca   120
gtcgcctggt accagcagaa gcctgggaaa gctccaaagc tgctgatcta cagtgcatca   180
ttcctgtatt caggagtgcc cagccggttt agcggcagca gatctggcac cgatttcaca   240
ctgactattt ctagtctgca gcctgaggac tttgccacat actattgcca gcagcactat   300
accacacccc ctactttcgg ccaggggacc aaagtggaga tcaagcgaac tgtggccgct   360
ccaagtgtct tcattttccc acccagcgat gaaagactga agtccggcac agcttctgtg   420
gtctgtctgc tgaacaattt ttaccccaga gaggccaaag tgcagtggaa ggtcgacaac   480
gctctgcaga gtggcaacag ccaggagagc gtgacagaac aggattccaa agactctact   540
tatagtctgt caagcaccct gacactgagc aaggcagact acgaaaagca taaagtgtat   600
gcctgtgagg tcacacatca ggggctgtca tcaccagtca ccaaatcatt caatcggggg   660
gagtgc                                                             666

<210> SEQ ID NO 17
<211> LENGTH: 107
<212> TYPE: PRT
<213> ORGANISM: Artificial Sequence
```

```
<220> FEATURE:
<223> OTHER INFORMATION: L1 clone 5034 VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 18
<211> LENGTH: 222
<212> TYPE: PRT
<213> ORGANISM: Artificial Sequence
<220> FEATURE:
<223> OTHER INFORMATION: L1 cone 5037 Full

<400> SEQUENCE: 18

Asp Tyr Lys Asp Asp Asp Lys Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Asp Val Asn Thr Ala Val Ala Trp Tyr Gln Gln Lys Pro
        35                  40                  45

Gly Lys Ala Pro Lys Leu Leu Ile Tyr Ser Ala Ser Phe Leu Tyr Ser
    50                  55                  60

Gly Val Pro Ser Arg Phe Ser Gly Ser Arg Ser Gly Thr Asp Phe Thr
65                  70                  75                  80

Leu Thr Ile Ser Ser Leu Gln Pro Glu Asp Phe Ala Thr Tyr Tyr Cys
                85                  90                  95

Gln Gln His Tyr Thr Thr Pro Pro Thr Phe Gly Gln Gly Thr Lys Val
            100                 105                 110

Glu Ile Lys Arg Thr Val Ala Ala Pro Ser Val Phe Ile Phe Pro Pro
        115                 120                 125

Ser Asp Glu Arg Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Lys Glu Ser Val Thr Glu Gln Asp Ser
                165                 170                 175

Lys Asp Ser Thr Tyr Ser Leu Ser Ser Arg Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220
```

<210> SEQ ID NO 19
<211> LENGTH: 666
<212> TYPE: DNA
<213> ORGANISM: Artificial Sequence
<220> FEATURE:
<223> OTHER INFORMATION: L1 clone 5037 Full

<400> SEQUENCE: 19

```
gactacaaag acgacgatga caaagatatc cagatgaccc agtcccctag ctccctgtcc     60
gcttctgtgg gcgatagggt cactattacc tgccgcgcat ctcaggacgt gaacaccgca    120
gtcgcctggt accagcagaa gcctgggaaa gctccaaagc tgctgatcta cagtgcatca    180
ttcctgtatt caggagtgcc agccggttt agcggcagca gatctggcac cgatttcaca    240
ctgactattt ctagtctgca gcctgaggac tttgccacat actattgcca gcagcactat    300
accacacccc ctactttcgg ccaggggacc aaagtggaga tcaagcgaac tgtggccgct    360
ccaagtgtct catttttcc acccagcgat gaaagactga agtccggcac agcttctgtg    420
gtctgtctgc tgaacaattt ttaccccaga gaggccaaag tgcagtggaa ggtcgacaac    480
gctctgcaga gtggcaacag caaggagagc gtgacagaac aggattccaa agactctact    540
tatagtctgt caagcagact gacactgagc aaggcagact acgaaaagca taaagtgtat    600
gcctgtgagg tcacacatca ggggctgtca tcaccagtca ccaaatcatt caatcggggg    660
gagtgc                                                               666
```

<210> SEQ ID NO 20
<211> LENGTH: 107
<212> TYPE: PRT
<213> ORGANISM: Artificial Sequence
<220> FEATURE:
<223> OTHER INFORMATION: L1 clone 5037 VL

<400> SEQUENCE: 20

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 21
<211> LENGTH: 6
<212> TYPE: PRT
<213> ORGANISM: Artificial Sequence
<220> FEATURE:
<223> OTHER INFORMATION: L1 clone 5037 CDRL1

<400> SEQUENCE: 21

```
Gln Asp Val Asn Thr Ala
1               5
```

<210> SEQ ID NO 22

```
<211> LENGTH: 9
<212> TYPE: PRT
<213> ORGANISM: Artificial Sequence
<220> FEATURE:
<223> OTHER INFORMATION: L1 clone 5037 CDRL3

<400> SEQUENCE: 22

Gln Gln His Tyr Thr Thr Pro Pro Thr
1               5

<210> SEQ ID NO 23
<211> LENGTH: 3
<212> TYPE: PRT
<213> ORGANISM: Artificial Sequence
<220> FEATURE:
<223> OTHER INFORMATION: L1 clone 5037 CDRL2

<400> SEQUENCE: 23

Ser Ala Ser
1

<210> SEQ ID NO 24
<211> LENGTH: 214
<212> TYPE: PRT
<213> ORGANISM: Artificial Sequence
<220> FEATURE:
<223> OTHER INFORMATION: L1 clone 3382 Full

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 642
```

<212> TYPE: DNA
<213> ORGANISM: Artificial Sequence
<220> FEATURE:
<223> OTHER INFORMATION: L1 clone 3382 Full

<400> SEQUENCE: 25

```
gatattcaga tgacccagtc cccaagctcc ctgagtgcct cagtgggcga ccgagtcacc      60
atcacatgca aggcttccca ggatgtgtct attggagtcg catggtacca gcagaagcca     120
ggcaaagcac ccaagctgct gatctatagc gcctcctacc ggtataccgg cgtgccctct     180
agattctctg gcagtgggtc aggaacagac tttactctga ccatctctag tctgcagcct     240
gaggatttcg ctacctacta ttgccagcag tactatatct acccagccac ctttggccag     300
gggacaaaag tggagatcaa ggactgtg ccgctccct ccgtcttcat ttttcccct         360
tctgacgaac agctgaaaag tggcacagcc agcgtggtct gtctgctgaa caatttctac     420
cctcgcgaag ccaaagtgca gtggaaggtc gataacgctc tgcagagcgg caacagccag     480
gagtctgtga ctaacagga cagtaaagat tcaacctata gcctgtcaag cacactgact      540
ctgagcaagg cagactacga gaagcacaaa gtgtatgcct gcgaagtcac acatcagggg     600
ctgtcctctc ctgtgactaa gagctttaac agaggagagt gt                        642
```

<210> SEQ ID NO 26
<211> LENGTH: 107
<212> TYPE: PRT
<213> ORGANISM: Artificial Sequence
<220> FEATURE:
<223> OTHER INFORMATION: L1 clone 3382 VL

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ala
                85                  90                  95

Thr Phe Gly Gln Gly Thr Lys Val Glu Ile Lys
            100                 105
```

<210> SEQ ID NO 27
<211> LENGTH: 6
<212> TYPE: PRT
<213> ORGANISM: Artificial Sequence
<220> FEATURE:
<223> OTHER INFORMATION: L1 clone 3382 CDRL1

<400> SEQUENCE: 27

```
Gln Asp Val Ser Ile Gly
1               5
```

<210> SEQ ID NO 28
<211> LENGTH: 9
<212> TYPE: PRT
<213> ORGANISM: Artificial Sequence
<220> FEATURE:

-continued

<223> OTHER INFORMATION: L1 clone 3382 CDRL3

<400> SEQUENCE: 28

Gln Gln Tyr Tyr Ile Tyr Pro Ala Thr
1               5

<210> SEQ ID NO 29
<211> LENGTH: 3
<212> TYPE: PRT
<213> ORGANISM: Artificial Sequence
<220> FEATURE:
<223> OTHER INFORMATION: L1 clone 3382 CDRL2

<400> SEQUENCE: 29

Ser Ala Ser
1

<210> SEQ ID NO 30
<211> LENGTH: 449
<212> TYPE: PRT
<213> ORGANISM: Artificial Sequence
<220> FEATURE:
<223> OTHER INFORMATION: H1 clone 5065 Full

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Glu Val Thr Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu

```
                 260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Val Tyr Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Ala Leu Val Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 31
<211> LENGTH: 1347
<212> TYPE: DNA
<213> ORGANISM: Artificial Sequence
<220> FEATURE:
<223> OTHER INFORMATION: H1 clone 5065 Full

<400> SEQUENCE: 31
gaggtgcagc tggtcgaaag cggaggagga ctggtgcagc caggagggtc actgcgactg    60
agctgcgcag cttccggctt caacatcaag gacacctaca ttcactgggt ccgccaggct   120
cctggaaaag gcctggagtg ggtggcacga atctatccaa ctaatggata cacccggtat   180
gccgactccg tgaagggccg gttcaccatt tctgcagata caagtaaaaa cactgcctac   240
ctgcagatga cagcctgcg agccgaagat acagccgtgt actattgcag ccgatgggga   300
ggcgacggct tctacgctat ggattattgg ggcagggaa ccctggtcac agtgagctcc   360
gcatcaacaa aggggcctag cgtgtttcca ctggccccct ctagtaaatc cacctctggg   420
ggaacagcag ccctgggatg tgaggtgacc gactacttcc cagagcccgt cactgtgagc   480
tggaactccg gcgccctgac atctggggtc catacttttc ctgctgtgct gcagtcaagc   540
ggcctgtaca gcctgtcctc tgtggtcact gtgccaagtt caagcctggg gactcagacc   600
tatatctgca acgtgaatca caagccatcc aataccaaag tcgacaagaa agtggaaccc   660
aagtcttgtg ataaaacaca tacttgcccc ccttgtcctg caccagagct gctgggagga   720
ccaagcgtgt tcctgttttcc acccaagcct aaagacaccc tgatgattag taggactcca   780
gaagtcacct gcgtggtcgt ggacgtgagc cacgaggacc ccgaagtcaa gttcaactgg   840
tacgtggatg gcgtcgaggt gcataatgcc aagacaaaac ccagggagga acagtacaac   900
tccacttatc gcgtcgtgtc tgtcctgacc gtgctgcacc aggactggct gaacggcaag   960
```

```
gagtataagt gcaaagtgag caataaggct ctgcccgcac ctatcgagaa aacaatttcc    1020
aaggctaaag ggcagcctag agaaccacag gtgtacgtgt accctccatc tagggacgag    1080
ctgaccaaga accaggtcag tctgacatgt ctggtgaaag ggttctatcc cagcgatatc    1140
gcagtggagt gggaatccaa tggacagcct gagaacaatt acaagaccac accccctgtg    1200
ctggactctg atggaagttt cgccctggtg agtaagctga ccgtcgataa atcacggtgg    1260
cagcagggca acgtgttcag ctgttcagtg atgcacgaag cactgcacaa ccactacacc    1320
cagaaaagcc tgtccctgtc ccccggc                                        1347
```

<210> SEQ ID NO 32
<211> LENGTH: 120
<212> TYPE: PRT
<213> ORGANISM: Artificial Sequence
<220> FEATURE:
<223> OTHER INFORMATION: H1 clone 5065 VH

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 33
<211> LENGTH: 8
<212> TYPE: PRT
<213> ORGANISM: Artificial Sequence
<220> FEATURE:
<223> OTHER INFORMATION: H1 clones 5065, 719 CDRH1 and H2 clone 720
      CDRH1

<400> SEQUENCE: 33

```
Gly Phe Asn Ile Lys Asp Thr Tyr
1               5
```

<210> SEQ ID NO 34
<211> LENGTH: 13
<212> TYPE: PRT
<213> ORGANISM: Artificial Sequence
<220> FEATURE:
<223> OTHER INFORMATION: H1 clones 5065, 719 CDRH3 and H2 clone 720
      CDRH3

<400> SEQUENCE: 34

```
Ser Arg Trp Gly Gly Asp Gly Phe Tyr Ala Met Asp Tyr
1               5                   10
```

<210> SEQ ID NO 35
<211> LENGTH: 8

-continued

```
<212> TYPE: PRT
<213> ORGANISM: Artificial Sequence
<220> FEATURE:
<223> OTHER INFORMATION: H1 clones 5065, 719 CDRH2 and H2 clone 720
      CDRH2

<400> SEQUENCE: 35

Ile Tyr Pro Thr Asn Gly Tyr Thr
1               5

<210> SEQ ID NO 36
<211> LENGTH: 448
<212> TYPE: PRT
<213> ORGANISM: Artificial Sequence
<220> FEATURE:
<223> OTHER INFORMATION: H1 clone 6586 Full

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
                20                  25                  30

Thr Met Asp Trp Val Arg Gln Ala Pro Gly Lys Gly Leu Glu Trp Val
            35                  40                  45

Gly Asp Val Asn Pro Asn Ser Gly Ser Ile Tyr Asn Gln Arg Phe
    50                  55                  60

Lys Gly Arg Phe Thr Phe Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
            305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Tyr Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 37
<211> LENGTH: 1344
<212> TYPE: DNA
<213> ORGANISM: Artificial Sequence
<220> FEATURE:
<223> OTHER INFORMATION: H1 clone 6586 Full

<400> SEQUENCE: 37
```

| | | | | | |
|---|---|---|---|---|---|
| gaggtgcagc | tggtggaatc | aggagggggc | ctggtgcagc | ccggagggtc | tctgcgactg | 60 |
| tcatgtgccg | cttctgggtt | cactttcgca | gactacacaa | tggattgggt | gcgacaggcc | 120 |
| cccggaaagg | gactggagtg | ggtgggcgat | gtcaacccta | ttctggcgg | gagtatctac | 180 |
| aaccagcggt | tcaaggggag | attcactttt | tcagtggaca | gaagcaaaaa | caccctgtat | 240 |
| ctgcagatga | acagcctgag | ggccgaagat | accgctgtct | actattgcgc | tcgcaatctg | 300 |
| ggccccagtt | tctactttga | ctattggggg | cagggaaccc | tggtgacagt | cagctccgct | 360 |
| agcactaagg | gccttccgt | gtttccactg | gctccctcta | gtaaatccac | ctctggaggc | 420 |
| acagctgcac | tgggatgtct | ggtgaaggat | tacttccctg | aaccagtcac | agtgagttgg | 480 |
| aactcagggg | ctctgacaag | tggagtccat | acttttcccg | cagtgctgca | gtcaagcgga | 540 |
| ctgtactccc | tgtcctctgt | ggtcaccgtg | cctagttcaa | gcctgggcac | ccagacatat | 600 |
| atctgcaacg | tgaatcacaa | gccatcaaat | acaaaagtcg | acaagaaagt | ggagcccaag | 660 |
| agctgtgata | aaactcatac | ctgcccacct | tgtccggcgc | cagaactgct | gggaggacca | 720 |
| agcgtgttcc | tgtttccacc | caagcctaaa | gacaccctga | tgatttcccg | gactcctgag | 780 |
| gtcacctgcg | tggtcgtgga | cgtgtctcac | gaggacccg | aagtcaagtt | caactggtac | 840 |
| gtggatggcg | tcgaagtgca | taatgccaag | accaaacccc | gggaggaaca | gtacaactct | 900 |
| acctatagag | tcgtgagtgt | cctgacagtg | ctgcaccagg | actggctgaa | tgggaaggag | 960 |
| tataagtgta | agtgagcaa | caaagccctg | cccgcccaa | tcgaaaaaac | aatctctaaa | 1020 |
| gcaaaaggac | agcctcgcga | accacaggtc | tacgtctacc | ccccatcaag | agatgaactg | 1080 |
| acaaaaaatc | aggtctctct | gacatgcctg | gtcaaaggat | tctacccttc | cgacatcgcc | 1140 |
| gtggagtggg | aaagtaacgg | ccagcccgag | aacaattaca | agaccacacc | ccctgtcctg | 1200 |
| gactctgatg | gagttttcgc | tctggtgtca | aagctgaccg | tcgataaaag | ccggtggcag | 1260 |
| cagggcaatg | tgtttagctg | ctccgtcatg | cacgaagccc | tgcacaatca | ctacacacag | 1320 |

```
aagtccctga gcctgagccc tggc                                          1344
```

<210> SEQ ID NO 38
<211> LENGTH: 119
<212> TYPE: PRT
<213> ORGANISM: Artificial Sequence
<220> FEATURE:
<223> OTHER INFORMATION: H1 clone 6586 VH

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Thr Met Asp Trp Val Arg Gln Ala Pro Gly Lys Gly Leu Glu Trp Val
        35                  40                  45

Gly Asp Val Asn Pro Asn Ser Gly Gly Ser Ile Tyr Asn Gln Arg Phe
    50                  55                  60

Lys Gly Arg Phe Thr Phe Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 39
<211> LENGTH: 8
<212> TYPE: PRT
<213> ORGANISM: Artificial Sequence
<220> FEATURE:
<223> OTHER INFORMATION: H1 clone 6586 CDRH1

<400> SEQUENCE: 39

Gly Phe Thr Phe Ala Asp Tyr Thr
1               5

<210> SEQ ID NO 40
<211> LENGTH: 12
<212> TYPE: PRT
<213> ORGANISM: Artificial Sequence
<220> FEATURE:
<223> OTHER INFORMATION: H1 clone 6586 CDRH3

<400> SEQUENCE: 40

Ala Arg Asn Leu Gly Pro Ser Phe Tyr Phe Asp Tyr
1               5                   10

<210> SEQ ID NO 41
<211> LENGTH: 8
<212> TYPE: PRT
<213> ORGANISM: Artificial Sequence
<220> FEATURE:
<223> OTHER INFORMATION: H1 clone 6586 CDRH2

<400> SEQUENCE: 41

Val Asn Pro Asn Ser Gly Gly Ser
1               5

<210> SEQ ID NO 42
<211> LENGTH: 226

```
<212> TYPE: PRT
<213> ORGANISM: Artificial Sequence
<220> FEATURE:
<223> OTHER INFORMATION: L2 clone 3904 Full

<400> SEQUENCE: 42

Tyr Pro Tyr Asp Val Pro Asp Tyr Ala Thr Gly Ser Asp Ile Gln Met
1               5                   10                  15

Thr Gln Ser Pro Ser Ser Leu Ser Ala Ser Val Gly Asp Arg Val Thr
            20                  25                  30

Ile Thr Cys Lys Ala Ser Gln Asp Val Ser Ile Gly Val Ala Trp Tyr
        35                  40                  45

Gln Gln Lys Pro Gly Lys Ala Pro Lys Leu Leu Ile Tyr Ser Ala Ser
    50                  55                  60

Tyr Arg Tyr Thr Gly Val Pro Ser Arg Phe Ser Gly Ser Gly Ser Gly
65                  70                  75                  80

Thr Asp Phe Thr Leu Thr Ile Ser Ser Leu Gln Pro Glu Asp Phe Ala
                85                  90                  95

Thr Tyr Tyr Cys Gln Gln Tyr Tyr Ile Tyr Pro Tyr Thr Phe Gly Gln
            100                 105                 110

Gly Thr Lys Val Glu Ile Lys Arg Thr Val Ala Ala Pro Ser Val Phe
        115                 120                 125

Ile Phe Pro Pro Ser Asp Glu Glu Leu Lys Ser Gly Thr Ala Ser Val
130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Glu Glu Ser Val Thr
                165                 170                 175

Glu Gln Asp Ser Lys Asp Ser Thr Tyr Ser Leu Ser Ser Thr Leu Glu
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

<210> SEQ ID NO 43
<211> LENGTH: 678
<212> TYPE: DNA
<213> ORGANISM: Artificial Sequence
<220> FEATURE:
<223> OTHER INFORMATION: L2 clone 3904 Full

<400> SEQUENCE: 43
tatccctacg atgtgcctga ctacgctact ggctccgata tccagatgac ccagtctcca      60
agctccctga gtgcatcagt gggggaccga gtcaccatca catgcaaggc ttcccaggat     120
gtgtctattg gagtcgcatg gtaccagcag aagccaggca agcacccaa gctgctgatc      180 tacagcgcct cctaccggta tactggggtg ccttccagat tctctggcag tgggtcagga     240
accgacttta ctctgaccat ctctagtctg cagcccgagg atttcgccac ctactattgc     300
cagcagtact atatctaccc ttataccttt ggccagggga caaaagtgga gatcaagagg     360
acagtggccg ctccaagtgt cttcattttt ccccccttccg acgaagagct gaaaagtgga    420
actgcttcag tggtctgtct gctgaacaat ttctaccccc gcgaagccaa agtgcagtgg    480
aaggtcgata acgctctgca gagcggcaat tccgaggagt ctgtgacaga acaggacagt    540
```

```
aaagattcaa cttatagcct gtcaagcaca ctggagctgt ctaaggcaga ctacgagaag    600
cacaaagtgt atgcctgcga agtcacccat cagggggctgt cctctcccgt gacaaagagc    660
tttaacagag gagagtgt                                                   678
```

<210> SEQ ID NO 44
<211> LENGTH: 107
<212> TYPE: PRT
<213> ORGANISM: Artificial Sequence
<220> FEATURE:
<223> OTHER INFORMATION: L2 clone 3904 VL

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 45
<211> LENGTH: 481
<212> TYPE: PRT
<213> ORGANISM: Artificial Sequence
<220> FEATURE:
<223> OTHER INFORMATION: H1 clone 719 Full

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Ser Gly Gly Ser Gly Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
```

```
                  165                 170                 175
Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Tyr Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Glu Asp Gly Ser Phe Ala Leu Val Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 46
<211> LENGTH: 1443
<212> TYPE: DNA
<213> ORGANISM: Artificial Sequence
<220> FEATURE:
<223> OTHER INFORMATION: H1 clone 719 Full

<400> SEQUENCE: 46
gacatccaga tgacccagtc tccatcctcc ctgtctgcat ctgtaggaga cagagtcacc      60
atcacttgcc gggcaagtca ggacgttaac accgctgtag cttggtatca gcagaaacca     120
gggaaagccc ctaagctcct gatctattct gcatcctttt tgtacagtgg ggtcccatca     180
aggttcagtg gcagtcgatc tgggacagat ttcactctca ccatcagcag tctgcaacct     240
```

```
gaagattttg caacttacta ctgtcaacag cattacacta ccccacccac tttcggccaa    300
gggaccaaag tggagatcaa aggtggttct ggtggtggtt ctggtggtgg ttctggtggt    360
ggttctggtg gtggttctgg tgaagtgcag ctggtggagt ctgggggagg cttggtacag    420
cctggcgggt ccctgagact ctcctgtgca gcctctggat tcaacattaa agatacttat    480
atccactggg tccggcaagc tccagggaag ggcctggagt gggtcgcacg tatttatccc    540
acaaatggtt acacacggta tgcggactct gtgaagggcc gattcaccat ctccgcagac    600
acttccaaga acaccgcgta tctgcaaatg aacagtctga gctgagga cacggccgtt     660 tattactgtt caagatgggg cggagacggt ttctacgcta tggactactg gggccaaggg    720
accctggtca ccgtctcctc agccgccgag cccaagagca cgataagac ccacacctgc     780 cctccctgtc cagctccaga actgctggga ggacctagcg tgttcctgtt tccccctaag    840
ccaaaagaca ctctgatgat ttccaggact cccgaggtga cctgcgtggt ggtggacgtg    900
tctcacgagg accccgaagt gaagttcaac tggtacgtgg atggcgtgga agtgcataat    960
gctaagacaa aaccaagaga ggaacagtac aactccactt atcgcgtcgt gagcgtgctg   1020
accgtgctgc accaggactg gctgaacggg aaggagtata agtgcaaagt cagtaataag   1080
gccctgcctg ctccaatcga aaaaaccatc tctaaggcca aggcagcc aagggagccc     1140 caggtgtaca catacccacc cagcagagac gaactgacca gaaccaggt gtccctgaca     1200 tgtctggtga aggcttcta tcctagtgat attgctgtgg agtgggaatc aaatggacag     1260
ccagagaaca attacaagac cacacctcca gtgctggacg aggatggcag cttcgccctg   1320
gtgtccaagc tgacagtgga taatctcga tggcagcagg ggaacgtgtt tagttgttca    1380
gtgatgcatg aagccctgca caatcattac actcagaaga gcctgtccct gtctcccggc   1440
aaa                                                                  1443
```

<210> SEQ ID NO 47
<211> LENGTH: 107
<212> TYPE: PRT
<213> ORGANISM: Artificial Sequence
<220> FEATURE:
<223> OTHER INFORMATION: H1 clone 719 VL

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 48
<211> LENGTH: 120
<212> TYPE: PRT
<213> ORGANISM: Artificial Sequence
<220> FEATURE:

<223> OTHER INFORMATION: H1 clone 719 VH

<400> SEQUENCE: 48

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 49
<211> LENGTH: 481
<212> TYPE: PRT
<213> ORGANISM: Artificial Sequence
<220> FEATURE:
<223> OTHER INFORMATION: H2 clone 720 Full

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220
```

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
            245                 250                 255

Thr His Thr Cys Pro Pro Cys Pro Ala Pro Glu Leu Leu Gly Gly Pro
        260                 265                 270

Ser Val Phe Leu Phe Pro Pro Lys Pro Lys Asp Thr Leu Met Ile Ser
    275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Glu
        340                 345                 350

Tyr Lys Cys Lys Val Ser Asn Lys Ala Leu Pro Ala Pro Ile Glu Lys
    355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Ile
385                 390                 395                 400

Cys Leu Val Lys Gly Phe Tyr Pro Ser Asp Ile Ala Val Glu Trp Glu
            405                 410                 415

Ser Asn Gly Gln Pro Glu Asn Arg Tyr Met Thr Trp Pro Pro Val Leu
        420                 425                 430

Asp Ser Asp Gly Ser Phe Phe Leu Tyr Ser Lys Leu Thr Val Asp Lys
    435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 50
<211> LENGTH: 1443
<212> TYPE: DNA
<213> ORGANISM: Artificial Sequence
<220> FEATURE:
<223> OTHER INFORMATION: H2 clone 720 Full

<400> SEQUENCE: 50
gacatccaga tgacccagtc tccatcctcc ctgtctgcat ctgtaggaga cagagtcacc      60
atcacttgcc gggcaagtca ggacgttaac accgctgtag cttggtatca gcagaaacca     120
gggaaagccc ctaagctcct gatctattct gcatcctttt tgtacagtgg ggtcccatca     180
aggttcagtg gcagtcgatc tgggacagat ttcactctca ccatcagcag tctgcaacct     240
gaagattttg caacttacta ctgtcaacag cattacacta ccccacccac tttcggccaa     300
gggaccaaag tggagatcaa aggtggttct ggtggtggtt ctggtggtgg ttctggtggt     360
ggttctggtg gtggttctgg tgaagtgcag ctggtggagt ctgggggagg cttggtacag     420
cctggcgggt ccctgagact ctcctgtgca gcctctggat tcaacattaa agatacttat     480
atccactggg tccggcaagc tccagggaag ggcctggagt gggtcgcacg tatttatccc     540

```
acaaatggtt acacacggta tgcggactct gtgaagggcc gattcaccat ctccgcagac    600
acttccaaga acaccgcgta tctgcaaatg aacagtctga gagctgagga cacggccgtt    660
tattactgtt caagatgggg cggagacggt ttctacgcta tggactactg gggccaaggg    720
accctggtca ccgtctcctc agccgccgag cccaagagca cgataagac ccacacctgc     780 cctccctgtc cagctccaga actgctggga ggacctagcg tgttcctgtt tccccctaag    840
ccaaaagaca ctctgatgat ttccaggact cccgaggtga cctgcgtggt ggtggacgtg    900
tctcacgagg accccgaagt gaagttcaac tggtacgtgg atggcgtgga agtgcataat    960
gctaagacaa aaccaagaga ggaacagtac aactccactt atcgcgtcgt gagcgtgctg   1020
accgtgctgc accaggactg gctgaacggg aaggagtata agtgcaaagt cagtaataag   1080
gccctgcctg ctccaatcga aaaaaccatc tctaaggcca aaggccagcc aagggagccc   1140
caggtgtaca cactgccacc cagcagagac gaactgacca gaaccaggt gtccctgatc    1200 tgtctggtga aaggcttcta tcctagtgat attgctgtgg agtgggaatc aaatggacag   1260
ccagagaaca gatacatgac ctggcctcca gtgctggaca gcgatggcag cttcttcctg   1320
tattccaagc tgacagtgga taaatctcga tggcagcagg ggaacgtgtt tagttgttca   1380
gtgatgcatg aagccctgca caatcattac actcagaaga gcctgtccct gtctcccggc   1440
aaa                                                                 1443

<210> SEQ ID NO 51
<211> LENGTH: 107
<212> TYPE: PRT
<213> ORGANISM: Artificial Sequence
<220> FEATURE:
<223> OTHER INFORMATION: H2 clone 720 VL

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 52
<211> LENGTH: 120
<212> TYPE: PRT
<213> ORGANISM: Artificial Sequence
<220> FEATURE:
<223> OTHER INFORMATION: H2 clone 720 VH

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120
```

<210> SEQ ID NO 53
<211> LENGTH: 448
<212> TYPE: PRT
<213> ORGANISM: Artificial Sequence
<220> FEATURE:
<223> OTHER INFORMATION: H2 clone 3041 Full

<400> SEQUENCE: 53

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
             35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270
```

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Leu Pro Pro Ser Arg Asp Glu Leu Thr Lys Asn Gln Val Ser Leu Leu
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Leu Thr Trp Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 54
<211> LENGTH: 1344
<212> TYPE: DNA
<213> ORGANISM: Artificial Sequence
<220> FEATURE:
<223> OTHER INFORMATION: H2 clone 3042 Full

<400> SEQUENCE: 54

| | |
|---|---|
| gaagtgcagc tggtcgaatc tggaggagga ctggtgcagc caggagggtc cctgcgcctg | 60 |
| tcttgcgccg ctagtggctt cacttttacc gactacacca tggattgggt gcgacaggca | 120 |
| cctggaaagg gcctggagtg ggtcgccgat gtgaacccaa atagcggagg ctccatctac | 180 |
| aaccagcggt tcaagggccg gttcaccctg tcagtggacc ggagcaaaaa caccctgtat | 240 |
| ctgcagatga atagcctgcg agccgaagat actgctgtgt actattgcgc ccggaatctg | 300 |
| gggccctcct tctactttga ctattggggg cagggaactc tggtcaccgt gagctccgcc | 360 |
| tccaccaagg gccttctgt gttcccactg gctccctcta gtaaatccac atctggggga | 420 |
| actgcagccc tgggctgtct ggtgaaggac tacttcccag agcccgtcac agtgtcttgg | 480 |
| aacagtggcg ctctgacttc tggggtccac acctttcctg cagtgctgca gtcaagcggg | 540 |
| ctgtacagcc tgtcctctgt ggtcaccgtg ccaagttcaa gcctgggaac acagacttat | 600 |
| atctgcaacg tgaatcacaa gccatccaat acaaaagtcg acaagaaagt ggaacccaag | 660 |
| tcttgtgata aaacccatac atgccccccct gtcctgcac agagctgct gggaggacca | 720 |
| agcgtgttcc tgtttccacc caagcctaaa gatacactga tgattagtag gacccccaga | 780 |
| gtcacatgcg tggtcgtgga cgtgagccac gaggaccccg aagtcaagtt taactggtac | 840 |
| gtggacggcg tcgaggtgca taatgccaag actaaaccca gggaggaaca gtacaacagt | 900 |
| acctatcgcg tcgtgtcagt cctgacagtg ctgcatcagg attggctgaa cgggaaagag | 960 |
| tataagtgca agtgagcaa taaggctctg cccgcaccta tcgagaaaac aatttccaag | 1020 |
| gcaaaaggac agcctagaga accacaggtg tacgtgctgc ctccatcaag ggatgagctg | 1080 |

```
acaaagaacc aggtcagcct gctgtgtctg gtgaaaggat tctatccctc tgacattgct   1140
gtggagtggg aaagtaatgg ccagcctgag aacaattacc tgacctggcc ccctgtgctg   1200
gactcagatg gcagcttctt tctgtatagc aagctgaccg tcgacaaatc ccggtggcag   1260
caggggaatg tgtttagttg ttcagtcatg cacgaggcac tgcacaacca ttacacccag   1320
aagtcactgt cactgtcacc aggg                                          1344
```

```
<210> SEQ ID NO 55
<211> LENGTH: 119
<212> TYPE: PRT
<213> ORGANISM: Artificial Sequence
<220> FEATURE:
<223> OTHER INFORMATION: H2 clone 3041 VH

<400> SEQUENCE: 55
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

```
<210> SEQ ID NO 56
<211> LENGTH: 448
<212> TYPE: PRT
<213> ORGANISM: Artificial Sequence
<220> FEATURE:
<223> OTHER INFORMATION: H1 clone 3057 Full

<400> SEQUENCE: 56
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
                340                 345                 350

Tyr Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 57
<211> LENGTH: 1344
<212> TYPE: DNA
<213> ORGANISM: Artificial Sequence
<220> FEATURE:
<223> OTHER INFORMATION: H1 clone 3057 Full

<400> SEQUENCE: 57
gaagtgcagc tggtcgaatc tggaggagga ctggtgcagc caggagggtc cctgcgcctg     60
tcttgcgccg ctagtggctt cacttttacc gactacacca tggattgggt cgacaggca    120 cctggaaagg gcctggagtg ggtcgccgat gtgaacccaa atagcggagg ctccatctac    180
aaccagcggt tcaagggccg gttcacccg tcagtggacc ggagcaaaaa caccctgtat    240
ctgcagatga atagcctgcg agccgaagat actgctgtgt actattgcgc ccggaatctg    300

-continued

```
gggccctcct tctactttga ctattggggg cagggaactc tggtcaccgt gagctccgcc    360
tccaccaagg gaccttctgt gttcccactg gctccctcta gtaaatccac atctgggga     420
actgcagccc tgggctgtct ggtgaaggac tacttcccag agcccgtcac agtgtcttgg    480
aacagtggcg ctctgacttc tggggtccac acctttcctg cagtgctgca gtcaagcggg    540
ctgtacagcc tgtcctctgt ggtcaccgtg ccaagttcaa gcctgggaac acagacttat    600
atctgcaacg tgaatcacaa gccatccaat acaaaagtcg acaagaaagt ggaacccaag    660
tcttgtgata aacccatac atgccccct tgtcctgcac cagagctgct gggaggacca     720
agcgtgttcc tgtttccacc caagcctaaa gatacactga tgattagtag acccccagaa    780
gtcacatgcg tggtcgtgga cgtgagccac gaggaccccg aagtcaagtt taactggtac    840
gtggacggcg tcgaggtgca taatgccaag actaaaccca gggaggaaca gtacaacagt    900
acctatcgcg tcgtgtcagt cctgacagtg ctgcatcagg attggctgaa cgggaaagag    960
tataagtgca agtgagcaa taaggctctg cccgcaccta tcgagaaaac aattccaag    1020
gcaaaaggac agcctagaga accacaggtg tacgtgtatc ctccatcaag ggatgagctg   1080
acaaagaacc aggtcagcct gacttgtctg gtgaaaggat tctatccctc tgacattgct   1140
gtggagtggg aaagtaatgg ccagcctgag acaattaca agaccacacc ccctgtgctg    1200
gactcagatg gcagcttcgc gctggtgagc aagctgaccg tcgacaaatc ccggtggcag   1260
caggggaatg tgtttagttg ttcagtcatg cacgaggcac tgcacaacca ttacacccag   1320
aagtcactgt cactgtcacc aggg                                          1344
```

<210> SEQ ID NO 58
<211> LENGTH: 119
<212> TYPE: PRT
<213> ORGANISM: Artificial Sequence
<220> FEATURE:
<223> OTHER INFORMATION: H1 clone 3057 VH

<400> SEQUENCE: 58

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Thr Met Asp Trp Val Arg Gln Ala Pro Gly Lys Gly Leu Glu Trp Val
        35                  40                  45
Ala Asp Val Asn Pro Asn Ser Gly Gly Ser Ile Tyr Asn Gln Arg Phe
    50                  55                  60
Lys Gly Arg Phe Thr Leu Ser Val Asp Arg Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asn Leu Gly Pro Ser Phe Tyr Phe Asp Tyr Trp Gly Gln Gly
            100                 105                 110
Thr Leu Val Thr Val Ser Ser
        115
```

<210> SEQ ID NO 59
<211> LENGTH: 475
<212> TYPE: PRT
<213> ORGANISM: Artificial Sequence
<220> FEATURE:
<223> OTHER INFORMATION: H1 clone 3317 Full

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Thr Asp Tyr Thr Met Asp Trp Val Arg
145                 150                 155                 160

Gln Ala Pro Gly Lys Gly Leu Glu Trp Val Ala Asp Val Asn Pro Asn
                165                 170                 175

Ser Gly Gly Ser Ile Tyr Asn Gln Arg Phe Lys Gly Arg Phe Thr Leu
                180                 185                 190

Ser Val Asp Arg Ser Lys Asn Thr Leu Tyr Leu Gln Met Asn Ser Leu
            195                 200                 205

Arg Ala Glu Asp Thr Ala Val Tyr Tyr Cys Ala Arg Asn Leu Gly Pro
        210                 215                 220

Ser Phe Tyr Phe Asp Tyr Trp Gly Gln Gly Thr Leu Val Thr Val Ser
225                 230                 235                 240

Ser Ala Ala Glu Pro Lys Ser Ser Asp Lys Thr His Thr Cys Pro Pro
                245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Val Tyr Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415
```

| Asn | Asn | Tyr | Lys | Thr | Thr | Pro | Pro | Val | Leu | Asp | Ser | Asp | Gly | Ser | Phe |
|-----|-----|-----|-----|-----|-----|-----|-----|-----|-----|-----|-----|-----|-----|-----|-----|
|     |     |     | 420 |     |     |     | 425 |     |     |     |     | 430 |     |     |     |

| Ala | Leu | Val | Ser | Lys | Leu | Thr | Val | Asp | Lys | Ser | Arg | Trp | Gln | Gln | Gly |
|-----|-----|-----|-----|-----|-----|-----|-----|-----|-----|-----|-----|-----|-----|-----|-----|
|     |     |     |     | 435 |     |     |     |     | 440 |     |     |     |     | 445 |     |

| Asn | Val | Phe | Ser | Cys | Ser | Val | Met | His | Glu | Ala | Leu | His | Asn | His | Tyr |
|-----|-----|-----|-----|-----|-----|-----|-----|-----|-----|-----|-----|-----|-----|-----|-----|
|     |     |     | 450 |     |     |     |     | 455 |     |     |     | 460 |     |     |     |

| Thr | Gln | Lys | Ser | Leu | Ser | Leu | Ser | Pro | Gly | Lys |
|-----|-----|-----|-----|-----|-----|-----|-----|-----|-----|-----|
| 465 |     |     |     | 470 |     |     |     | 475 |     |     |

<210> SEQ ID NO 60
<211> LENGTH: 1425
<212> TYPE: DNA
<213> ORGANISM: Artificial Sequence
<220> FEATURE:
<223> OTHER INFORMATION: H1 clone 3317 Full

<400> SEQUENCE: 60

| gacattcaga | tgacccagag | ccctagctcc | ctgagtgcct | cagtcgggga | cagggtgact | 60 |
| atcacctgca | aggcttcaca | ggatgtcagc | attggcgtgg | catggtacca | gcagaagcca | 120 |
| gggaaagcac | ccaagctgct | gatctatagc | gcctcctaca | ggtatacagg | cgtgccatcc | 180 |
| cgcttctctg | gcagtgggtc | aggaactgac | tttacactga | ctatttctag | tctgcagccc | 240 |
| gaagatttcg | ccacatacta | ttgccagcag | tactatatct | acccttatac | ttttggccag | 300 |
| gggaccaaag | tggagattaa | ggcggagga | ggctccggag | gaggagggtc | tggaggagga | 360 |
| ggaagtgagg | tccagctggt | ggaatctgga | ggaggactgg | tgcagccagg | agggtccctg | 420 |
| aggctgtctt | gtgccgctag | tggcttcacc | tttacagact | acacaatgga | ttgggtgcgc | 480 |
| caggcaccag | aaagggact | ggaatgggtc | gctgatgtga | accctaatag | cggaggctcc | 540 |
| atctacaacc | agcggttcaa | aggacggttc | accctgtcag | tggaccggag | caagaacacc | 600 |
| ctgtatctgc | agatgaacag | cctgagagcc | gaggatactg | ctgtgtacta | ttgcgccagg | 660 |
| aatctgggcc | caagcttcta | ctttgactat | tgggggcagg | gaacactggt | cactgtgtca | 720 |
| agcgcagccg | aacccaaatc | tctgataag | actcacacct | gcccaccttg | tccagctcca | 780 |
| gagctgctgg | gaggacctag | cgtgttcctg | tttccaccca | agccaaaaga | cactctgatg | 840 |
| atttctagaa | cccctgaagt | gacatgtgtg | gtcgtggacg | tcagtcacga | ggaccccgaa | 900 |
| gtcaaattca | actggtacgt | ggatggcgtc | gaggtgcata | atgccaagac | caaaccccga | 960 |
| gaggaacagt | acaactcaac | ctatcgggtc | gtgagcgtcc | tgacagtgct | gcatcaggac | 1020 |
| tggctgaacg | gcaaggagta | taagtgcaaa | gtgagcaaca | aggctctgcc | tgcaccaatc | 1080 |
| gagaagacca | tttccaaggc | taagggcag | ccccgcgaac | tcaggtctac | cgtgtatcct | 1140 |
| ccaagccgag | atgagctgac | aaaaaaccag | gtctccctga | cttgtctggt | gaagggattt | 1200 |
| tacccaagtg | acatcgcagt | ggagtgggaa | tcaaatggcc | agcccgaaaa | caattataag | 1260 |
| accacacccc | ctgtgctgga | ctctgatggg | agtttcgcac | tggtctccaa | actgaccgtg | 1320 |
| gacaagtctc | ggtggcagca | gggaaacgtc | tttagctgtt | ccgtgatgca | cgaggccctg | 1380 |
| cacaatcatt | acacacagaa | atctctgagt | ctgtcacctg | gcaag |      | 1425 |

<210> SEQ ID NO 61
<211> LENGTH: 107
<212> TYPE: PRT
<213> ORGANISM: Artificial Sequence
<220> FEATURE:
<223> OTHER INFORMATION: H1 clone 3317 VL

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 62
<211> LENGTH: 119
<212> TYPE: PRT
<213> ORGANISM: Artificial Sequence
<220> FEATURE:
<223> OTHER INFORMATION: H1 clone 3317 VH

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 63
<211> LENGTH: 480
<212> TYPE: PRT
<213> ORGANISM: Artificial Sequence
<220> FEATURE:
<223> OTHER INFORMATION: H2 clone 5244 Full

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
```

```
             65                  70                  75                  80
Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys Gly Gly Ser Gly Gly
                100                 105                 110

Gly Ser Gly Gly Gly Ser Gly Gly Gly Ser Gly Gly Gly Ser Gly Glu
                115                 120                 125

Val Gln Leu Val Glu Ser Gly Gly Gly Leu Val Gln Pro Gly Gly Ser
            130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
        290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Val
    370                 375                 380

Leu Pro Pro Ser Arg Asp Glu Leu Thr Lys Asn Gln Val Ser Leu Leu
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Leu Thr Trp Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
        450                 455                 460

Ala Leu His Asn His Tyr Thr Gln Lys Ser Leu Ser Leu Ser Pro Gly
465                 470                 475                 480

<210> SEQ ID NO 64
```

```
<211> LENGTH: 1440
<212> TYPE: DNA
<213> ORGANISM: Artificial Sequence
<220> FEATURE:
<223> OTHER INFORMATION: H2 clone 5244 Full

<400> SEQUENCE: 64
gacattcaga tgacacagag ccccagctcc ctgagtgctt cagtcggcga cagggtgact      60
atcacctgcc gcgcatccca ggatgtcaac accgctgtgg catggtacca gcagaagcct     120
ggaaaagccc caaagctgct gatctacagc gcttccttcc tgtattctgg cgtgccaagt     180
cggttttctg gaagtagatc aggcactgac ttcacactga ctatctctag tctgcagccc     240
gaagattttg ccacctacta ttgccagcag cactatacca cacccctac attcggacag      300
ggcactaaag tggagattaa gggcgggtca ggcggaggga gcggaggagg gtccggagga     360
gggtctggag gagggagtgg agaggtccag ctggtggaat ctggaggagg actggtgcag     420
cctggaggct cactgcgact gagctgtgcc gcttccggct ttaacatcaa agacacatac     480
attcattggg tcaggcaggc accagggaag ggactggaat gggtggcccg catctatccc     540
acaaatgggt acactcgata tgccgacagc gtgaaaggac ggtttaccat ttctgctgat     600
accagtaaga cacagcata cctgcagatg aacagcctgc gcgcagagga tacagccgtg      660
tactattgca gtcgatgggg gggagacggc ttctacgcca tggattattg gggccagggg     720
actctggtca ccgtgtcaag cgcagccgaa cctaaatcct ctgacaagac ccacacatgc     780
ccaccctgtc ctgctccaga gctgctggga ggaccatccg tgttcctgtt cctccaaag     840
cctaaagata cactgatgat tagccgcact cccgaagtca cctgtgtggt cgtggacgtg     900
tcccacgagg accccgaagt caagttcaac tggtacgtgg acggcgtcga ggtgcataat     960
gccaagacta aaccaagaga ggaacagtac aattcaacct ataggggtcgt gagcgtcctg    1020
acagtgctgc atcaggattg gctgaacggc aaggagtata gtgcaaagt gtctaacaag      1080
gccctgcccg ctcctatcga gaagactatt agcaaggcaa aagggcagcc acgggaaccc     1140
caggtctacg tgctgccccc tagcagagac gagctgacca aaaaccaggt ctccctgctg     1200
tgtctggtga agggctttta tcctagtgat atcgctgtgg agtgggaatc aaatgggcag     1260
ccagaaaaca attacctgac atggccaccc gtgctggaca gcgatgggtc cttctttctg     1320
tattccaaac tgactgtgga caagtctaga tggcagcagg gaaacgtctt cagctgttcc     1380
gtgatgcacg aggccctgca caatcattac acccagaagt ctctgagtct gtcacccggc    1440

<210> SEQ ID NO 65
<211> LENGTH: 107
<212> TYPE: PRT
<213> ORGANISM: Artificial Sequence
<220> FEATURE:
<223> OTHER INFORMATION: H2 clone 5244 VL

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys
            100                 105
```

<210> SEQ ID NO 66
<211> LENGTH: 120
<212> TYPE: PRT
<213> ORGANISM: Artificial Sequence
<220> FEATURE:
<223> OTHER INFORMATION: H2 clone 5244 VH

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 67
<211> LENGTH: 6
<212> TYPE: PRT
<213> ORGANISM: Artificial Sequence
<220> FEATURE:
<223> OTHER INFORMATION: H2 clones 5244,720 CDRL1 and L1 clone 5034
      CDRL1 and H1 clone 719 CDRL1

<400> SEQUENCE: 67

```
Gln Asp Val Asn Thr Ala
1               5
```

<210> SEQ ID NO 68
<211> LENGTH: 3
<212> TYPE: PRT
<213> ORGANISM: Artificial Sequence
<220> FEATURE:
<223> OTHER INFORMATION: H2 clones 5244,720 CDRL2 and L1 clone 5034
      CDRL2 and H1 clone 719 CDRL2

<400> SEQUENCE: 68

```
Ser Ala Ser
1
```

<210> SEQ ID NO 69
<211> LENGTH: 9
<212> TYPE: PRT
<213> ORGANISM: Artificial Sequence
<220> FEATURE:
<223> OTHER INFORMATION: H2 clones 5244,720 CDRL3 and L1 clone 5034
      CDRL3 and H1 clone 719 CDRL3

```
<400> SEQUENCE: 69

Gln Gln His Tyr Thr Thr Pro Pro Thr
1               5

<210> SEQ ID NO 70
<211> LENGTH: 8
<212> TYPE: PRT
<213> ORGANISM: Artificial Sequence
<220> FEATURE:
<223> OTHER INFORMATION: H1 clone 5244 CDRH1

<400> SEQUENCE: 70

Gly Phe Asn Ile Lys Asp Thr Tyr
1               5

<210> SEQ ID NO 71
<211> LENGTH: 8
<212> TYPE: PRT
<213> ORGANISM: Artificial Sequence
<220> FEATURE:
<223> OTHER INFORMATION: H1 clone 5244 CDRH2

<400> SEQUENCE: 71

Ile Tyr Pro Thr Asn Gly Tyr Thr
1               5

<210> SEQ ID NO 72
<211> LENGTH: 13
<212> TYPE: PRT
<213> ORGANISM: Artificial Sequence
<220> FEATURE:
<223> OTHER INFORMATION: H1 clone 5244 CDRH3

<400> SEQUENCE: 72

Ser Arg Trp Gly Gly Asp Gly Phe Tyr Ala Met Asp Tyr
1               5                   10

<210> SEQ ID NO 73
<211> LENGTH: 8
<212> TYPE: PRT
<213> ORGANISM: Artificial Sequence
<220> FEATURE:
<223> OTHER INFORMATION: Variant 1582,15084,15081 CDRH2

<400> SEQUENCE: 73

Val Asn Pro Asn Ser Gly Tyr Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Variant 15085, 15083 and 15080, 15084, 15081
      CDRDH1

<400> SEQUENCE: 74

Gly Phe Thr Phe Gln Asp Tyr Thr
1               5

<210> SEQ ID NO 75
<211> LENGTH: 12
<212> TYPE: PRT
<213> ORGANISM: Artificial Sequence
<220> FEATURE:
<223> OTHER INFORMATION: Variant 15085, 15084 CDRH3
```

```
<400> SEQUENCE: 75

Ala Arg Asn Leu Gly Pro Trp Phe Tyr Phe Asp Tyr
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Variant 15083 and 15080, 15079, 15081 CDRL3

<400> SEQUENCE: 76

Gln Gln Tyr Tyr Ile Tyr Pro Gly Thr
1               5

<210> SEQ ID NO 77
<211> LENGTH: 8
<212> TYPE: PRT
<213> ORGANISM: Artificial Sequence
<220> FEATURE:
<223> OTHER INFORMATION: Variant 15079 CDRH1

<400> SEQUENCE: 77

Gly Phe Thr Phe Tyr Asp Tyr Thr
1               5

<210> SEQ ID NO 78
<211> LENGTH: 119
<212> TYPE: PRT
<213> ORGANISM: Artificial Sequence
<220> FEATURE:
<223> OTHER INFORMATION: Variant 7133 VH

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 79
<211> LENGTH: 107
<212> TYPE: PRT
<213> ORGANISM: Artificial Sequence
<220> FEATURE:
<223> OTHER INFORMATION: Variant 7133 VL

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
```

```
            20                  25                  30
Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ala
                85                  90                  95

Thr Phe Gly Gln Gly Thr Lys Val Glu Ile Lys
            100                 105

<210> SEQ ID NO 80
<211> LENGTH: 119
<212> TYPE: PRT
<213> ORGANISM: Artificial Sequence
<220> FEATURE:
<223> OTHER INFORMATION: Variant 15082 VH

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Tyr Ser Ile Tyr Asn Gln Arg Phe
50                  55                  60

Lys Gly Arg Phe Thr Leu Ser Val Asp Arg Ser Trp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 81
<211> LENGTH: 107
<212> TYPE: PRT
<213> ORGANISM: Artificial Sequence
<220> FEATURE:
<223> OTHER INFORMATION: Variant 15082 and 15085 VL

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95
```

Thr Phe Gly Gln Gly Thr Lys Val Glu Ile Lys
        100                 105

<210> SEQ ID NO 82
<211> LENGTH: 119
<212> TYPE: PRT
<213> ORGANISM: Artificial Sequence
<220> FEATURE:
<223> OTHER INFORMATION: Variant 15085 VH

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gln Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Trp Phe Tyr Phe Asp Tyr Trp Gly Gln Gly
            100                 105                 110

Thr Leu Val Thr Val Ser Ser
        115

<210> SEQ ID NO 83
<211> LENGTH: 119
<212> TYPE: PRT
<213> ORGANISM: Artificial Sequence
<220> FEATURE:
<223> OTHER INFORMATION: Variant 15083 VH

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gln Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 84
<211> LENGTH: 107
<212> TYPE: PRT
<213> ORGANISM: Artificial Sequence
<220> FEATURE:
<223> OTHER INFORMATION: Variant 15083,15080,15079 and 15081 VL

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Trp Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Gly
                85                  90                  95

Thr Phe Gly Gln Gly Thr Lys Val Glu Ile Lys
            100                 105

<210> SEQ ID NO 85
<211> LENGTH: 119
<212> TYPE: PRT
<213> ORGANISM: Artificial Sequence
<220> FEATURE:
<223> OTHER INFORMATION: Variant 15080 VH

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gln Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Trp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 86
<211> LENGTH: 119
<212> TYPE: PRT
<213> ORGANISM: Artificial Sequence
<220> FEATURE:
<223> OTHER INFORMATION: Variant 15079 VH

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Tyr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

-continued

Lys Gly Arg Phe Thr Leu Ser Val Asp Arg Ser Trp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 87
<211> LENGTH: 119
<212> TYPE: PRT
<213> ORGANISM: Artificial Sequence
<220> FEATURE:
<223> OTHER INFORMATION: Variant 15084 VH

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gln Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Tyr Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Trp Phe Tyr Phe Asp Tyr Trp Gly Gln Gly
            100                 105                 110

Thr Leu Val Thr Val Ser Ser
        115

<210> SEQ ID NO 88
<211> LENGTH: 107
<212> TYPE: PRT
<213> ORGANISM: Artificial Sequence
<220> FEATURE:
<223> OTHER INFORMATION: Variant 15084 VL

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Trp Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 89

```
<211> LENGTH: 119
<212> TYPE: PRT
<213> ORGANISM: Artificial Sequence
<220> FEATURE:
<223> OTHER INFORMATION: Variant 15081 VH

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gln Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Tyr Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115
```